US011878009B2

(12) United States Patent
Chen et al.

(10) Patent No.: US 11,878,009 B2
(45) Date of Patent: Jan. 23, 2024

(54) ANTICANCER COMBINATION OF CHIDAMIDE AND CELECOXIB SALTS

(71) Applicant: Great Novel Therapeutics Biotech & Medicals Corporation, Taipei (TW)

(72) Inventors: Jia-Shiong Chen, Taipei (TW); Mu-Hsuan Yang, Taipei (TW); Cheng-Han Chou, Taipei (TW); Yi-Hong Wu, Taipei (TW); Sz-Hao Chu, Taipei (TW); Ye-Su Chao, Taipei (TW); Chia-Nan Chen, Taipei (TW)

(73) Assignee: GREAT NOVEL THERAPEUTICS BIOTECH & MEDICALS CORPORATION, Taipei (TW)

( * ) Notice: Subject to any disclaimer, the term of this patent is extended or adjusted under 35 U.S.C. 154(b) by 0 days.

(21) Appl. No.: 16/566,744

(22) Filed: Sep. 10, 2019

(65) Prior Publication Data
US 2021/0069163 A1    Mar. 11, 2021

(51) Int. Cl.
| A61K 31/4406 | (2006.01) |
| A61K 31/415 | (2006.01) |
| A61P 35/00 | (2006.01) |
| A61K 39/00 | (2006.01) |
| C07K 16/28 | (2006.01) |

(52) U.S. Cl.
CPC ........ *A61K 31/4406* (2013.01); *A61K 31/415* (2013.01); *A61P 35/00* (2018.01); *C07K 16/2818* (2013.01); *C07K 16/2827* (2013.01); *A61K 2039/507* (2013.01); *C07K 2317/76* (2013.01)

(58) Field of Classification Search
CPC .. A61K 31/155; A61K 31/192; A61K 31/405; A61K 31/415; A61K 2300/00; A61K 31/02; A61K 39/3955; A61K 2039/505; A61K 31/4406; A61K 2039/507; C07D 487/00; C07D 401/14; C07D 413/14; C07D 417/14; C07D 471/04; C07D 491/107; C07D 495/04; C07D 403/04; C07D 405/14; C07D 407/14; C07D 409/14; C07D 413/04; C07D 471/08; C07D 471/14; C07D 487/08; C07D 487/10; C07D 491/048; C07D 491/056; C07D 491/113; C07D 493/04; C07D 498/10; C07D 513/04; C07D 519/00; A61P 35/00; C07K 16/2818; C07K 16/2827; C07K 2317/76
USPC ........................................................ 514/603
See application file for complete search history.

(56) References Cited

U.S. PATENT DOCUMENTS

| 9,573,901 | B2 * | 2/2017 | Lu ............................ A61P 17/06 |
| 10,246,462 | B2 * | 4/2019 | Beck ..................... C07D 487/04 |
| 10,287,353 | B2 * | 5/2019 | Bissonnette ......... A61K 31/167 |
| 10,385,131 | B2 * | 8/2019 | Bissonnette ....... C07K 16/2827 |
| 10,548,889 | B1 * | 2/2020 | Brands ..................... A61P 35/00 |
| 10,624,968 | B2 * | 4/2020 | Bennett ................... A61P 35/00 |
| 2015/0299126 | A1 | 10/2015 | Lu et al. |
| 2017/0327583 | A1 * | 11/2017 | Bissonnette ..... A61K 39/39558 |
| 2018/0355041 | A1 | 12/2018 | Sazinsky et al. |
| 2018/0355042 | A1 * | 12/2018 | Bissonnette ......... A61K 31/506 |
| 2019/0021103 | A1 | 1/2019 | Zhang et al. |
| 2019/0211103 | A1 * | 7/2019 | Chen .................... A61K 31/155 |

FOREIGN PATENT DOCUMENTS

| EP | 2860174 B1 | 11/2017 |
| EP | 3508224 A1 | 7/2019 |
| JP | 2019142841 A | 8/2019 |
| RU | 2603138 C1 | 11/2016 |
| WO | 2012/016111 A1 | 2/2012 |
| WO | 2014082354 A1 | 6/2014 |

OTHER PUBLICATIONS

Julius E. Remenar et al. (CrystEngComm, 2011, 13, 1081-1089, Celecoxib sodium salt: engineering crystal forms for performance, https://doi.org/10.1039/C0CE00475H).*
Tam Nm Dinh et al. (Am J Clin Exp Immunol, May 15, 2017;6(3):27-42. eCollection 2017).*
International Search Report and Written Opinion in International Patent Application No. PCT/CN2019/105421, dated Jun. 16, 2020 in 13 pages.
Office Action and Search report in Taiwan Counterpart Application No. 108132885, dated Dec. 10, 2020, in 6 pages; English translation provided.
U.S. Department of Health and Human Services Food and Drug Administration Center for Drug Evaluation and Research (CDER) Center for Biologies Evaluation and Research (CBER), "M9 Biopharmaceutics Classification System-Based Biowaivers, Guidance for Industry," May 2021, ICH.
Baghel, Shrawan, "An Investigation into the Solubility and Stability of Amorphous Solid Dispersions of BCS Class II Drugs," submitted to Waterford Institute of Technology for the Degree of Doctor of Philosophy, Waterford, Ireland, [Unpublished Degree of Doctor of Philosophy].
U.S. Department of Health and Human Services Food and Drug Administration Center for Drug Evaluation and Research (CDER), "Regulatory Classification of Pharmaceutical Co-Crystals, Guidance for Industry," Feb. 2018, Pharmaceutical Quality/CMC, Revision 1.
Bharate, S.S.,Recent developments in pharmaceutical salts: FDA approvals from 2015 to 2019, Drug Discovery Today (2020), doi: https://doi.org/10.1016/j.drudis.2020.11.016.

(Continued)

*Primary Examiner* — Kara R McMillian
(74) *Attorney, Agent, or Firm* — Prosyla Group PC

(57) ABSTRACT

The present invention relates to a combination of a histone deacetylase (HDAC) inhibitor, chidamide in an acidic salt form, and a nonsteroidal anti-inflammatory drugs (NSAIDs), celecoxib in a basic salt form. The present invention also relates to methods which significantly regulate tumor microenvironment and therefore dramatically improve anti-cancer activity.

17 Claims, 79 Drawing Sheets

(56) References Cited

OTHER PUBLICATIONS

Gupta, Deepak, "Salts of Therapeutic Agents: Chemical, Physicochemical, and Biological Considerations," Molecules 2018, 23, 1719; doi:10.3390/molecules23071719.

Anderson, Bradley D., Wermuth, C.G. Edition, Latest Medicinal Chemistry Volume, p. 347-365, Technomic Inc., 1999.cited as background reference.

Bastin, Richard J. et al.: "Salt selection and Optimisation Procedures for Pharmaceutical New Chemical Entities", Organic Process Research & Development, 2000, vol. 4, p. 427-435, DOI: 10.1021/op000018u).

Hirayama, Reiaki et al., Handbook of Organic Compound Crystal Preparation, 2008, pp. 17-23, 37-40, 45-51, and 57-65.

Julius F. Remenar et.al., "Celecoxib sodium salt: engineering crystal forms for performance", CrystEngComm, 2011, 13, pp. 1081-1089).

Office Action dated Jan. 31, 2023, in corresponding Russian patent application No. 2022109453.

Office Action dated May 9, 2023, in corresponding Japan patent application No. 2022-515831.

Sherry L.Morissette et al., "High-throughput crystallization: polymorphs, salts, co-crystals and solvates of pharmaceutical solids", Advanced Drug Delivery Reviews, 2004, v.56, pp. 275-300 (section1, 3.1).

\* cited by examiner

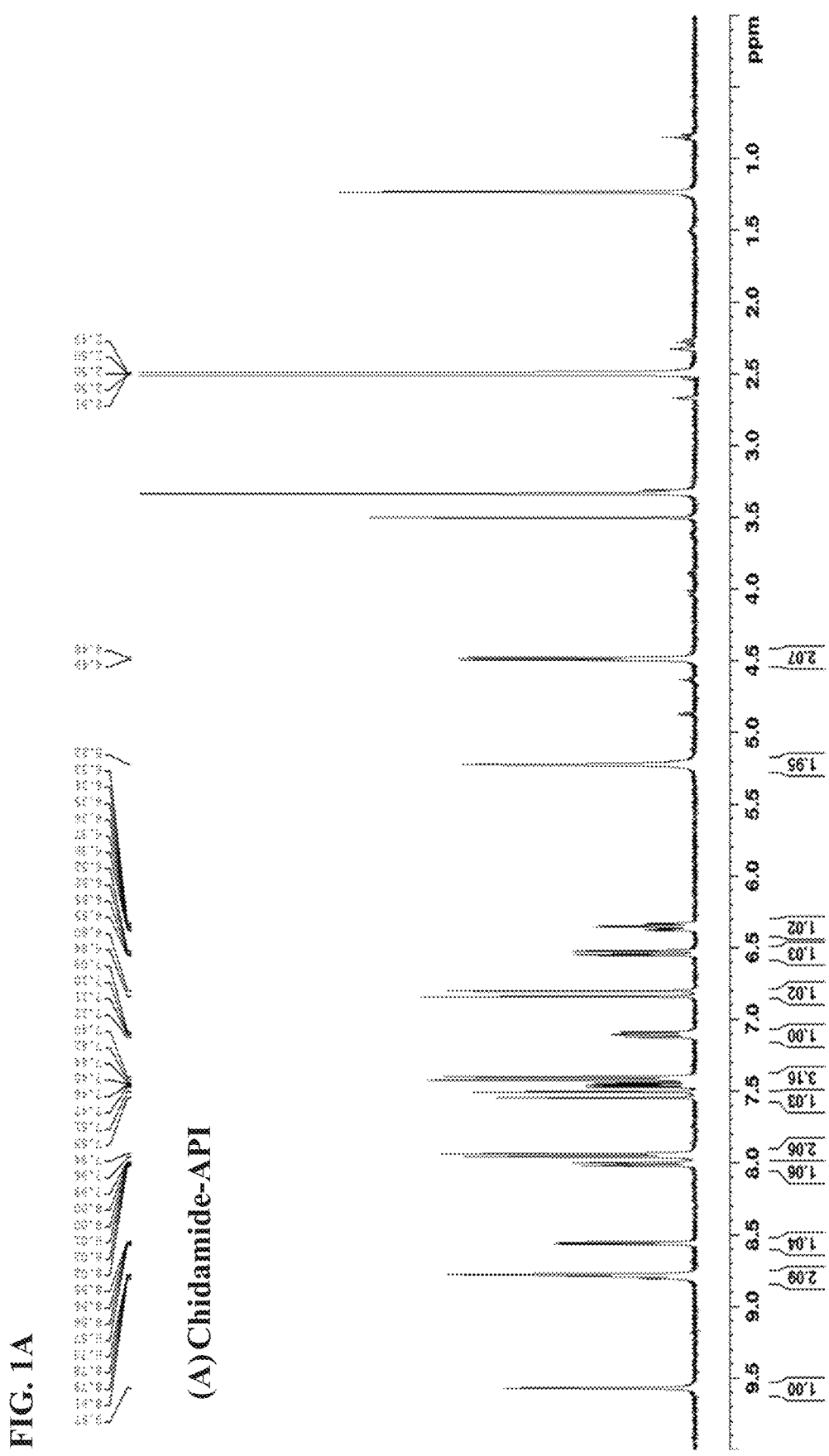
FIG. 1A (A) Chidamide-API

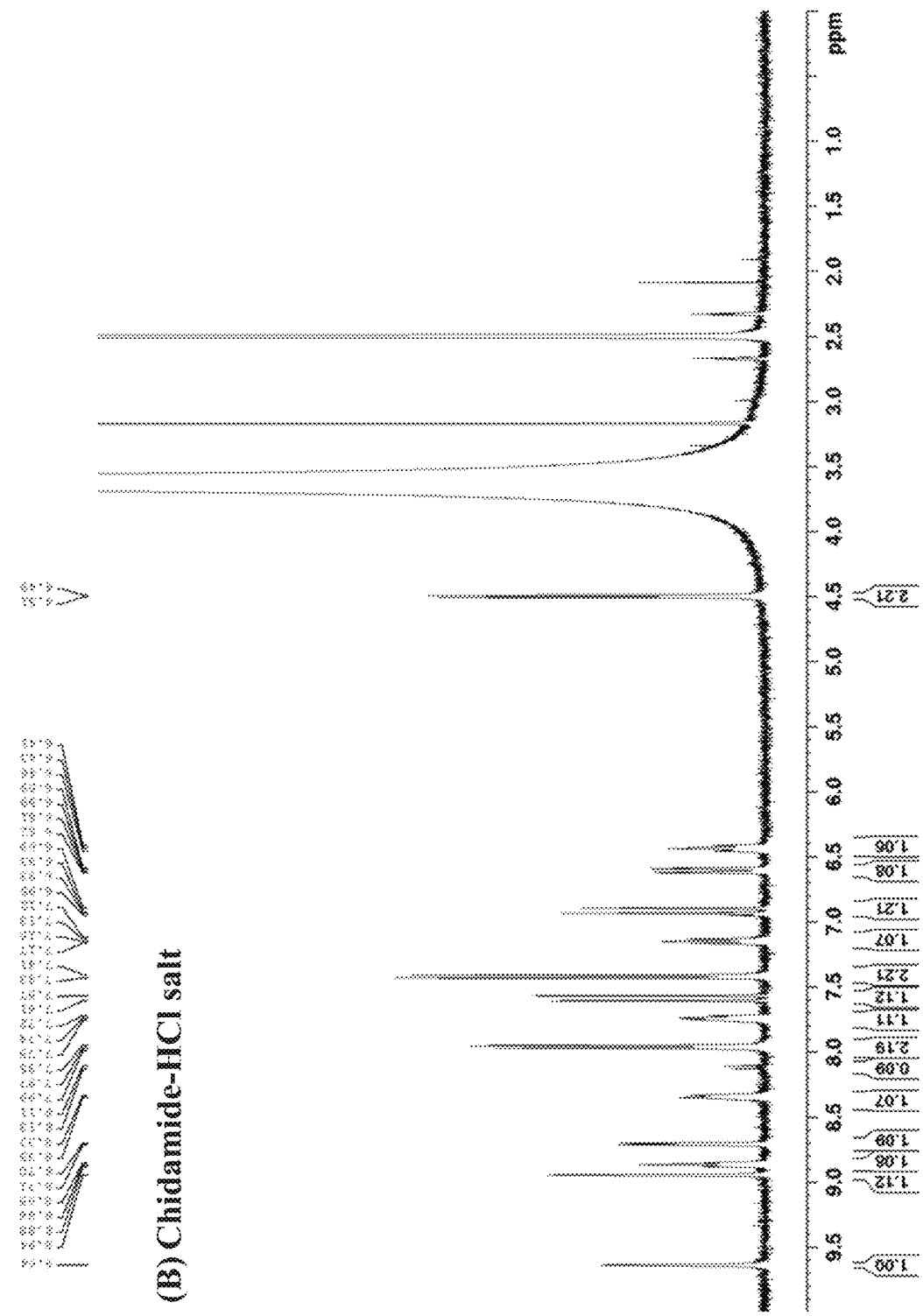
FIG. 1B (B) Chidamide-HCl salt

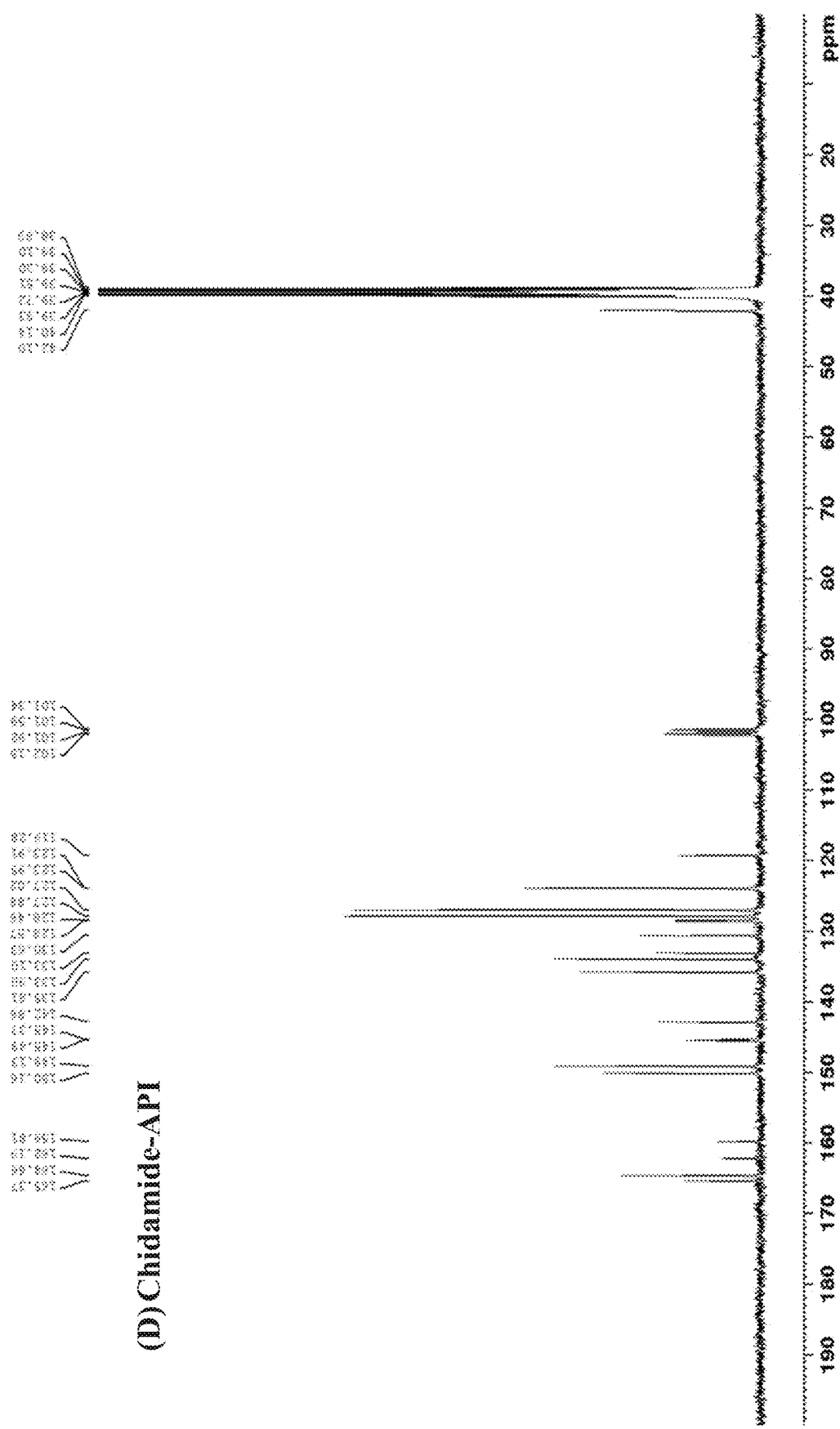
FIG. 1D (D) Chidamide-API (E) Chidamide-HCl salt

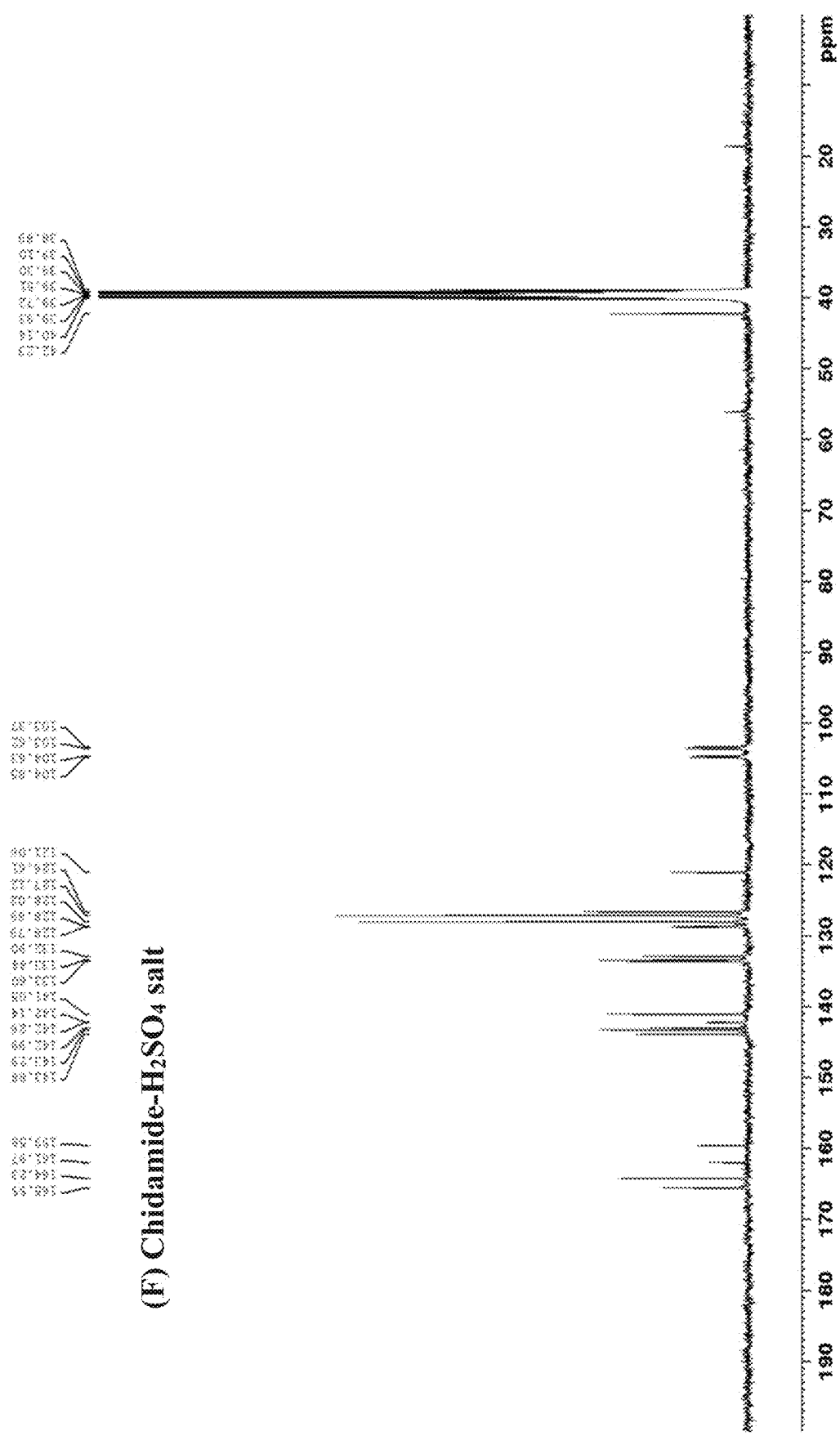
FIG. 1F (F) Chidamide-H₂SO₄ salt

FIG. 1G

| $^{13}$C NMR | Chidamide-API | Chidamide-HCl salt | Chidamide-H$_2$SO$_4$ salt |
|---|---|---|---|
| Chemical shift (δ) | 42.05, 101.42, 101.99, 119.25, 123.89, 126.97(2C), 127.82(2C), 128.44, 130.59, 133.06, 133.93, 135.74, 142.81, 145.35, 149.07, 150.11, 160.95, 162.13, 164.60, 165.30 | 42.15, 108.10, 110.71, 125.45, 127.06(2C), 127.79, 128.13, 128.96, 129.06, 132.40, 132.82, 133.69, 134.21, 141.56, 142.06, 142.20, 143.18, 158.44, 160.85, 164.06, 165.43 | 42.23, 103.50, 104.74, 121.06, 126.61, 127.12(2C), 128.02(2C), 128.74, 132.90, 133.44, 133.60, 141.05, 142.20, 142.99, 143.29, 143.88, 159.58, 162.19, 164.23, 165.55 |

FIG. 3D

| XRD | Chidamide-API | Chidamide-HCl salt | Chidamide-H$_2$SO$_4$ salt |
|---|---|---|---|
| 2θ | 4.19, 6.65, 8.45, 12.72, 16.97, 17.87, 18.36, 19.32, 20.12, 20.60, 21.59, 23.98, 25.55, 27.04, 27.60, 27.95, 28.27, 29.59, 29.96 | 16.12, 19.02, 21.08, 21.62, 23.38, 23.76, 25.58, 27.82, 28.18, 30.16 | 14.74, 17.00, 18.49, 19.45, 21.15, 22.00, 23.55, 24.65, 26.69, 27.94 |

FIG. 4D

| FTIR | Chidamide-API | Chidamide-HCl salt | Chidamide-H$_2$SO$_4$ salt |
|---|---|---|---|
| Wavenumbers (cm$^{-1}$) | 3412, 3309, 3275, 3194, 3045, 2357, 2336, 1651, 1639, 1612, 1497, 1439, 1428, 1417, 1332, 1314, 1296, 1278, 1266, 1235, 1221, 1196, 1165, 1120, 1070, 1037, 1026, 1014 | 3162, 3059, 3036, 2751, 2588, 2359, 2341, 1667, 1658, 1639, 1620, 1610, 1562, 1517, 1508, 1485, 1468, 1444, 1431, 1307, 1282, 1265, 1243, 1220, 1182, 1145, 1074, 1046 | 3249, 3067, 2578, 2360, 1689, 1664, 1647, 1614, 1568, 1521, 1510, 1486, 1467, 1434, 1412, 1388, 1354, 1328, 1283, 1266, 1252, 1226, 1184, 1099, 1059, 1034, 1022 |

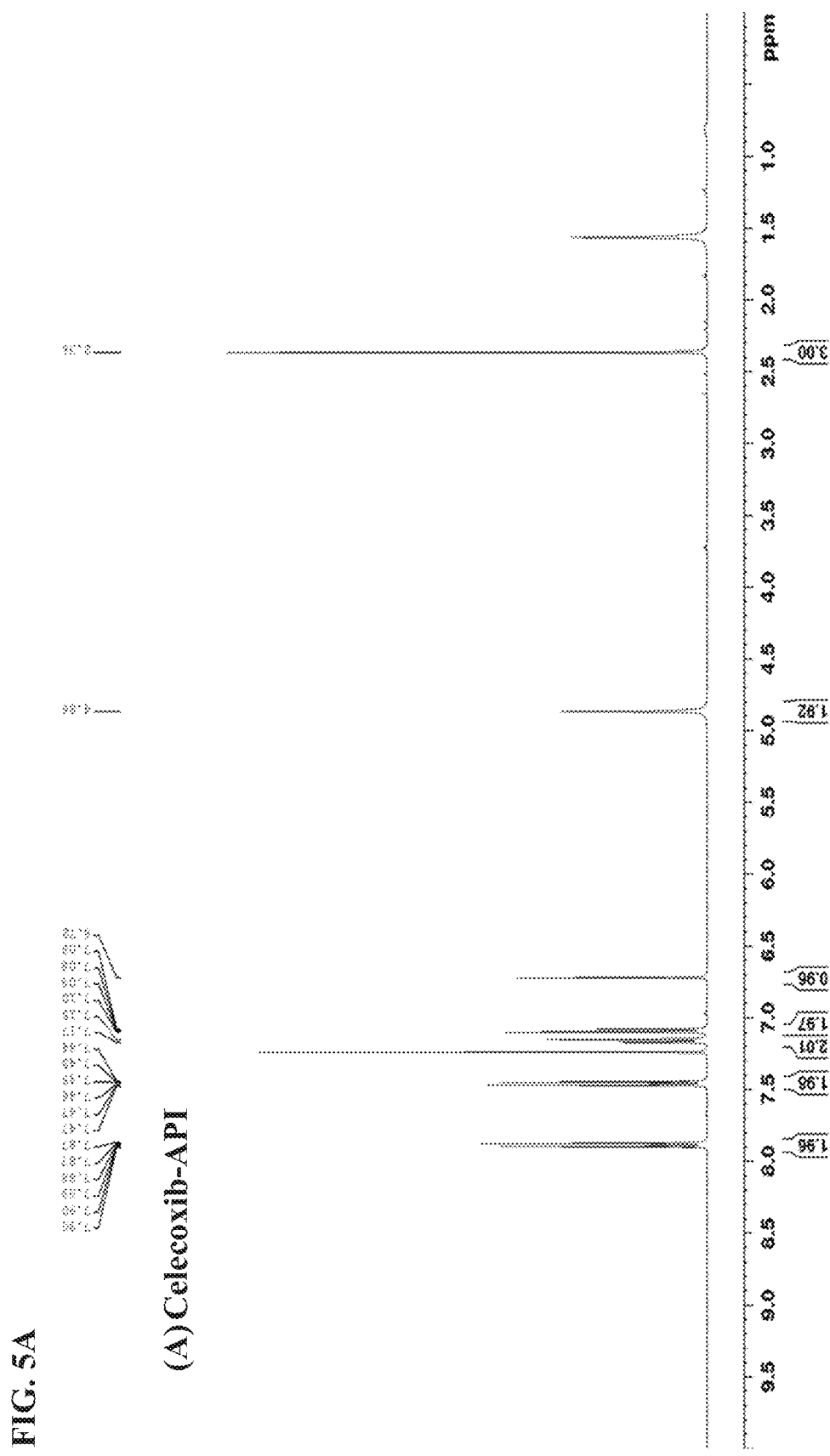
FIG. 5A (A) Celecoxib-API

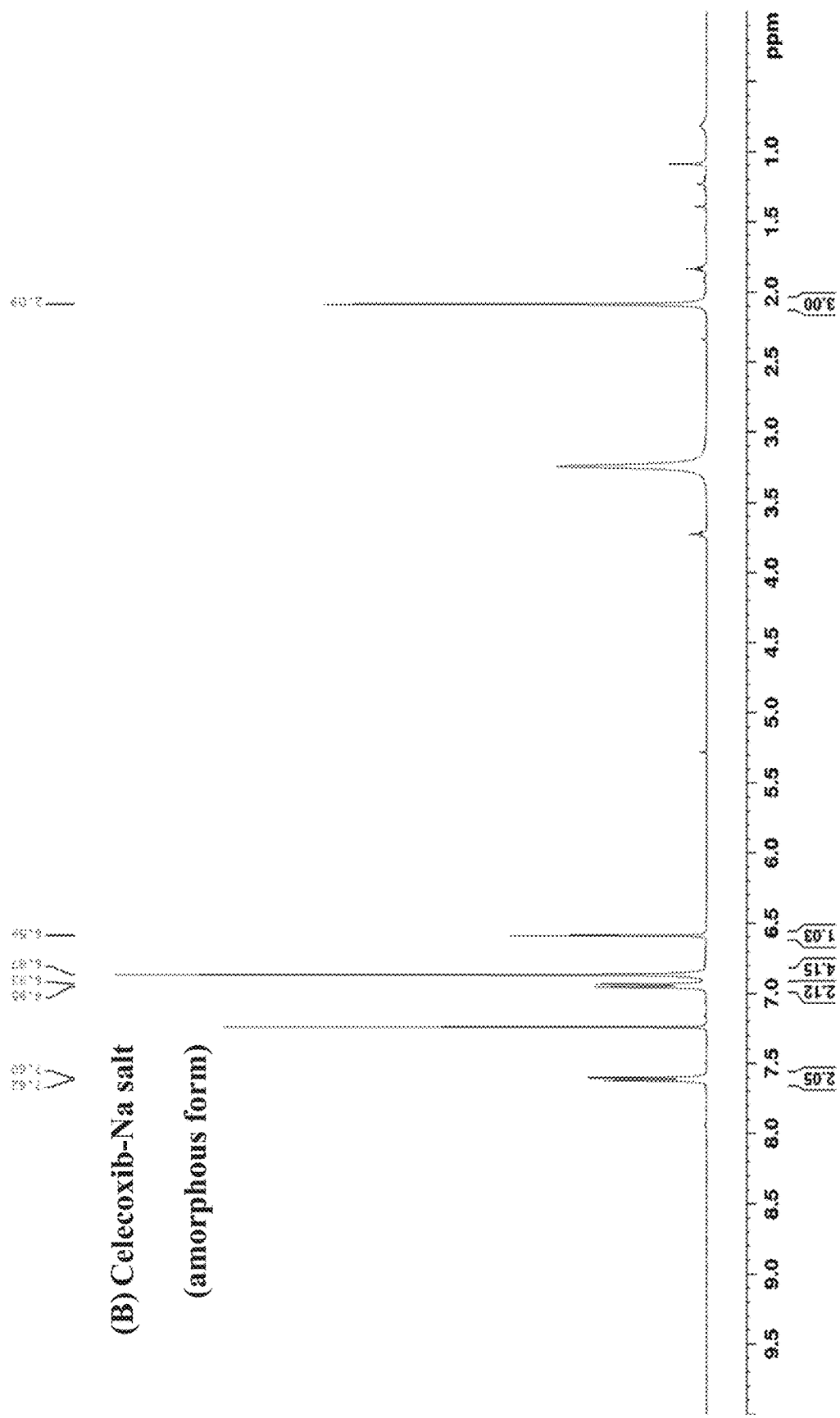
FIG. 5B (B) Celecoxib-Na salt (amorphous form)

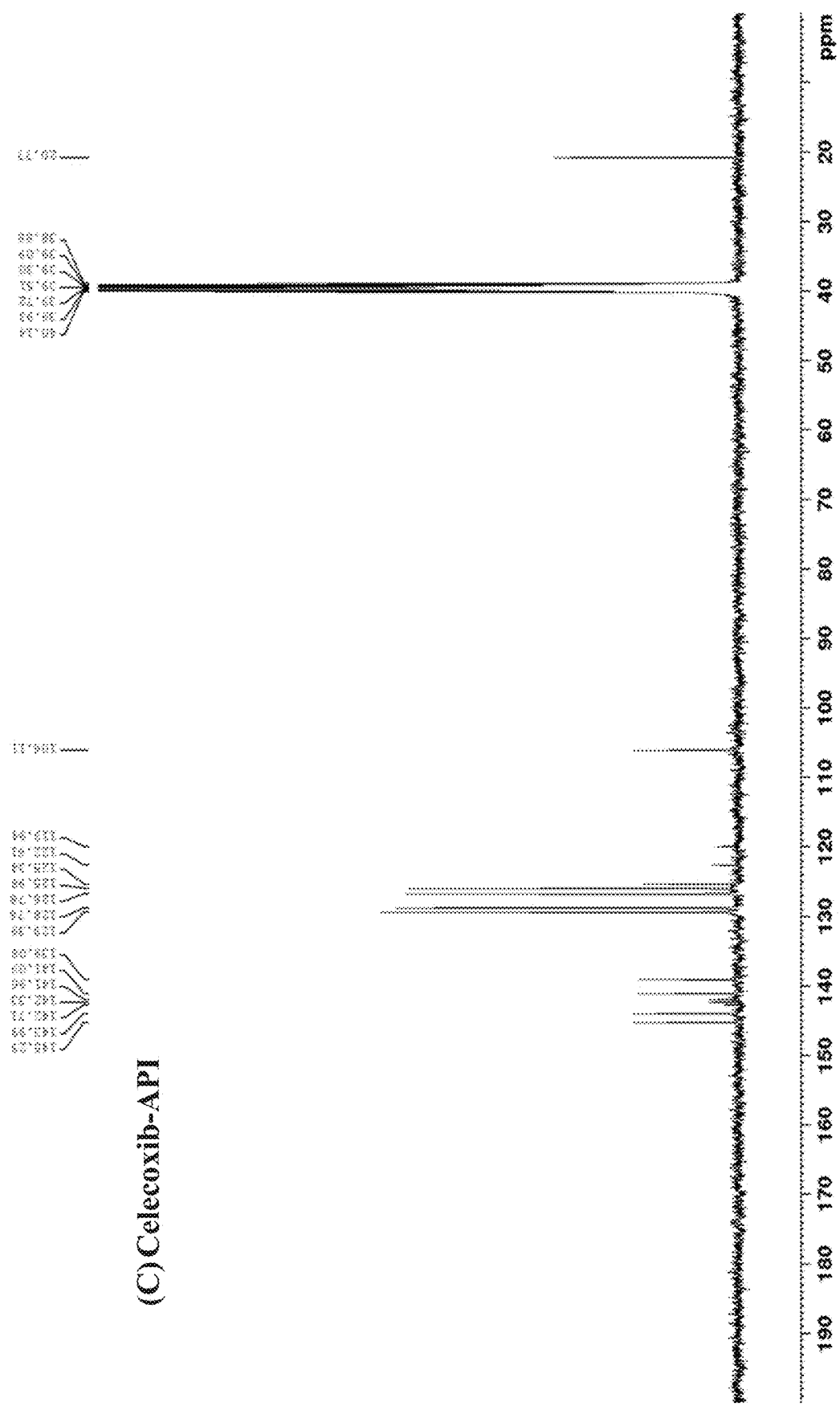
FIG. 5C (C) Celecoxib-API

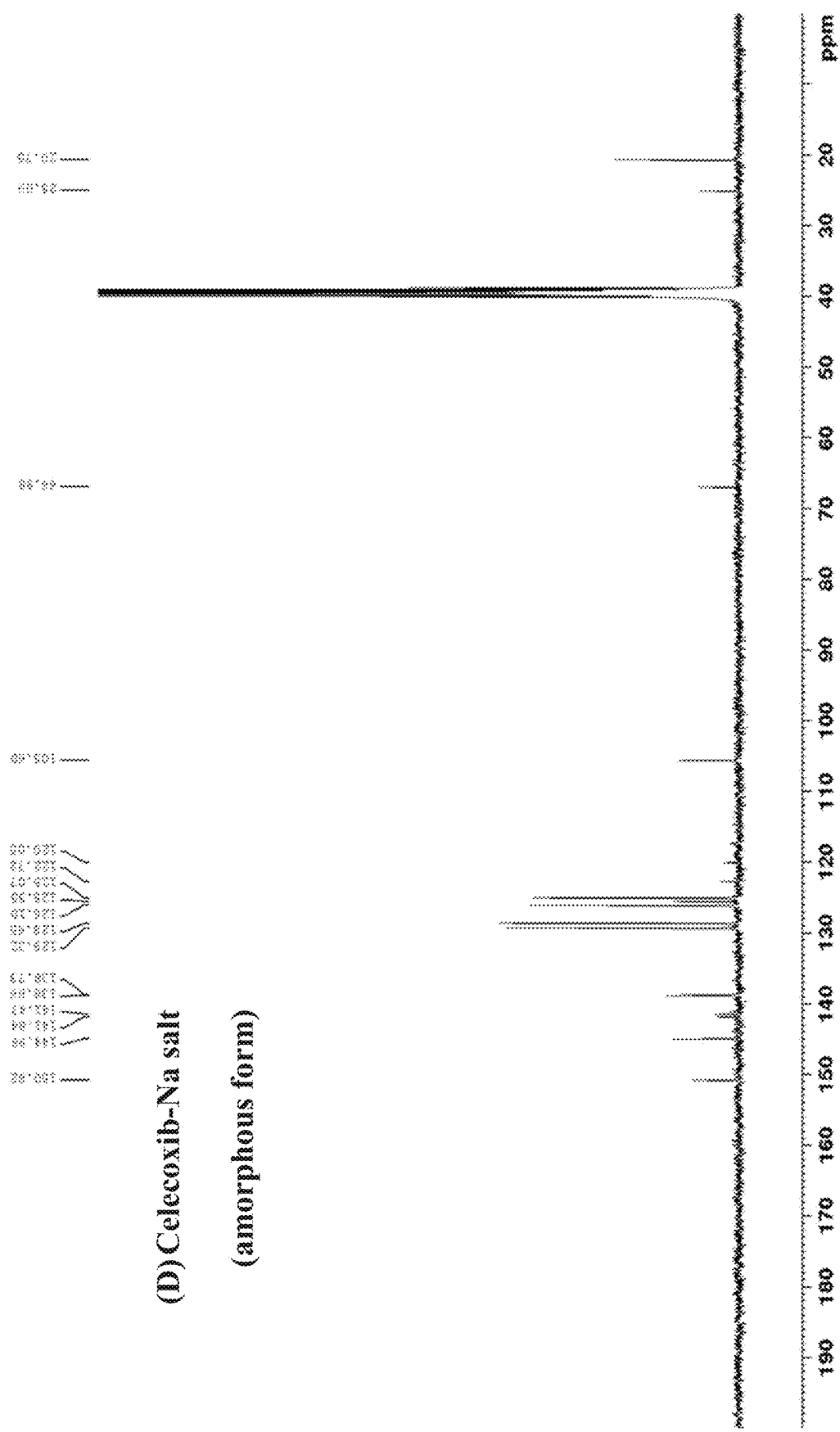
FIG. 5D (D) Celecoxib-Na salt (amorphous form)

FIG. 5E

| $^{13}$C NMR | Celecoixb-API | Celecoxib-Na salt |
|---|---|---|
| Chemical shift (δ) | 20.77, 106.11, 119.94, 122.61, 125.34, 125.98, 126.78, 128.76, 129.39, 139.08, 141.09, 141.96, 142.33, 142.71, 143.96, 145.23 | 25.09, 66.98, 105.60, 120.05, 122.72, 125.07, 125.55, 126.10, 128.65, 129.32, 138.73, 138.86, 141.47, 141.84, 144.98, 150.82 |

FIG. 7D

| XRD | Celecoxib-API | Celecoxib-Na salt (amorphous form) | Celecoxib-Na salt (crystalline form) |
|---|---|---|---|
| $2\theta$ | 14.84, 16.12, 17.93, 18.71, 19.66, 21.50, 22.37, 23.46, 25.36, 29.48 | Amorphous | 10.95, 14.05, 14.601, 17.20, 18.25, 19.85, 20.51, 21.51, 22.55, 25.80, 27.30 |

FIG. 8D

| FTIR | Celecoxib-API | Celecoxib-Na salt (amorphous form) | Celecoxib-Na salt (crystalline form) |
|---|---|---|---|
| Wavenumbers ($cm^{-1}$) | 3341, 3234, 1497, 1472, 1446, 1374, 1346, 1274, 1229, 1163, 1135, 1102, 1093, 1016, 981, 969, 906, 845, 834, 818, 792, 761, 742 | 1653, 1596, 1558, 1541, 1521, 1498, 1472, 1449, 1406, 1374, 1272, 1235, 1160, 1132, 1096, 1021, 974, 967, 841, 826, 806, 759, 742 | 1597, 1498, 1472, 1449, 1408, 1374, 1272, 1236, 1160, 1132, 1096, 975, 967, 881, 842, 826, 806, 759, 742 |

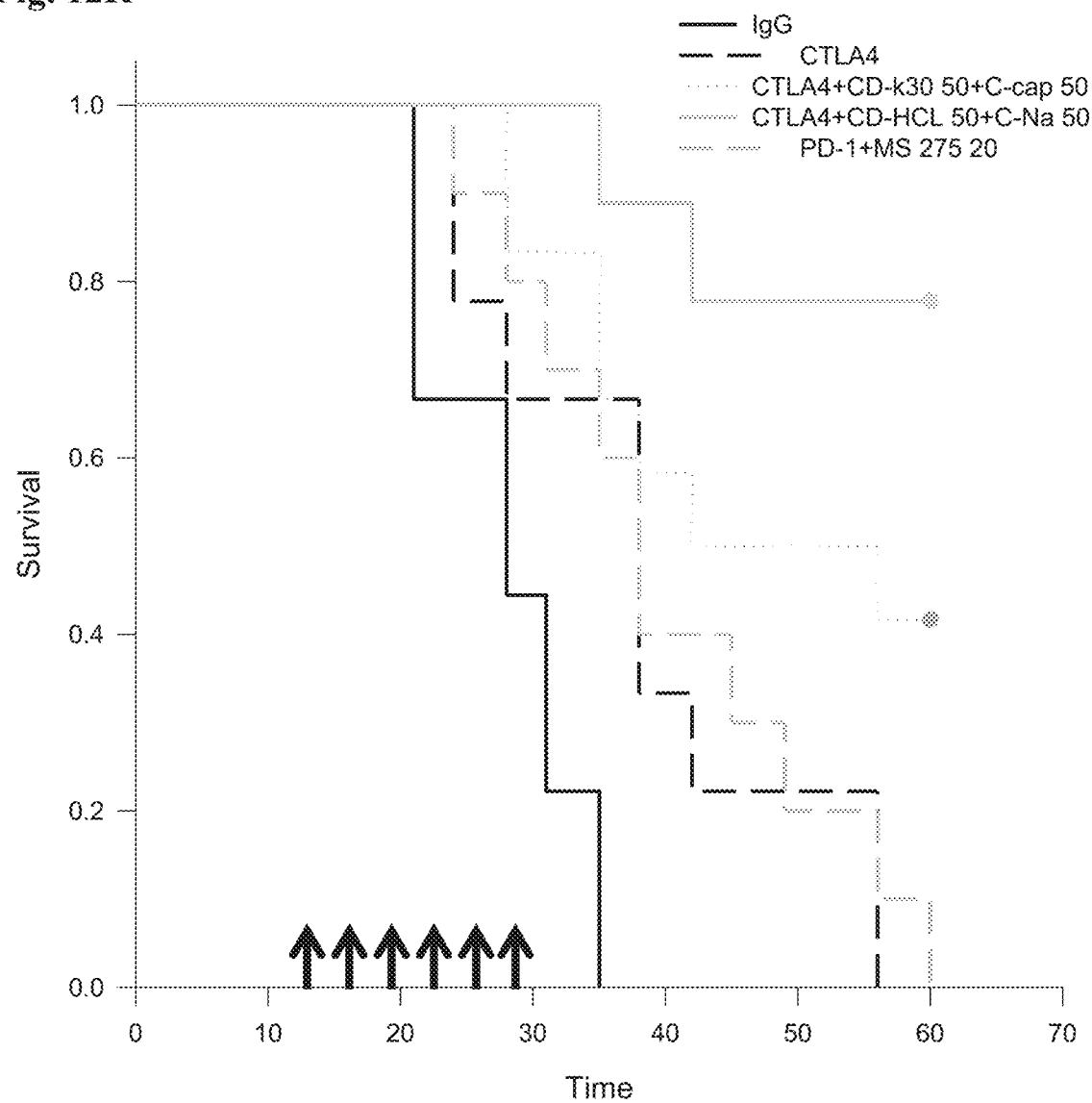

ANTICANCER COMBINATION OF CHIDAMIDE AND CELECOXIB SALTS

FIELD OF THE INVENTION

This disclosure relates to the field of cancer therapy. Particularly, this disclosure provides a combination comprising chidamide and celecoxib in selected salt forms and its applications in the regulation of the tumor microenvironment and cancer immunotherapy.

BACKGROUND OF THE INVENTION

Cancer immune therapy is a rapidly developing field that has yielded impressive and promising breakthroughs. The discovery of the existence of tumor-associated antigens has now raised the possibility of using a host's immune system to intervene in tumor growth. Various mechanisms of harnessing both the humoral and cellular arms of the immune system are currently being explored for cancer immunotherapy.

Several strategies have been proposed to break immune tolerance including adoptive transfer of immune effectors, immunomodulatory therapy, and vaccination. But, these strategies still do not prevent immune escape. The main escape pathway occurs in cancer cells including anti-apoptotic signaling, mitogen-activated protein kinase (MAPK), and cyclic adenosine monophosphate (cAMP) related mechanisms. The tumor microenvironment is an important field of research because it is dynamic and complex in the process of tumor progression. Tumors evolve mechanisms to escape immune control by a process called immune editing, which provides a selective pressure in the tumor microenvironment that can lead to malignant progression. In the tumor-promoting phase referred to as 'immune escape,' the immune system can further tumor progression either by selecting cancer cells that are more capable of surviving the host's immunocompetence or by modifying the tumor microenvironment in such a way that tumor outgrowth is facilitated. The distinct properties of tumor microenvironment have the involvement of different factors such as hypoxia, acidic pH, vascular architect, metabolic state, immunosuppressive function of many immune cells, and cytokine or chemokine. These factors control the immune escape and decrease the immune response. Therefore, to control the tumor microenvironment is one of the important strategies for anticancer treatment, especially for immunotherapy.

Immune system homeostasis includes the presence of both stimulatory and inhibitory mechanisms to control the balance in immune system response. The inhibitory mechanisms include cytotoxic T lymphocyte associated antigen-4 (CTLA-4, a CD28 homolog), and programmed cell death protein-1 (PD-1) or its ligand (PD-L1), TIM-3 (T cell immunoglobulin-3), BTLA (B and T lymphocyte attenuator), VISTA (V-domain Ig suppressor of T cell activation) and LAG-3 (lymphocyte-activation gene 3). The stimulatory mechanisms include cluster of differentiation 28 (CD28), Tumor necrosis factor receptor superfamily, member 4 (TNFRSF4), also known as CD134 or called OX40, glucocorticoid-induced TNFR family related gene (GITR), a member of the tumor necrosis factor (TNF) receptor family (CD137; 4-1BB), a member of the tumor necrosis factor receptor superfamily (CD27), herpesvirus entry mediator (HVEM). Currently, many immune checkpoint inhibitors monoclonal antibodies-including anti-CTLA-4, anti-PD-1, and anti-PD-L1 antibodies have been approved by the US FDA, EMA, PMDA, and NMPA for therapeutic use in several oncological indications. However, for these immune checkpoint inhibitors, about 20%-30% of cancer patients have provided tumor response for monotherapy. The efficacy is still unsatisfactory. The strategies of new drug combination with immune checkpoint inhibitors are the recent approaches of boosting the response rate of these immune checkpoint inhibitors. This will give opportunities to assess the benefits of immunotherapy for patients with varieties of advanced cancers. On the other hand, the drug resistance to immune checkpoint inhibitors has caused the benefits of treatment to be less than expected. Many promising combination approaches have been underway in pre-clinical studies and clinical trials. The efforts of these promising combination regimens bring hope for solving the problem of drug resistance by improving the immune response rate and the efficacy.

There remains a need to develop a therapeutic solution to control the tumor microenvironment and improve the anticancer efficacy of immunotherapy.

SUMMARY OF THE INVENTION

The present disclosure provides a combination comprising a selected salt of chidamide and a selected salt of celecoxib and methods of regulating tumor microenvironment, dramatically improving immune response and anticancer activity by administering a selected chidamide salt in combination with a selected celecoxib salt thereof.

In one aspect, the present disclosure provides a combination comprising an acidic salt of chidamide and a basic salt of celecoxib.

In one embodiment, the amounts of the acidic salt of chidamide and the basic salt of celecoxib ranges from about 5% (w/w) to about 80% (w/w) and about 95% (w/w) to about 20% (w/w), respectively. In one embodiment, the amounts of the acidic salt of chidamide and the basic salt of celecoxib are in a weight ratio of about 8:1, about 4:1, about 3:1, about 2:1, about 1:1, about 1:2, about 1:3, about 1:4 or about 1:8.

In one embodiment, the acidic salt of chidamide and the basic salt of celecoxib are contained in a same dosage form or independently contained in separate dosage forms. In a further embodiment, the dosage form is a tablet or capsule.

In one embodiment, the acidic salt of chidamide is a hydrochloride salt or a sulfate salt. In another embodiment, the acidic salt of chidamide is in a crystalline or amorphous form.

In one embodiment, the hydrochloride salt of chidamide is in a crystalline form (Form A) having an X-ray powder diffraction (XRPD) pattern with peaks comprising 2-theta values at about 16.12 degree, about 19.02 degree, about 21.62 degree, about 23.38 degree and about 30.16 degree. In another embodiment, the XRPD pattern of Form A further has peaks comprising 2-theta values at about 21.08 degree, about 23.76 degree, about 25.58 degree, about 27.82 degree and about 28.18 degree In yet another embodiment, the hydrochloride salt of chidamide is in a crystalline form (Form A) having a Fourier-transform infrared spectroscopy (FTIR) pattern with peaks at about 3162 cm$^{-1}$, about 3059 cm$^{-1}$, about 3036 cm$^{-1}$, about 2751 cm$^{-1}$, about 2588 cm$^{-1}$, about 2359 cm$^{-1}$, about 2341 cm$^{-1}$, about 1667 cm$^{-1}$, about 1658 cm$^{-1}$, about 1639 cm$^{-1}$, about 1620 cm$^{-1}$, about 1610 cm$^{-1}$, about 1562 cm$^{-1}$, about 1517 cm$^{-1}$, about 1508 cm$^{-1}$, about 1485 cm$^{-1}$, about 1468 cm$^{-1}$, about 1444 cm$^{-1}$, about 1431 cm$^{-1}$, about 1307 cm$^{-1}$, about 1282 cm$^{-1}$, about 1265 cm$^{-1}$, about 1243 cm$^{-1}$, about 1220 cm$^{-1}$, about 1182 cm$^{-1}$, about 1145 cm$^{-1}$, about 1074 cm$^{-1}$, about 1046 cm$^{-1}$.

In a further embodiment, Form A is further characterized as exhibiting an XRPD pattern substantially the same as that shown in FIG. 3B or a FTIR pattern substantially the same as that shown in FIG. 4B.

In one embodiment, the sulfate salt of chidamide is in a crystalline form (Form B) having an X-ray powder diffraction (XRPD) pattern with peaks comprising 2-theta values at about 21.15 degree, about 24.65 degree, about 17.00 degree, about 18.49 degree and about 26.69 degree. In another embodiment, the XRPD pattern of Form B further has peaks comprising 2-theta values at about 14.74 degree, about 19.45 degree, about 22.00 degree, about 23.55 degree and about 27.94 degree.

In one embodiment, the sulfate salt of chidamide is in a crystalline form (Form B) having a FTIR pattern with peaks at about 3249 cm$^{-1}$, about 3067 cm$^{-1}$, about 2578 cm$^{-1}$, about 2360 cm$^{-1}$, about 1689 cm$^{-1}$, about 1664 cm$^{-1}$, about 1647 cm$^{-1}$, about 1614 cm$^{-1}$, about 1568 cm$^{-1}$, about 1521 cm$^{-1}$, about 1510 cm$^{-1}$, about 1486 cm$^{-1}$, about 1467 cm$^{-1}$, about 1434 cm$^{-1}$, about 1412 cm$^{-1}$, about 1388 cm$^{-1}$, about 1354 cm$^{-1}$, about 1328 cm$^{-1}$, about 1283 cm$^{-1}$, about 1266 cm$^{-1}$, about 1252 cm$^{-1}$, about 1226 cm$^{-1}$, about 1184 cm$^{-1}$, about 1099 cm$^{-1}$, about 1059 cm$^{-1}$, about 1034 cm$^{-1}$ and about 1022 cm$^{-1}$.

In a further embodiment, Form B is further characterized as exhibiting an XRPD pattern substantially the same as that shown in FIG. 3C or a FTIR pattern substantially the same as that shown in FIG. 4C.

In one embodiment, the basic salt of celecoxib is a sodium salt of celecoxib. In another embodiment, the sodium salt of celecoxib is in an amorphous form or a crystalline form. In another embodiment, the amorphous form of the sodium salt of celecoxib has an XRPD pattern substantially the same as that shown in FIG. 7B.

In one embodiment, the sodium salt of celecoxib is in a crystalline form (Form I) having an X-ray powder diffraction (XRPD) pattern with peaks comprising 2-theta values at about 19.85 degree, about 20.51 degree, about 21.51 degree, about 22.55 degree and about 18.25 degree. In another embodiment, the XRPD pattern of Form I further has peaks comprising 2-theta values at about 10.95 degree, about 14.05 degree, about 14.60 degree, about 17.2 degree, about 25.80 degree and about 27.30 degree. In a further embodiment, Form I is further characterized as exhibiting an XRPD pattern substantially the same as that shown in FIG. 7C.

In one embodiment, the combination further comprises an immune checkpoint inhibitor and/or a chemotherapeutic agent. In some embodiment, the immune checkpoint inhibitor is an anti-CTLA-4 antibody, anti-PD-1 antibody or an anti-PD-L1 antibody. Certain embodiments of the immune checkpoint inhibitor include pembrolizumab, pidilizumab, nivolumab, durvalumab, avelumab, atezolizumab, toripalimab, sintilimab, camrelizumab, and MIHI.

In one aspect, the present disclosure provides a method of treating a cancer through regulation of microenvironment and improvement of immune response, comprising administering an effective amount of chidamide in combiantion with an effective amount of celecoxib. In a further embodiment, chidamide and celecoxib are administered concurrently, separately or sequentially.

In one aspect, the present disclosure provides a method of regulating microenvironment in cancer immunotherapy, comprising administering an effective amount of a combination described herein to a subject. In one embodiment, the acidic salt of chidamide and the basic salt of celecoxib are administered concurrently, separately or sequentially.

In another aspect, the present disclosure provides a method of treating a cancer, comprising administering an effective amount of a combination described herein to a subject. In one embodiment, the cancer is treated through regulation of microenvironment and improvement of immune response. In one embodiment, the method further comprises administering an immune checkpoint inhibitor. In another embodiment, the combination of the disclosure and the immune checkpoint inhibitor are administered concurrently, separately or sequentially. Examples of the immune checkpoint inhibitor are those described herein.

In one embodiment, the administration of the acidic salt of chidamide and the basic salt of celecoxib improves the pharmacokinetics profile compared with that of chidamide free base and celecoxib free acid.

Certain embodiments of the cancer include glioblastoma, liver cancer, colorectal carcinoma, glioblastoma, gastric cancer, colorectal cancer, esophageal cancer, lung cancer, pancreatic cancer, renal cell carcinoma, benign prostate hyperplasia, prostate cancer, ovarian cancer, melanoma, breast cancer, chronic lymphocytic leukemia (CLL), Merkel cell carcinoma, Non-Hodgkin lymphoma, acute myeloid leukemia (AML), gallbladder cancer, cholangiocarcinoma, urinary bladder cancer, and uterine cancer.

BRIEF DESCRIPTION OF THE DRAWINGS

FIGS. 1A to 1G represent the $^1$H-NMR and $^{13}$C-NMR spectra for chidamide-API, chidamide-HCl salt, and chidamide-H$_2$SO$_4$ salt.

FIG. 1A is the $^1$H-NMR spectra of chidamide-API (Active Pharmaceutical Ingredient).

FIG. 1B is the $^1$H-NMR spectra of chidamide-HCl salt.
FIG. 1C is the $^1$H-NMR spectra of chidamide-H$_2$SO$_4$ salt.
FIG. 1D is the $^{13}$C-NMR spectra of chidamide-API.
FIG. 1E is the $^{13}$C-NMR spectra of chidamide-HCl salt.
FIG. IF is the $^{13}$C-NMR spectra of chidamide-H$_2$SO$_4$ salt.
FIG. 1G is the data of $^{13}$C-NMR spectra of different forms of chidamide.

FIG. 2A is the ESI-MS spectra of chidamide-HCl salt in positive ion mode.

FIG. 2B is the ESI-MS spectra of chidamide-HCl salt in negative ion mode.

FIG. 2C is the ESI-MS spectra of chidamide-H$_2$SO$_4$ salt in positive ion mode.

FIG. 2D is the -MS spectra of chidamide-H$_2$SO$_4$ saltin negative ion mode.

FIGS. 3A to 3D represent the X-ray Powder Diffraction (XRD) spectra for chidamide-API, chidamide-HCl salt, and chidamide-H$_2$SO$_4$ salt.

FIG. 3A is the XRD spectra of chidamide-API.
FIG. 3B is the XRD spectra of chidamide-HCl salt.
FIG. 3C is the XRD spectra of chidamide-H$_2$SO$_4$ salt.
FIG. 3D is the comparison of the 2-theta values of chidamide-API, chidamide-HCl salt, and chidamide-H$_2$SO$_4$ salt.

FIGS. 4A to 4D show the Fourier-Transform Infrared Spectroscopy (FTIR) spectra for chidamide-API, chidamide-HCl salt, and chidamide-H$_2$SO$_4$ salt.

FIG. 4A is the FTIR spectra of chidamide-API.
FIG. 4B is the FTIR spectra of chidamide-HCl salt.

FIG. 4C is the FTIR spectra of chidamide-$H_2SO_4$ salt.

FIG. 4D shows the comparison of the characterization of chidamide-API, chidamide-HCl salt, and chidamide-$H_2S_4$ salt.

FIGS. 5A to 5E show the $^1$H-NMR and $^{13}$C-NMR spectra for celecoxib-API and celecoxib-Na salt.

FIG. 5A is the $^1$H-NMR spectra (400 MHz, $CDCl_3$) of celecoxib-API (Active Pharmaceutical Ingredient).

FIG. 5B is the $^1$H-NMR spectra (400 MHz, $CDCl_3$) of celecoxib-Na salt.

FIG. 5C is the $^{13}$C-NMR spectra of celecoxib-API.

FIG. 5D is the $^{13}$C-NMR spectra of celecoxib-Na salt.

FIG. 5E is the data of $^{13}$C-NMR spectra (100 MHz, DMSO-$d_6$) of celecoxib-API and celecoxib-Na salt. Celecoxib-Na salt can be prepared as amorphous or crystalline form by different processes. The $^1$H-NMR and $^{13}$C-NMR spectra of amorphous celecoxib-Na salt have the same patterns as those of crystalline salt form.

FIGS. 7A to 7D show the X-ray Powder Diffraction (XRD) spectra for celecoxib-API and amorphous and crystalline forms of celecoxib-Na salt.

FIG. 7A shows the XRD spectra of celecoxib-API.

FIG. 7B shows the XRD spectra of amorphous form of celecoxib-Na salt.

FIG. 7C shows the XRD spectra of crystalline form of celecoxib-Na salt.

FIG. 7D shows the comparison of XRD spectra of the various forms of celecoxib-Na. It was markedly different in term of diffraction peaks between amorphous form and crystalline form.

FIGS. 8A to 8D show the Fourier-Transform Infrared Spectroscopy (FTIR) spectra for celecoxib-API and amorphous and crystalline forms of celecoxib-Na salt.

FIG. 8A shows the FTIR spectra of celecoxib-API.

FIG. 8B shows the FTIR spectra of celecoxib-Na salt in a crystal form.

FIG. 8C shows the FTIR spectra of amorphous form of celecoxib-Na.

FIG. 8D shows the characterization of FTIR patterns between celecoxib-API and celecoxib-Na salts.

FIGS. 9A and 9B show the total tumor volumes and fold change of tumor size.

FIGS. 9C-9H show the individual tumor volumes.

FIG. 9I shows the CT26 tumor-bearing mice body weight.

FIG. 9J shows the animal survival rate. CT26 tumor-bearing mice were treated as indicated and euthanized when tumor volume reached 3000 $mm^3$ after tumor implantation. Means and SDs are shown. The number of animals used in each experimental arm and P values are also indicated. *$P<0.05$ (vs IgG); #$P<0.05$ (vs PD-1). P-values were calculated using Student's t-test that compared tumor size at indication group with IgG group. Differences of survival rates between different treatment groups were analyzed by the one-way ANOVA, followed by Tukey's multiple comparisons test.

FIGS. 10A and 10B show the total tumor volumes and fold change of tumor size.

FIGS. 10C to 10H show the individual tumor volumes.

FIG. 10I shows the percentages of tumor-free mice.

FIG. 10J shows the CT26 tumor bearing-mice body weight.

FIG. 10K shows the animal survival rate. CT26 tumor bearing mice were treated as indicated and euthanized when tumor volume reached 3000 $mm^3$ after tumor implantation. Means and SDs are shown. The number of animals used in each experimental arm and P values are also indicated. *$P<0.05$ (vs IgG); #$P<0.05$ (vs PD-1). P-values were calculated using Student's t-test that compared tumor size at indication group with IgG group. Differences of survival rates between different treatment groups were analyzed by the one-way ANOVA followed by Tukey's multiple comparisons test.

FIGS. 11A to 11D show the total tumor volumes and fold change of tumor size.

FIG. 11N shows the animal survival rate. CT26 tumor bearing mice were treated as indicated and euthanized when tumor volume reached 3000 $mm^3$ after tumor implantation. Means and SDs are shown. The number of animals used in each experimental arm and P values are also indicated. *$P<0.05$ (vs IgG); #$P<0.05$ (vs PD-1). P-values were calculated using Student's t-test that compared tumor size at indication group with IgG group. Differences of survival rates between different treatment groups were analyzed by the one-way ANOVA followed by Tukey's multiple comparisons test.

FIGS. 12A to 12R show that the resistance to PD-1 checkpoint blockade therapy is overcome by using anti-PD-1 or anti-CTLA-4 Ab combined with chidamide-HCl salt plus celecoxib-Na salt in CT26 tumor-bearing mice. The CT-26-bearing mice (the average tumor size about 120 mm³) were treated with first line of therapy of anti-PD-1 antibody (2.5 mg/kg) administered twice (twice weekly). When tumors met the failure criteria of first line therapy, which was defined as when tumor size increased three times to average about 360 mm³ and tumor volume <600 mm³, the mice were reenrolled for the second line of therapy study. These anti-PD-1 resistance mice were treated with seven different regimens (n=9-11 mice/group) as indicated: IgG, Anti-IgG control (vehicle, 2.5 mg/kg); PD-1, Anti-PD-1 monoclonal antibody (2.5 mg/kg); CTLA-4, anti-CTLA-4 monoclonal antibody (2.5 mg/kg); CD-HCl, chidamide-HCl salt (50 mg/kg); C—Na, amorphous celecoxib-Na salt (50 mg/kg); MS275, entinostat (20 mg/kg).

FIGS. 12A to 12E show the total tumor volumes and fold change of tumor size.

FIGS. 12Q and 12R show the animal survival rate. CT26 tumor bearing mice were treated as indicated and euthanized when tumor volume reached 3000 mm³ after tumor implantation. Means and SDs are shown. The number of animals used in each experimental arm and P values are also indicated. *P<0.05 (vs IgG); #P<0.05 (vs PD-1). P-values were calculated using Student's t-test that compared tumor size at indication group with IgG group. Differences of survival rates between different treatment groups were analyzed by the one-way ANOVA, followed by Tukey's multiple comparisons test.

FIGS. 13A to 13E show the total tumor volumes and fold change of tumor size.

FIGS. 13Q and 13R show the animal survival rate (D) were recorded. CT26 tumor bearing mice were treated as indicated and euthanized when tumor volume reached 3000 mm³ after tumor implantation. Means and SDs are shown. The number of animals used in each experimental arm and P values are also indicated. *P<0.05 (vs IgG); #P<0.05 (vs PD-1). P-values were calculated using Student's t-test that compared tumor size at indication group with IgG group. Differences of survival rates between different treatment groups were analyzed by the one-way ANOVA, followed by Tukey's multiple comparisons test.

FIGS. 14A and 14B show the comparison of PK profile between chidamide-K30 and chidamide-HCl salt.

FIG. 14C shows the comparison of PK profile between celecoxib/cap and amorphous celecoxib-Na salt.)

FIGS. 14D and 14E show the t comparison of chidamide PK profiles of chidamide-K30 plus celecoxib/cap vs. chidamide-HCl salt plus amorphous celecoxib-Na salt.

FIG. 14F shows the comparison of celecoxib PK profiles of chidamide-K30 plus celecoxib/cap vs. chidamide-HCl salt plus celecoxib-Na salt.

FIGS. 14G and 14H show the comparison of chidamide PK profiles of chidamide-K30 vs. chidamide-HCl salt vs. chidamide-K30 plus celecoxib/cap vs. chidamide-HCl salt plus celecoxib-Na salt.

FIG. 14I shows the comparison of celecoxib PK profiles of celecoxib/cap vs. celecoxib-Na salt vs. chidamide-K30 plus celecoxib/cap vs. chidamide-HCl salt plus celecoxib-Na salt.

DETAILED DESCRIPTION OF THE INVENTION

Figure 1C:
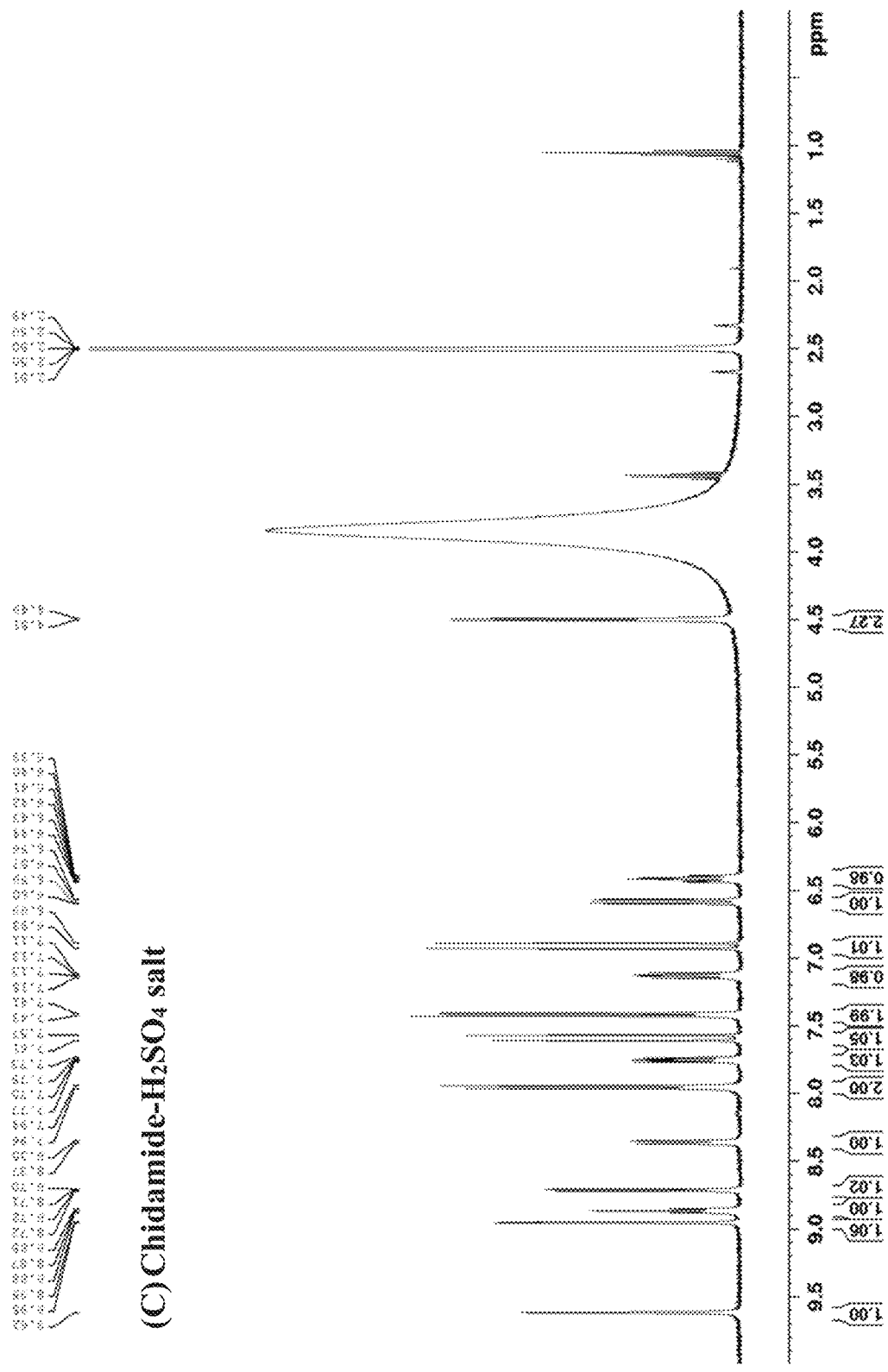

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

Reference to "about" a value or parameter herein includes (and describes) embodiments that are directed to that value or parameter per se. For example, description referring to "about X" includes description of "X." For example, the term "about X°" of a 2-theta value in a XRPD pattern refers to +/−0.2 degrees of 2-theta value.

The term "a" and "an" refers to one or to more than one (i.e., to at least one) of the grammatical object of the article. By way of example, "an element" means one element or more than one element. The use of "or" means "and/or," unless specifically stated otherwise.

The term "polymorph" refers to a crystalline form of a compound (e.g., Compound 1), or a hydrate or solvate thereof, in a particular crystal packing arrangement. All polymorphs of a particular compound have the same elemental composition. The term "crystalline," as used herein, refers to a solid state form which consists of orderly arrangement of structural units. Different crystalline forms of the same compound, or a hydrate, or solvate thereof, arise from different packing of the molecules in the solid state, which results in different crystal symmetries and/or unit cell parameter. Different crystalline forms usually have different X-ray diffraction patterns, infrared spectra, melting points, densities, hardness, crystal shapes, optical and electrical properties, stabilities, and/or solubility.

The term "substantially as shown in" when referring, for example, to an XRPD pattern, refers to a graph that is not necessarily identical to those depicted herein, but that falls within the limits of experimental error or deviations when considered by one of ordinary skill in the art.

As used herein, "subject," "individual" and "patient" are used interchangeably to refer to a vertebrate, preferably a mammal, more preferably a human. Mammals include, but are not limited to, murines, simians, humans, farm animals, sport animals, and pets. Tissues, cells and their progeny of a biological entity obtained in vitro or cultured in vitro are also encompassed.

As used herein, "therapeutically effective amount" means an amount sufficient to treat a subject afflicted with a disease (e.g., a neurodegenerative disease) or to alleviate a symptom or a complication associated with the disease.

As used herein, the terms "treat," treating," "treatment," and the like refer to reducing or ameliorating a disorder, and/or symptoms associated therewith. It will be appreciated that, although not precluded, treating a disorder or condition does not require that the disorder, condition or symptoms associated therewith be completely eliminated.

As used herein, the term "immunotherapy" refers to the treatment of a subject afflicted with, or at risk of contracting or suffering a recurrence of, a disease by a method comprising inducing, enhancing, suppressing or otherwise modifying an immune response.

As used herein, the term "programmed cell death protein 1 (PD-1)" refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

As used herein, the term "programmed death-ligand1 (PD-L1)" is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

As used herein, an "antibody" and "antigen-binding fragments thereof" encompass naturally occurring immunoglobulins (e.g., IgM, IgG, IgD, IgA, IgE, etc.) as well as non-naturally occurring immunoglobulins, including, for example, single chain antibodies, chimeric antibodies (e.g., humanized murine antibodies), heteroconjugate antibodies (e.g., bispecific antibodies), Fab', F(ab').sub.2, Fab, Fv, and rIgG. As used herein, an "antigen-binding fragment" is a portion of the full-length antibody that retains the ability to specifically recognize the antigen, as well as various combinations of such portions.

As used herein, the term "cancer" refers to a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. "Cancer" as used herein refers to primary, metastatic and recurrent cancers.

The tumor microenvironment is an important aspect of cancer biology that contributes to tumor initiation, tumor progression and responses to therapy. The tumor microenvironment is composed of a heterogeneous cell population that includes malignant cells and cells that support tumor proliferation, invasion, and metastatic potential though extensive crosstalk. Tumor cells often induce an immunosuppressive microenvironment, which favors the development of immunosuppressive populations of immune cells, such as myeloid-derived suppressor cells (MDSCs), tumor-associated macrophage (TAM), and regulatory T cells (Tregs). Therefore, targets within the tumor microenvironment have been uncovered that can help direct and improve the actions of various cancer therapies, notably immunotherapies that work by potentiating host antitumor immune responses.

The present invention surprisingly found that a combination of a histone deacetylase (HDAC) inhibitor (such as chidamide or an acidic salt thereof) and a nonsteroidal anti-inflammatory drugs (NSAIDs) (such as celecoxib or a basic salt thereof) significantly improves immune response, regulates tumor microenvironment and therefore dramatically improve anti-cancer activity. The two active pharmaceutical ingredients are preferably in salt form or a crystalline form or an amorphous form.

Chidamide (Epidaza®) is known as a histone deacetylase (HDAC) inhibitor and inhibits Class I HDAC1, HDAC2, HDAC3, as well as Class IIb HDAC10. The chemical name of chidamide is 4-(((E)-3-(pyridin-3-yl)acrylamido)methyl)-N-(2-amino-4-fluorophenyl)benzamide with the following structure.

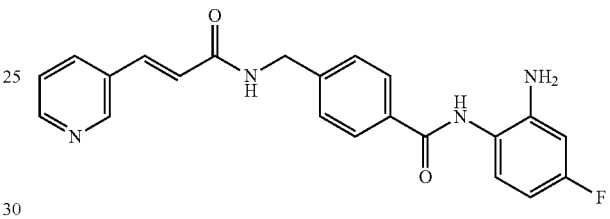

Celecoxib, sold under the brand name Celebrex® among others, is a COX-2 selective nonsteroidal anti-inflammatory drug (NSAID). The chemical name of celecoxib is 4-[5-(4-Methylphenyl)-3-(trifluoromethyl)pyrazol-1-yl]benzenesulfonamide with the following structure.

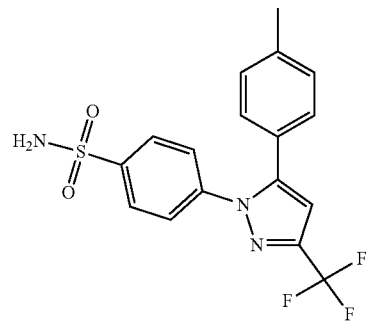

In the present disclosure, an acidic salt of chidamide (such as chidamide-HCl or chidamide-$H_2SO_4$ salts) and a basic form of celecoxib (such as celecoxib-Na salt) are used. Preferably, the salt form of chidamide is in a crystalline form and the salt form of celecoxib is in an amorphous form.

In particular, a crystalline form of chidamide-HCl salt (crystalline form A) and a crystalline form of chidamide-$H_2SO_4$ salt (Form B) are described herein.

XRPD patterns and FTIR patterns are depicted and described herein for Form A and Form B. As used herein, the "largest peak" refers to the peak in a diffraction pattern with the highest intensity. As used herein, the term "major intensity peak" includes any peak having an intensity that is in the top 20% of the peaks in a particular X-ray powder diffraction pattern.

Crystalline form A has an XRPD patter with peaks comprising 2-theta values as described herein. Alternatively, the hydrochloride salt of chidamide is in a crystalline form (Form A) having a Fourier-transform infrared spectroscopy (FTIR) pattern with peaks as described herein. Furthermore, Form A is further characterized as exhibiting an XRPD pattern substantially the same as that shown in FIG. 3B or a FTIR pattern substantially the same as that shown in FIG. 4B.

Crystalline form B has an XRPD patter with peaks comprising 2-theta values as described herein. Alternatively, the sulfate salt of chidamide is in a crystalline form (Form B) having a FTIR pattern with peaks as described herein. Furthermore, Form B is further characterized as exhibiting an XRPD pattern substantially the same as that shown in FIG. 3C or a FTIR pattern substantially the same as that shown in FIG. 4C.

The basic salt of celecoxib is a sodium salt of celecoxib, which is in an amorphous form or a crystalline form. In one embodiment, the amorphous form of the sodium salt of celecoxib has an XRPD pattern substantially the same as that shown in FIG. 7B.

The sodium salt of celecoxib in a crystalline form (Form I) has an X-ray powder diffraction (XRPD) pattern with peaks as described herein. In a further embodiment, Form I is further characterized as exhibiting an XRPD pattern substantially the same as that shown in FIG. 7C.

Chidamide acidic salt is prepared by a strong acidic condition (Arrhenius acid with pKa<3) during the manufacturing process and through specific process to generate novel crystal forms of chidamide-HCl and chidamide-$H_2SO_4$ salts. These salts significantly improve water solubility and pharmacokinetic profile, greatly boosting efficacy in immunotherapy when combined with celecoxib-Na salt and an immune checkpoint inhibitor. The production processes of the crystalline forms of chidamide-HCl and chidamide-$H_2SO_4$ salts are illustrated in the Examples herein.

Celecoxib basic salt is prepared by metal hydride such as NaH during the manufacturing process and through specific processes to generate "anhydrous" amorphous and crystal forms of celecoxib-Na salts. The amorphous celecoxib-Na salt possesses significant water solubility and novel pharmacokinetic profile, and exerts influence on boosting efficacy in immunotherapy when combined with the chidamide acidic salt and an immune checkpoint inhibitor. Similar results were also observed with crystal form of celecoxib-Na salt. The production processes of the amorphous form and crystalline form of celecoxib-Na salt are illustrated in the Examples herein.

In some embodiments, the amount of the chidamide-HCl or chidamide-$H_2S_4$ salt in the combination ranges from about 5% (w/w) to about 80% (w/w), about 30% to about 80% (w/w), about 40% to about 80% (w/w), about 20% to about 60% (w/w), about 30% to about 60% (w/w), about 40% to about 60% (w/w) or about 35% to about 60% (w/w).

In some embodiments, the amount of the celecoxib-Na salt in the combination ranges from about 5% to about 80% (w/w), about 30% to about 80% (w/w), about 40% to about 80% (w/w), about 20% to about 60% (w/w), about 30% to about 60% (w/w), about 40% to about 60% (w/w) or about 35% to about 60% (w/w).

US 20180355042 and US 20190211103 provide combinations that include an HDACi and a PD-1 inhibitor that are useful for treating cancer, including reducing and/or preventing cancer metastasis.

In one embodiment, the combination of the present disclosure is produced with a different ratio of chidamide-HCl salt or chidamide-$H_2SO_4$ salt (can be called chidamide salt) and celecoxib-Na salt (can be called celecoxib salt). The pharmacokinetic property of chidamide salt and celecoxib salt was improved when compared with chidamide-K30 (original formulation of chidamide product Epidaza®) and celecoxib/capsule (original formulation of celecoxib product) Celebrex®.

Furthermore, in combination with an immune checkpoint inhibitor, the combination (chidamide salt plus celecoxib salt) dramatically improved the anti-cancer activity compared with chidamide-K30 plus celecoxib/capsule. Treatment with the combination of the present disclosure in combination with an immune checkpoint inhibitor significantly augments the efficacy in inhibiting tumor growth in comparison with the immune checkpoint inhibitor alone, chidamide-K30 plus celecoxib/capsule, and even both further combined. Furthermore, the combination of the combo and an immune checkpoint inhibitor significantly eradicates the tumor and augments survival rate up to about 80-100%.

The immune checkpoint inhibitor can be used in combination with the combination of the present disclosure described herein to stimulate an immune system against cancer cells and treat a cancer. The Immune checkpoint inhibitors suitable for use in the present disclosure include antagonists of an inhibitory receptor which inhibits the PD-1, PD-L1, CTLA-4, T cell immunoglobulin-3 (TIM3), B and T lymphocyte attenuator (BTLA), V-domain Ig suppressor of T cell activation (VISTA) or lymphocyte-activation gene 3 (LAG3) pathway, such as anti-PD-1 antibodies, anti-PD-L1 antibodies, anti-CTLA-4 antibodies, anti-TIM-3 antibodies, anti-BTLA antibodies, anti-VISTA antibodies and anti-LAG-3 antibodies. Examples of PD-1 or PD-L1 inhibitors include, but are not limited to, humanized antibodies blocking human PD-1 such as pembrolizumab (anti-PD-1 Ab, trade name Keytruda®), nivolumab (anti-PD-1 Ab, Opdivo®) or pidilizumab (anti-PD-1 Ab, CT-011), toripalimab (anti-PD-1 Ab, trade name Tuo Yi®), sintilimab (anti-PD-1 Ab, trade name Tyvyt), camrelizumab (anti-PD-1 Ab), Bavencio (anti-PD-L1 Ab, avelumab), Imfinzi (anti-PD-L1 Ab, durvalumab), and Tecentriq (anti-PD-L1 Ab, atezolizumab), as well as fully human antibodies such as nivolumab (anti-PD-1 Ab, trade name Opdivo®) and cemiplimab-rwlc (anti-PD-1 Ab, trade name Libtayo®). Other PD-1 inhibitors may include presentations of soluble PD-1 ligand including without limitation PD-L2 Fc fusion protein also known as B7-DC-Ig or AMP-244 and other PD-1 inhibitors presently under investigation and/or development for use in therapy. In addition, immune checkpoint inhibitors may include—without limitation—humanized or fully human antibodies blocking PD-L1 such as durvalumab and MIH1 and other PD-L1 inhibitors presently under investigation. In some embodiments, the amount of the immune checkpoint inhibitor ranges from about 0.5% (w/w) to about 15% (w/w), 0.5% (w/w) to about 10% (w/w), 0.5% (w/w) to about 5% (w/w), 1.0% (w/w) to about 20% (w/w), 1.0% (w/w) to about 15% (w/w), 1.0% (w/w) to about 10% (w/w) or 1.0% (w/w) to about 5% (w/w).

In some embodiments of the present disclosure, the chidamide-HCl or chidamide-$H_2SO_4$ salts, the celecoxib-Na salt, and the immune checkpoint inhibitor are administered simultaneously. In some embodiments, the chidamide-HCl or chidamide-$H_2SO_4$ salts, the celecoxib-Na salt, and the immune checkpoint inhibitor are administered sequentially in either order or in alternation.

The pharmaceutical combination of the present invention may be formulated with a "carrier." As used herein, "carrier"

includes any solvent, dispersion medium, vehicle, coating, diluent, antibacterial and/or antifungal agent, isotonic agent, absorption delaying agent, buffer, carrier solution, suspension, colloid, and the like. The use of such media and/or agents for pharmaceutical active substances is well known in the art. For example, the pharmaceutical combinations can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, lotion, gel, ointment, or a controlled-release patch or spray applied to the skin; (4) intravaginally or intrarectally, for example, as a pessary, cream, suppository or foam; (5) sublingually; (6) ocularly; (7) transdermally; (8) transmucosally; or (9) nasally.

The combination of the present disclosure can be used to regulate tumor microenvironment, and in cancer immunotherapy. Examples of the cancer includes, but are not limited to, glioblastoma, liver cancer (such as hepatocellular carcinoma), colorectal carcinoma, glioblastoma, gastric cancer, colorectal cancer, esophageal cancer, lung cancer (such as non-small cell lung cancer (NSCLC) and small cell lung cancer), pancreatic cancer, renal cell carcinoma, benign prostate hyperplasia, prostate cancer, ovarian cancer, melanoma, breast cancer, chronic lymphocytic leukemia (CLL), Merkel cell carcinoma, Non-Hodgkin lymphoma, acute myeloid leukemia (AML), gallbladder cancer, cholangiocarcinoma, urinary bladder cancer, and uterine cancer.

The pharmaceutical combination of the present disclosure may be provided in a single formulation. In other embodiments, the pharmaceutical combination of the present disclosure may be provided in separate formulations. A pharmaceutical combination may be formulated in a variety of and/or a plurality of forms adapted to one or more preferred routes of administration. Thus, a pharmaceutical combination can be administered via one or more known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical combination, or a portion thereof, can be administered to a mucosal surface, such as by administration to, for example, the nasal or respiratory mucosa (e.g., by spray or aerosol). A pharmaceutical combination, or a portion thereof, also can be administered via a sustained or delayed release.

A pharmaceutical combination of the present disclosure may be conveniently presented in unit dosage form and may be prepared by methods well known in the art of pharmacy. Methods of preparing a combination with a pharmaceutically acceptable carrier include the step of bringing the pharmaceutical combination of the present disclosure into association with a carrier that constitutes one or more accessory ingredients. In general, a pharmaceutical combination of the present disclosure may be prepared by uniformly and/or intimately bringing the active compound into association with a liquid carrier, a finely divided solid carrier, or both, and then, if necessary, shaping the product into the desired formulations.

In some embodiments, the method can include administering a sufficient amount of the pharmaceutical combination of the present disclosure to provide a dose of, for example, from about 10 mg/kg to about 1,000 mg/kg to the subject.

The present invention is illustrated by the following examples. It is to be understood that the particular examples, materials, amounts, and procedures are to be interpreted broadly in accordance with the scope and spirit of the invention as set forth herein.

EXAMPLE

Materials and Methods

Materials and Equipment. Chidamide-API, chidamide-K30, chidamide-HCl salt, chidamide-$H_2SO_4$ salt and celecoxib-Na salt were provided by GNT Biotech & Medicals Co. Ltd (Taiwan). Celecoxib-API was purchased from Aarti Drugs Ltd (India). Celecoxib capsule product (Celebrex®, 200 mg) was purchased from (Pfizer, Taiwan). The following antibodies and reagents were used for animal experiments: mouse anti-PD-L1 (B7-H1) monoclonal antibody (10F.9G2; Bio X Cell), mouse anti-PD-1 (CD279) monoclonal antibody (RMP1-14; Bio X Cell), mouse anti-CTLA4 (CD152) monoclonal antibody (BE0164; Bio X Cell), and rat anti-IgG2a isotype control monoclonal antibody (2A3; Bio X Cell). LC/MS-grade methanol, HPLC-grade of acetonitrile, 1-heptanesulfonic acid sodium salt, talc, and ethylenediaminetetraacetic acid were all purchased from J.T.Baker® (USA). Formic acid, sodium chloride, lactose, magnesium stearate, polyvinylpyrrolidone, and sodium phosphate tribasic dodecahydrate were purchased from Sigma-Aldrich (USA). Sodium lauryl sulfate was purchased from Showa Chemical Co., Ltd (Japan). Distilled water was purified using a Milli-Q distillation system (Merck Millipore®, France). Hydrochloric acid S.G. (HCl) was purchased from Fisher chemical, USA. Sodium hydride (NaH), THF 99.5% molecular sieve was purchased from Acros, Belgium. Ethyl ether anhydrous was purchased from ECHO chemical co., LTD, Taiwan. Filter paper was purchased from Toyo Roshi Kaisha, LTD, Japan. $^1H$ NMR and $^{13}C$ NMR were recorded on a Bruker AVANCE 400 MHz PLUS instrument. FTIR spectra were recorded on a Perkin Elmer Spotlight 200i Sp2 with AutoATR System (Perkin Elmer IR spectrophotometer). Powder X-ray diffraction measurement was carried out on a PANalytical EMPYREAN X-ray diffractometer. Electrospray Ionization Mass was recorded on a Bruker microTOF. Fast atom bombardment mass were recorded on a JEOL JMS-700. Gibco RPMI 1640 and DMEM with L-glutamine were purchased from Invitrogen Life Technologies. HyClone FBS was purchased from Thermo Scientific.

Preparation of Chidamide-HCl Salt. One gram of Chidamide-API (Active pharmaceutical ingredient) was placed in flask and 3-5 ml of 6-8N HCl (aq) was added and stirred until fully dissolved by visual inspection. Then solid precipitation was generated without stirring condition. The solid precipitate was separated by suction filtration process, and further purified by forming slurry four times to remove the impurities with diethyl ether. The pure solid was condensed and concentrated to dryness. Then the solid product was dried at 50-60° C. for 16 hours in oven and ground into powder to pass a sieve of 100 mesh. The chidamide-HCl salt was prepared and further characterized by analyses of HPLC, $^1H$-NMR, $^{13}C$-NMR, XRD, saturation solubility, MS and FTIR, etc. The chidamide-HCl salts were also prepared by the following processes.

65 mg of chidamide-API was suspended in 50~150 ml of EtOH, MeOH, DCM, THF, or $H_2O$, then 2-6 drops of 37% HCl were added with stirring until fully dissolved. The mixture was concentrated to remove the solvent until 1 ml of liquid remained, which was then dropped into 50 ml ether and solid salt was precipitated.

500 mg chidamide-API was added into 4-10 ml of 4~8N HCl (aq) and stirred until fully dissolved. Then 10~20 ml EtOH was added and then 10~20 ml ether until foggy appearance was formed. The process of crystallization was continued at 4° C. for 12 hr. The salt was collected by filtration and washed with ether, and then dried in oven at 60° C. for 5 hr.

Preparation of Chidamide-$H_2SO_4$ Salt. One gram of Chidamide-API was placed in flask and 3~5 ml of 3~5M $H_2SO_4$(aq) was added and stirred until fully dissolved by visual inspection. The solution was slowly dropped into 150~200 ml of ethanol and the solid was precipitated. The solid was separated by suction filtration process, and rinsed three times with ethanol. The solid was purified through slurry process three times with ethanol, and the solid was further to remove the excess moisture with diethyl ether. The pure solid was condensed and concentrated to dryness. Then the solid product was dried at 50~60° C. for 16 hours in oven and ground into powder to pass a sieve of 100 mesh. The chidamide-$H_2SO_4$ salt was prepared and further characterized by analyses of HPLC, $^1$H-NMR, $^{13}$C-NMR, XRD, saturation solubility, MS and FTIR, etc.

Preparation of Celecoxib-Na Salt. Five gram of celecoxib-API was placed in a round bottom flask and 150-200 ml of THF was added under air-free condition in the presence of nitrogen gas. The compound was fully dissolved by visual inspection. 450-500 mg of NaH (sodium hydride) was added into the solution and stirred vigorously. The solid precipitate was formed in about 70-90 min. The THF was removed by suction filtration process and the solid was rinsed for three times with 20 ml THF. Then the solid was dissolved in 300 ml dichloride methane (DCM), and the solution was filtered by suction process to remove any undissolved. The filtrate was collected and then condensed and concentrated to dryness by rotary evaporator with pressure 30-50 mbar and spin rate 140 rpm for solid generation. The pure solid was dried at 60° C. for 16 hours and ground powder to pass a sieve of 100 mesh. The anhydrous amorphous celecoxib-Na salt was prepared and further analyzed by the spectra of $^1$H-NMR, $^{13}$C-NMR, XRD, MS, FTIR, etc.

And other process to generate anhydrous amorphous celecoxib-Na salt is described as below. One gram of celecoxib-API was placed in a round bottom flask and 6 ml of THF was added under air-free condition in the presence of nitrogen gas. The compound was fully dissolved by visual inspection. 75~100 mg of NaH (sodium hydride) was added into the solution and stirred vigorously. The solid precipitate was formed in about 40~80 min. The THF was removed by suction filtration process and the solid was rinsed for three times with diethyl ether. The solid was purified through slurry process three times with diethyl ether. Then the solid was dissolved in 150~200 ml dichloride methane (DCM), and the solution was filtered by suction process to remove any undissolved. The filtrate was collected and then condensed and concentrated to dryness. During condensation process the initial pressure was set at 400~430 mbar until there is no distillate. The pressure was then set at 10~30 mbar until the solid salt precipitated. The pure solid was dried at 60° C. for 16 hours and ground into powder to pass a sieve of 100 mesh. The amorphous celecoxib-Na salt was prepared and further characterized by analyses of HPLC, $^1$H-NMR, $^{13}$C-NMR, XRD, saturation solubility, MS, and FTIR, etc.

The anhydrous crystalline celecoxib-Na salt was also prepared at the process described as above except that during condensation process pressure was set at 10~30 mbar until the solid salt precipitated.

Determination of Saturation Solubility of Chidamide-HCl, Chidamide-$H_2SO_4$, and Celecoxib-Na Salts. Sample of 5 mg of chidamide-HCl, chidamide-$H_2SO_4$, or celecoxib-Na salts was added to 5 ml volumetric flasks containing ddH2O and shook at 100 rpm in an incubator at 25° C. for 90 minutes. The resulting suspension was filtered through a 0.22 μm filter. The concentrations of chidamide-HCl, chidamide-$H_2SO_4$, and celecoxib-Na salts were determined spectrophotometrically at 256 nm, 256 nm, and 253 nm, respectively. The saturation solubility of each sample was determined in triplicates and the mean value and standard deviation were reported. Preparation of standard curves is described as below. The stock of Chidamide and celecoxib were prepared in 99.99% MeOH. The $\lambda_{max}$ was found to be at 256 nm and 253 nm, respectively. The calibration curve showed good linearity characterized by coefficient of correlation ($R^2$) equal to 0.9998 over the Beer's concentration range of 0-20 μg/ml.

Cell Lines. CT26 (CRL-2638; murine colorectal adenocarcinoma) were purchased from ATCC. CT26 tumor cell lines were grown in McCoy's 5A supplemented with 10% (vol/vol) FBS at 37° C., 5% $CO_2$.

Anti-cancer Activity in Animal Models. Animal study was approved and overseen by The Taipei Medical University Institutional Animal Care and Use Committee (TMU IACUC, NO: LAC-2018-0340). Six- to eight-wk-old male BALB/C mice (BioLASCO Taiwan) were used for all animal experiments. CT26 ($5 \times 10^6$) cancer cells were inoculated by s.c. into the right flank of each mouse. Tumors were allowed to grow for 10-11 d (tumor size about 200-300 mm$^3$) before randomization and treatment. CT26-bearing mice were given 2.5 mg/kg of anti-IgG (Lot #65481701), anti-PD-1 (Lot #640517M1 and Lot #717918D1), anti-PD-L1 (Lot #720619F1) or anti-CTLA-4 (Lot #702418A2B) antibody by i.p. administration on days 11, 14, 17, 20, 23, and 26 post-tumor implantation, and all antibodies were diluted to appropriate concentrations in 100 μL of sterile PBS (pH 7.4) (Invitrogen Life Technologies). Chidamide-K30, chidamide-HCl salt, chidamide-$H_2SO_4$ salt, celecoxib (capsule/Celebrex®, 200 mg), and celecoxib-Na salt (amorphous or crystalline form) were administrated orally on day 11 post-tumor implantation. Chidamide-K30, chidamide-HCl salt, and chidamide-$H_2SO_4$ salt was orally administered to treat tumor bearing mice at various doses of 12.5, 25, and 50 mg/kg daily from days 11 to 26. Daily treatment with celecoxib (capsule/Celebrex®, 200 mg) or celecoxib-Na salt at various doses of 12.5, 25.0, and 50 mg/kg was performed from days 11 to 26. The anti-cancer activity was measured from the start of the treatment until the tumor volume reached 3,000 mm$^3$. Tumor volume was calculated as length×width×0.5.

Survival Rate in Animal Models. The administration of antibody or drugs was performed from days 11 to 25 or 26. The tumor continued to grow in the tumor bearing mice. The tumor volume of the mice was measured once every three or four days (twice/week). The tumor bearing mice were regarded as dead when the tumor volume reached 3,000 mm$^3$. All treatment groups were recorded and analyzed.

To Overcome the Resistance to First Line PD-1 Checkpoint Blockade Therapy. Animal research was approved and overseen by The Taipei Medical University Institutional Animal Care and Use Committee (TMU IACUC, NO: LAC-2018-0340). Six- to eight-wk-old male BALB/C mice (BioLASCO Taiwan) were used for all animal experiments. CT26 ($5\times10^6$) cancer cells were inoculated by s.c. into the right flank of each mouse. Tumors were allowed to grow for 8 d (tumor size average about 120 mm$^3$) before first line treatment of anti-PD-1 antibody (2.5 mg/kg) administered twice (3 days between two administrations). When tumors met the failure criteria of consecutive increase three fold in 3 days (tumor size average 360 mm$^3$) after the second dose of anti-PD-1 antibody during first line therapy and the tumor volumes were <600 mm$^3$, the mice were reenrolled. These mice with resistance to anti-PD-1 Ab were further randomized. The mice with resistance to anti-PD-1 Ab were treated by seven different regimens, including anti-IgG (2.5 mg/kg; Lot #65481701), anti-PD-1 Ab (2.5 mg/kg; Lot #640517M1), anti-PD-1 Ab (2.5 mg/kg) combined with entinostat (20 mg/kg), anti-PD-1 Ab (2.5 mg/kg) combined with chidamide-HCl salt (50 mg/kg) plus celecoxib-Na salt (50 mg/kg), chidamide-HCl salt (50 mg/kg) plus celecoxib-Na salt (50 mg/kg), anti-CTLA-4 Ab (2.5 mg/kg; Lot #702418A2B) alone or combined with chidamide-HCl salt (50 mg/kg) plus celecoxib-Na salt (50 mg/kg). Antibodies were administered by intraperitoneally (i.p.) on days 14, 17, 20, 23, 26, and 29 (six treatments, 3 days between treatments) and all antibodies were diluted to appropriate concentrations in 100 µL of sterile PBS (pH 7.4) (Invitrogen Life Technologies). Celecoxib-Na salt, chidamide-HCl salt, and entinostat were administered orally from days 14 to 29. Celecoxib-Na salt (50 mg/kg), chidamide-HCl salt (50 mg/kg) was daily given, however entinostat (20 mg/kg) was given every two days. The anti-cancer activity was measured from the start of the treatment until the tumor volume reached 3,000 mm$^3$. Tumor volume was calculated as length×width×0.5. The animal study was designed and showed the potential treatment option for failure of first line therapy with anti-PD-1 antibody in human cancer patients developing primary/secondary resistance to anti-PD-1 antibody therapy.

To Overcome the Resistance to First Line PD-L1 Checkpoint Blockade Therapy. In vivo animal study was approved and overseen by The Taipei Medical University Institutional Animal Care and Use Committee (TMU IACUC, NO: LAC-2018-0340). Six- to eight-wk-old male BALB/C mice (BioLASCO Taiwan) were used for all animal experiments. CT26 ($5\times10^6$) cancer cells were inoculated by s.c. into the right flank of each mouse. Tumors were allowed to grow for 8 d (tumor size average about 160 mm$^3$) before first line treatment of anti-PD-L1 antibody (2.5 mg/kg) administered twice (3 days between two administrations). When tumors met the failure criteria of consecutive increase two fold in 3 days (tumor size average 320 mm$^3$) after the last anti-PD-L1 (Lot #720619F1) antibody administration and the tumor volumes were <600 mm$^3$, the mice were reenrolled. These mice with resistance to anti-PD-L1 Ab were further randomized. The mice with resistance to anti-PD-L1 Ab were treated by seven different regimens, including anti-IgG (2.5 mg/kg; Lot #65481701), anti-PD-1 Ab (2.5 mg/kg; Lot #717918D1), anti-PD-1 Ab (2.5 mg/kg) combined with entinostat (20 mg/kg), anti-PD-1 Ab (2.5 mg/kg) combined with chidamide-HCl salt (50 mg/kg) plus celecoxib-Na salt (50 mg/kg), chidamide-HCl salt (50 mg/kg) plus celecoxib-Na salt (50 mg/kg), anti-CTLA-4 Ab (2.5 mg/kg; Lot #702418A2B) alone or combined with chidamide-HCl salt (50 mg/kg) plus celecoxib-Na salt (50 mg/kg). Antibodies were administered by intraperitoneally (i.p.) on days 14, 17, 20, 23, 26, and 29 (six treatments, 3 days between treatments) and all antibodies were diluted to appropriate concentrations in 100 µL of sterile PBS (pH 7.4) (Invitrogen Life Technologies). Celecoxib-Na salt, chidamide-HCl salt, and entinostat were administered orally from days 14 to 29. Celecoxib-Na salt (50 mg/kg), chidamide-HCl salt (50 mg/kg) was daily given, however entinostat (20 mg/kg) was given every two days. The anti-cancer activity was measured from the start of the treatment until the tumor volume reached 3,000 mm$^3$. Tumor volume was calculated as length×width×0.5. The animal study was designed and showed the potential treatment option for failure of first line therapy with anti-PD-L1 antibody in human cancer patients developing primary/secondary resistance to anti-PD-L1 antibody therapy.

Analysis of PK Profile (Pharmacokinetics) of Chidamide-HCl Salt and Celecoxib-Na Salt in Wistar Rat. The pharmacokinetic studies of chidamide, celecoxib and their salt forms (Chidamide-HCl salt and celecoxib-Na salt) were performed in Wistar male rats of 7 weeks old, by administering compounds orally at a dose of 50 mg/kg in water. Wistar male rats were purchased from BioLasco (Taiwan). Prior to pharmacokinetic studies, animals were fasted for 12 h with free access to water. Blood samples were collected (n>5/time point) at 0.08, 0.25, 0.5, 0.75, 1, 1.5, 2, 4, 6, 8, 10, 12, 24, 48 and 72 h, post dose. At each time point, about 250 µL of blood was collected from jugular vein into a labeled Microtainer™ Tube with EDTA. The blood samples were processed to obtain the plasma samples within 30 min of scheduled sampling time. All plasma samples were stored below −80° C. until analysis. The plasma samples were analyzed for treatments with chidamide-k30, chidamide-HCl salt, celecoxib (capsule/Celebrex®, 200 mg), and amorphous form celecoxib-Na salt by using a liquid chromatography-mass spectrometry (LC-MS/MS, 6470 Agilent Tech., USA) method with a limit of quantification of 14.2 ng/mL (Chidamide) and 45.5 ng/mL (Celecoxib). The PK parameters of chidamide-k30, chidamide-HCl salt, celecoxib/Celebrex®, and celecoxib-Na salt were calculated using trapezoidal rule and the noncompartmental analysis tool of validated Phoenix WinNonlin software (version 6.3). The pharmacokinetic studies were conducted at Taipei Medical University and approved by the Institutional Animal Care and Use Committee (IACUC Approval No: LAC-2017-0331). Samples were prepared and analyzed as described below. To 50 µL calibration standards or plasma samples, 150 µL acetonitrile (containing 10% methanol) was added and the samples were vortexed for 1 min to precipitate protein. After centrifugation at 4° C., 21,130×g for 15 min, 5 µL of the supernatant was injected directly into LC-MS/MS for analysis. The analysis was performed with a 6470 Series liquid chromatograph (Agilent Tech., USA) equipped with a quaternary pump (1260 Infinity II Quaternary Pump LC system), a degasser, an autosampler, a thermostatted column compartment and a LC-MS/MS-6470 mass spectrometer (Agilent Tech, USA). Chromatographic separation was achieved on LiChrospher® 60 RP-select B column (5 µm, 125×4.6 mm, Merck, Germany) at 40° C. and a mobile phase gradient as described in the table below. The flow rate was 0.5 mL/min. The overall run time was 10 min. Drying gas flow and nebulizing gas flow were set at 6 and 1.5 L/min. Dry gas temperature and capillary voltage of the system were adjusted to 250° C. and 3000 V, respectively. LC-MS/MS was performed with multiple reactions monitoring mode using target ions at m/z 391.1 and 265.1 for chidamide in positive ion electrospray ionization interface, and at m/z 380 and m/z 316 for celecoxib in negative ion electrospray ionization interface. Gradient Table of LC/MS

| Time (min) | 2.5% formic acid | water | acetonitrile |
|---|---|---|---|
| 0-3 | 2% | 68% | 30% |
| 3.01-5 | 2% | 48% | 50% |
| 5.01-9 | 2% | 38% | 60% |
| 9.01-12 | 2% | 68% | 30% |

Statistics. Means and standard errors were calculated for all data points from at least four independent experiments. Pairwise comparisons of tumor size between each of the experimental condition and the IgG control group were performed using a *Student's two-sample t test* (Systat Software, San Jose, Calif., USA). The Student's test or ANOVA was performed for the analysis of animal efficacy data. The Kaplan-Meier curves and the log rank test were generated using sigma stat 3.5 software. All P values<0.05 were considered statistically significant.

Example 1

Characterization of Novel Crystal Form of Chidamide-HCl Salt

Figure 1E:
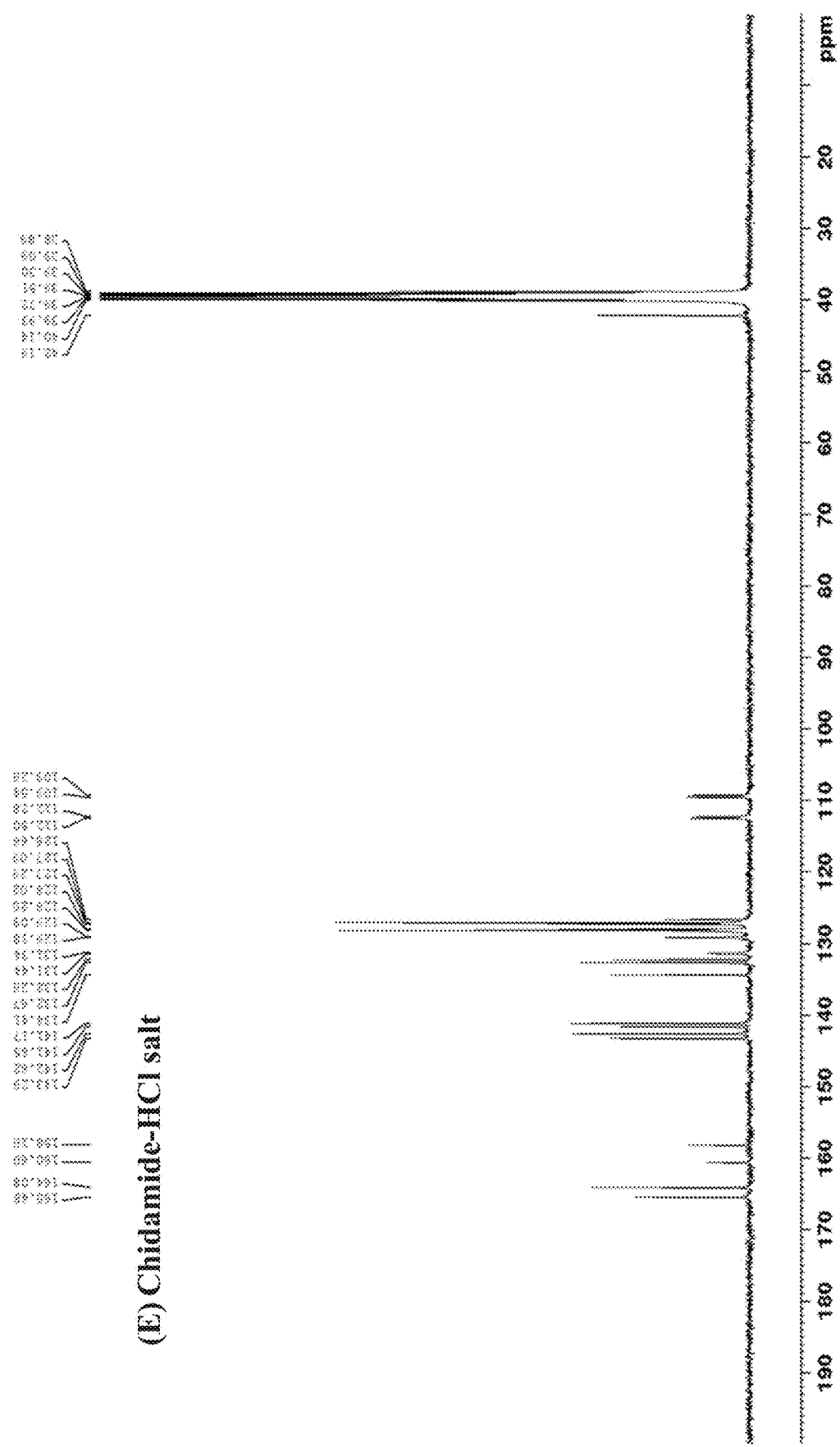
Figure 2A:
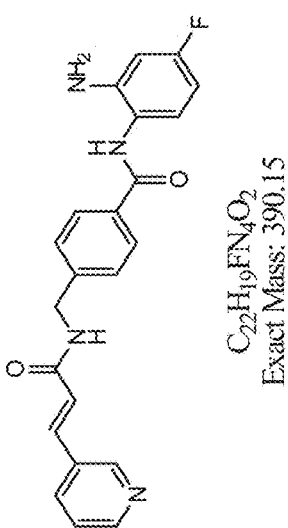
FIGS. 2A to 2D represent both the positive and negative ion ESI-MS spectra for chidamide-HCl salt and chidamide-H$_2$SO$_4$ salt.
Figure 2A:
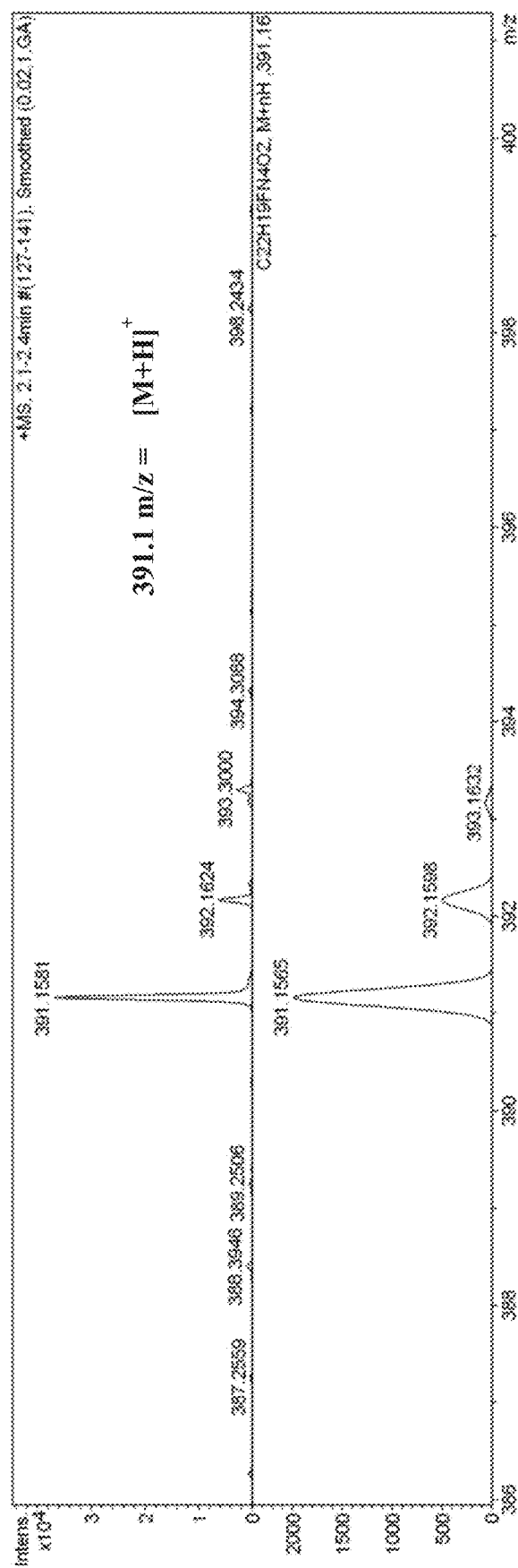
Figure 2B:
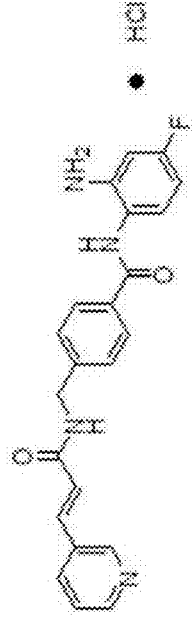
Figure 2B:
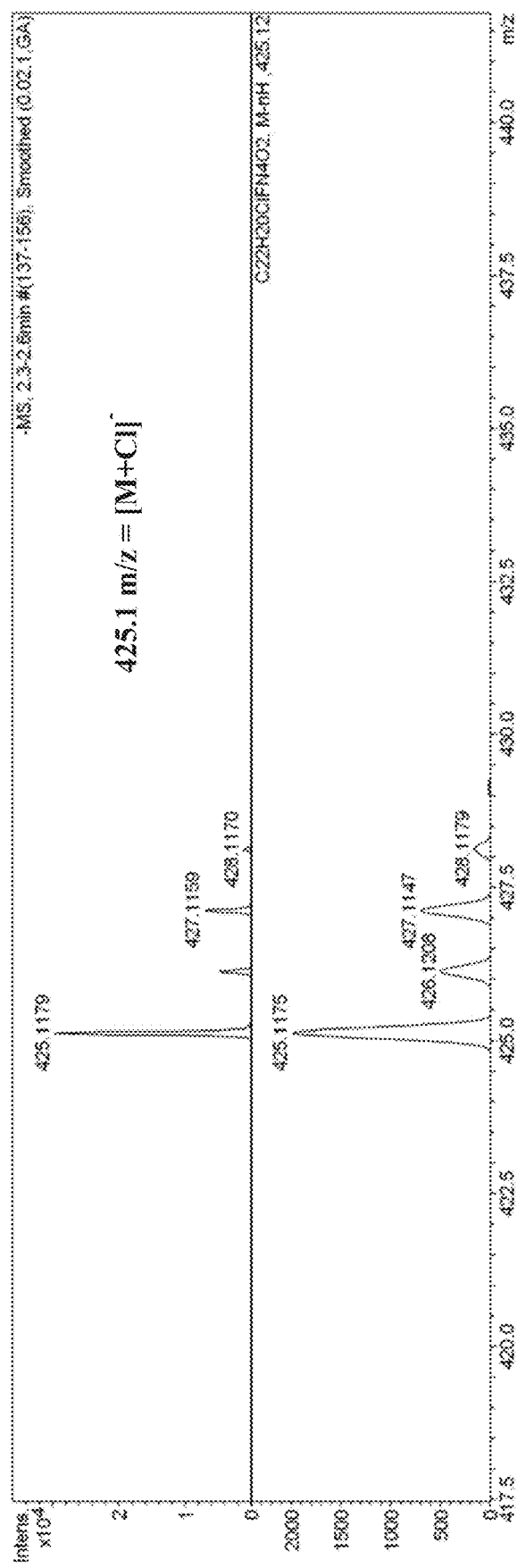
Figure 3A:
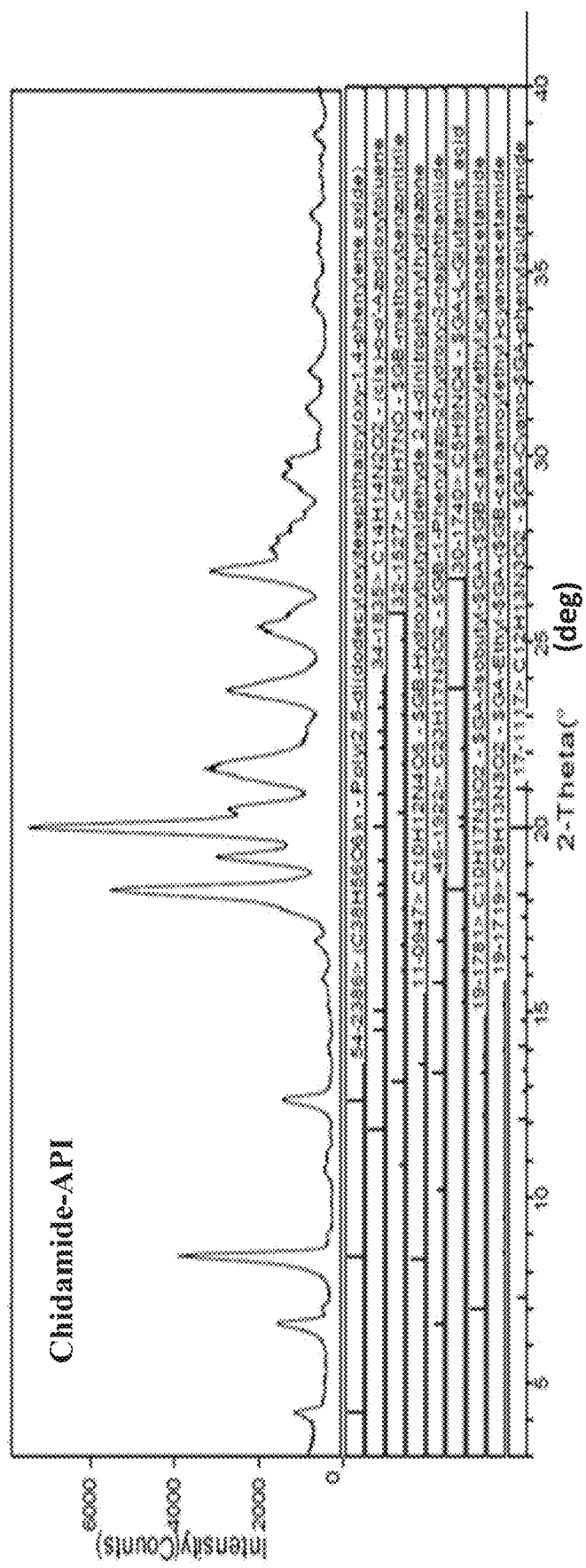
Figure 3B:
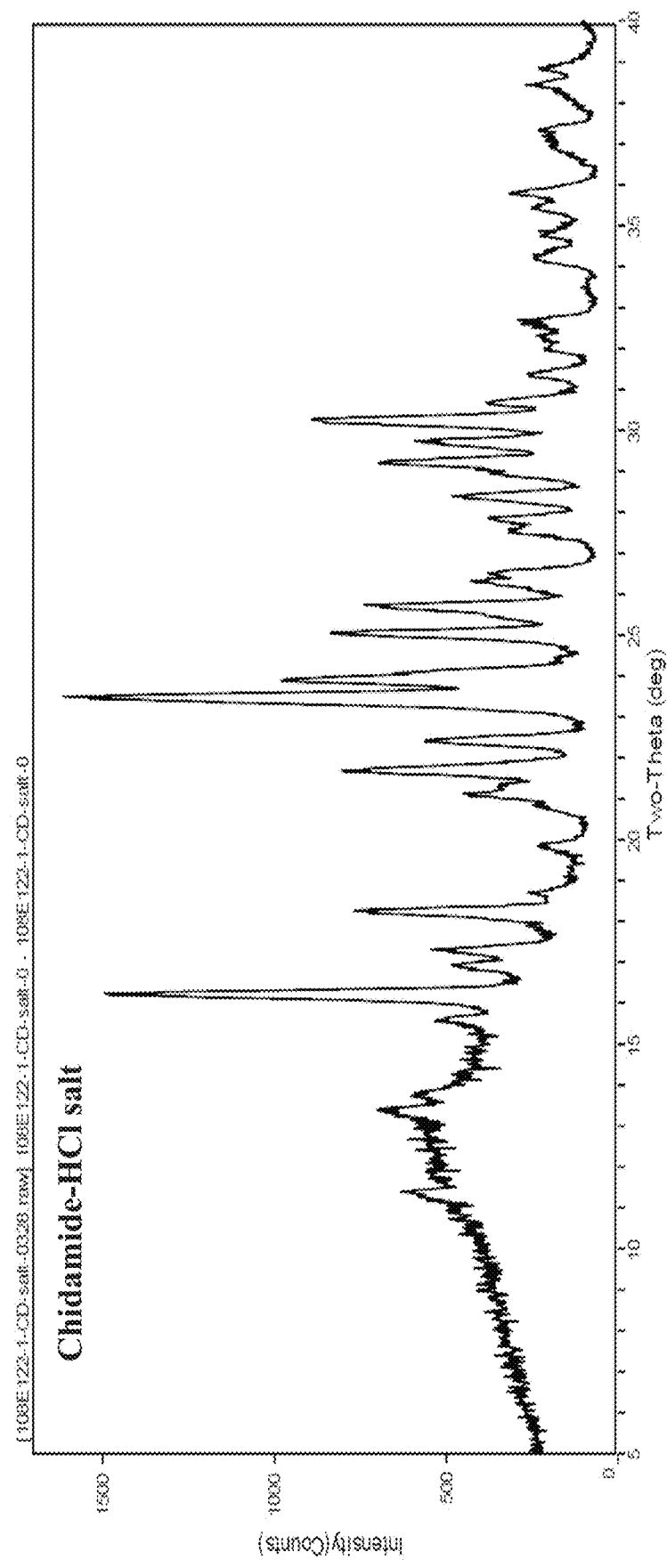
Figure 3C:
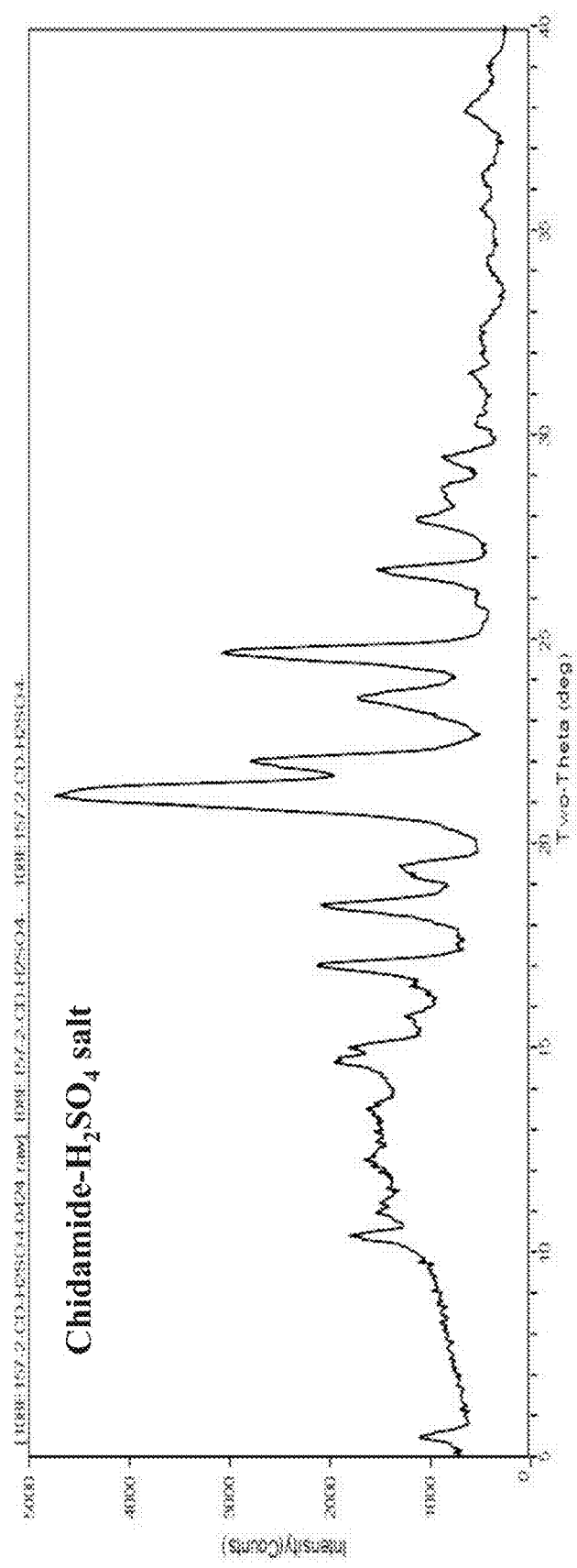
Figure 4A:
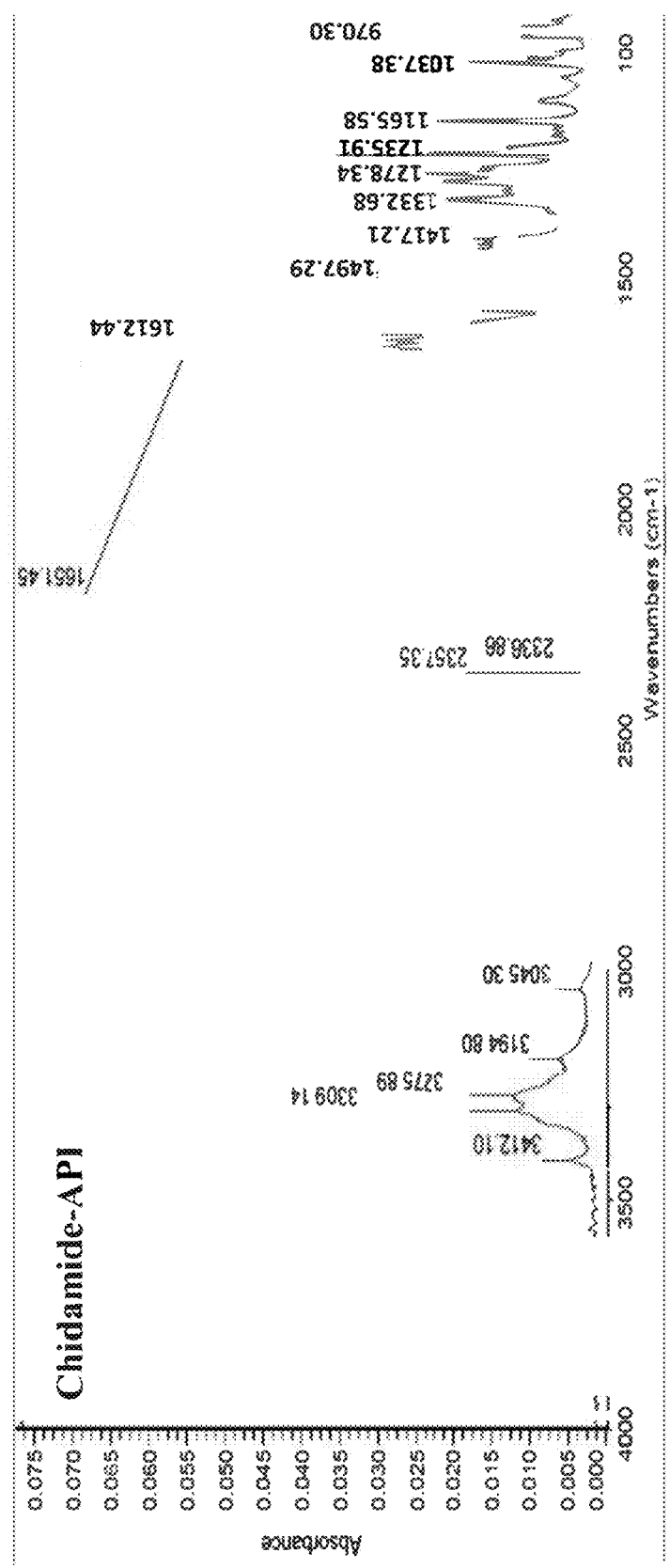
Figure 4B:
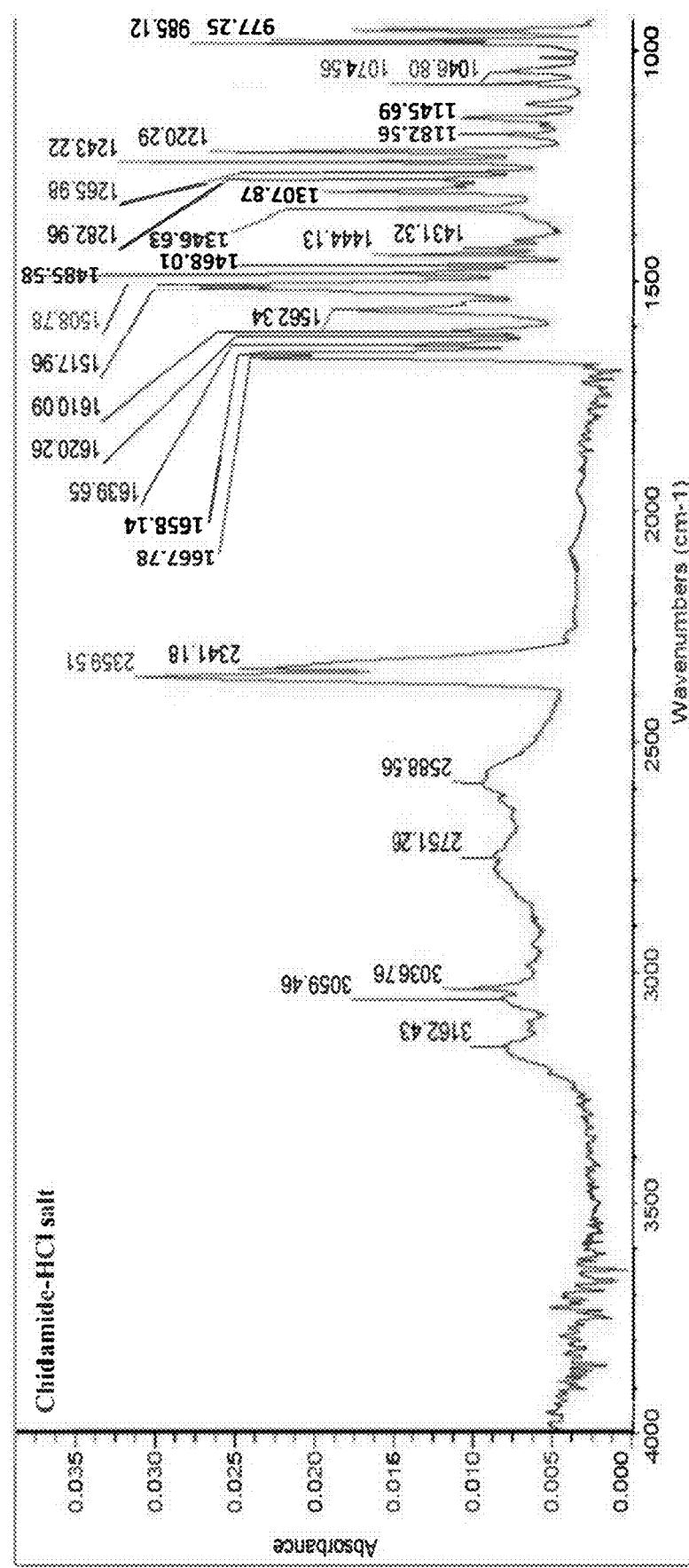

Chidamide has been approved by the China CFDA (NMPA) for relapsed or refractory peripheral T-cell lymphoma (PTCL) in 2014. Chidamide (trade name, Epidaza®) is available as tablets for oral use, containing 5 mg of Chidamide, and the recommended dose is 30 mg twice weekly with an interval more than 3 days. The tablet contains chidamide-API coated on polyvinylpyrrolidone k30 (PVP-K30) to improve its water solubility and oral bioavailability. In this invention, we developed formulations for chidamide API to produce chidamide-HCl and chidamide-$H_2SO_4$ salts in novel crystal forms. The properties of chidamide-HCl and chidamide-$H_2SO_4$ salts could significantly improve the water solubility and oral bioavailability. The structure of chidamide salts was identified by $^1$H-NMR and $^{13}$C-NMR as shown in FIG. 1A. $^1$H NMR was recorded by using a Bruker AVANCE 400 MHz PLUS instrument using solvent dimethyl sulfoxide (DMSO-d6). $^{13}$C NMR spectra were recorded at 100 MHz. The $^1$H-NMR data demonstrated that the chemical shift signal $\delta_H$ 5.20 of $NH_2$ group in aniline disappeared in chidamide-HCl salt in comparison with chidamide-API as shown in FIGS. 1A and 1B. This result demonstrated that the salt form was generated in the position of C21-$NH_2$. It can be described as C21-$NH_3^+$ $Cl^-$ or chidamide-HCl salt. The $^{13}$C-NMR data of chidamide-API and chidamide-HCl salt are shown in FIGS. 1D and 1E. The details of the chemical shift data of chidamide-API and chidamide-HCl salt are described as shown in Table 1 and FIG. 1G. Further, ESI-MS was used to determine the molecular weight. Mass spectra of Chidamide-HCl salt were recorded using a Bruker microTOF with ESI source and ion polarity: positive/negative mode. The positive ion mode ESI-MS spectra of chidamide-HCl salt was determined and shown in FIG. 2A. The most abundant peak has m/z 391.158 $[M+H]^+$. However, the negative ion mode ESI-MS spectra for chidamide-HCl salt, was determined and shown in FIG. 2B. The most abundant peak has m/z 425.118 $[M-Cl]^-$. Next, the crystal form of chidamide-HCl salt was characterized by XRD. The comparison of XRD profile between chidamide-API and chidamide-HCl salt was analyzed. XRD measurements were carried out on a PANalytical EMPYREAN X-ray diffractometer. For X-ray radiation source, a Cu ($\lambda$=45 kV, 40 mA) anode was used, range 20 between 3 and 40° with scan rate l/min. The XRD data demonstrated that chidamide-API and chidamide-HCl salt have different XRD profiles as shown in FIGS. 3A (chidamide-API) and 3B (chidamide-HCl salt). The 2-theta values were different between chidamide-API and chidamide-HCl salt as shown in FIG. 3D. This data indicated that chidamide-HCl salt has novel crystal form different from that of chidamide-API. The two different crystal forms of chidamide-API and chidamide-HCl salt were analyzed in saturation solubility study. Chidamide-HCl salt was much more water-soluble than chidamide-API and chidamide-K30 as shown in Table 2. Chidamide-API was water-insoluble, and chidamide-K30, the formulation of chidamide tablet (Epidaza®), showed low water solubility (about 26.03 µg/mL). Three independent batches of chidamide-HCl salt were tested and showed the saturation solubility about 554.83, 566.90, and 536.06m/mL, respectively. These results demonstrated that chidamide-HCl salt markedly improved the water solubility over 20 times compared with chidamide-K30 as shown in Table 2. The improvement of water solubility of chidamide-HCl salt may increase the oral bioavailability, which then would improve the PK profile and the anti-cancer efficacy. The structure of chidamide-HCl salt was further confirmed by FTIR analysis as shown in FIGS. 4A-4B. FTIR spectra were recorded on a Perkin Elmer Spotlight 200i Sp2 with AutoATR System (Perkin Elmer IR spectrophotometer). FTIR spectra were scans over the range of 4000-700 $cm^{-1}$. The profile of chidamide-HCl salt lost the signal of the N-H stretching of aniline in 3275 and 3309 wavenumber in $cm^{-1}$ as shown in FIG. 4B. The comparison of FTIR data of chidamide-API (FIG. 4A) and chidamide-HCl salt is represented in FIG. 4D.

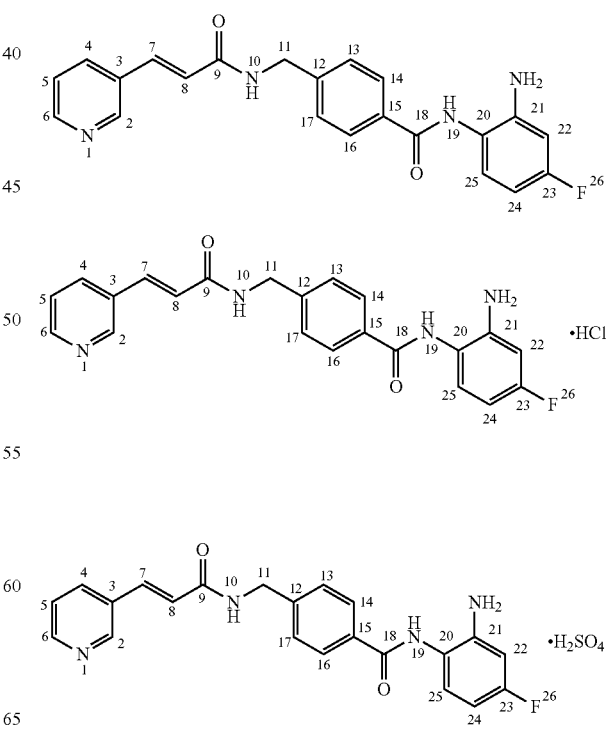

TABLE 1

$^1$H-NMR Spectroscopic Data (400 MHz, $d_6$-DMSO) for chidamide-API, Chidamide-HCl salt and Chidamide-H$_2$SO$_4$ salt.

| | Chidamide-API | | Chidamide-HCl salt | | Chidamide-H$_2$SO$_4$ salt | |
|---|---|---|---|---|---|---|
| position | | $\delta_H$ (J in Hz) | | $\delta_H$ (J in Hz) | | $\delta_H$ (J in Hz) |
| 11 | CH2 | 4.49, d | CH2 | 4.5, d | CH2 | 4.5, d |
| 21 | NH2 | 5.20, s | | | | |
| 24 | CH | 6.35, td | CH | 6.41, td | CH | 6.57, t |
| 22 | CH | 6.55, dd | CH | 6.58, dd | CH | 6.72, dd |
| 25 | CH | 6.82, d | CH | 6.91, d | CH | 6.99, d |
| 5 | CH | 7.12, dd | CH | 7.13, dd | CH | 7.22, t |
| 14, 16 | CH2 | 7.42, d | CH2 | 7.42, d | CH2 | 7.42, d |
| 7 | CH | 7.44, dd | CH | 7.59, d | CH | 7.62, d |
| 6 | CH | 7.52, d | CH | 7.76, dd | CH | 7.90, dd |
| 13, 17 | CH2 | 7.95, d | CH2 | 7.95, d | CH2 | 7.99, d |
| 4 | CH | 8.01, dt | CH | 8.37, d | CH | 8.54, d |
| 8 | CH | 8.56, dd | CH | 8.72, dd | CH | 8.79, dd |
| 2 | CH | 8.74, d | CH | 8.96, d | CH | 9.04, d |
| 10 | NH | 8.79, t | NH | 8.87, t | NH | 8.97, t |
| 19 | NH | 9.57, s | NH | 9.62, s | NH | 9.8, s |

TABLE 2

Saturation solubility study of chidamide-API, chidamide-HCl salt, and chidamide-H$_2$SO$_4$ salt

| Substances | Saturation & Solubility (μg/mL) |
|---|---|
| Chidamide-API | BDL |
| Chidamide/k30 (1:5) | 26.03 ± 0.24 |
| Chidamide-HCl salt NO. 190116 | 554.83 ± 23.90 |
| Chidamide-HCl salt NO. 190199 | 566.90 ± 20.60 |
| Chidamide-HCl salt NO. 190318 | 536.06 ± 0.94 |
| Chidamide-H$_2$SO$_4$ salt NO. 190119 | 597.39 ± 36.60 |
| Chidamide-H$_2$SO$_4$ salt NO. 190418 | 652.90 ± 14.35 |
| Chidamide-H$_2$SO$_4$ salt NO. 190504 | 561.50 ± 42.60 |

*BDL: Below detection limit

Example 2

Characterization of Novel Crystal Form of Chidamide-H$_2$SO$_4$ Salt

Figure 2C:
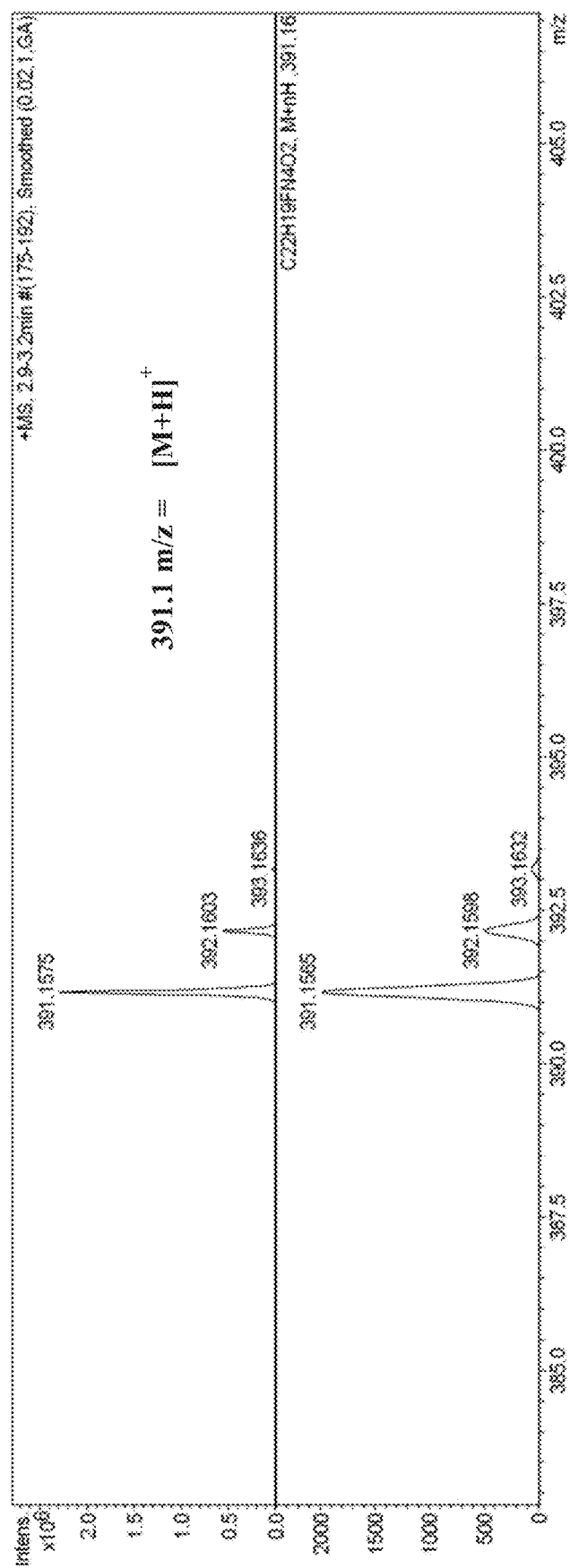
Figure 2D:
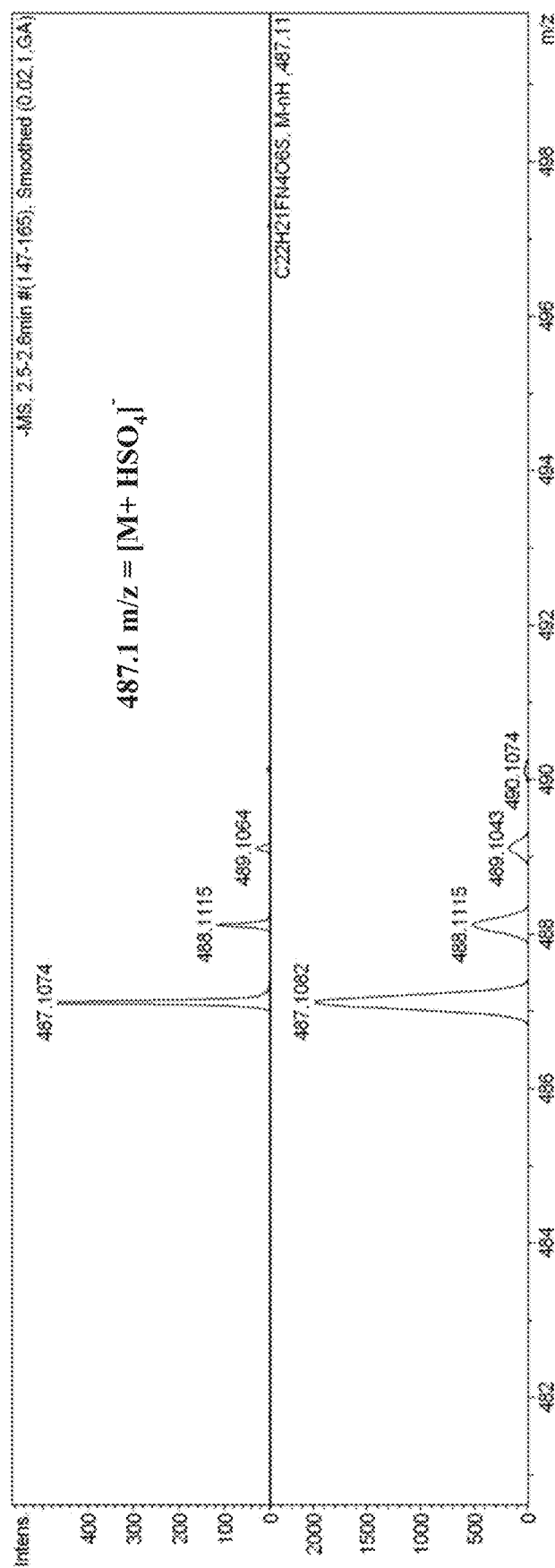
Figure 4C:
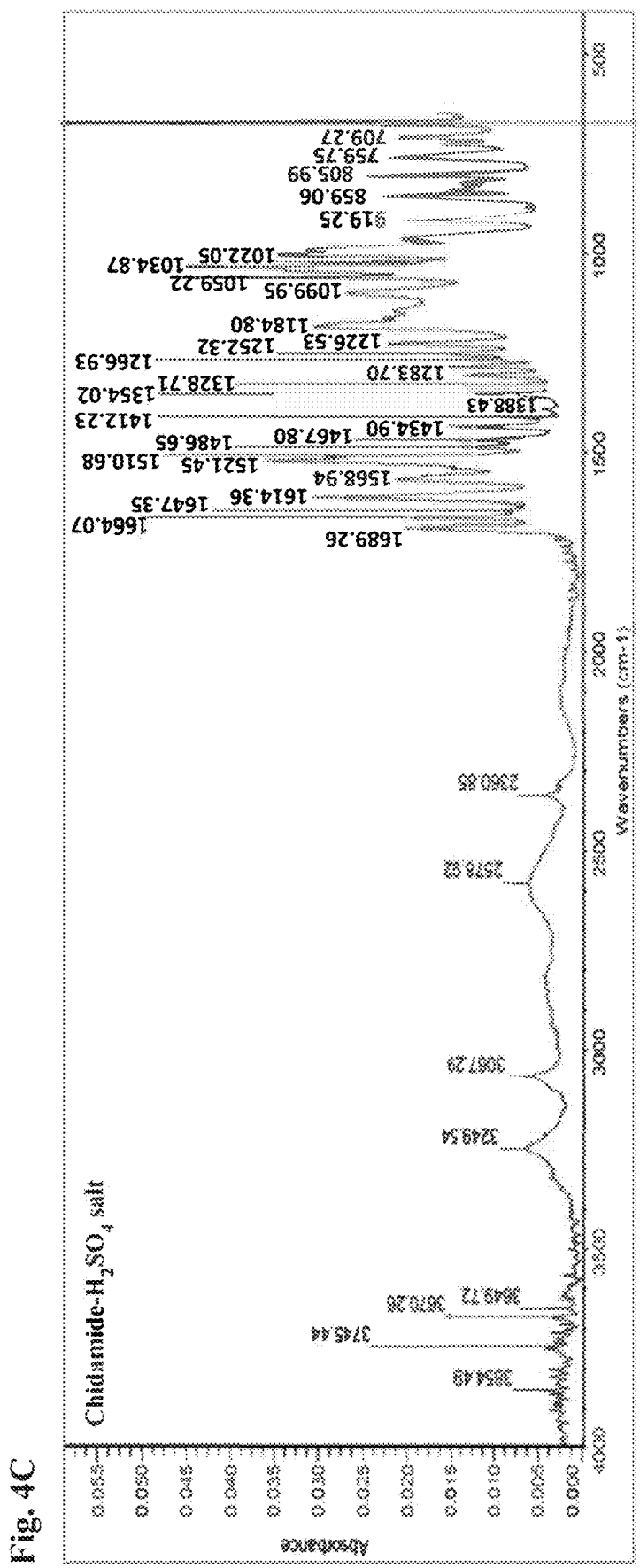

The second salt form of chidamide was prepared with H$_2$SO$_4$. The structure of chidamide-H$_2$SO$_4$ salt was identified by $^1$H-NMR and $^{13}$C-NMR as shown in FIGS. 1C and 1F. $^1$H NMR was recorded by using a Bruker AVANCE 400 MHz PLUS instrument using solvent dimethyl sulfoxide (DMSO-d6). $^{13}$C NMR spectra were recorded at 100 MHz. The $^1$H-NMR data demonstrated that the chemical shift signal $\delta_H$ 5.20 of NH$_2$ group in aniline disappeared in chidamide-H$_2$S$_4$ salt in comparison with chidamide-API as shown in FIGS. 1C and 1A. This result demonstrated that the salt form was generated in the position of C21-NH$_2$. It can be described C21-NH$_3^+$ HSO$_4^-$ or chidamide-H$_2$S$_4$ salt. The detailed chemical shift data of chidamide-API and chidamide-H$_2$S$_4$ salt were shown in Table 1 and FIG. 1G. Further, ESI-MS was used to determine the molecular weight. Mass spectra of chidamide-H$_2$S$_4$ salt were recorded using a Bruker microTOF with ESI source and ion polarity: positive/negative mode. The positive ion mode ESI-MS spectra of chidamide-H$_2$S$_4$ salt was determined and shown in FIG. 2C. The most abundant peak has m/z 391.16 [M+H]$^+$. However, the negative ion mode ESI-MS spectra for chidamide-H$_2$S$_4$ salt was determined and shown in FIG. 2D. The most abundant peak has m/z 487.12 [M+HSO$_4$]$^-$. Next, the crystal form of chidamide-H$_2$S$_4$ salt was characterized by XRD. The comparison of XRD profile between chidamide-API and chidamide-H$_2$SO$_4$ salt was analyzed. XRD measurements were carried out on a PANalytical EMPYREAN X-ray diffractometer. For X-ray radiation source, a Cu ($\lambda$=45 kV, 40 mA) anode was used, range 2θ between 3 and 40° with scan rate 1/min. The XRD data demonstrated that chidamide-API and chidamide-H$_2$SO$_4$ salt have different XRD profiles as shown in FIGS. 3A (chidamide-API) and 3C (chidamide-H$_2$S$_4$ salt). The 2-theta values were different between chidamide-API and chidamide-H$_2$S$_4$ salt as shown in FIG. 3D. This data indicated that chidamide-H$_2$S$_4$ salt has novel crystal form different from that of chidamide-API. The two different crystal forms of chidamide-API and chidamide-H$_2$SO$_4$ salt were analyzed in saturation solubility study. Chidamide-H$_2$SO$_4$ salt was much more water-soluble than chidamide-API and chidamide-K30 as shown in Table 2. Chidamide-API was water-insoluble, and chidamide-K30, the formulation of chidamide tablet (Epidaza®), showed low water solubility (about 26.03 μg/mL). Three independent batches of chidamide-H$_2$SO$_4$ salt were tested and showed the saturation solubility about 597.39, 652.90, and 561.5 μg/mL, respectively. These results demonstrated that chidamide-H$_2$SO$_4$ salt markedly improved the water solubility over 20 times compared with chidamide-K30 as shown in Table 2. The improvement of water solubility of chidamide-H$_2$SO$_4$ salt may increase the oral bioavailability, which then would improve the PK profile and the anti-cancer efficacy. The structure of chidamide-H$_2$SO$_4$ salt was further confirmed by FTIR analysis as shown in FIG. 4C. FTIR spectra were recorded on a Perkin Elmer Spotlight 200i Sp2 with AutoATR System (Perkin Elmer IR spectrophotometer). FTIR spectra were scans over the range of 4000-700 cm$^{-1}$. The profile of chidamide-H$_2$SO$_4$ salt lost the signal of the N—H stretching of aniline in 3412 and 3309 wavenumber in cm$^{-1}$ as shown in FIG. 4C. The comparison of FTIR data of chidamide-API (FIG. 4A) and chidamide-H$_2$SO$_4$ salt is represented in FIG. 4D.

Example 3

Characterization of Novel Amorphous Form of Celecoxib-Na Salt

Figure 6:
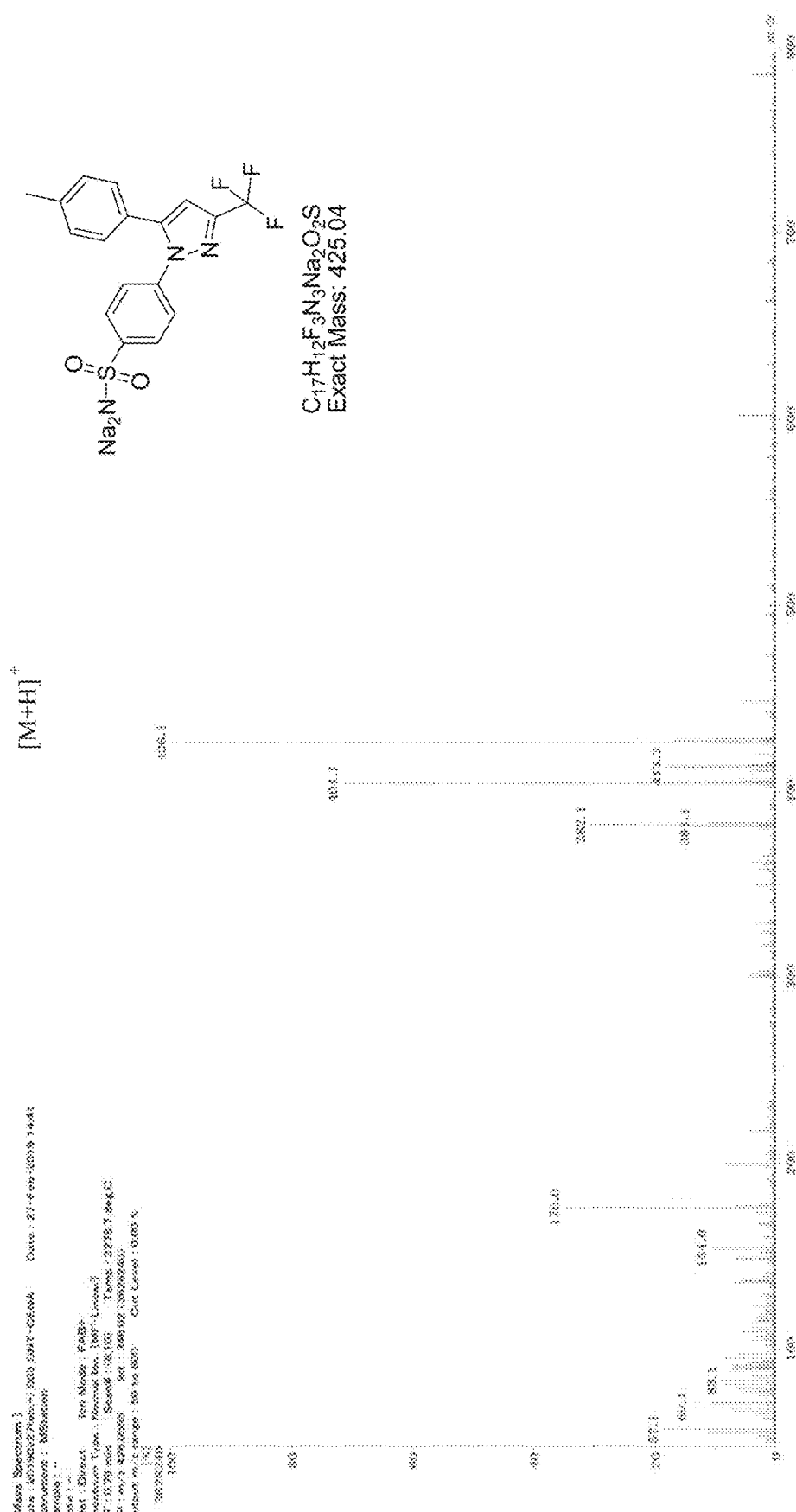
FIG. 6 shows the Fast Atom Bombardment Mass Spectrometry (FAB-MS) spectra of celecoxib-Na salt. The FAB-MS spectra of amorphous celecoxib-Na salt have the same pattern as that of crystalline salt form.
Figure 7A:
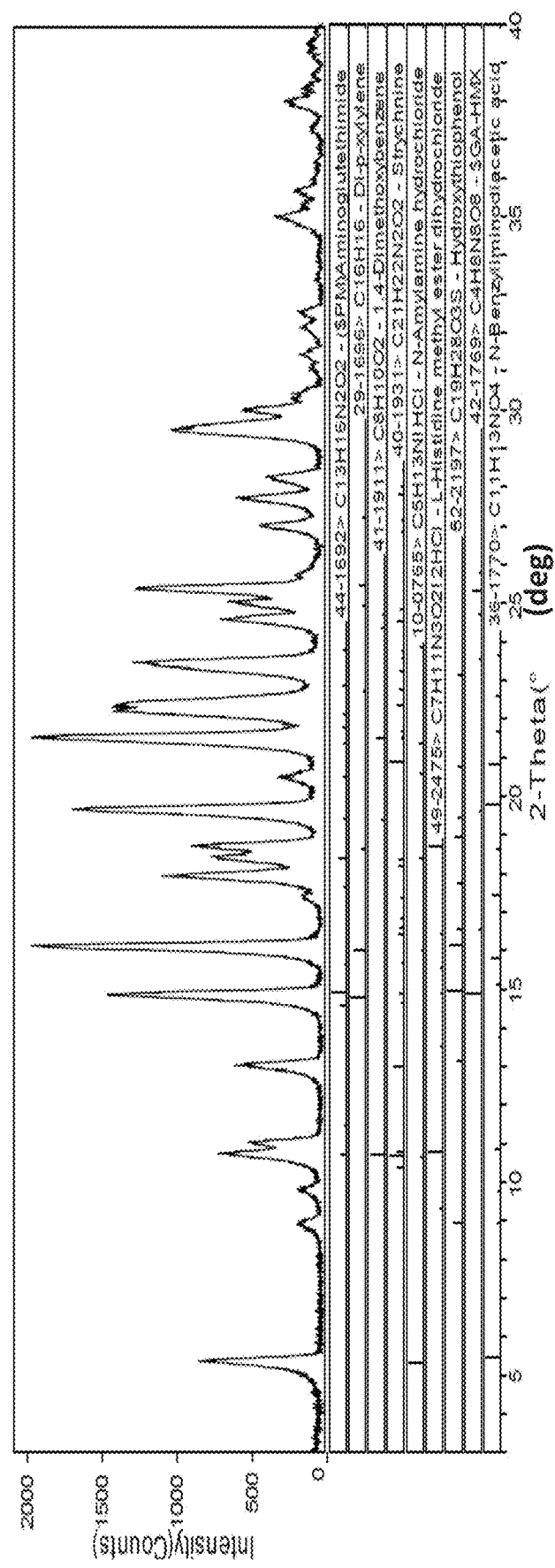
Figure 7B:
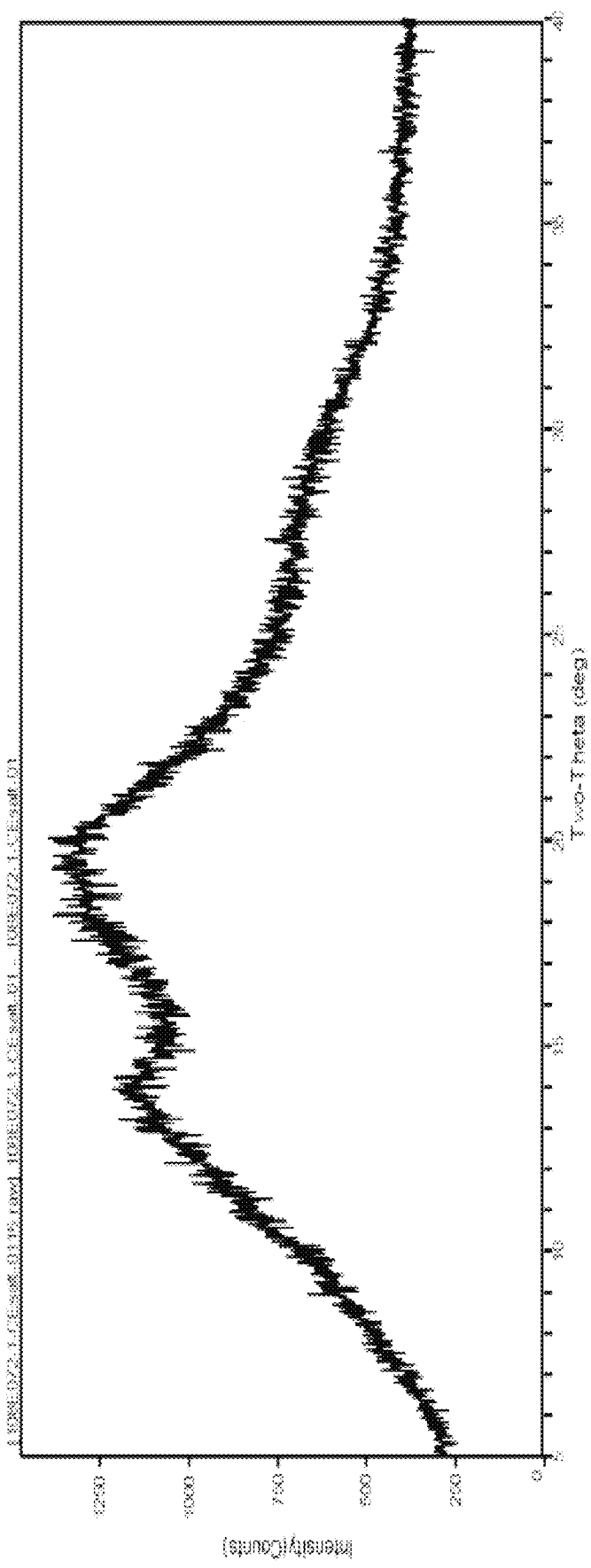
Figure 7C:
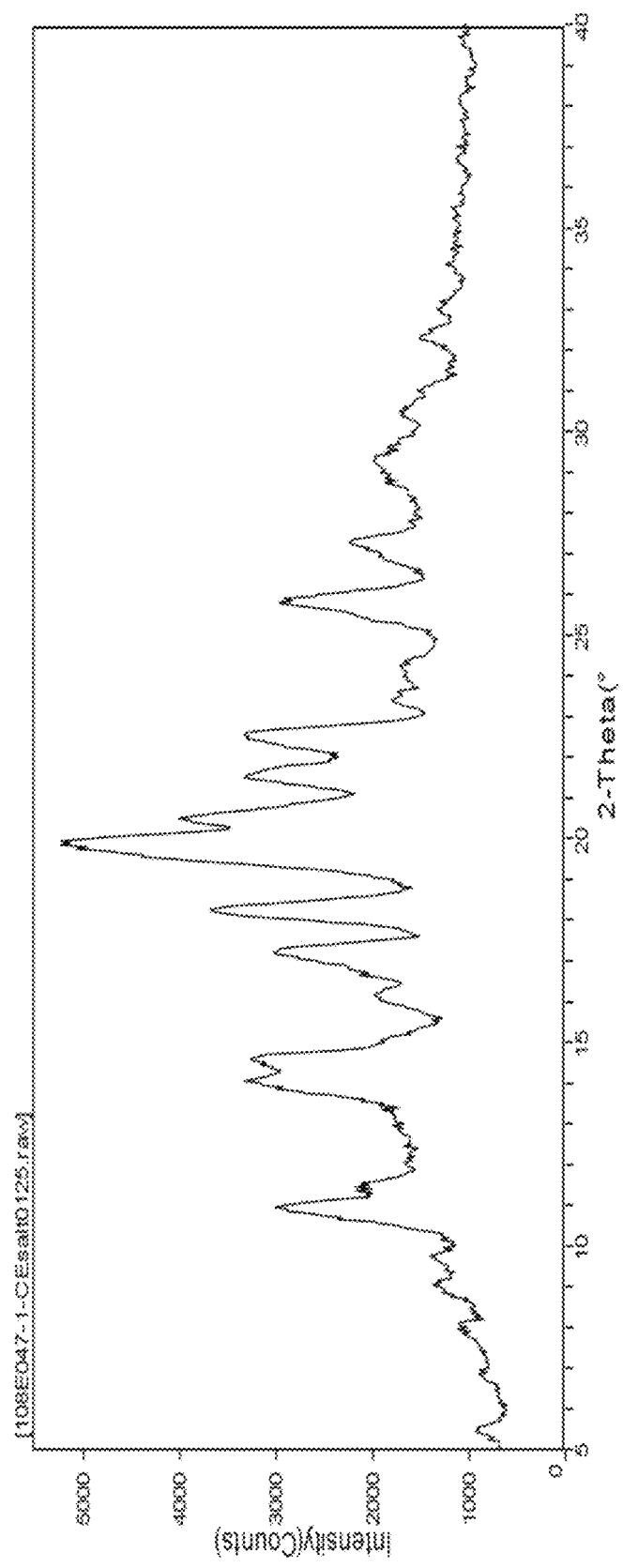
Figure 8A:
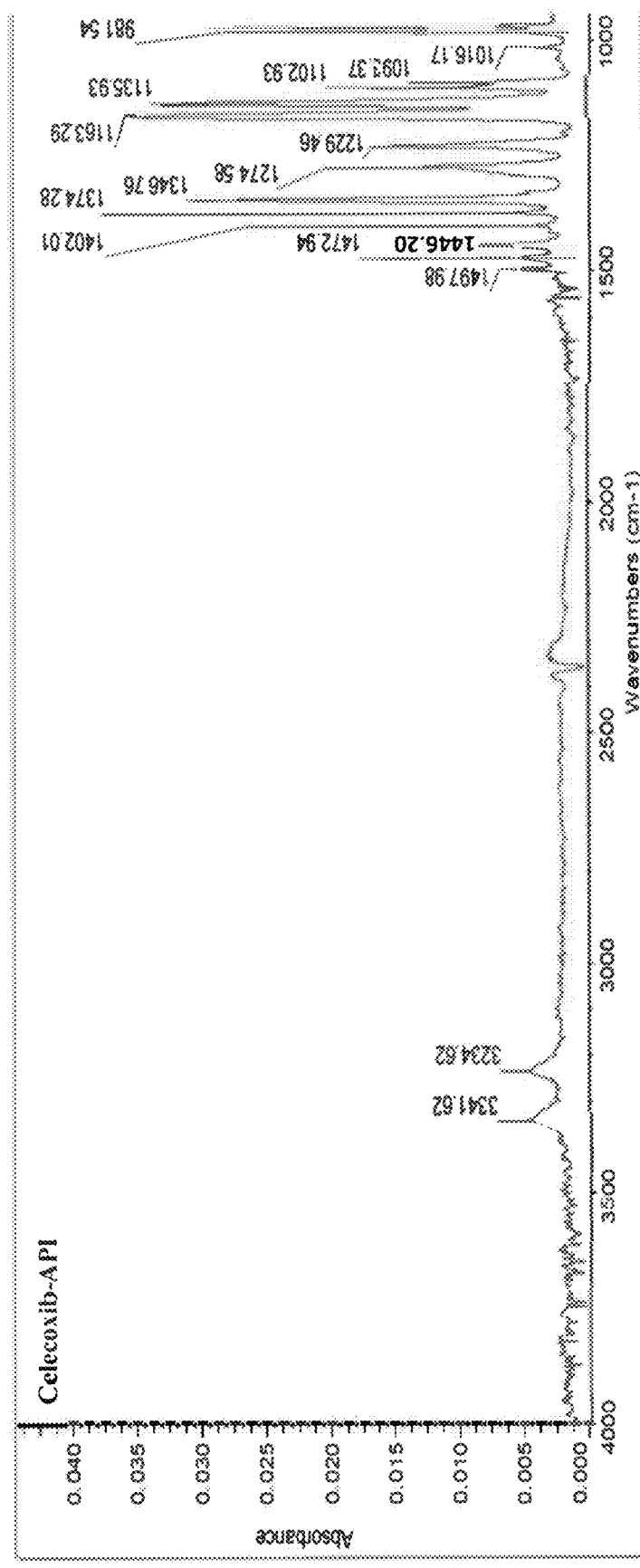
Figure 8B:
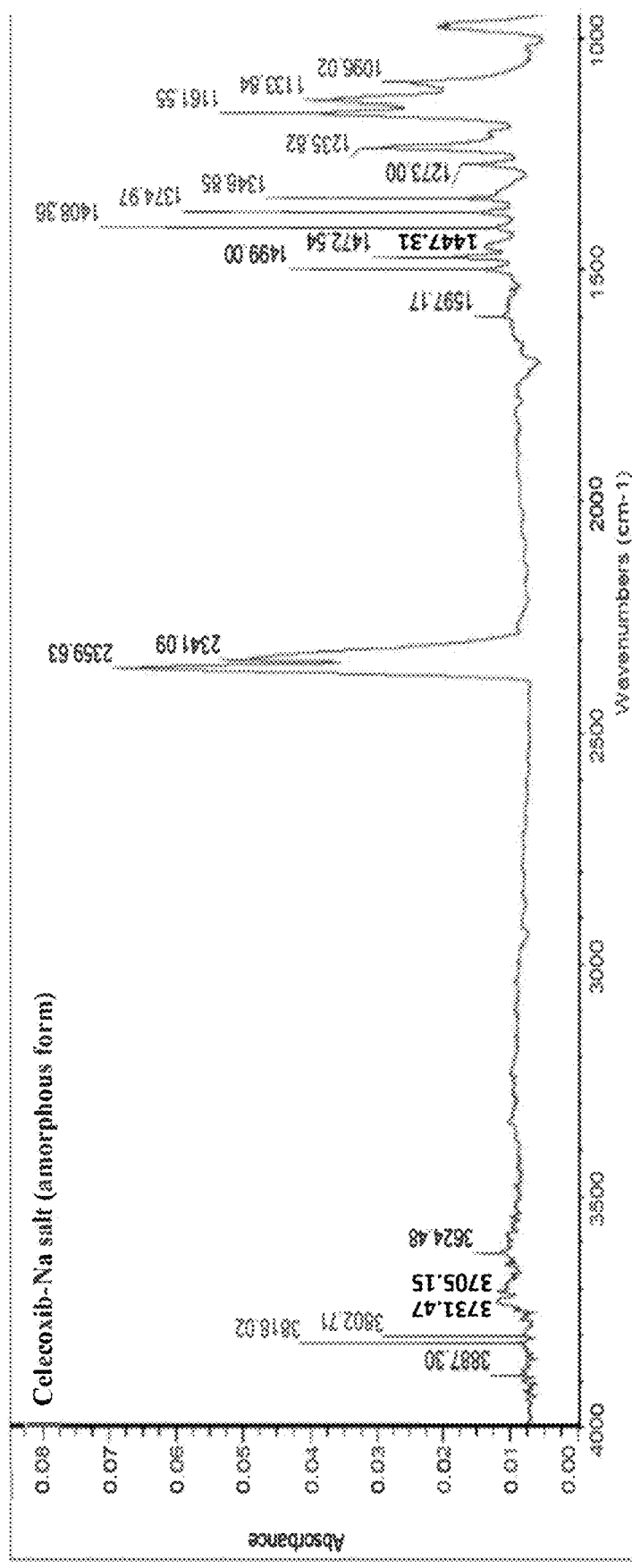

Amorphous forms are characterized by having a short-range molecular order unlike crystal forms having a long-range order of molecular packing. Celecoxib has been classified as class II of BCS (biopharmaceutical classification system). It was low solubility and high permeability properties. Most commercialized drugs have appropriate permeability; dissolution is the rate limiting step for absorption of these drugs. On the other hand, the solubility was another important issue in drug development; the preparation of amorphous form provides an efficient solution for the low solubility issue. We have designed and tested a unique method to generate the amorphous form of celecoxib-Na salt. In NaH strong base condition the replacement of hydrogen from sulfonamide group of Celecoxib-API by Na occurred and through multiple steps including purification and condensation the novel amorphous celecoxib-Na salt was produced. First, $^1$H-NMR spectra of celecoxib-API and celecoxib-Na salt was compared and shown in FIGS. 5A and 5B. It was clearly shown that two hydrogen signal in sulfonamide disappeared as shown in FIG. 5B. It suggested that two Na atoms replaced two hydrogen atoms from sulfonamide group to produce the novel celecoxib-Na salt. The $^1$H NMR data (400 MHz, CDCl$_3$) of celecoxib-API was described as: δ 2.36 (3H, s), 4.86 (2H, s), 6.72 (1H, s), 7.09 (2H, dd), 7.16 (2H, d), 7.46 (2H, m), 7.89 (2H, m). The $^1$H NMR data (400 MHz, CDCl$_3$) of celecoxib-Na salt was described as: δ2.09 (3H, s), 6.59 (1H, s), 6.87 (4H, s), 6.94 (2H, d), 7.61 (2H, d). The $^1$H-NMR data demonstrated that the chemical shift signal $δ_H$ 4.86 of NH$_2$ group in Sulfonamides disappeared in Celecoxib-Na salt in comparison with Celecoxib-API as shown in FIGS. 5B and 5A. Furthermore, $^{13}$C-NMR data was demonstrated in FIGS. 5C, 5D, and 5E. Next, we used FAB-MS to confirm the molecular weight of celecoxib-Na salt as shown in FIG. 6. Mass spectra of celecoxib-Na salt were recorded by using a JEOL JMS-700 with FAB Source and Ion Polarity: Positive mode. The data demonstrated that the found m/z was 426.1 [M+H$^+$]. It was suggested that celecoxib-Na salt was C$_{17}$H$_{12}$F$_3$N$_3$Na$_2$O$_2$S, with molecular weight 425.04. The calculated m/z for C$_{17}$H$_{12}$F$_3$N$_3$Na$_2$O$_2$S was 425.04, and it was found 426.1 (M+H)$^+$ in FAB-MS. The data again confirmed the celecoxib-Na salt contained two sodium to replace two hydrogens. Next, the water solubility of amorphous celecoxib-Na salt was evaluated. As shown in Table 3, celecoxib-API was water-insoluble, but celecoxib-capsule (Celebrex®) was slightly water-insoluble (about 1.19 μg/mL). Three independent batches of amorphous form of celecoxib-Na salt were tested to have saturation solubility about 54.72, 54.45, and 56.72 μg/mL, respectively. The water solubility of celecoxib-Na salt was significantly improved in comparison with celecoxib-API and celecoxib-capsule. This result suggested that the improved water solubility property of amorphous salt form of celecoxib-Na may increase the oral bioavailability, and therefore increase the therapeutic efficacy. Furthermore, as shown in FIGS. 7A-7D, the XRD data have indicated that celecoxib-API has specific crystal pattern (FIG. 7A), but amorphous celecoxib-Na salt has amorphous diffraction pattern as shown in FIG. 7B. This result indicated that amorphous celecoxib-Na salt possessed specific form with marked improvement of the saturation water solubility. Many researches were devoted to make the amorphous form of celecoxib by using different polymers as carriers. The structure of amorphous celecoxib-Na salt was reconfirmed by analysis of FTIR as shown in FIG. 8B. The amorphous celecoxib-Na salt lost the N—H stretching of sulfonamide in 3234 and 3341 wavenumber in cm$^{-1}$ as shown in FIGS. 8A and 8B. The comparison of FTIR data between celecoxib-API and amorphous celecoxib-Na salt is presented in FIG. 8D.

TABLE 3

Saturation solubility study of celecoxib-API, celecoxib-capsule, and celecoxib-Na salt (amorphous form or crystalline form).

| Substances | Saturation & Solubility (μg/mL) |
| --- | --- |
| Celecoxib-API | BDL |
| Celecoxib-capsule (Celebrex ®) | 1.19 ± 0.05 |
| Celecoxib-Na salt NO. 1903261 (amo) | 54.72 ± 1.0 |
| Celecoxib-Na salt NO. 1903262 (amo) | 54.45 ± 1.8 |
| Celecoxib-Na salt NO. 1903263 (amo) | 56.72 ± 0.8 |
| Celecoxib-Na salt NO. 190307 (cry) | 111.5 ± 5.7 |
| Celecoxib-Na salt NO. 1903282 (cry) | 133.63 ± 1.8 |
| Celecoxib-Na salt NO. 1903283 (cry) | 95.34 ± 5.7 |

*BDL: Below detection limit
amo: amorphous;
cry: crystalline

Example 4

Characterization of Crystalline Form of Celecoxib-Na Salt

Figure 8C:
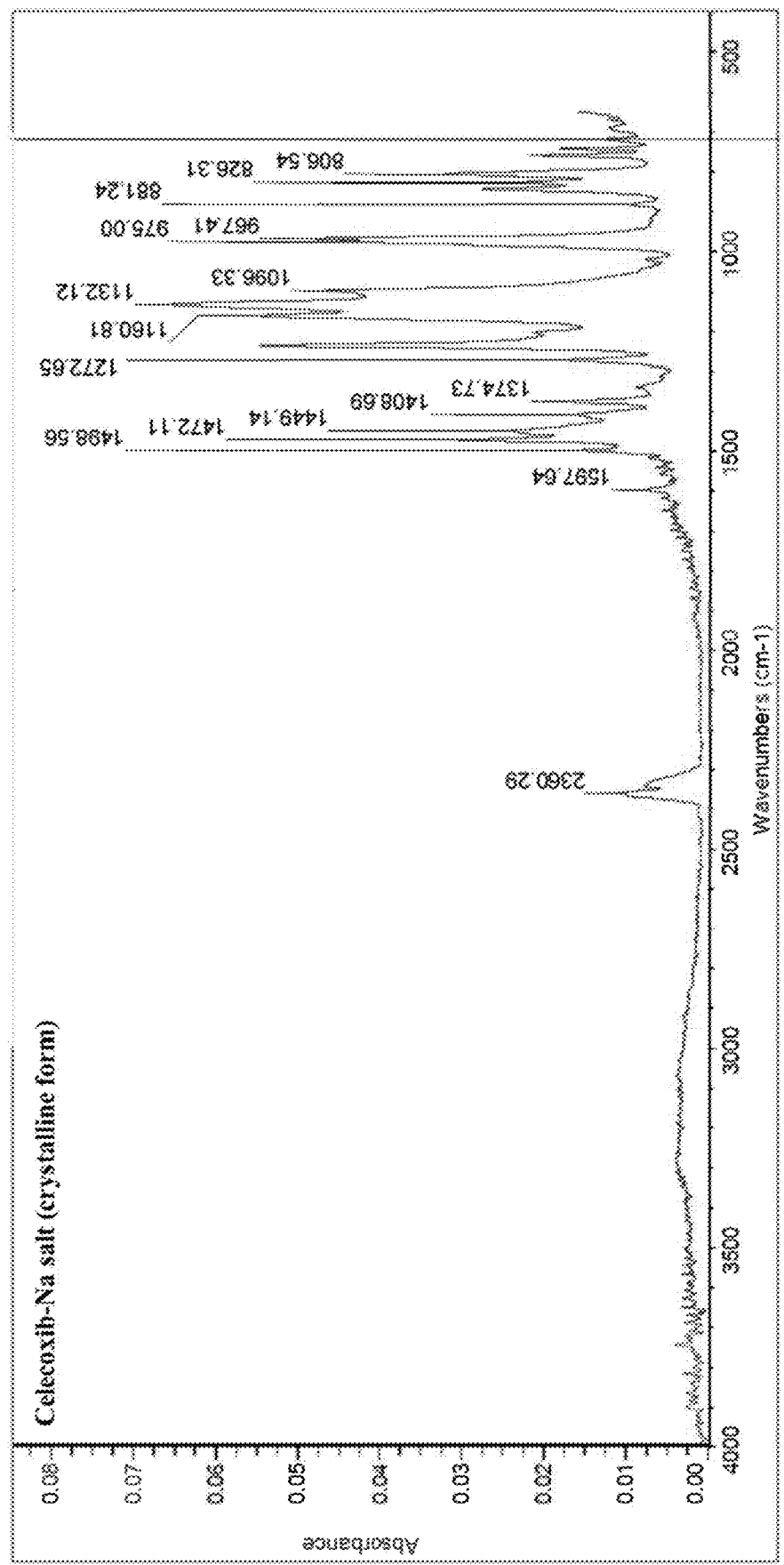

The crystalline celecoxib-Na salt was prepared and analyzed by $^1$H-NMR, $^{13}$C-NMR, XRD, MS, FTIR. As shown in Table 3, the water solubility of crystalline form of celecoxib-Na salt from three different batches was shown to be about 111.5, 133.63, and 95.34 μg/mL. As shown in FIGS. 7C and 7D, the crystal diffraction pattern of crystalline celecoxib-Na salt is different from that of celecoxib-API. This result indicated that crystalline celecoxib-Na salt possessed specific crystal form which caused the marked improvement of water solubility. The structure of crystalline celecoxib-Na salt was reconfirmed by the analysis of FTIR as shown in FIG. 8C. The celecoxib-Na salt lost the N—H stretching of sulfonamide in 3234 and 3341 wavenumber in cm$^{-1}$ as shown in FIGS. 8C and 8D, as compared with celecoxib-API.

Example 5

Figure 9A:
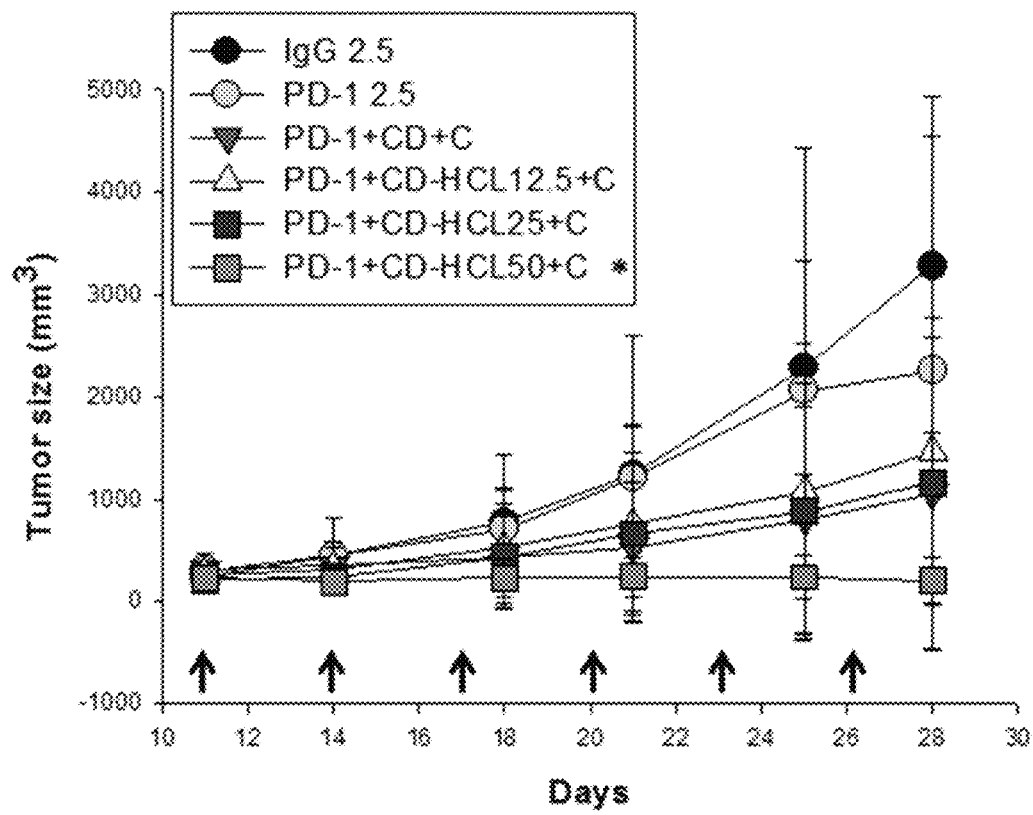
FIGS. 9A to 9J show the therapeutic response of chidamide-HCl salt plus celecoxib-cap combined with anti-PD-1 antibody in CT26 tumor-bearing mice. BALB/c mice bearing a CT26 colon tumor were treated with various therapeutic modalities as indicated. IgG, Anti-IgG control (vehicle, 2.5 mg/kg); PD-1, Anti-PD-1 monoclonal antibody (2.5 mg/kg); CD-HCl, chidamide-HCl salt 12.5, 25, 50 mg/kg; CD-K30, chidamide-K30 (chidamide coated on polyvinylpyrrolidone K30, 50 mg/kg); C-cap 50, celecoxib product from capsule (50 mg/kg, Celebrex®).
Figure 9B:
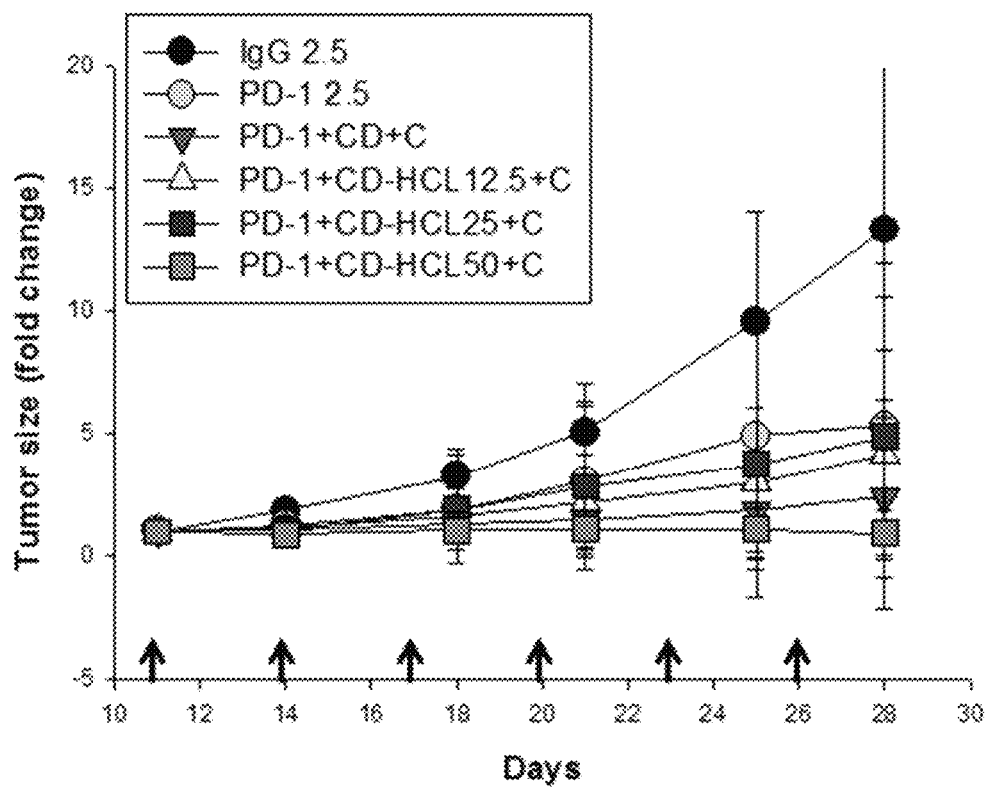
Figure 9C:
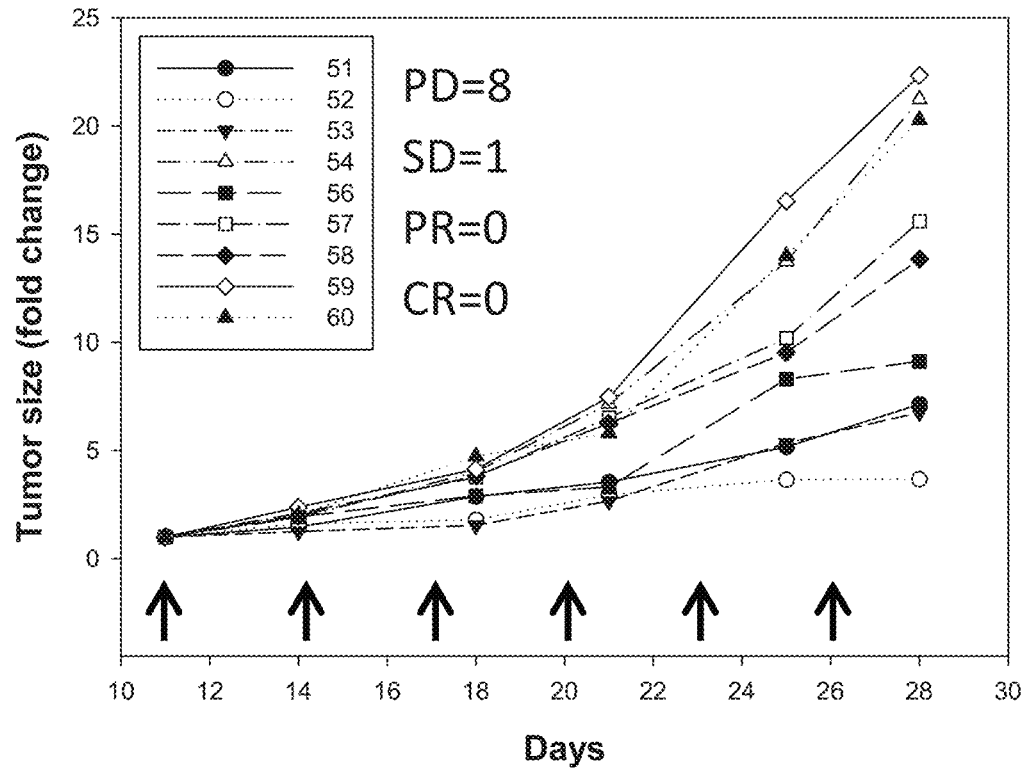
Figure 9D:
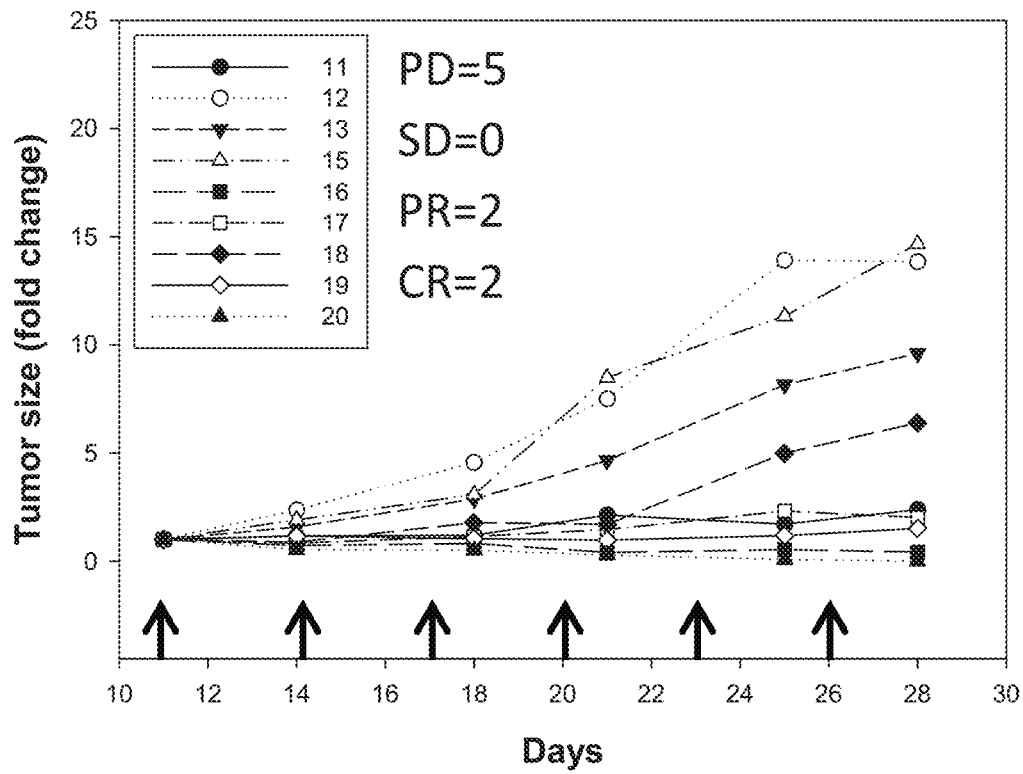
Figure 9E:
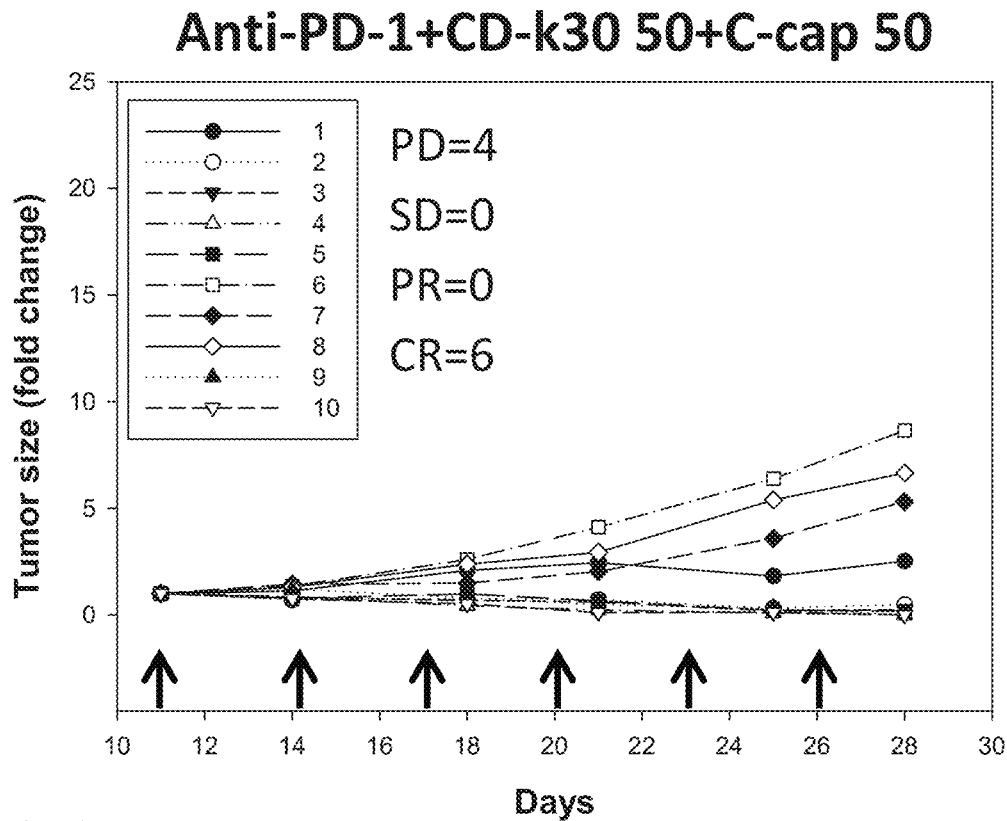
Figure 9F:
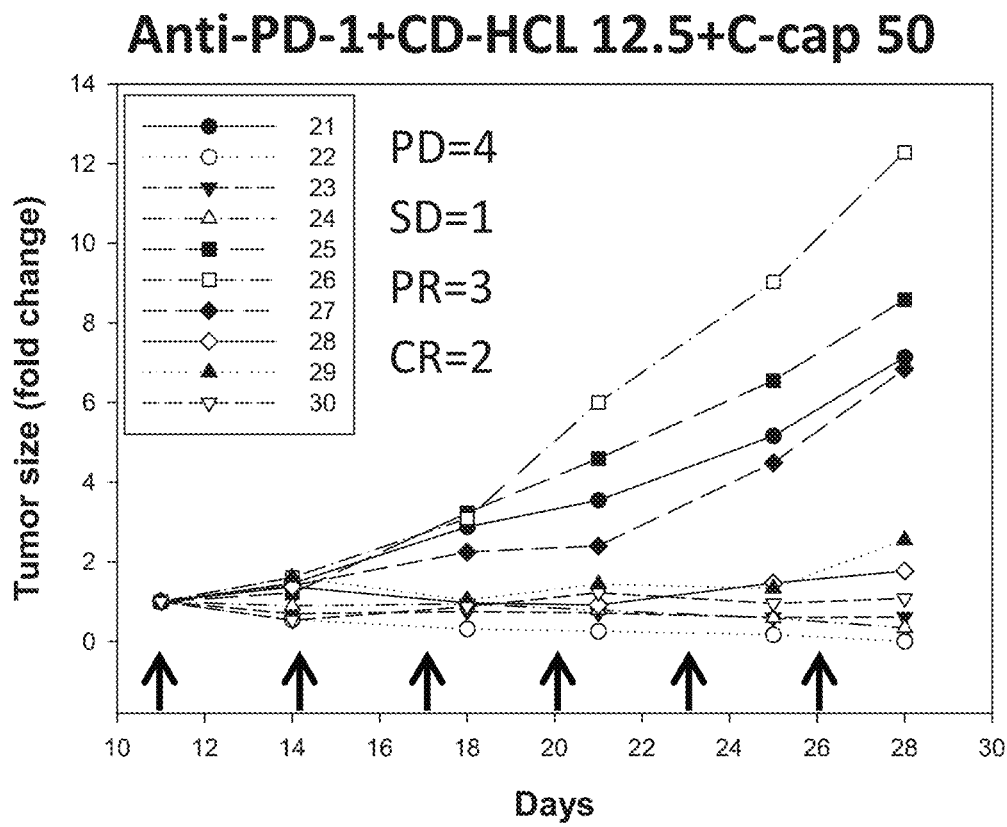
Figure 9G:
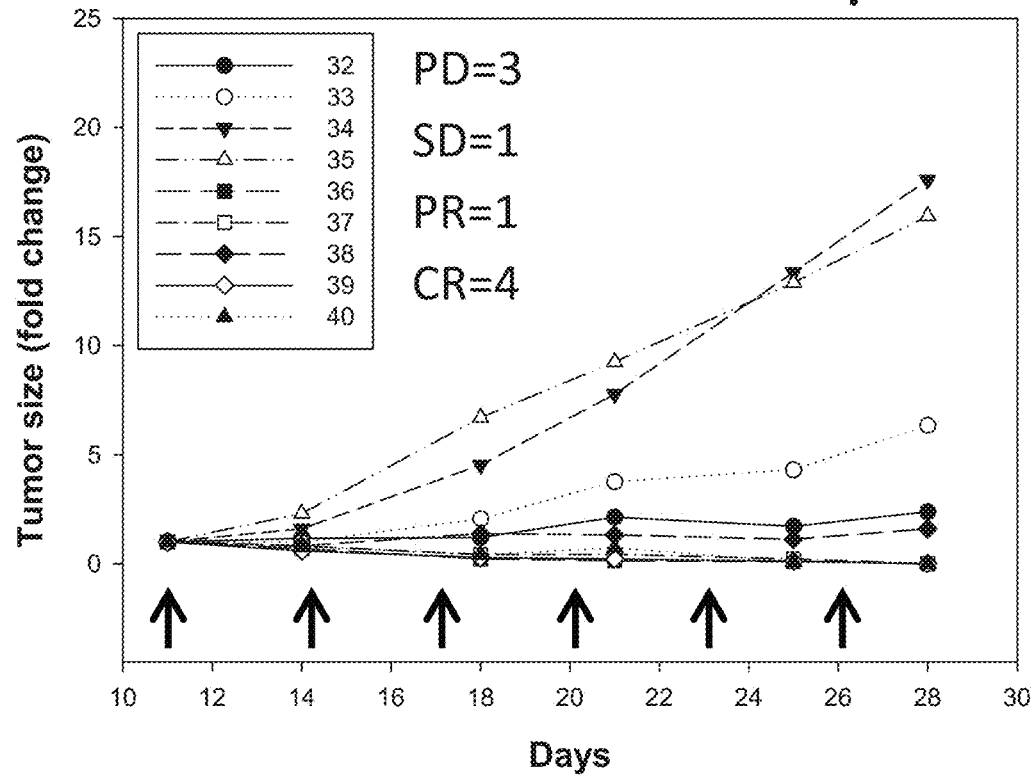
Figure 9H:
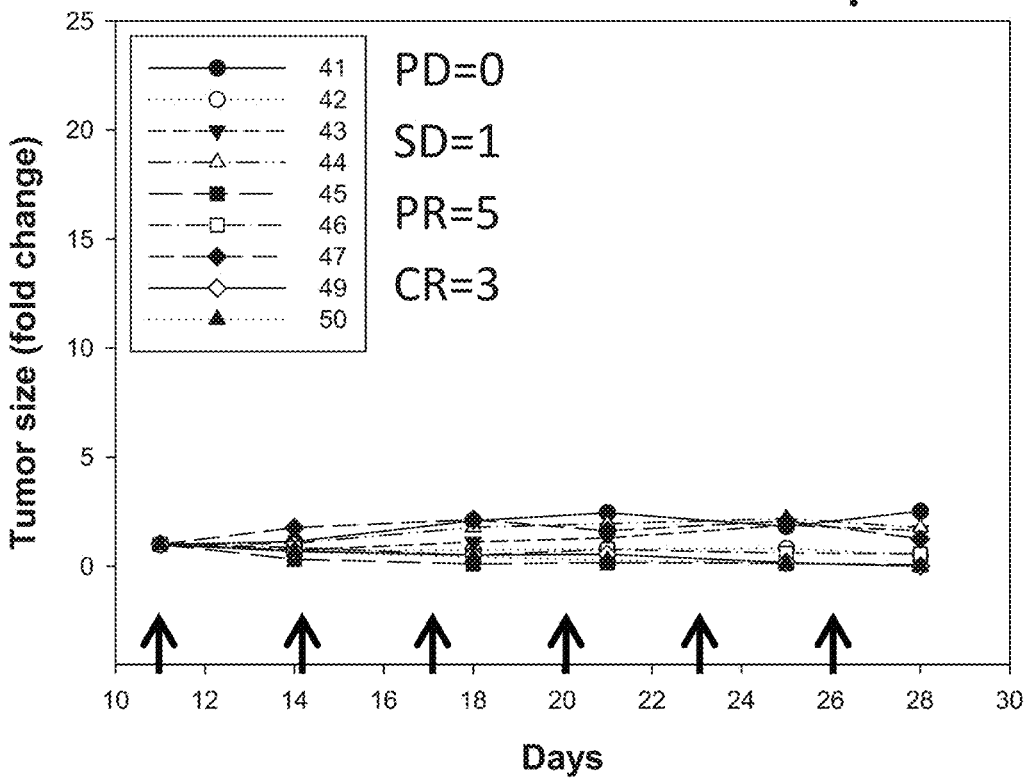

The Comparison of Anti-Cancer Activity Between Chidamide-K30 and Chidamide-HCl Salt When Combined with Celecoxib-capsule and Anti-PD-1 Ab in CT26-Bearing Mice To investigate whether chidamide salt form will increase the potency for tumor inhibition, we evaluated the therapeutic effect of chidamide-K30 plus celecoxib-capsule vs. chidamide-HCl salt plus celecoxib-capsule in combination with anti-PD-1 antibody (2.5 mg/kg; Lot #640517M1) in CT26-bearing mice. As shown in FIGS. 9A-9J, the tumor size in the CT26 tumor-bearing mice grew to about 200-250 mm$^3$ at day 11. Then the mice were treated with 6 different regimens as shown. As shown in FIGS. 9A and 9B, chidamide-K30 50 mg/kg plus celecoxib-capsule 50 mg/kg in combination with anti-PD-1 Ab significantly inhibited tumor growth in the CT26-bearing mice in comparison with the anti-PD-1 Ab group. The results of chidamide-HCl salt at dose of 12.5, 25, or 50 mg/kg plus celecoxib-capsule 50 mg/kg in combination with anti-PD-1 Ab also showed significant inhibition of tumor growth in the CT26 tumor-bearing mice in comparison with the anti-PD-1 Ab group. To compare the anti-cancer activity between chidamide salt form and chidamide-K30, the efficacy was evaluated by the following grading. In this study, we defined Complete Response (CR, ≤0.5 time tumor growth in the tumor bearing mice at the end of the treatment); Partial Response (PR, tumor size >0.5 time tumor growth, but ≤2 times tumor growth in the tumor bearing mice at the end of the treatment); Stable Disease (SD, between 2 and 5 times tumor growth in the tumor bearing mice at the end of the treatment); Progressive Disease (PD, equal to or greater than 5 times tumor growth in the tumor bearing mice at the end of the treatment).

Figure 9I:
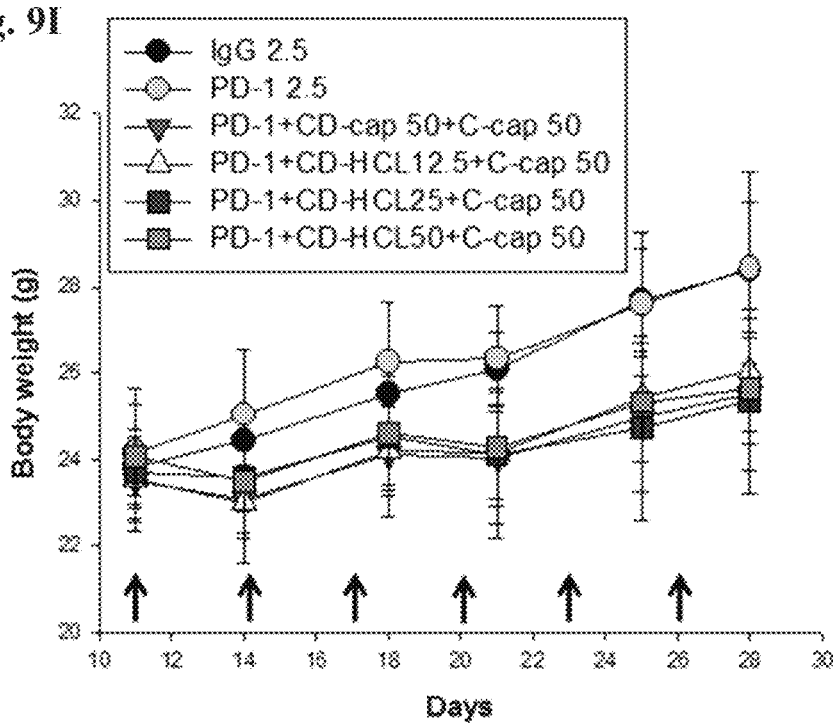
Figure 9J:
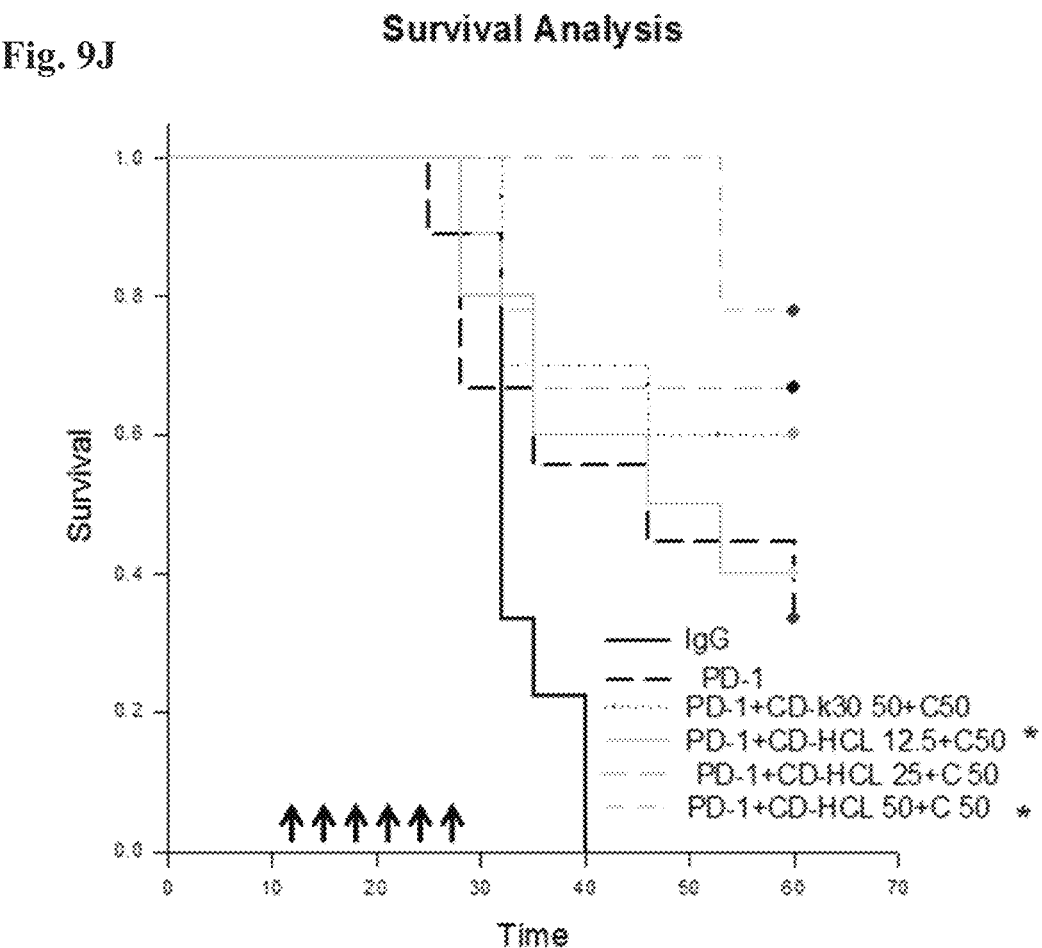

As shown in FIGS. 9C to 9H, chidamide-HCl salt 50 mg/kg plus celecoxib-capsule 50 mg/kg combined with the anti-PD-1 Ab 2.5 mg/kg is even more effective in inhibiting tumor growth in the CT26 tumor-bearing mice in comparison with the chidamide-K30 50 mg/kg plus celecoxib-capsule 50 mg/kg combined with anti-PD-1 Ab group. The treatment with chidamide-K30 50 mg/kg plus celecoxib-capsule 50 mg/kg combined with anti-PD-1 Ab achieved 6 mice of CR (60%) and 4 mice of PD with moderate tumor growth, and treatment with chidamide-HCl salt 50 mg/kg plus celecoxib-HCl salt 50 mg/kg in combination with anti-PD-1 Ab achieved response rate of 89% with 5 mice of PR and 3 mice of CR and without mice of PD. These results suggested that chidamide-HCl salt form was more efficient than chidamide-K30 due to higher water solubility and oral bioavailability, which therefore improved the therapeutic efficacy. In FIGS. 9A and 9B and 9C to 9H it also showed that in combination with anti-PD-1 Ab, chidamide-HCl salt 12.5 mg/kg plus celecoxib-capsule 50 mg/kg was enough to influence the tumor microenvironment and reactivate cytotoxic T-lymphocytes to kill the tumor. As shown in FIG. 9I, none of the mice in the treatment groups lost any body weight. After the treatment was stopped at day 26, the tumor in the CT26 tumor-bearing mice grew faster in the IgG control group. However, chidamide-HCl salt plus celecoxib-Na salt combined with an immune checkpoint inhibitor regimen was very potent in inhibiting tumor growth and thus significantly increased survival rate (FIG. 9J). As shown in FIG. 9J, chidamide-HCl salt 50 mg/kg plus celecoxib-capsule 50 mg/kg combined with anti-PD-1 Ab significantly increased the survival rate to about 77.7%, however chidamide-K30 50 mg/kg plus celecoxib-capsule 50 mg/kg combined with anti-PD-1 Ab only achieved 60% survival rate in the CT26-bearing tumor mice model. It is noteworthy that chidamide-HCl salt 25 mg/kg plus celecoxib-capsule 50 mg/kg combined with anti-PD-1 Ab significantly increased the survival rate to about 66.6%. This result suggested that chidamide-HCl salt plus celecoxib-capsule were more powerful than chidamide-K30 plus celecoxib-capsule to control and regulate the tumor microenvironment and boost immunotherapy to some extent.

This study also proved that chidamide-HCl salt plus celecoxib-capsule combined with immune checkpoint inhibitor was more potent to boost anti-cancer immune response than chidamide-K30 plus celecoxib-capsule. On the other hand, the head to head comparison between chidamide-HCl salt plus celecoxib-capsule and chidamide-K30 plus celecoxib-capsule when combined with anti-PD-1 Ab has demonstrated that the anti-cancer activity of combination regimen with chidamide-HCl salt plus celecoxib-Na salt is better than that of combination regimen with chidamide-K30 plus celecoxib-capsule.

Example 6

Figure 10A:
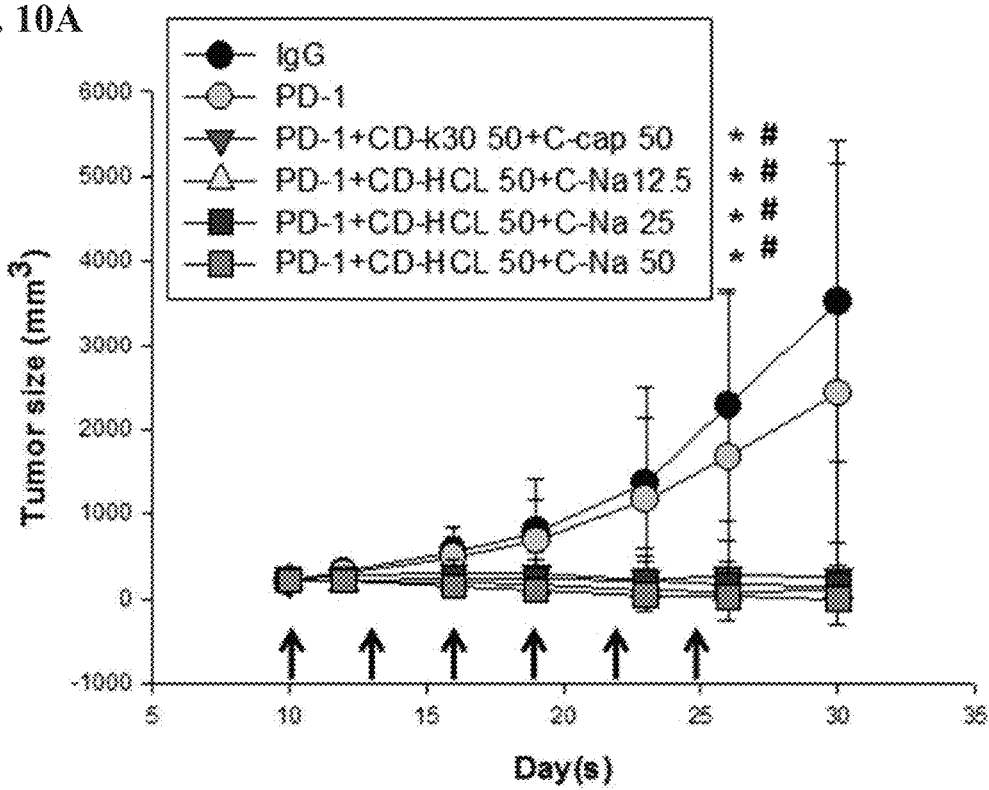
FIGS. 10A to 10K show the therapeutic response of chidamide-HCl salt plus celecoxib-Na salt combined with anti-PD-1 antibody in CT26 tumor-bearing mice. BALB/c mice bearing a CT26 colon tumor were treated with various therapeutic modalities as indicated. IgG, Anti-IgG control (vehicle, 2.5 mg/kg); PD-1, Anti-PD-1 monoclonal antibody (2.5 mg/kg); CD-HCl, chidamide-HCl salt (50 mg/kg); C—Na, amorphous celecoxib-Na salt (12.5, 25, and 50 mg/kg); CD-K30, chidamide-K30 (chidamide coated on polyvinylpyrrolidone K30, 50 mg/kg); C-capsule 50, celecoxib product from capsule (50 mg/kg, Celebrex®).
Figure 10B:
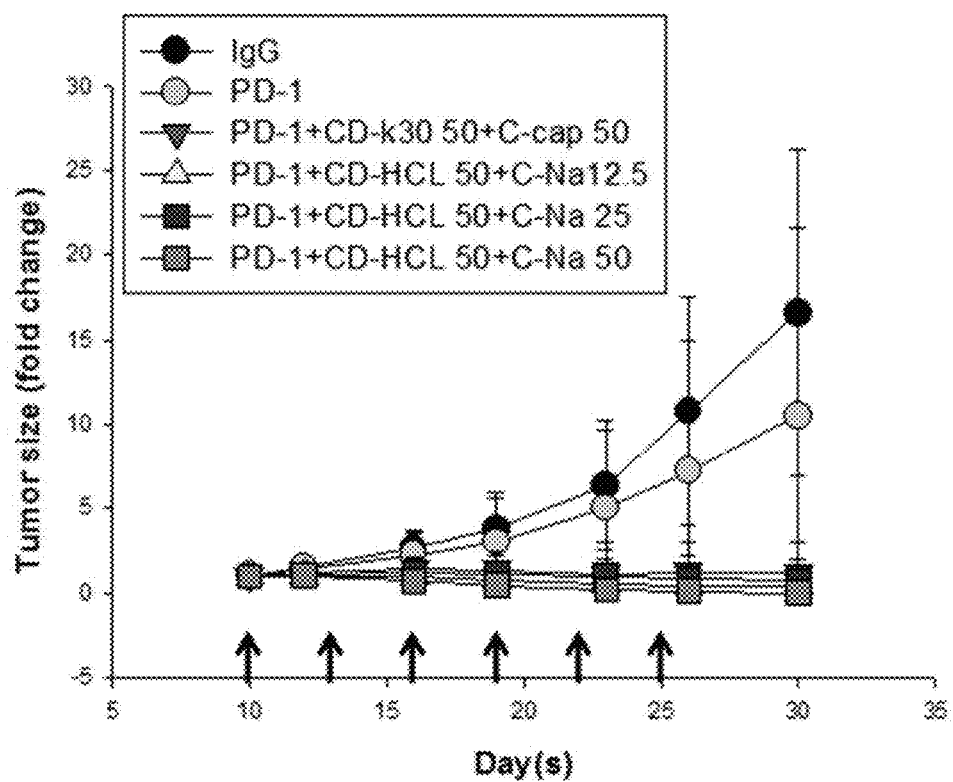
Figure 10C:
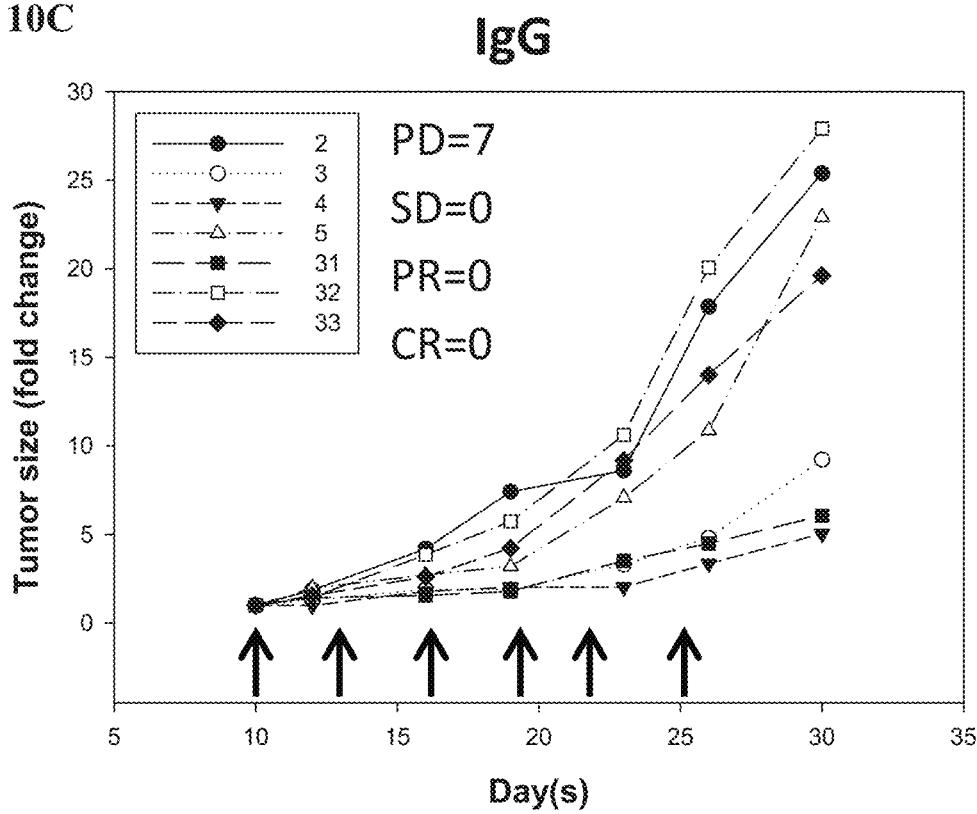
Figure 10D:
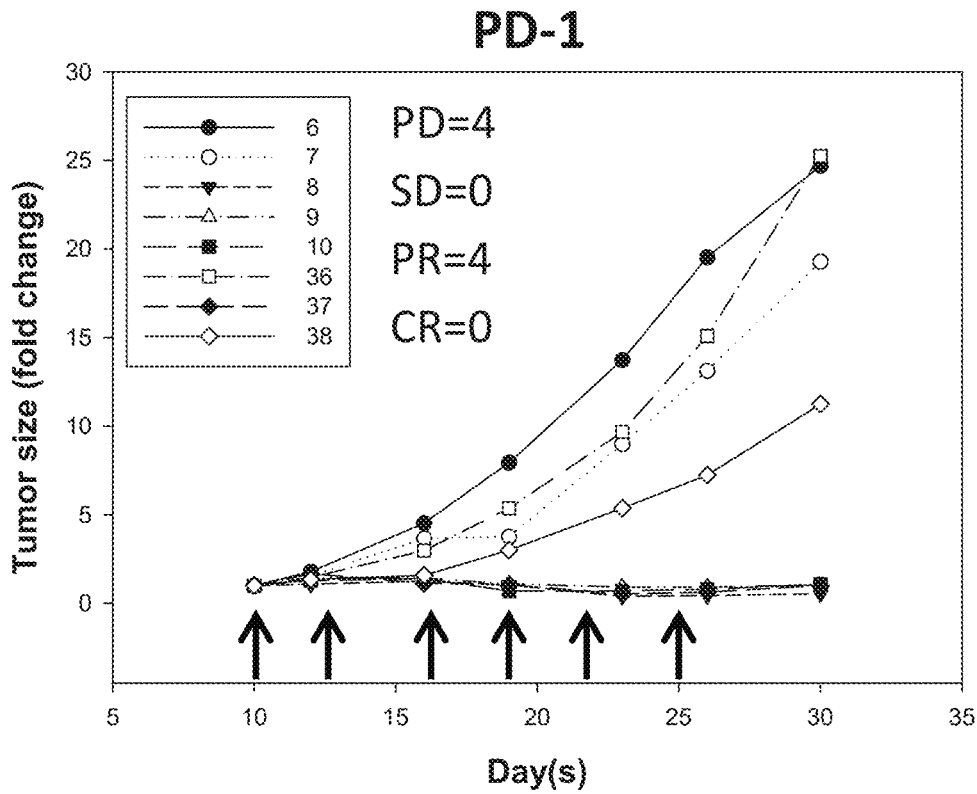
Figure 10E:
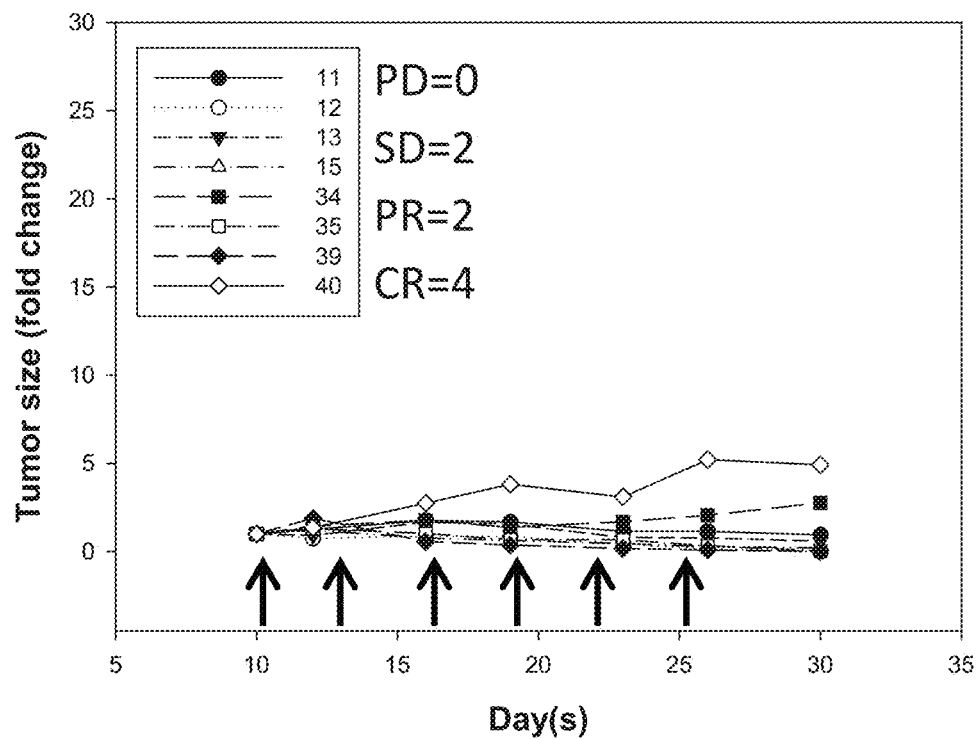
Figure 10F:
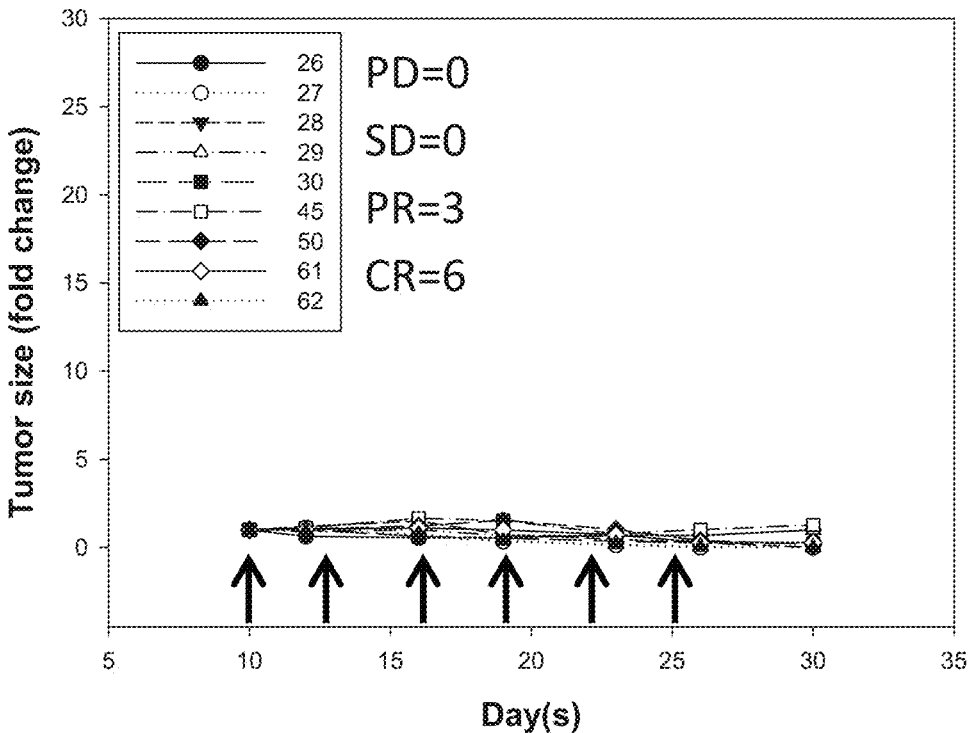
Figure 10G:
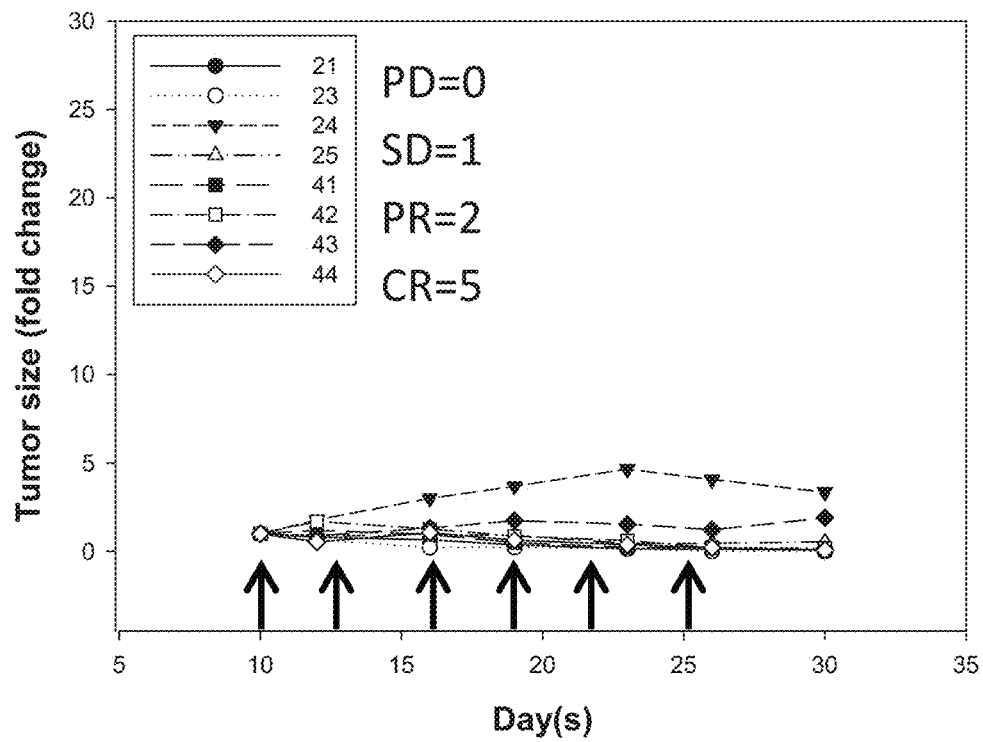
Figure 10H:
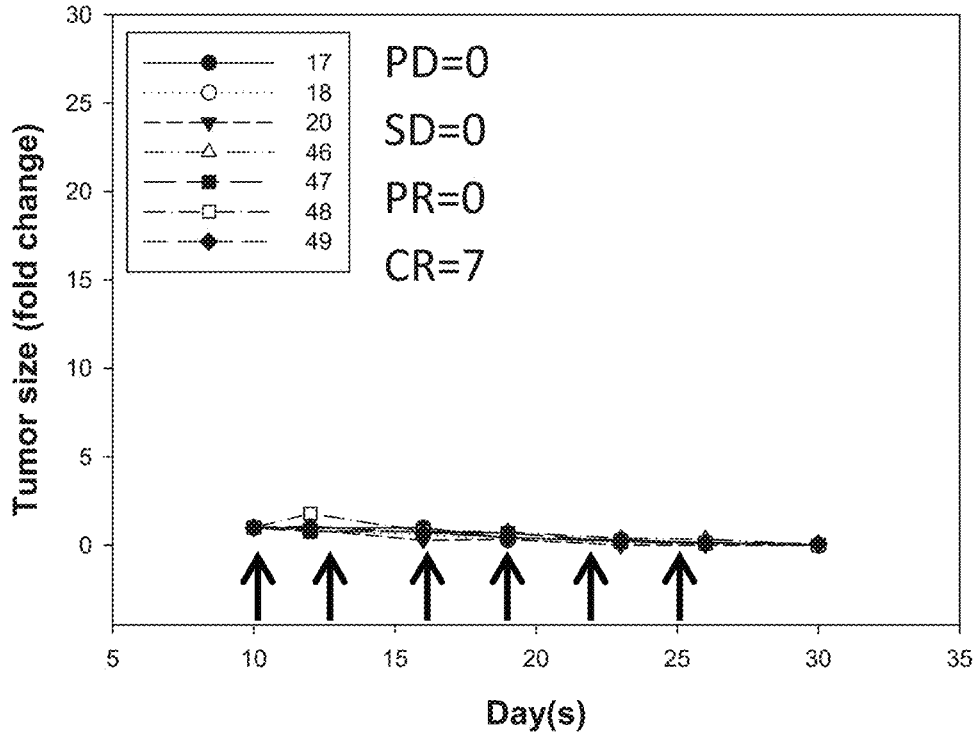

The Comparison of Anti-Cancer Effect between Chidamide-K30 Plus Celecoxib-capsule and Chidamide-HCl Salt Plus Celecoxib-Na Salt in Combination with Anti-PD-1 Ab in CT26-Bearing Mice To demonstrate the improvement of tumor-inhibitory activity, we evaluated the therapeutic effects of chidamide-K30 plus celecoxib-capsule vs. chidamide-HCl salt plus celecoxib-Na salt in combination with anti-PD-1 antibody (2.5 mg/kg; Lot #640517M1) in CT26-bearing mice. As shown in FIGS. 10A-10K, each study group was treated when the tumor size in the CT26-bearing mice grew to about 200-250 mm$^3$ at day 10. First, chidamide-K30 50 mg/kg plus celecoxib-capsule 50 mg/kg in combination with anti-PD-1 Ab significantly inhibited tumor growth in the CT26-bearing mice in comparison with the anti-PD-1 Ab group (FIGS. 10A and 10B). The results of chidamide-HCl salt 50 mg/kg plus amorphous celecoxib-Na salt at various doses of 12.5, 25, and 50 mg/kg in combination with anti-PD-1 Ab showed significant inhibition of tumor growth in the CT26-bearing mice in comparison with the anti-PD-1 Ab group (FIGS. 10A and 10B). In FIGS. 10C to 10H, it was demonstrated that chidamide-HCl salt 50 mg/kg plus different doses of celecoxib-Na salt combined with the anti-PD-1 Ab 2.5 mg/kg is even more effective in inhibiting tumor growth in the CT26-bearing mice in comparison with the chidamide-K30 50 mg/kg plus celecoxib-capsule 50 mg/kg combined with anti-PD-1 Ab 2.5 mg/kg. These results suggested that chidamide-HCl salt and celecoxib-Na salt were more efficient than chidamide-K30 and celecoxib-capsule because these salt forms possessed higher water solubility and oral bioavailability and therefore improved the therapeutic efficacy.

Figure 10I:
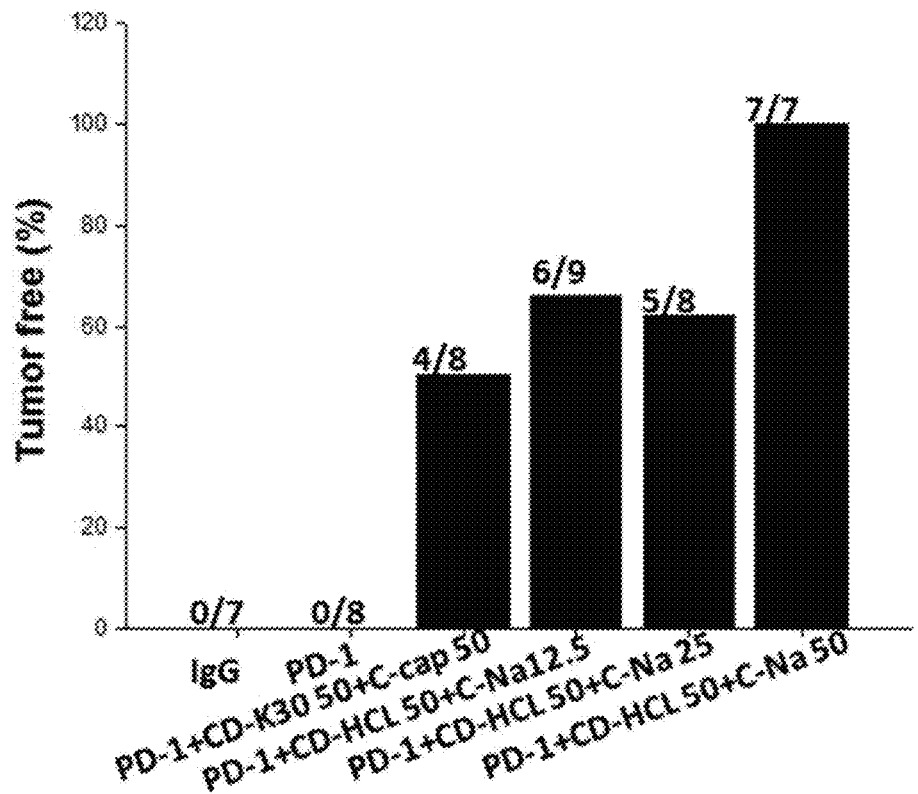
Figure 10J:
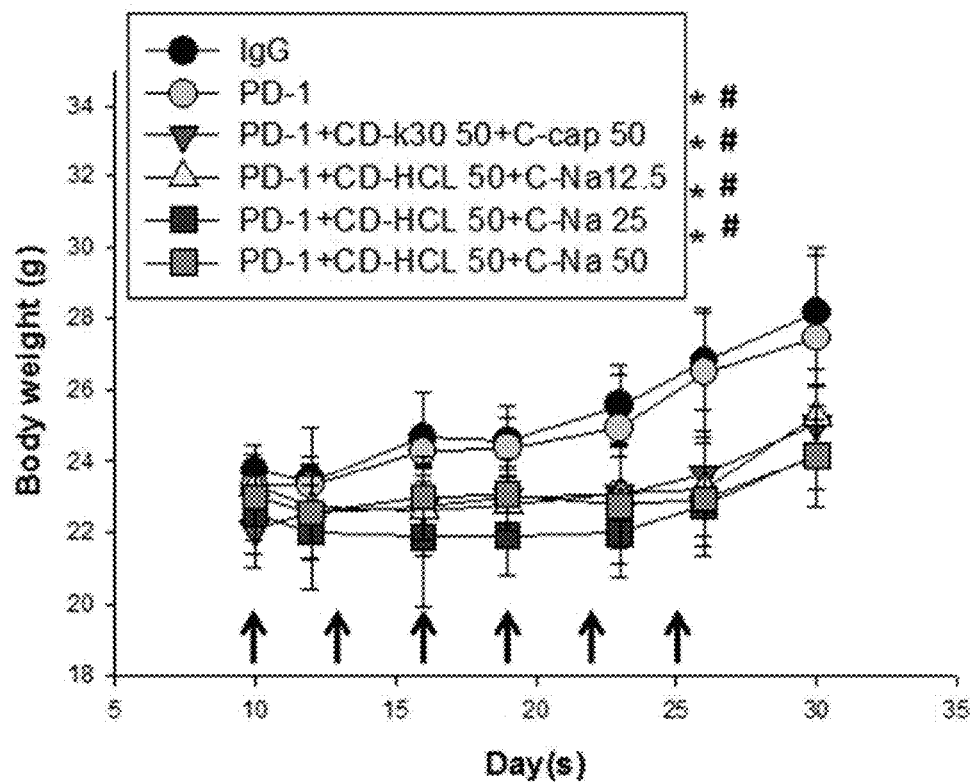

In 10A and 10B and 10C to 10H it showed that chidamide-HCl salt 50 mg/kg combined with celecoxib-Na salt 12.5 mg/kg was enough to influence the tumor microenvironment and reactivate cytotoxic T-lymphocytes to kill the tumor. The head to head comparison of the anti-cancer effects between the same dose (50 mg/kg) of chidamide-K30 plus celecoxib-capsule (achieved 4 mice of CR, 50%) and chidamide-HCl salt plus celecoxib-Na salt in combination with anti-PD-1 Ab 2.5 mg/kg showed that the latter combination with salt form regimen had better potency of tumor growth inhibition in CT26-bearing mice and achieved 7 mice of CR (100%) as shown in FIGS. 10C to 10H. Furthermore, as shown in FIG. 10I that the percentage of tumors-free animals (CR) was evaluated in different treatment groups. In combination with anti-PD-1 Ab, all salt form regimens were more potent to inhibit tumor growth (have higher percentage of tumor-free) when compared with chidamide-K30 plus celecoxib-capsule. These results suggested that celecoxib-Na salt was more potent for inhibition of tumor growth than celecoxib-capsule in combination with immune checkpoint inhibitor in CT26-bearing mice model. The similar result was also demonstrated in chidamide-HCl compared with chidamide-K30. This finding also demonstrated that the dose of chidamide-HCl salt plus celecoxib-Na salt can be reduced in combination with immune checkpoint inhibitor for potent reactivation of cytotoxic T-lymphocytes in the tumor microenvironment to inhibit tumor growth as shown in FIGS. 10A and 10B and 10C to 10H. As shown in FIG. 10J, none of the mice in the treatment groups lost any body weight.

Figure 10K:
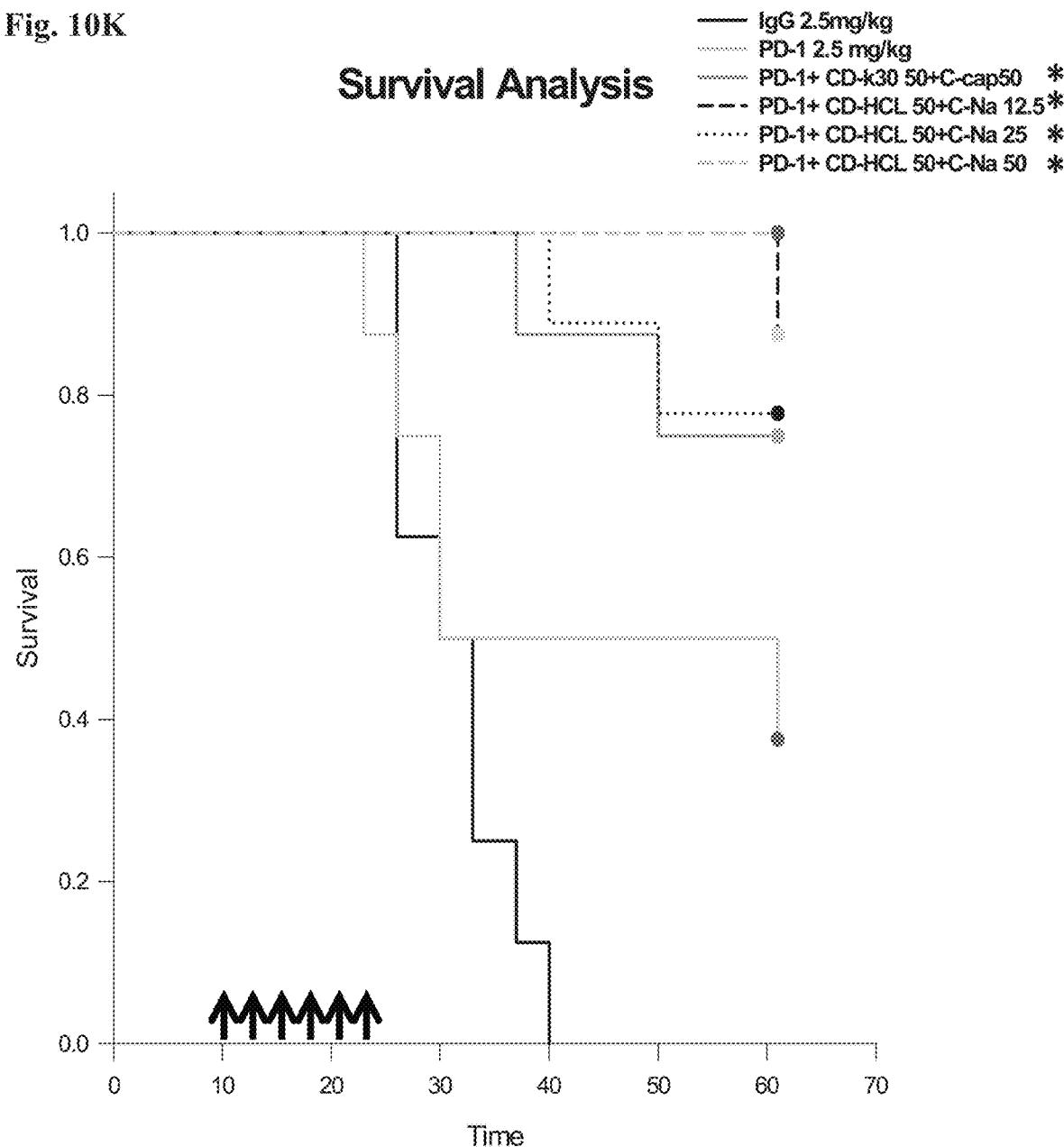

After the treatment was stopped at day 25, the tumor in the CT26-bearing tumor mice grew faster in the IgG (2.5 mg/kg; Lot #65481701) control group. As shown in FIG. 10K, in combination with anti-PD-1 Ab, chidamide-HCl salt 50 mg/kg plus celecoxib-Na salt 50 mg/kg group significantly increased the survival rate to about 100% in comparison with chidamide-K30 plus celecoxib-capsule (about 75%) in the CT26-bearing tumor mice model. The survival rate was only 37.5% for anti-PD-1 group. This result suggested that chidamide-HCl salt plus celecoxib-Na salt were more powerful than chidamide-K30 plus celecoxib-capsule to control and regulate the tumor microenvironment and boost immune response to some extent. In conclusion, chidamide-HCl salt plus celecoxib-Na salt combined with an immune checkpoint inhibitor regimen was very potent in inhibiting tumor growth and thus significantly increased survival rate (FIG. 10K). This study proved that chidamide-HCl salt plus celecoxib-Na salt combined with immune checkpoint inhibitor was more potent to boost anti-cancer immune response than chidamide-K30 plus celecoxib-capsule. On the other hand, the head to head comparison between chidamide-HCl salt plus celecoxib-Na salt and chidamide-K30 plus celecoxib-capsule when combined with anti-PD-1 Ab has demonstrated that the anti-cancer activity of combination regimen with chidamide-HCl salt plus celecoxib-Na salt is better than that of combination regimen with chidamide-K30 plus celecoxib-capsule.

Example 7

Figure 11B:
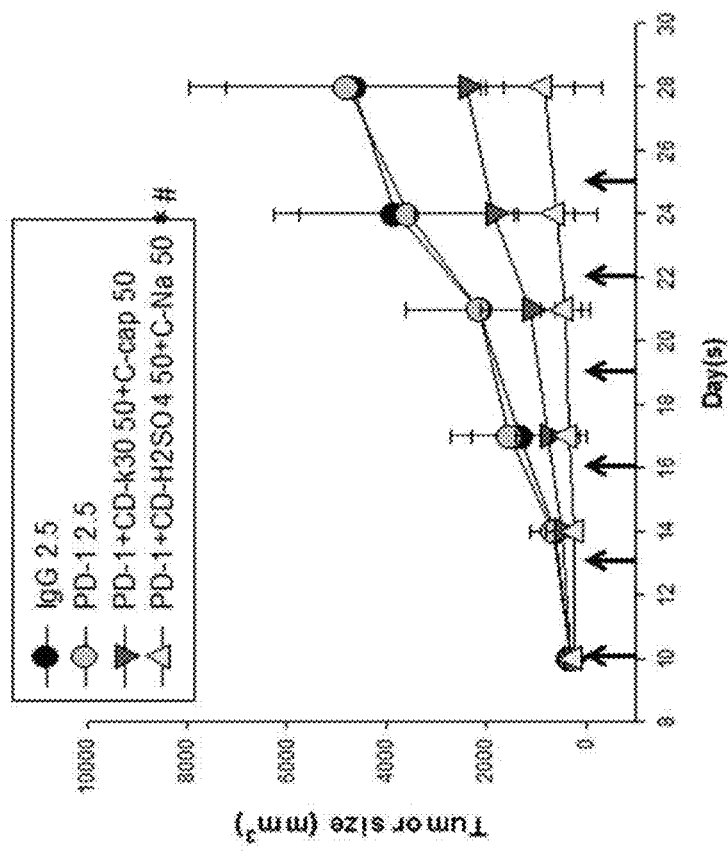
Figure 11A:
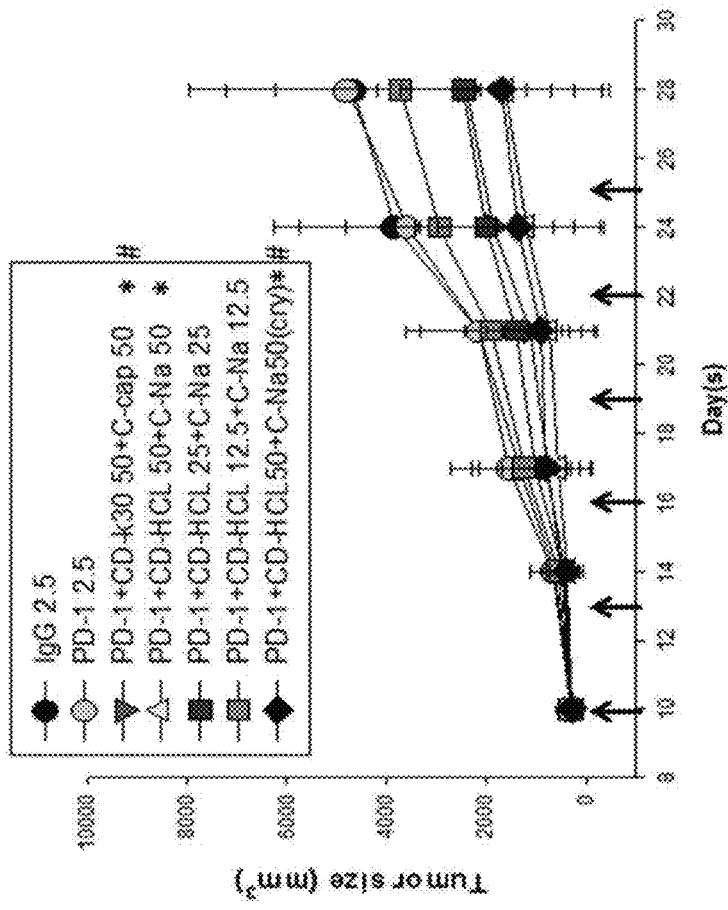
FIGS. 11A to 11N confirm the optimal therapeutic response doses of chidamide-HCl salt plus celecoxib-Na salt combined with anti-PD-1 antibody and evaluate the therapeutic response of chidamide-$H_2SO_4$ salt plus celecoxib-Na salt combined with anti-PD-1 antibody in CT26 tumor-bearing mice. BALB/c mice bearing a CT26 colon tumor the tumor size about 300 $mm^3$ were treated with various therapeutic modalities as indicated. IgG, Anti-IgG control (vehicle, 2.5 mg/kg); PD-1, Anti-PD-1 monoclonal antibody (2.5 mg/kg); CD-HCl, chidamide-HCl salt (12.5, 25, and 50 mg/kg); C—Na, amorphous celecoxib-Na salt (12.5, 25, and 50 mg/kg); C—Na cry, crystalline celecoxib-Na salt (50 mg/kg); CD-$H_2SO_4$, chidamide-$H_2SO_4$ salt (50 mg/kg); CD-K30, chidamide-K30 (chidamide coated on polyvinylpyrrolidone K30, 50 mg/kg); C-cap, celecoxib product from capsule (50 mg/kg, Celebrex®).
Figure 11D:
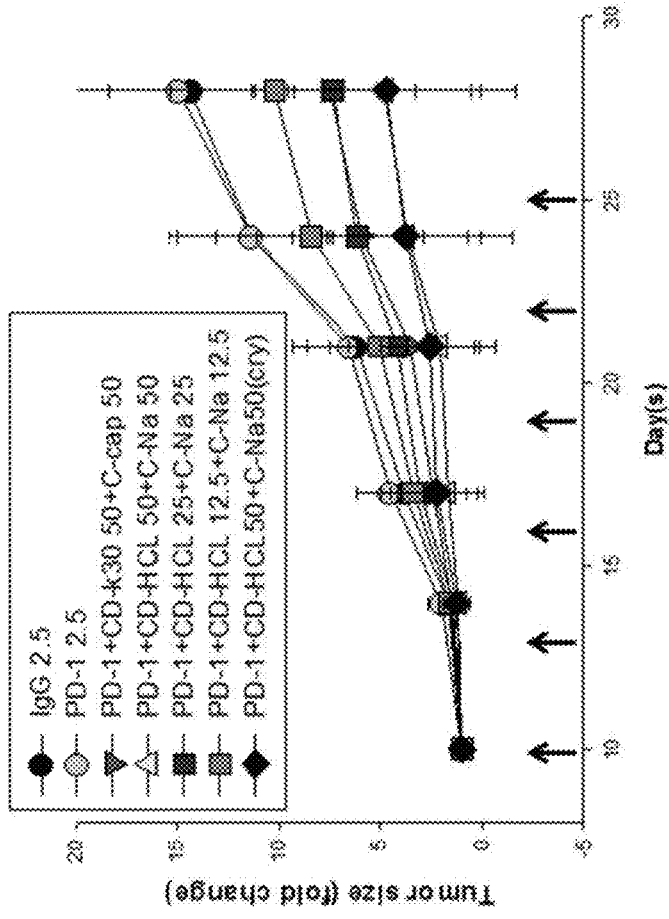
Figure 11C:
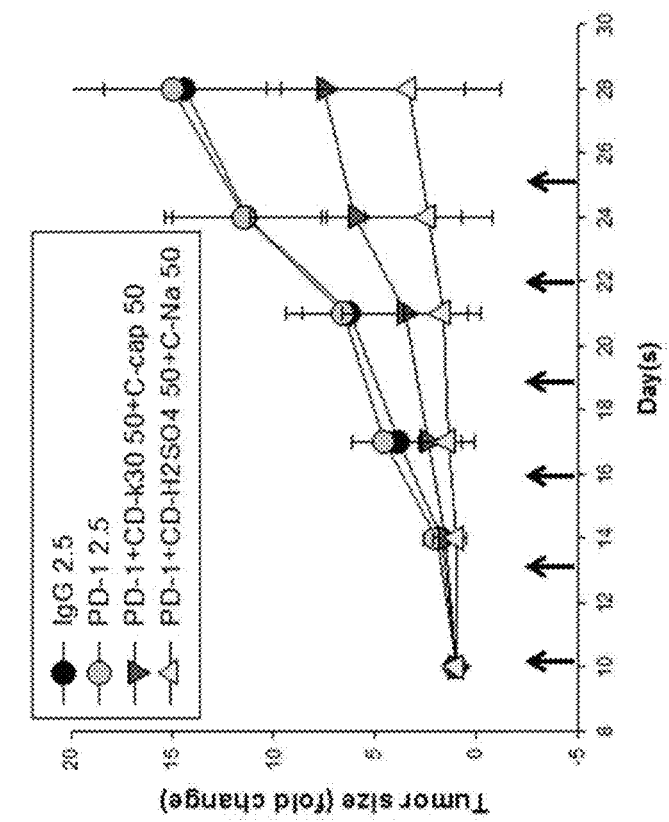
Figure 11E:
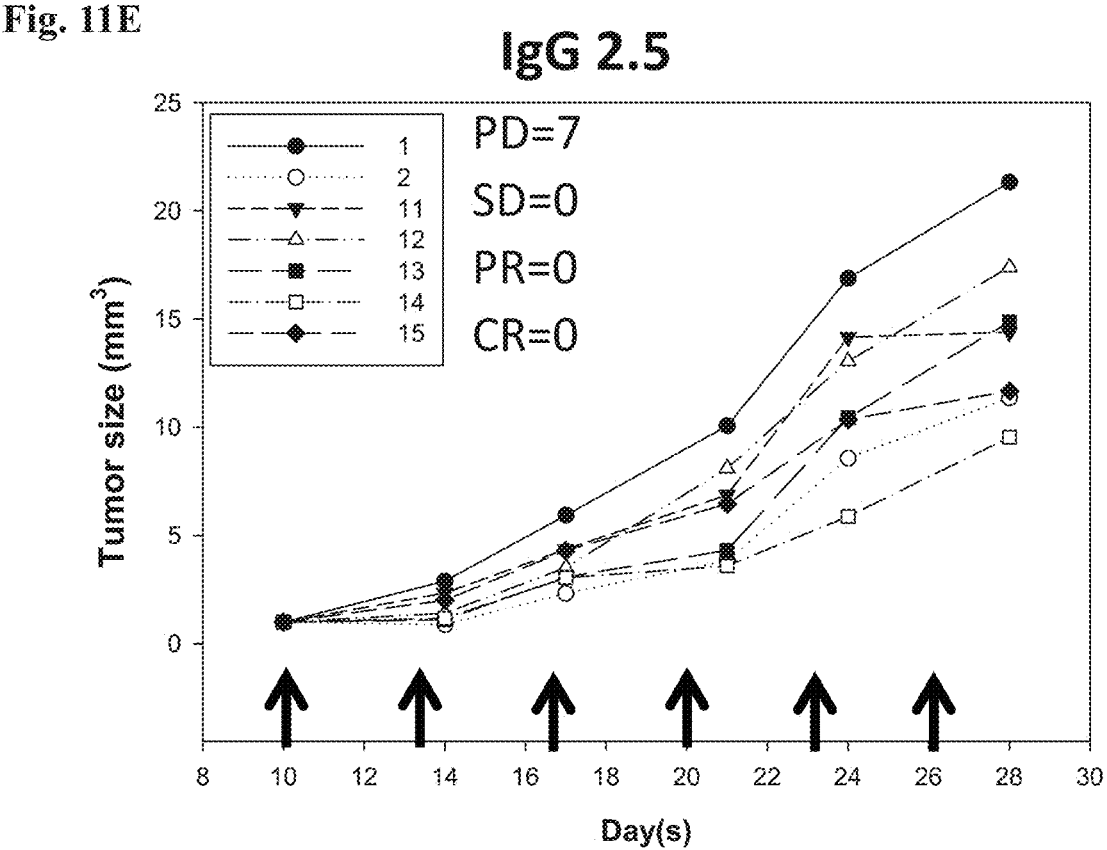
FIGS. 11E to 11L show the individual tumor volumes.
Figure 11F:
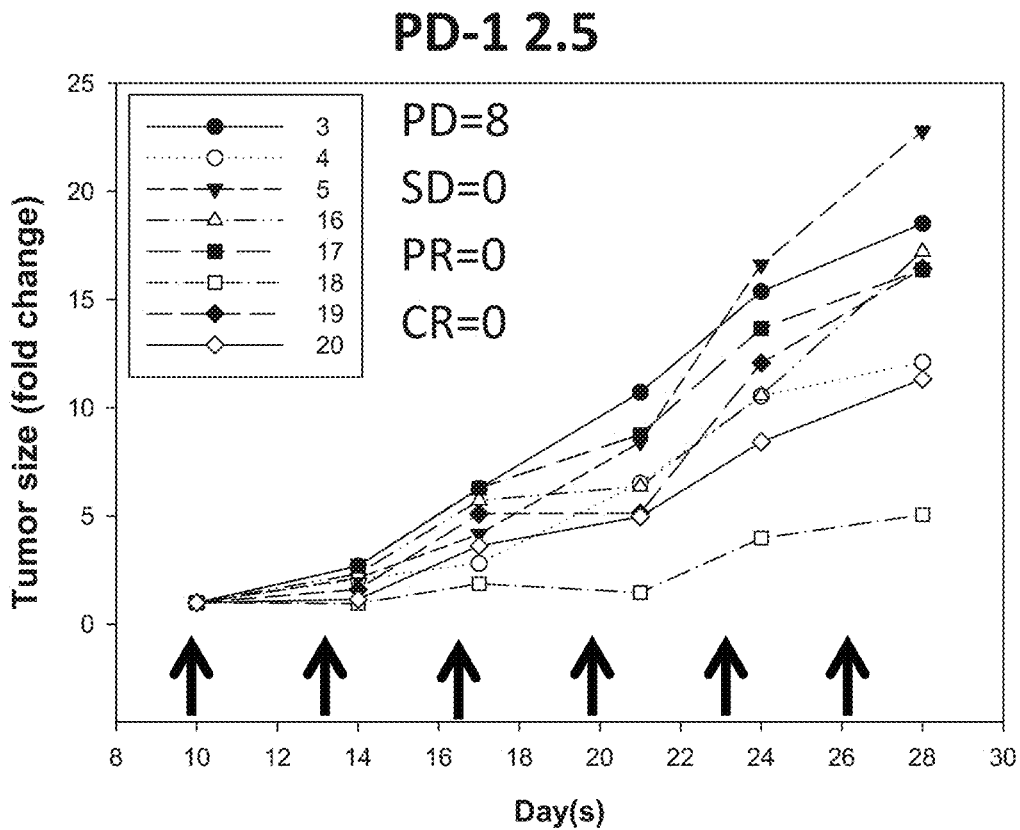
Figure 11G:
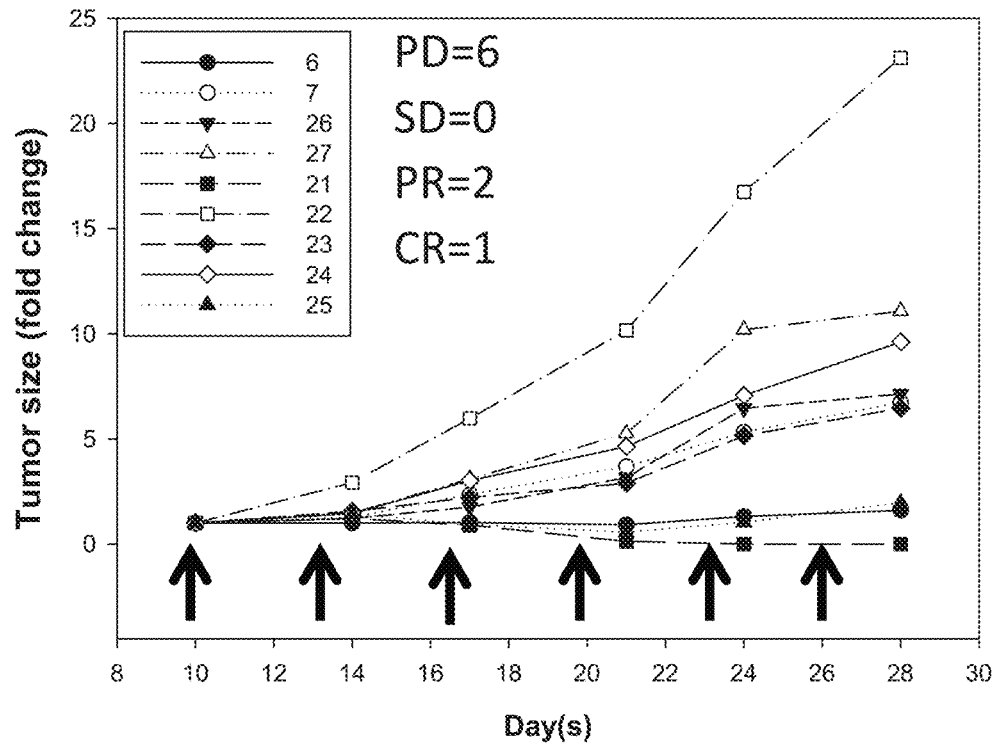
Figure 11H:
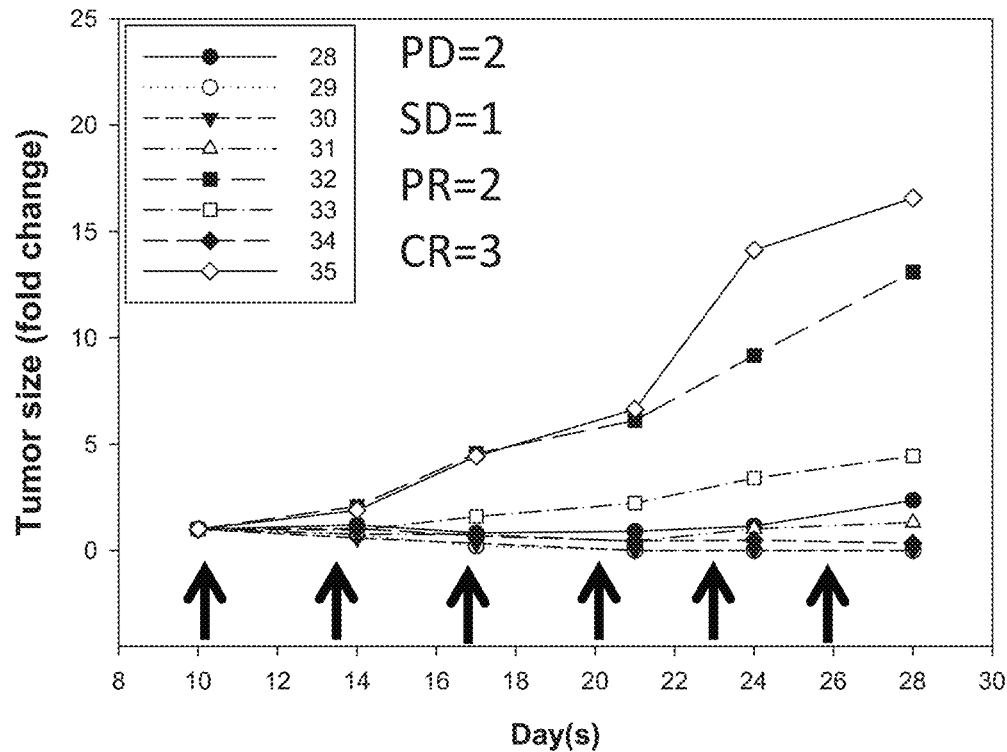
Figure 11I:
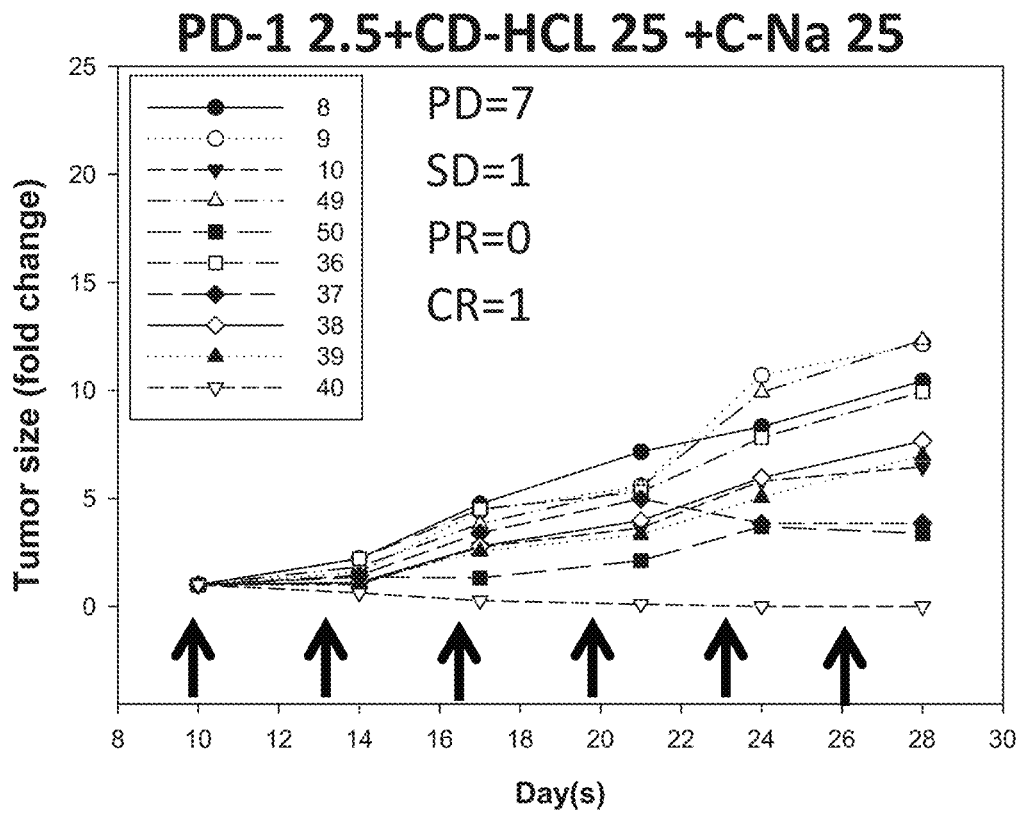
Figure 11J:
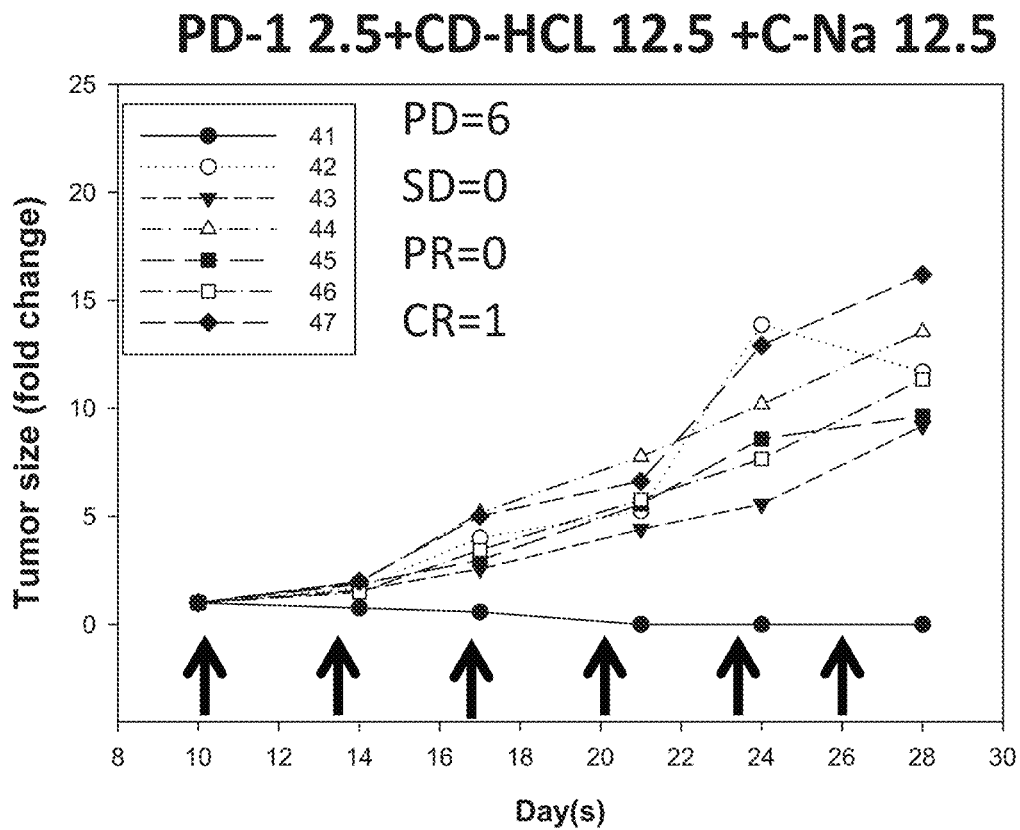
Figure 11K:
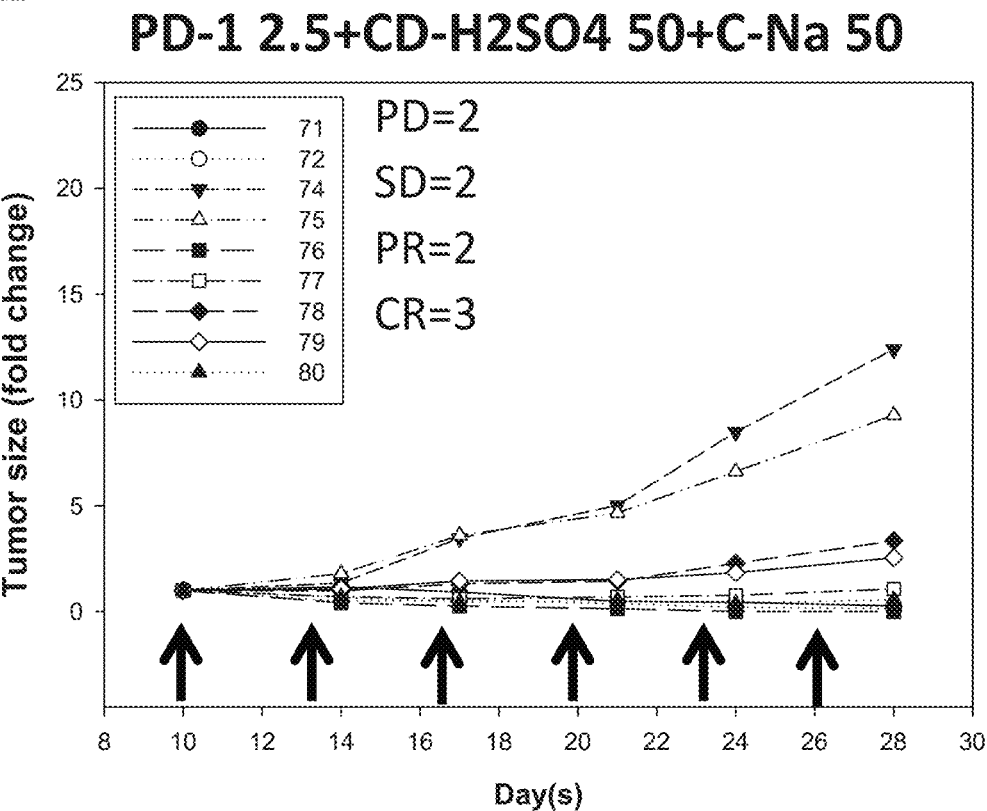
Figure 11L:
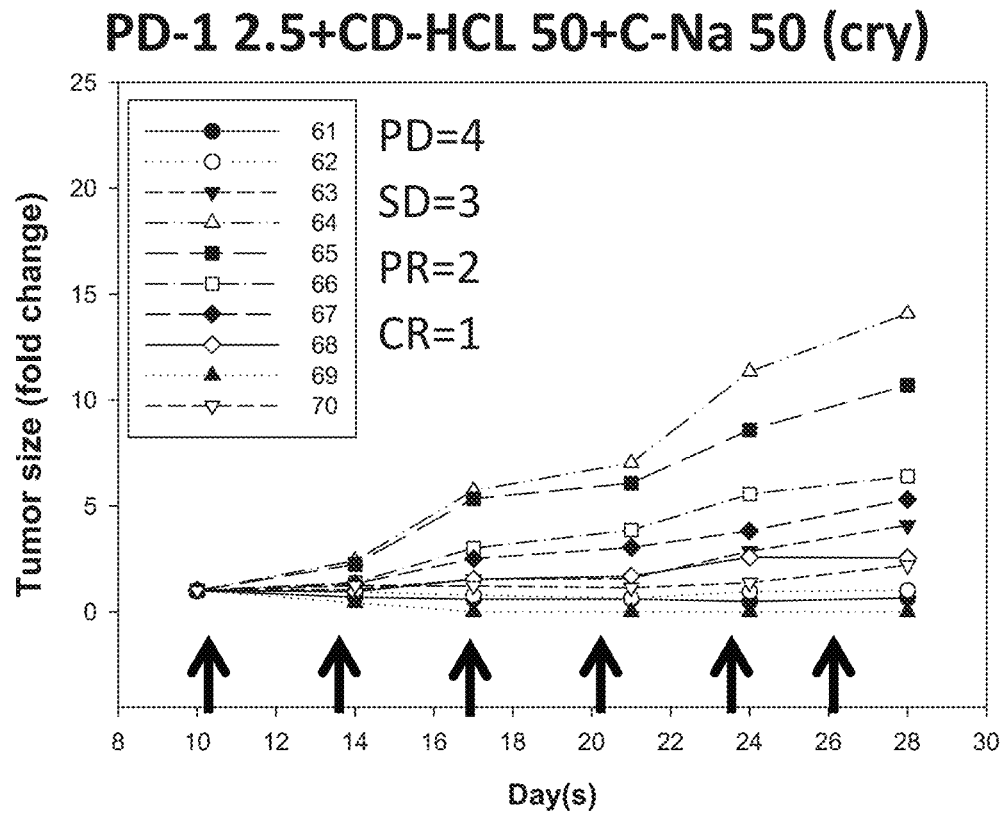
Figure 11M:
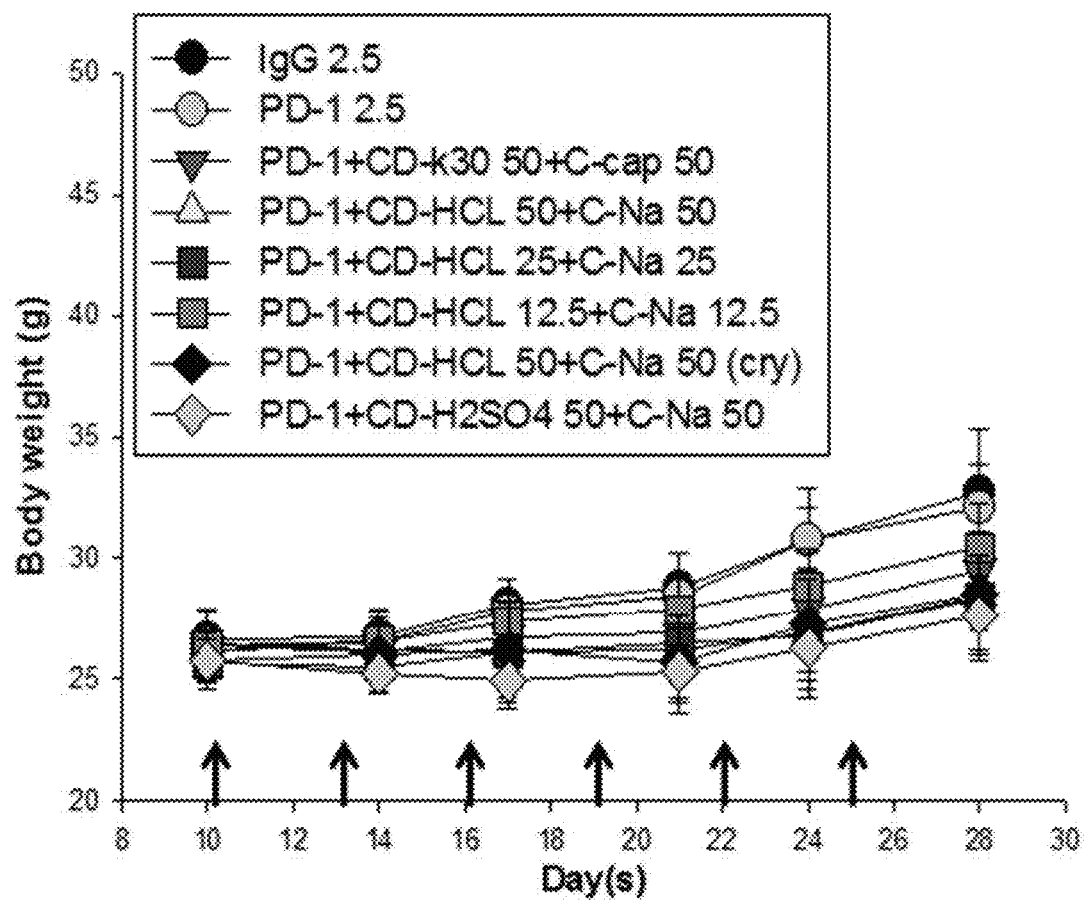
FIG. 11M shows the CT26 tumor-bearing mice body weight.

To Confirm the Optimal Therapeutic Response Doses of Chidamide-HCl Salt Plus Celecoxib-Na Salt Combined with Anti-PD-1 Antibody and Evaluate the Chidamide-$H_2SO_4$ Salt Plus Celecoxib-Na Salt Combined with Anti-PD-1 Antibody in CT26 tumor-Bearing Mice To test the optimal therapeutic response doses of chidamide-HCl salt plus celecoxib-Na salt combined with anti-PD-1 antibody in CT26 tumor-bearing mice, mice with the tumor size about 300 mm$^3$ were treated with different doses of chidamide-HCl salt plus celecoxib-Na salt combined with anti-PD-1 antibody. As shown in FIGS. 11A to 11D, chidamide-HCl salt plus amorphous celecoxib-Na salt at dose of 50 mg/kg combined with anti-PD-1 antibody (2.5 mg/kg; Lot #717918D1) was better than at dose of 25 mg/kg and 12.5 mg/kg. This result also showed that chidamide-HCl salt plus celecoxib-Na salt at doses of 25 mg/kg combined with anti-PD-1 antibody (2.5 mg/kg) possessed similar therapeutic response when compared with chidamide-K30 plus celecoxib-capsule at doses of 50 mg/kg combined with anti-PD-1 antibody (2.5 mg/kg). It was suggested that chidamide-HCl salt plus celecoxib-Na salt possessed more potent anticancer activity than chidamide-K30 plus celecoxib-capsule at the same dose when combined with anti-PD-1 antibody in CT26 tumor-bearing mice. In addition, in combination with anti-PD-1 antibody, chidamide-HCl salt plus crystalline celecoxib-Na salt possessed decreased potency of anti-cancer activity when compared with chidamide-HCl salt plus amorphous celecoxib-Na salt at the same dose in CT26 tumor-bearing mice as shown in FIGS. 11E to 11L. On the other hand, the chidamide-$H_2SO_4$ salt plus celecoxib-Na salt combined with anti-PD-1 antibody possessed potent anti-cancer activity similar to that of chidamide-HCl salt plus celecoxib-Na salt combined with anti-PD-1 antibody as shown in FIGS. 11E to 11L. In this experiment, because tumors had reached an average volume of about 300 mm$^3$ before different treatments and anti-PD-1 antibody protein activity was lower as compared with previous studies, the anti-cancer therapeutic effect of anti-PD-1 antibody treatment was shown to be very poor in this study. As shown in FIGS. 11E to 11L, the optimal dose of chidamide-HCl salt 50 mg/kg or chidamide-$H_2SO_4$ salt 50 mg/kg plus celecoxib-Na salt at dose of 50 mg/kg combined with anti-PD-1 antibody (2.5 mg/kg) possessed best therapeutic response in this study. Furthermore, amorphous celecoxib-Na salt achieved better response rate than crystalline celecoxib-Na salt in the combination regimen. When tumor size was average about 300 mm$^3$ before treatment, chidamide-K30 plus celecoxib-capsule combined with anti-PD-1 antibody only achieved response rate about 33%. However, chidamide-HCl salt or chidamide-$H_2SO_4$ salt plus celecoxib-Na salt combined with anti-PD-1 antibody significantly improved the response rate up to 62.5% and 55.5%, respectively. These results demonstrated that salt forms of chidamide and celecoxib were more potent to boost immune response rate than chidamide-K30 and celecoxib-capsule in CT26 tumor-bearing mice. As shown in FIG. 11M, none of the mice in the treatment groups lost any body weight.

Figure 11N:
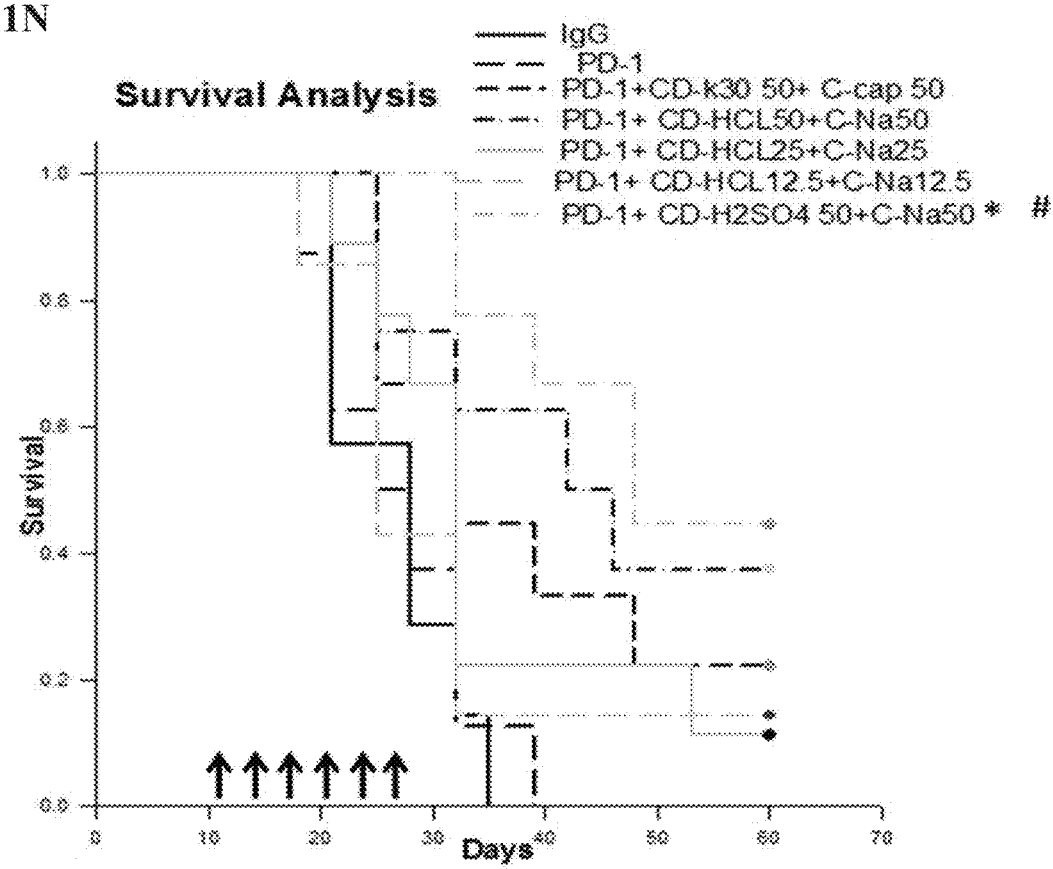
Figure 11N:
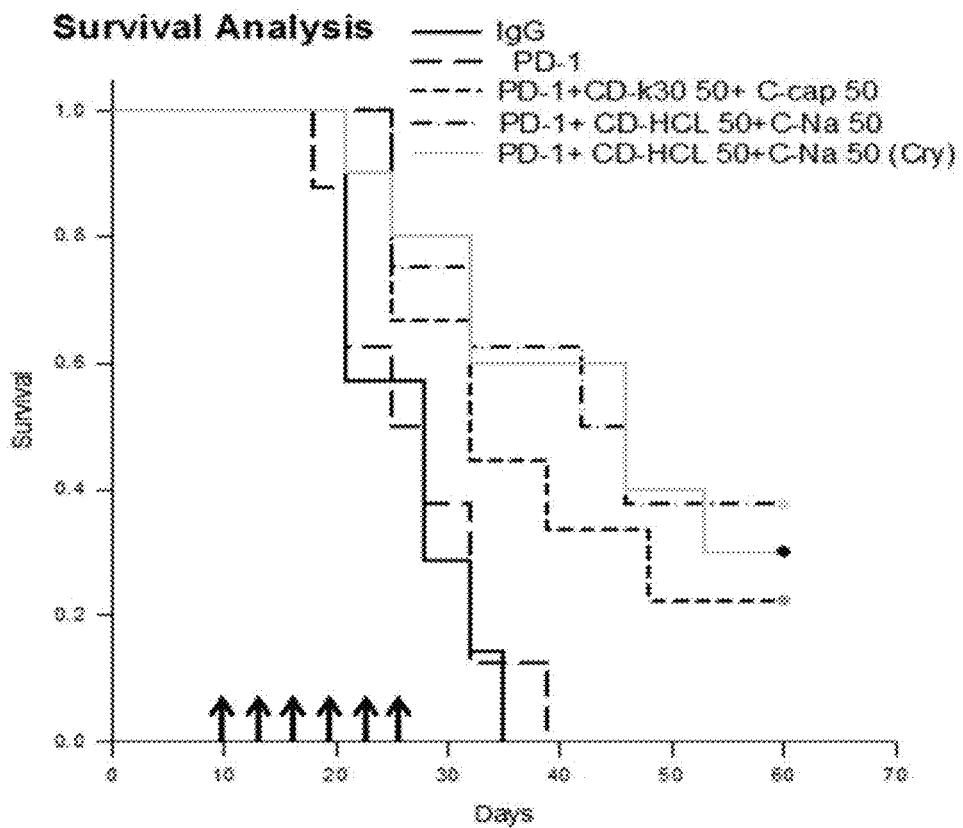

After the treatment was stopped at day 26, the tumor in the CT26-bearing tumor mice grew faster in the IgG control group. However, chidamide-HCl salt or chidamide-$H_2SO_4$ salt plus celecoxib-Na salt combined with an immune checkpoint inhibitor regimen was very potent in inhibiting tumor growth and thus significantly increased survival rate (FIG. 11N). As shown in FIG. 11N, chidamide-K30 50 mg/kg plus celecoxib-capsule 50 mg/kg combined with anti-PD-1 antibody group increased the survival rate to only about 22% in this study because that anti-PD-1 antibody anti-cancer activity was lower as compared with previous results. On the other hand, chidamide-HCl salt or chidamide-$H_2SO_4$ salt 50 mg/kg plus celecoxib-Na salt 50 mg/kg combined with anti-PD-1 antibody group significantly increased the survival rate to about 37.5% or 44.4%, respectively in the CT26-bearing tumor mice model. This result suggested that chidamide-HCl salt or chidamide-$H_2SO_4$ salt plus celecoxib-Na salt combined with anti-PD-1 antibody were more potent than chidamide-K30 plus celecoxib-capsule combined with anti-PD-1 antibody to control and regulate the tumor microenvironment and boost immune response to some extent. This study also proved that chidamide-HCl salt or chidamide-$H_2SO_4$ salt plus celecoxib-Na salt combined with immune checkpoint inhibitor was more potent to boost anti-cancer immune response than chidamide-K30 plus celecoxib-capsule combined with immune checkpoint inhibitor. On the other hand, the head to head comparison between chidamide-HCl salt plus celecoxib-Na salt and chidamide-K30 plus celecoxib-capsule when combined with anti-PD-1 Ab has demonstrated that the anti-cancer activity of combination regimen with chidamide-HCl salt plus celecoxib-Na salt is better than that of combination regimen with chidamide-K30 plus celecoxib-capsule.

Example 8

The Resistance to First Line Anti-PD-1 Ab Treatment was Overcome by

Second Line Treatment with Anti-PD-1/anti-CTLA-4 Ab Combined with Chidamide-HCl Salt Plus Celecoxib-Na Salt in CT26-bearing Mice In this study, the mice were treated with second line therapy to mimic the treatment for first line drug resistance occurring in human first line cancer therapy, in which a great portion of human cancer patients receiving first line anti-PD-1 antibody therapy will develop resistance, for the evaluation of the anti-cancer potency of second line therapy with chidamide-HCl salt plus celecoxib-Na salt combined with anti-PD-1/anti-CTLA-4 antibody when first line anti-PD-1 antibody therapy failed. Whether chidamide-HCl salt plus celecoxib-Na salt could improve the immune checkpoint inhibitors sensitivity through the regulation of tumor microenvironment was evaluated. Tumors were allowed to grow for 8 d (tumor size average about 120 mm$^3$) before first line treatment with anti-PD-1 antibody (2.5 mg/kg; Lot #717918D1) administered twice (3 days between two administrations). When tumors met the treatment failure criteria of consecutive increase three folds in 3 days (tumor size average 360 mm$^3$) after the second dose of first line anti-PD-1 antibody therapy and the tumor volumes were <600 mm$^3$, the mice were reenrolled. These mice with resistance to anti-PD-1 Ab were further randomized. There were ten different treatment regimens (n=9-11 mice/group) as indicated. These mice were randomized into different second line treatment groups, including anti-IgG Ab (2.5 mg/kg; Lot #65481701), anti-PD-1 Ab (2.5 mg/kg; Lot #717918D1), entinostat (20 mg/kg) combined with anti-PD-1 Ab (2.5 mg/kg) as positive control, chidamide-K30 plus celecoxib-capsule, chidamide-HCl salt (50 mg/kg) plus celecoxib-Na salt (50 mg/kg), chidamide-K30 plus celecoxib-capsule combined with anti-PD-1 Ab, chidamide-HCl salt (50 mg/kg) plus celecoxib-Na salt (50 mg/kg) combined with anti-PD-1 Ab (2.5 mg/kg), anti-CTLA-4 Ab (2.5 mg/kg; Lot #702418A2B), chidamide-K30 plus celecoxib-capsule combined with anti-CTLA-4 Ab (2.5 mg/kg), chidamide-HCl salt (50 mg/kg) plus celecoxib-Na salt (50 mg/kg) combined with anti-CTLA-4 Ab (2.5 mg/kg) groups. Antibodies were treated by intraperitoneally (i.p) six times (3 days between two injections). Entinostat was orally administered eight times (given every 2 days). Chidamide-K30 or Chidamide-HCl salt and celecoxib-capsule or celecoxib-Na salt were treated by oral administration 16 times (daily). As shown in FIGS. 12A to 12E and 12F to 12O, there was no mouse in anti-PD-1 Ab group achieved PR (response rate 0%) and 8 mice of PD with fast tumor growth. Treatment with chidamide-HCl salt plus celecoxib-Na salt was more potent to inhibit tumor growth compared with chidamide-K30 plus celecoxib-capsule. The treatment with chidamide-HCl salt plus celecoxib-Na salt showed that 3 mice achieved CR and 4 mice achieved PD with fast tumor growth (response rate 33.3%). However the treatment with chidamide-K30 plus celecoxib-capsule showed that only 1 mouse achieved PR and 8 mice achieved PD with fast tumor growth (response rate 10%). When chidamide-HCl salt plus celecoxib-Na salt combined with anti-PD-1 Ab, the result demonstrated that 4 mice achieved CR (response rate 36.3%) and 6 mice achieved PD with much slower tumor growth. However the treatment with chidamide-K30 plus celecoxib-capsule combined with anti-PD-1 Ab showed that only 1 mouse achieved PR and 9 mice achieved PD with moderate tumor growth (response rate 10%). This result suggested that anti-PD-1 Ab had no anti-cancer activity in mice with resistance to anti-PD-1 Ab. Moreover, chidamide-HCl salt plus celecoxib-Na salt regimen was very potent to control the tumor microenvironment and increase the anti-PD-1 Ab sensitivity in mice with resistance to anti-PD-1 Ab. And the treatment with chidamide-K30 plus celecoxib-capsule showed much less anti-cancer activity compared with the salt forms combination of chidamide-HCl salt plus celecoxib-Na salt. As shown in FIGS. 12F to 12O, anti-CTLA-4 Ab group moderately inhibited tumor growth compared with anti-PD-1 Ab group, but there was no mouse has ever achieved CR or PR and 7 mice achieved PD with moderate tumor growth. However, in chidamide-HCl salt plus celecoxib-Na salt combined with anti-CTLA-4 Ab group, the result demonstrated that 4 mice achieved CR, 2 mice achieved PR (response rate 60%) and no PD mice. And in chidamide-K30 plus celecoxib-capsule combined with anti-CTLA-4 Ab group, the result demonstrated that 2 mice achieved CR, 1 mouse achieved PR (response rate 25%) and 5 mice achieved PD with moderate tumor growth. Finally, in the positive control group entinostat combined with anti-PD-1 Ab, there was 1 mouse achieved PR (response rate 9%) and 8 mice achieved PD with fast tumor growth. Taken together, chidamide-HCl salt plus celecoxib-Na salt regimen was potent to boost the response rate in mice with resistance to anti-PD-1 Ab. Furthermore, chidamide-HCl salt plus celecoxib-Na salt was more potent to boost response rate when combined with anti-CTLA-4 Ab than combined with anti-PD-1 Ab in mice with resistance to anti-PD-1 Ab.

Figure 12A:
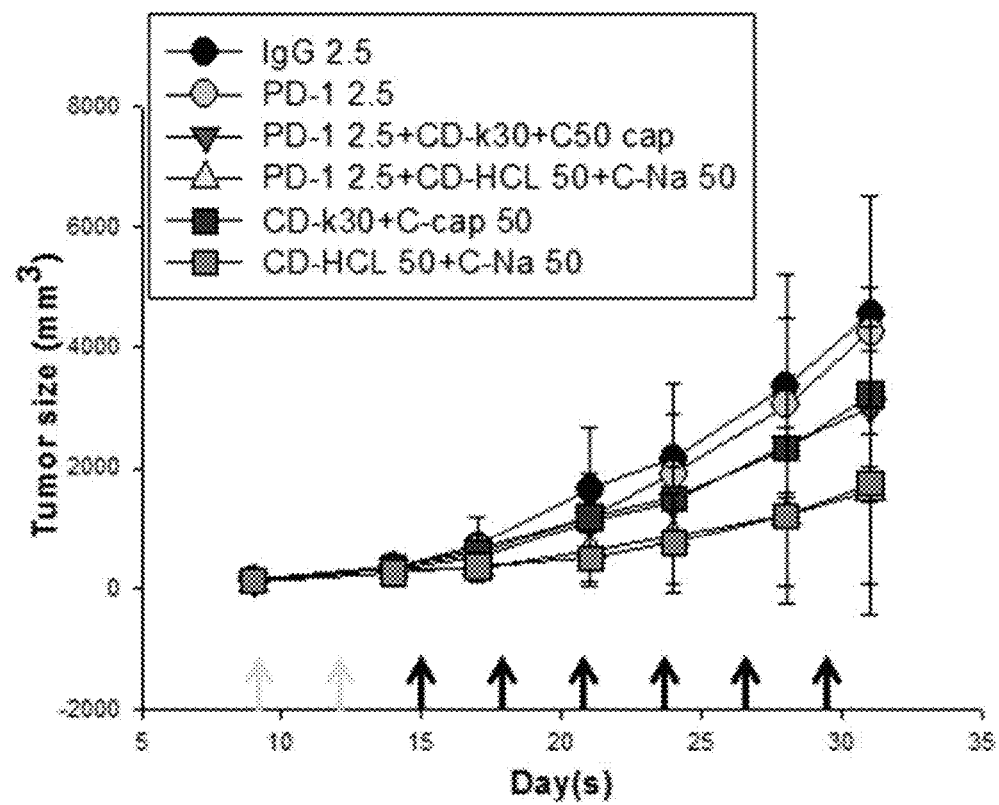
Figure 12B:
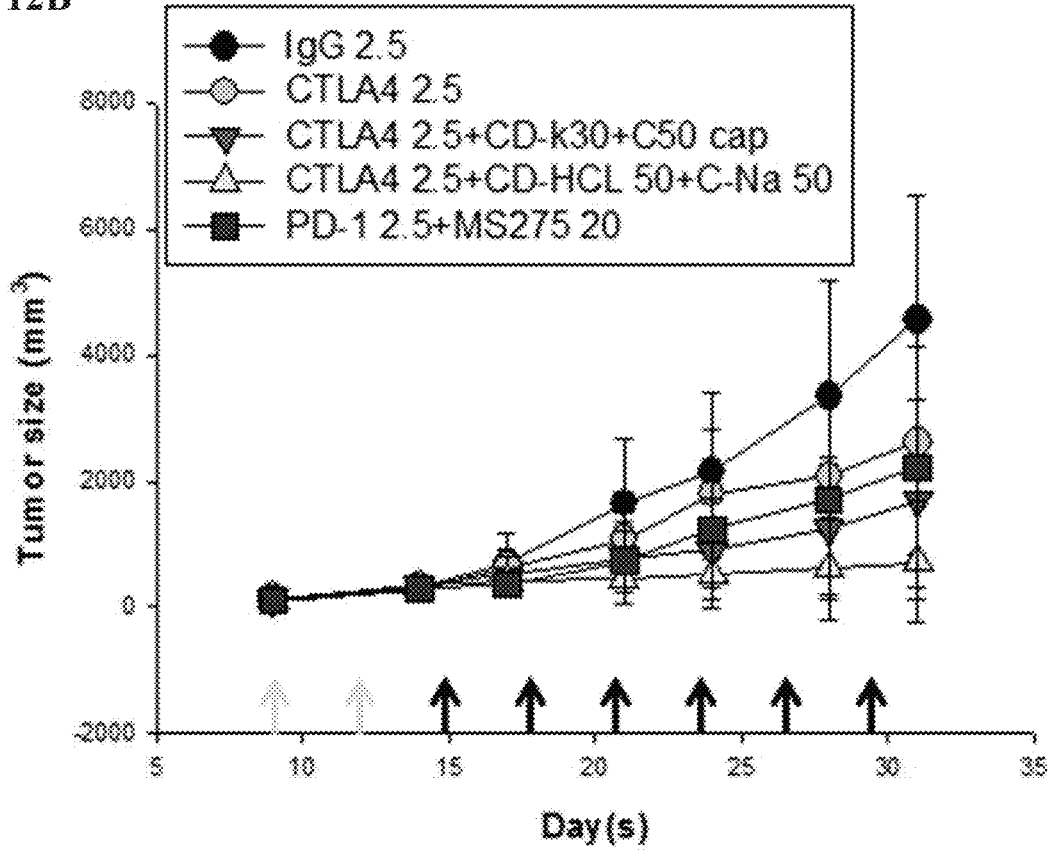
Figure 12C:
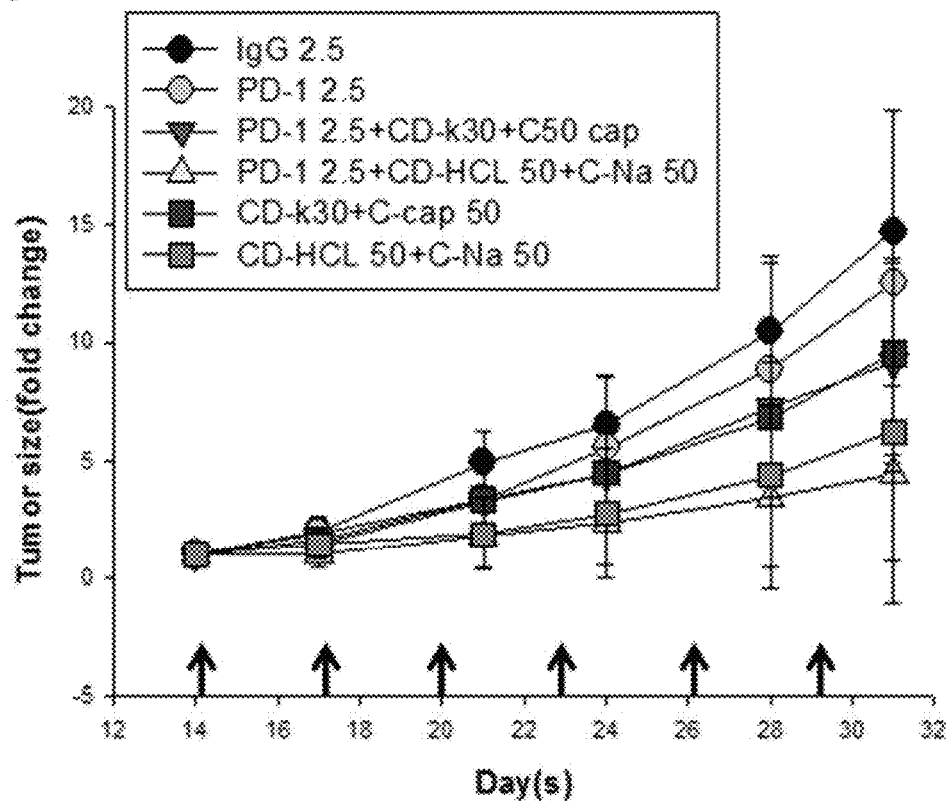
Figure 12D:
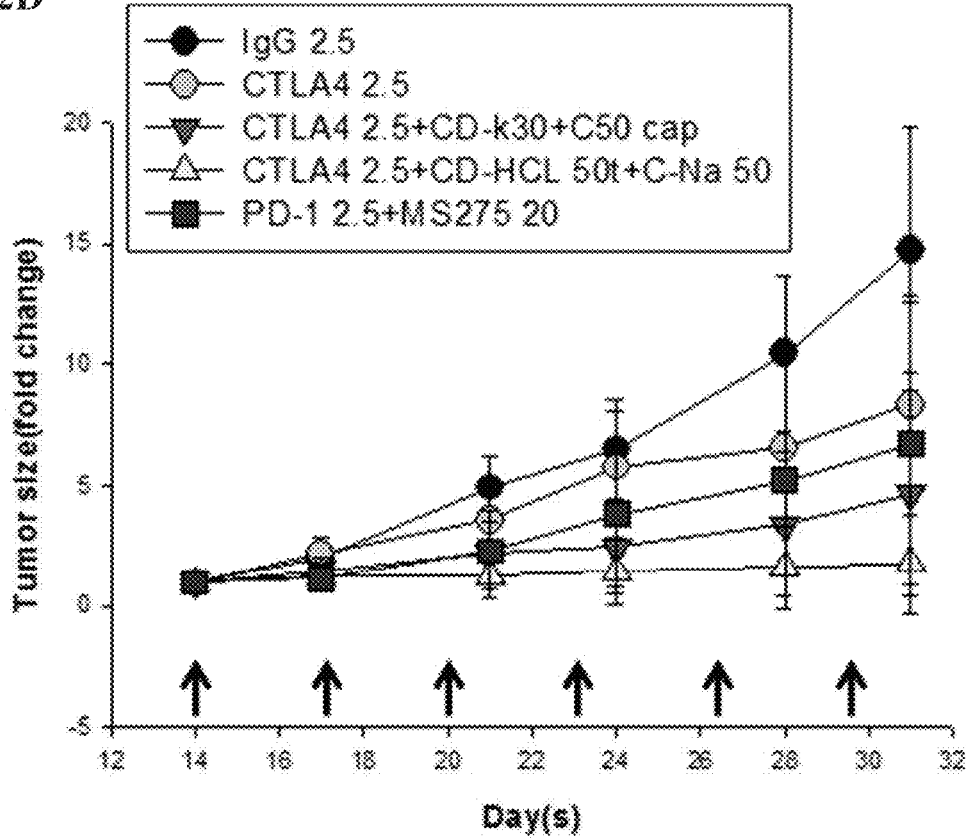
Figure 12E:
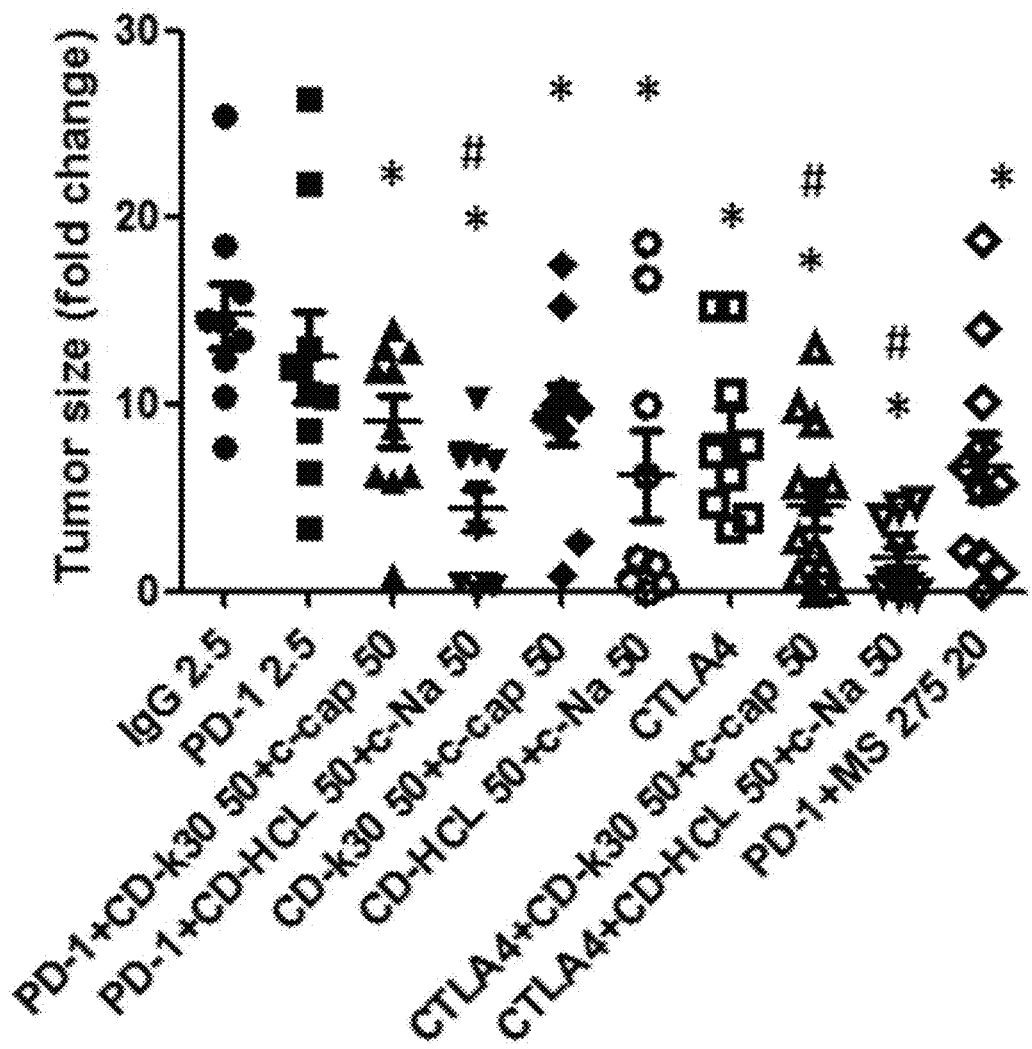
Figure 12F:
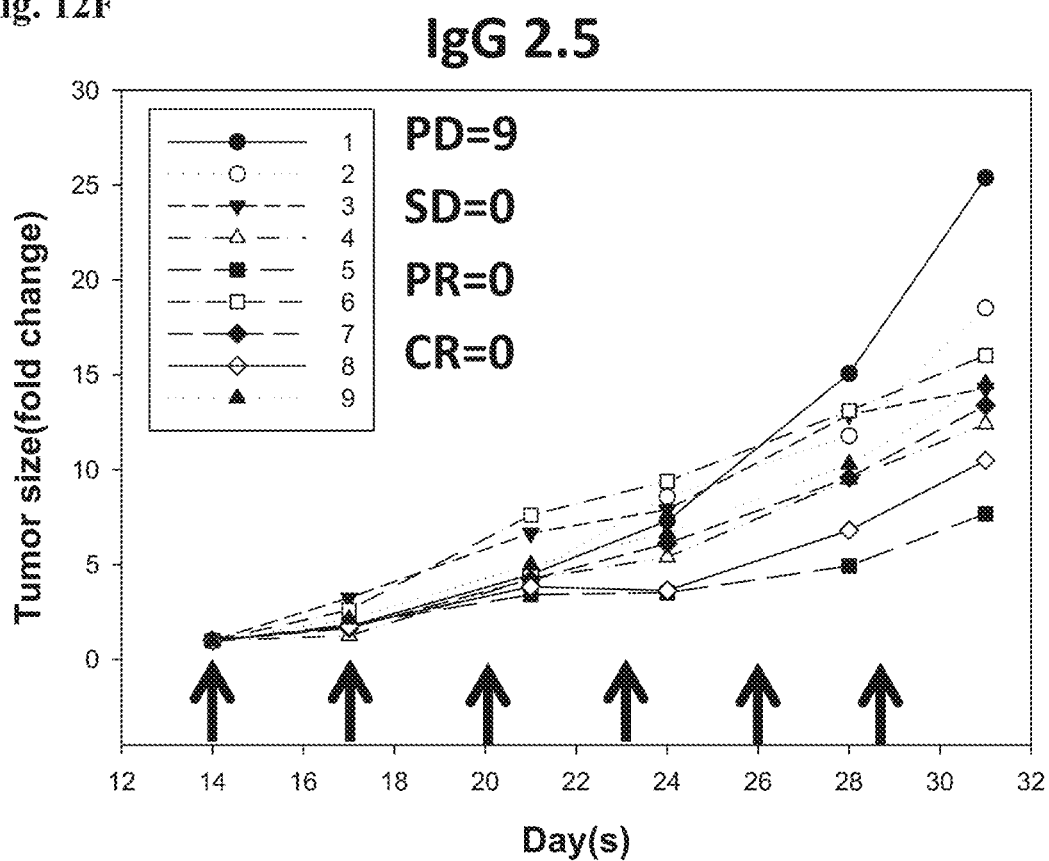
FIGS. 12F to 12O show the individual tumor volumes.
Figure 12G:
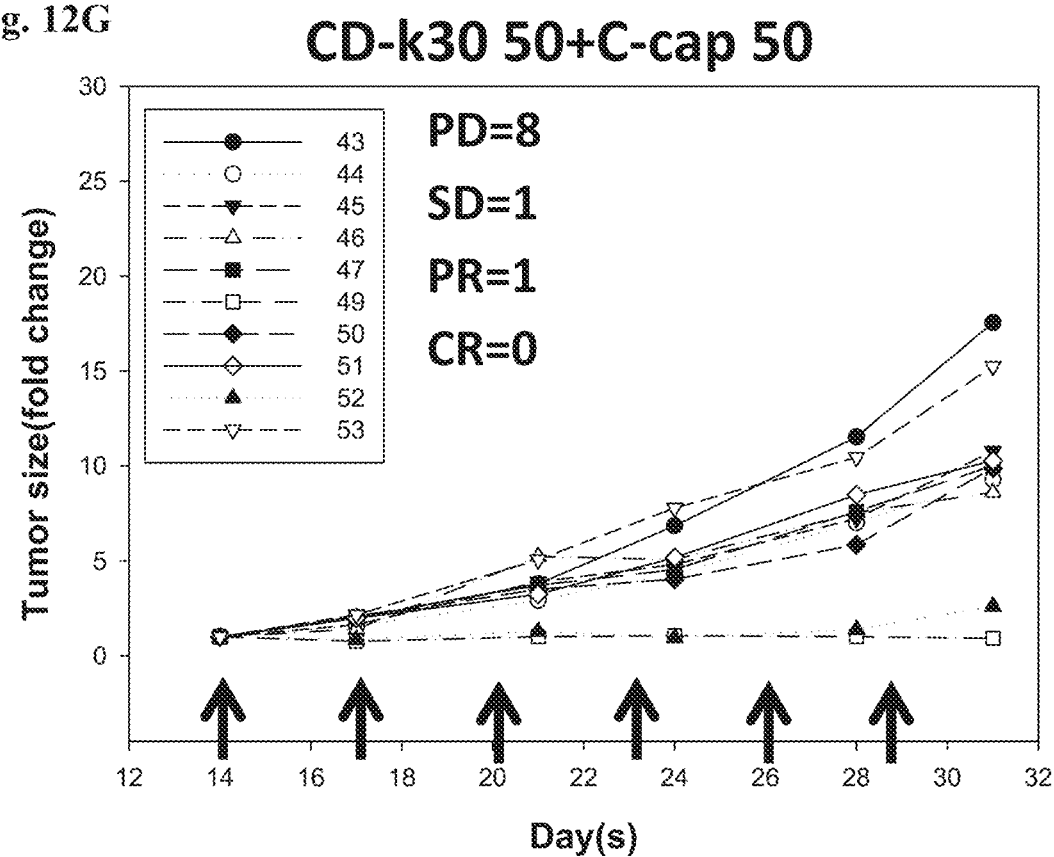
Figure 12H:
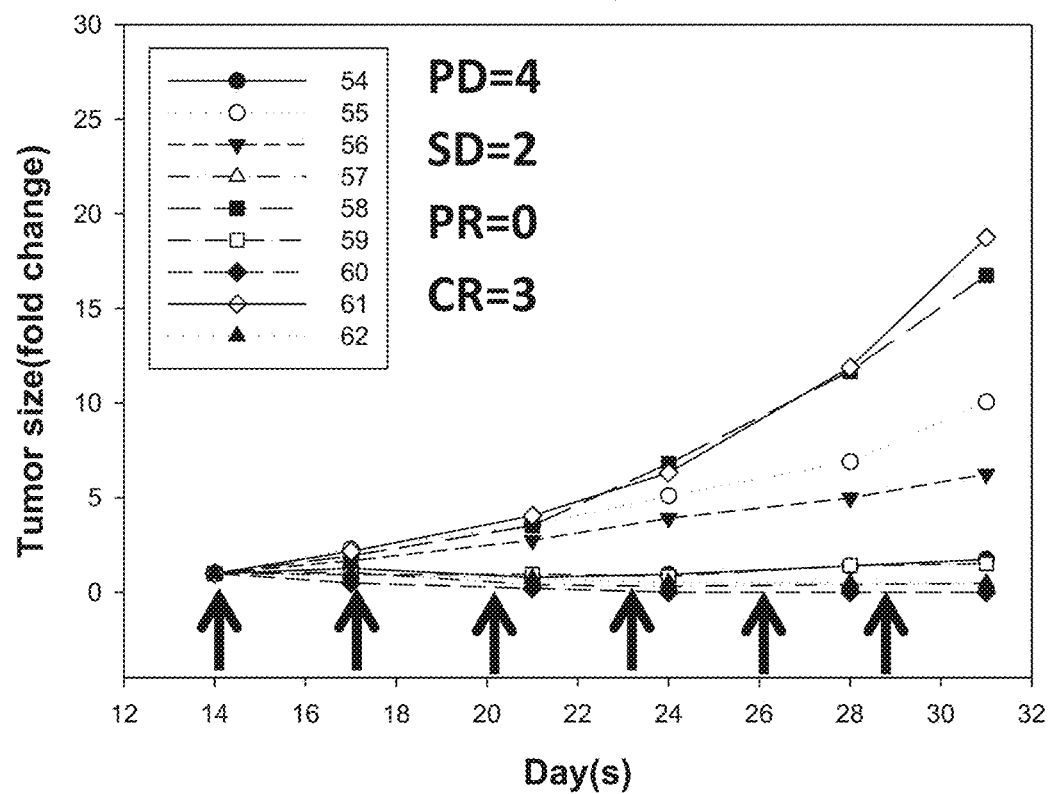
Figure 12I:
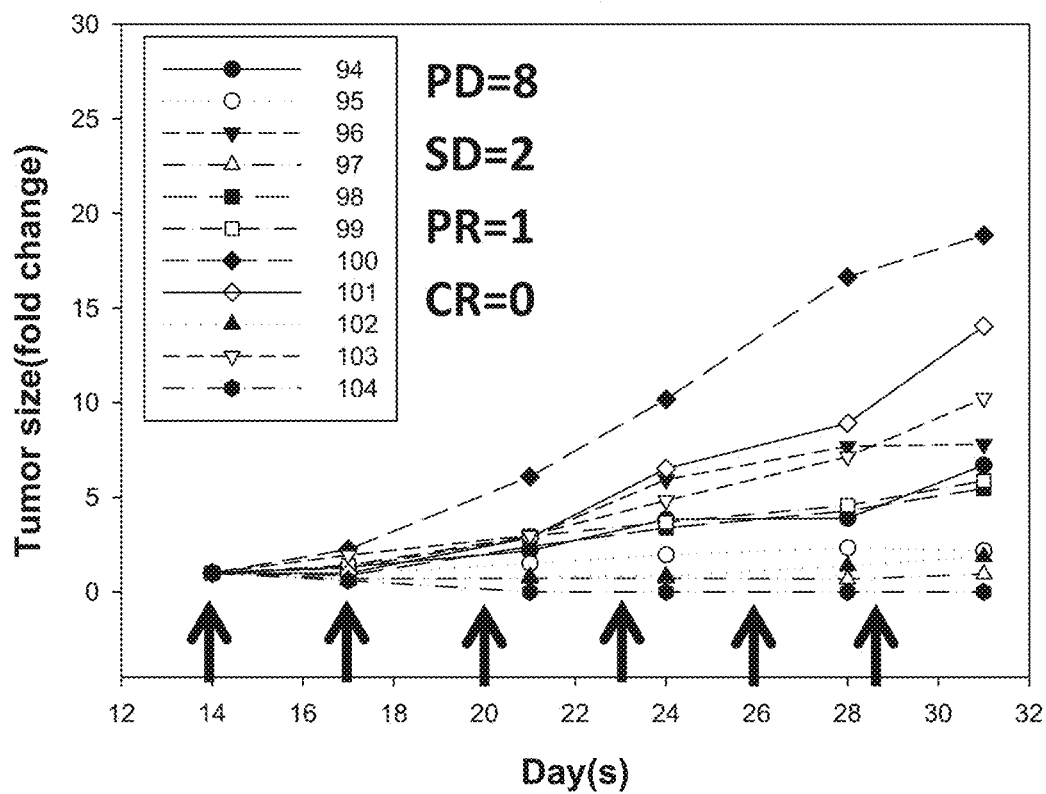
Figure 12J:
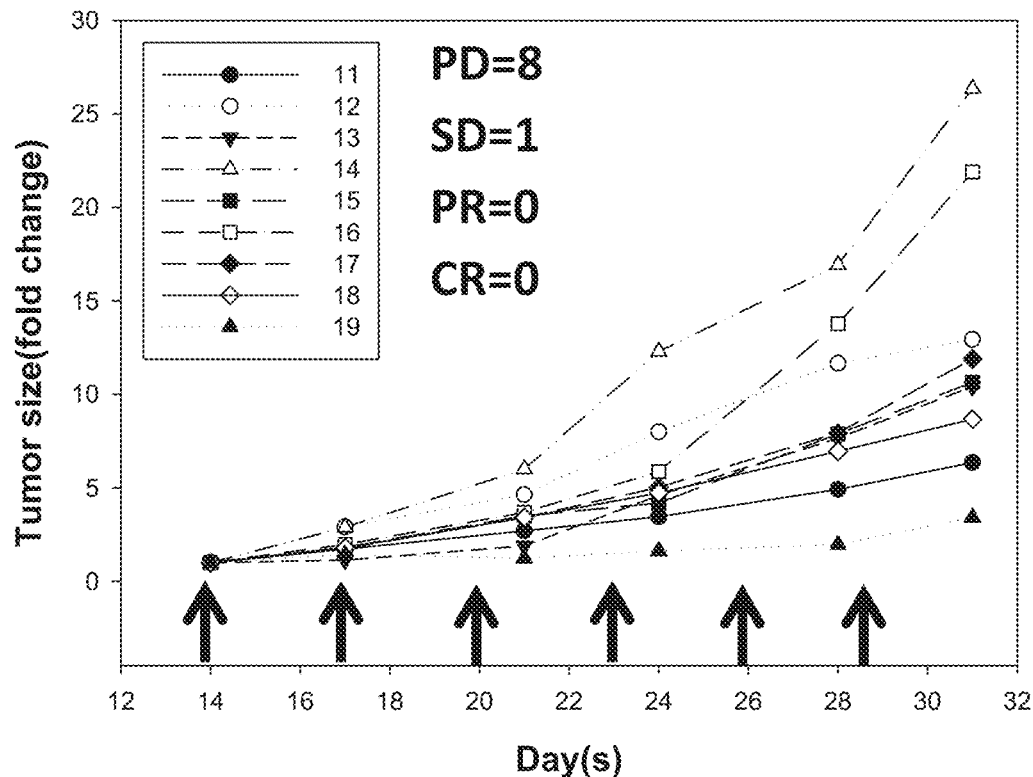
Figure 12K:
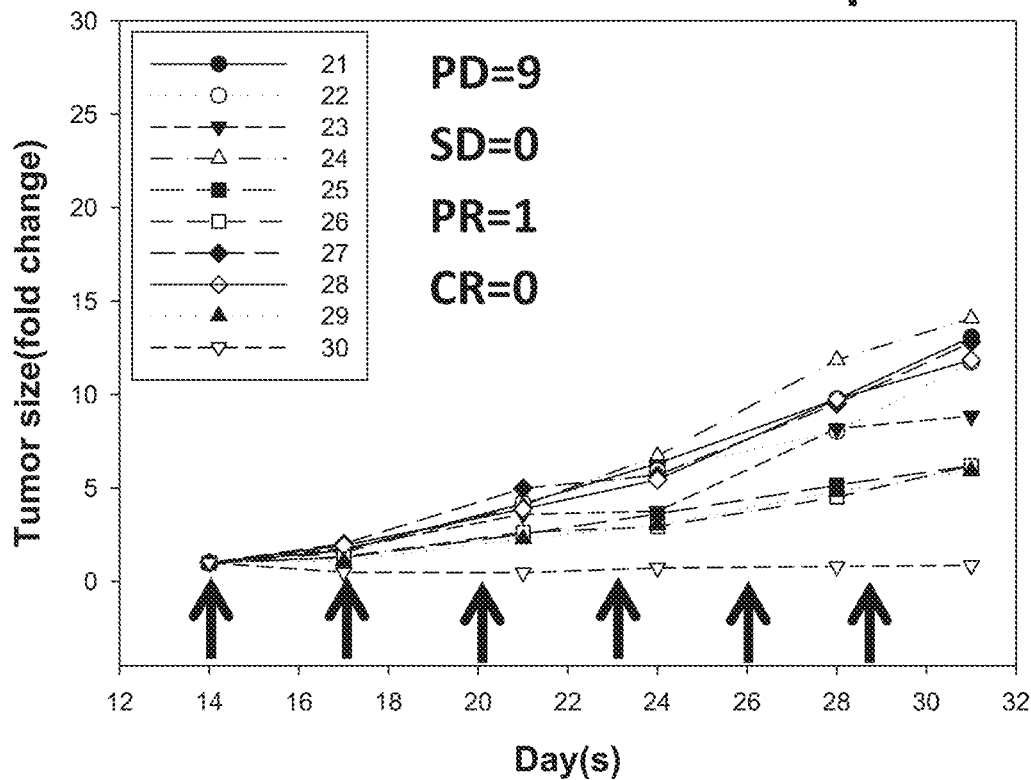
Figure 12L:
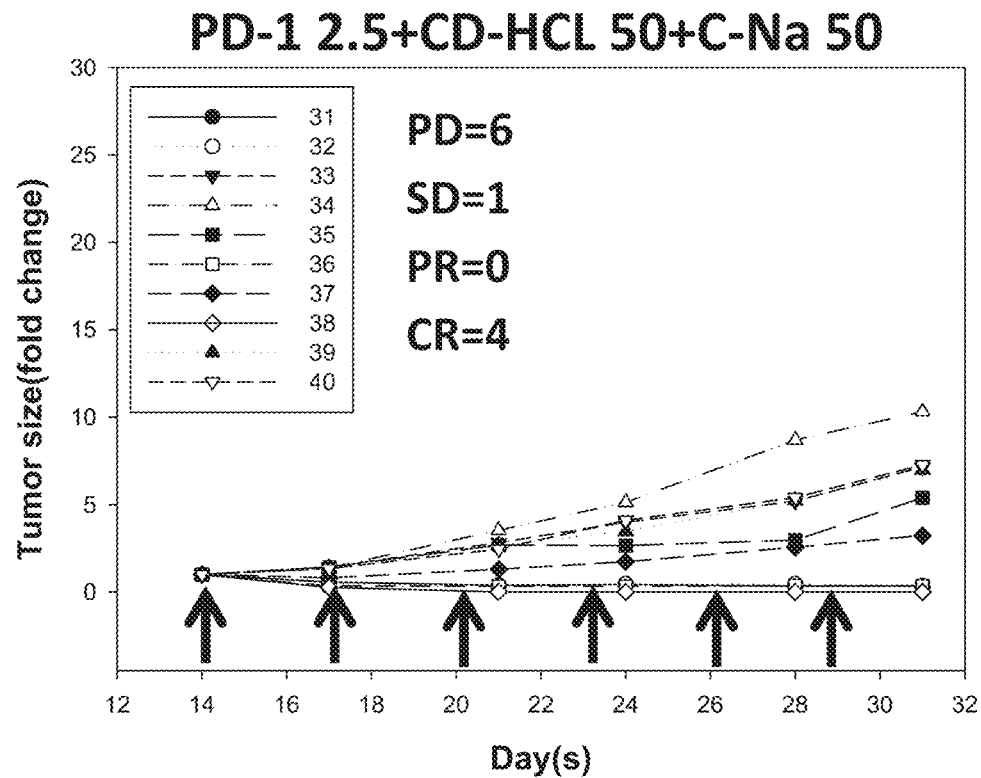
Figure 12M:
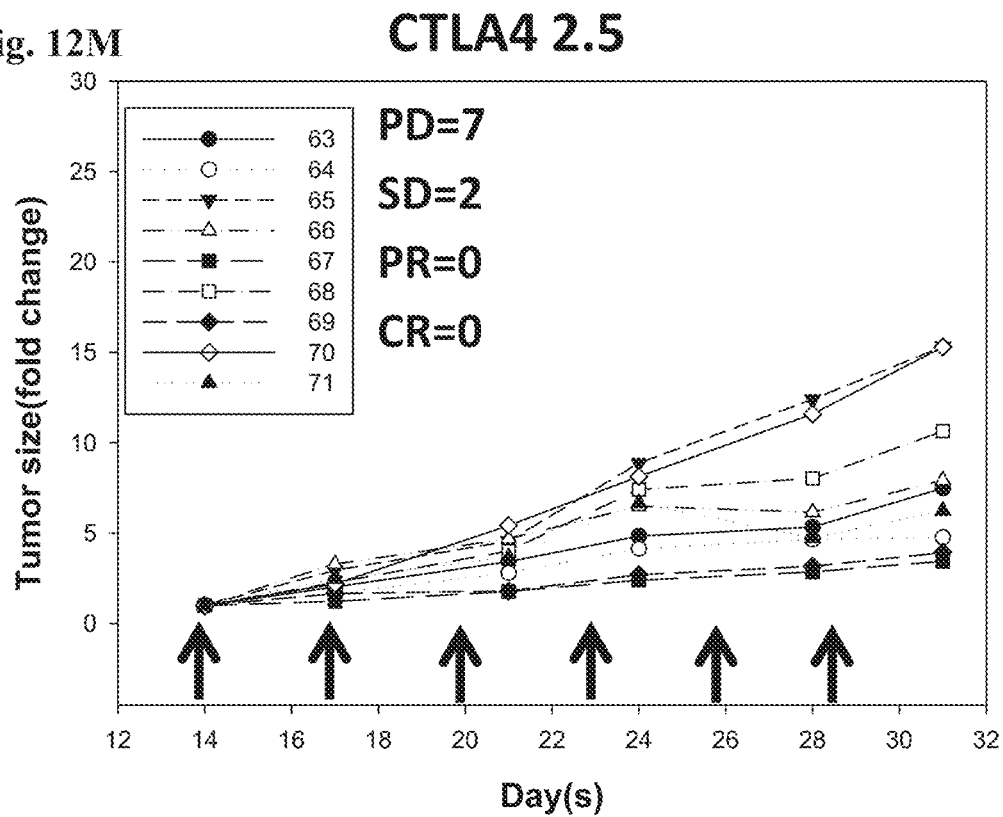
Figure 12N:
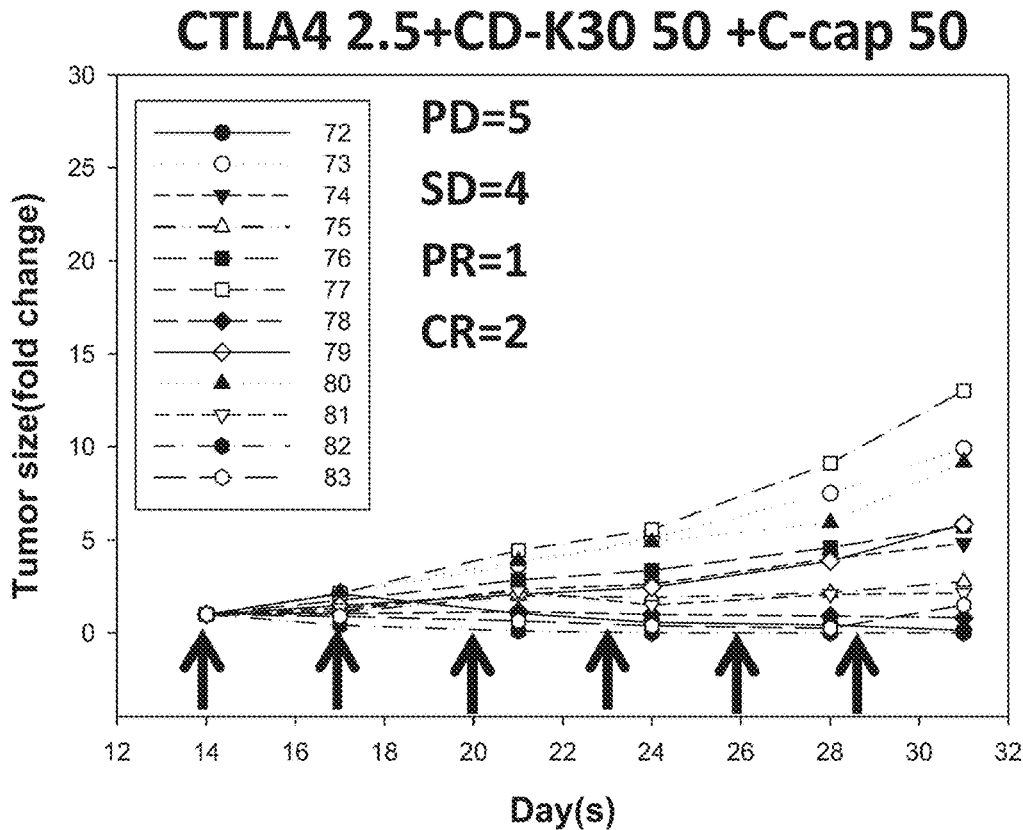
Figure 12O:
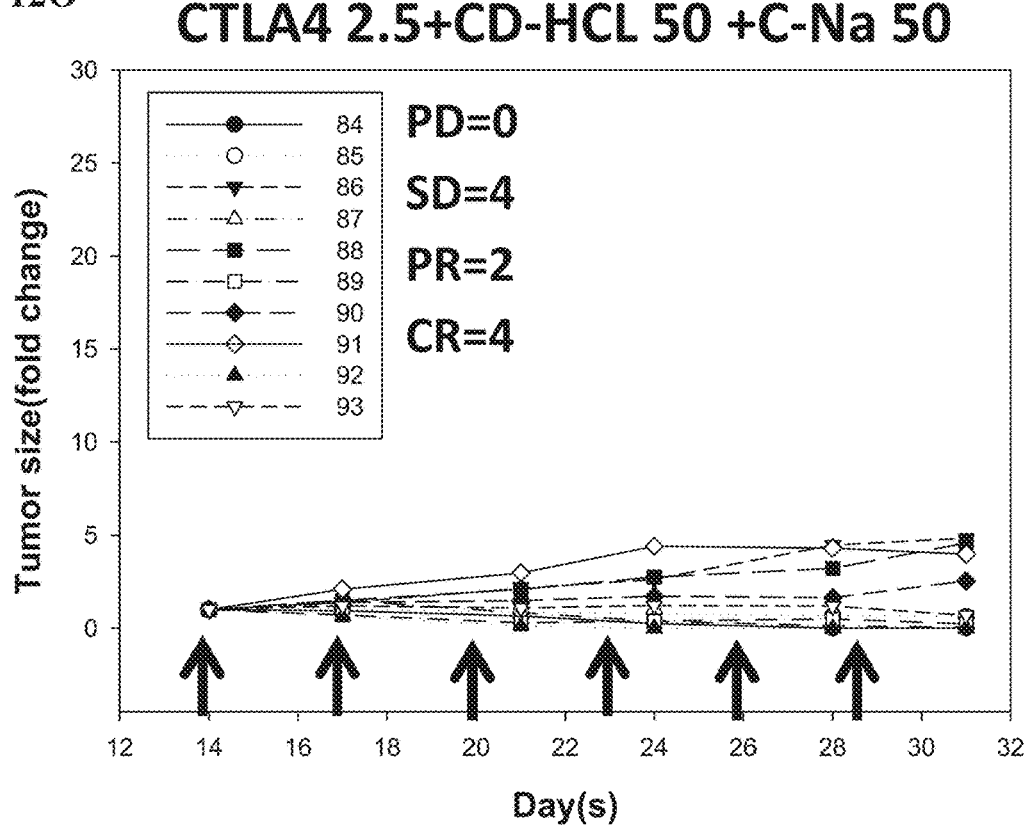
Figure 12P:
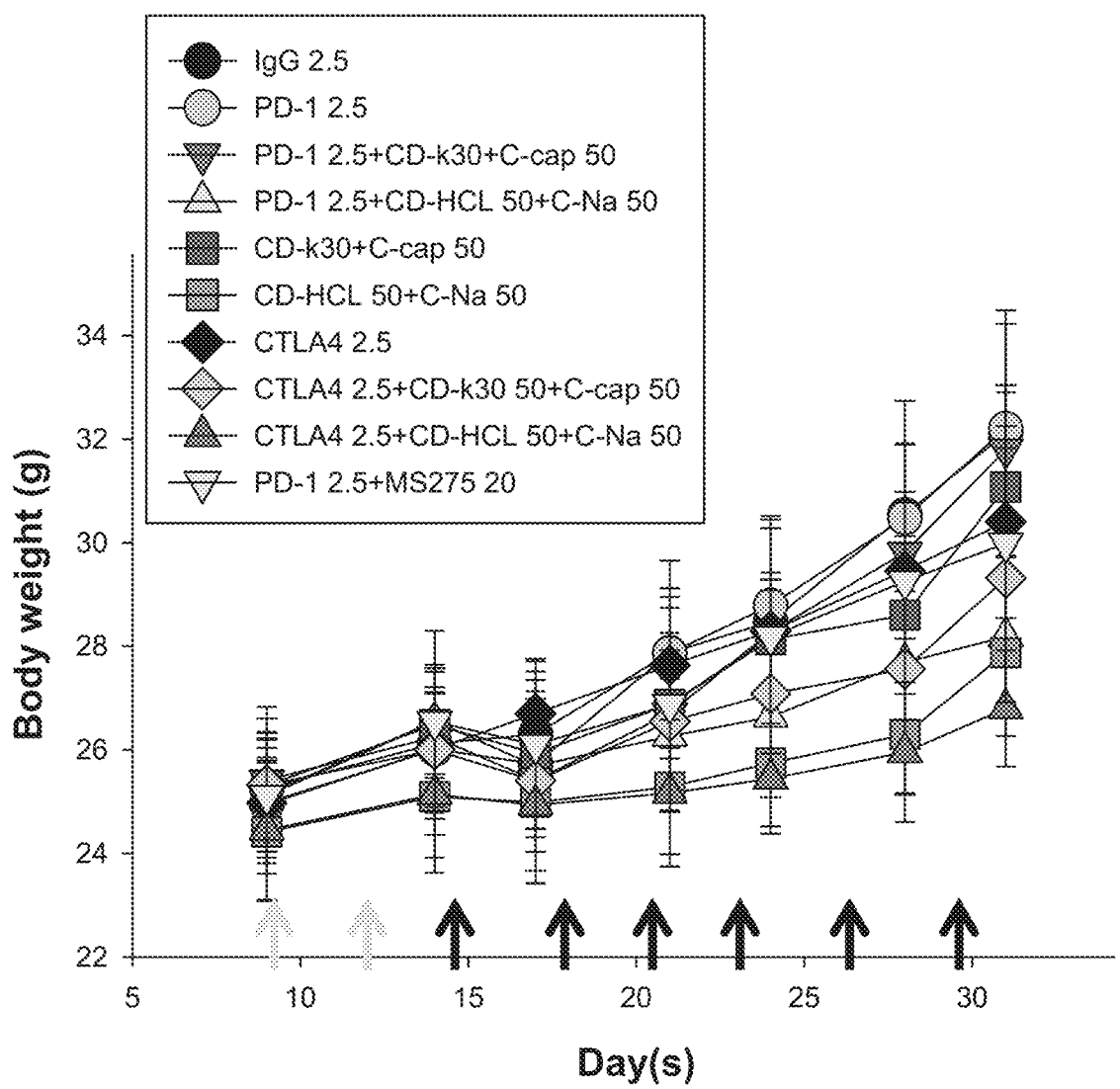
FIG. 12P shows the CT26 tumor-bearing mice body weight.
Figure 12Q:
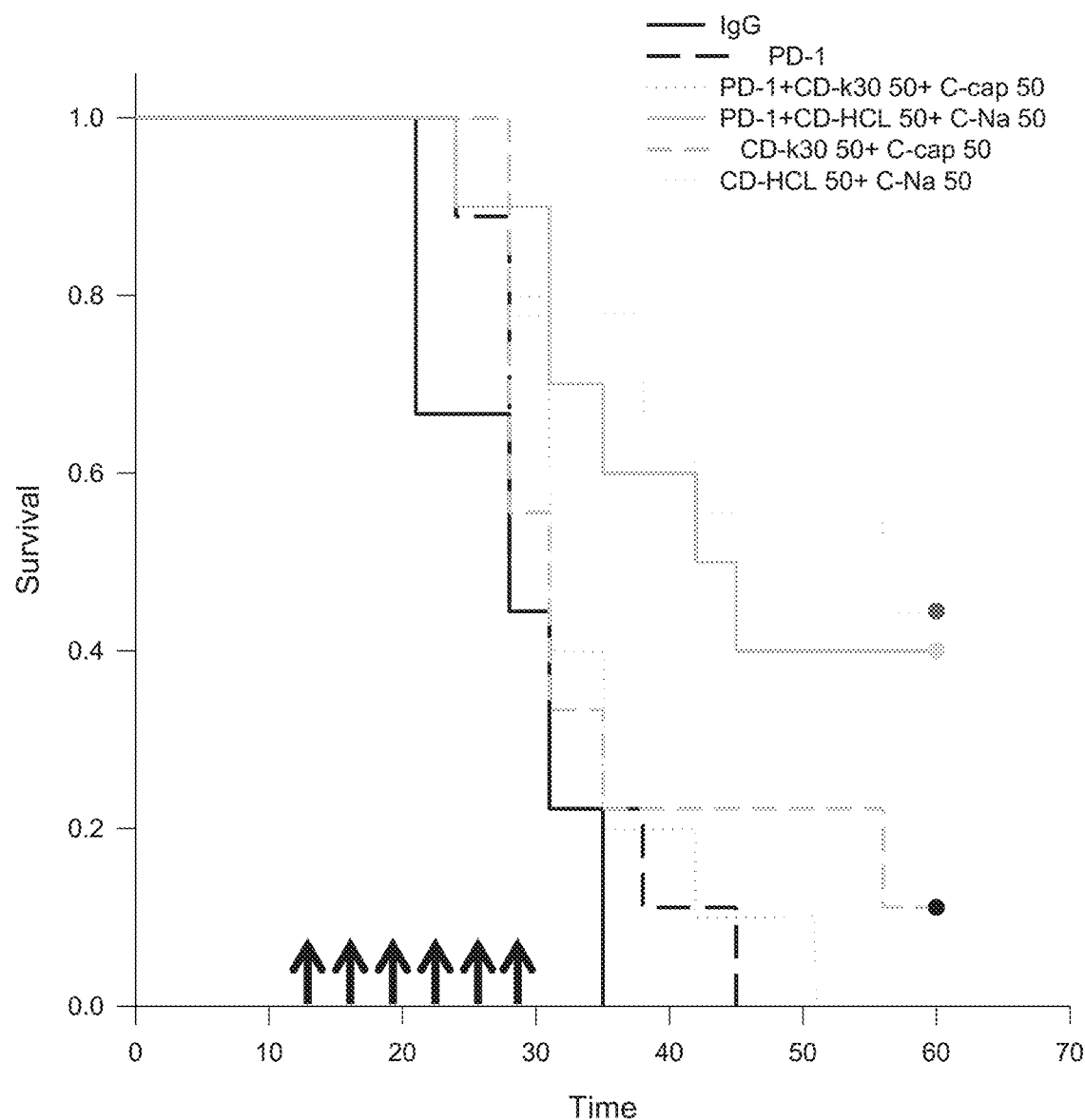

After the treatment was stopped at day 31, the tumors in the CT26 tumor-bearing mice grew faster in the anti-PD-1 and anti-CTLA-4 groups (FIGS. 12Q and 12R). The survival rate was evaluated at day 60. The treatment with chidamide-K30 plus celecoxib-capsule without combination with anti-PD-1 Ab showed better survival rate than combination with anti-PD-1 Ab, achieving 11.1% and 0%, respectively. And the treatment with chidamide-HCl salt plus celecoxib-Na salt without combination with anti-PD-1 Ab showed better survival rate than combination with anti-PD-1 Ab, achieving 44% and 40%, respectively. The result indicated that after treatment stopped chidamide-K30 plus celecoxib-capsule or chidamide-HCl salt plus celecoxib-Na salt in combination with anti-PD-1 Ab unexpectedly showed a faster tumor growth than chidamide-K30 plus celecoxib-capsule or chidamide-HCl salt plus celecoxib-Na salt. This study also proved that chidamide-HCl salt plus celecoxib-Na salt combined with anti-CTLA-4 Ab was more potent to boost anti-cancer immune response than chidamide-HCl plus celecoxib-Na combined with anti-PD-1 Ab. However, chidamide-HCl salt plus celecoxib-Na salt combined with anti-CTLA-4 Ab was more potent in inhibiting tumor growth than chidamide-K30 plus celecoxib-capsule combined with anti-CTLA-4 Ab, achieving survival rate 77.8% and 41.6%, respectively (FIGS. 12Q and 12R). On the other hand, the head to head comparison between chidamide-HCl salt plus celecoxib-Na salt and MS-275 when combined with anti-PD-1 Ab has demonstrated that the anti-cancer activity of combination regimen with chidamide-HCl salt plus celecoxib-Na salt is better than that of combination regimen with MS-275 in anti-PD-1 resistance condition.

Example 9

The Resistance to First Line Anti-PD-L1 Ab Treatment was Overcome by Second Line Treatment with Anti-PD-1/anti-CTLA-4 Ab Combined with Chidamide-HCl Salt Plus Celecoxib-Na Salt in CT26-Bearing Mice In this study, we further tested the second line combination treatment for the incidence of drug resistance after treatment with anti-PD-L1 Ab first line therapy, and evaluated the anti-cancer potency of second line therapy with chidamide-HCl salt plus celecoxib-Na salt combined with anti-PD-1/anti-CTLA-4 antibodies when first line anti-PD-L1 antibody therapy failed. Whether chidamide-HCl salt plus celecoxib-Na salt could improve sensitivity of the immune checkpoint inhibitors through the regulation of tumor microenvironment after drug resistance to first line anti-PD-L1 antibody treatment was tested. CT-26 tumor-bearing mice (the average tumor size about 160 mm$^3$) were treated with first line therapy of anti-PD-L1 antibody (2.5 mg/kg; Lot #720619F1) two times (3 days between the two injections). When tumors met the treatment failure criteria of consecutive increase three folds in 3 days (tumor size average 320 mm$^3$) after the second dose of first line anti-PD-L1 antibody therapy and the tumor volumes were <600 mm$^3$, the mice were reenrolled. These mice with resistance to anti-PD-L1 Ab were further randomized. There were ten different treatment regimens (n=9-11 mice/group) as indicated. These mice were randomized into different second line treatment groups, including anti-IgG Ab (2.5 mg/kg; Lot #65481701), anti-PD-1 Ab (2.5 mg/kg; Lot #717918D1), entinostat (20 mg/kg) plus celecoxib-capsule combined with anti-PD-1 Ab (2.5 mg/kg) as positive control, chidamide-K30 plus celecoxib-capsule, chidamide-HCl salt (50 mg/kg) plus celecoxib-Na salt (50 mg/kg), chidamide-K30 plus celecoxib-capsule combined with anti-PD-1 Ab, chidamide-HCl salt (50 mg/kg) plus celecoxib-Na salt (50 mg/kg) combined with anti-PD-1 Ab (2.5 mg/kg), anti-CTLA-4 Ab (2.5 mg/kg; Lot #702418A2B), chidamide-K30 plus celecoxib-capsule combined with anti-CTLA-4 Ab (2.5 mg/kg), chidamide-HCl salt (50 mg/kg) plus celecoxib-Na salt (50 mg/kg) combined with anti-CTLA-4 Ab (2.5 mg/kg) groups. Antibodies were treated by intraperitoneally (i.p) six times (administered every 3 days). Entinostat was orally administered eight times (administered every 2 days). Chidamide-K30 or Chidamide-HCl salt and celecoxib-capsule or celecoxib-Na salt were treated by oral administration 16 times (daily). As shown in FIGS. 13A to 13E and 13F to 13O, in control group anti-IgG group, 2 mice achieved PR and 3 mice achieved PD with fast tumor growth (response rate 28.6%), this was because mice responsive to first line anti-PD-L1 therapy were mistaken to be resistant to anti-PD-L1 Ab treatment due to delayed response to the first line treatment. However in anti-PD-1 Ab group, 1 mouse achieved PR, 2 mice achieved CR and 3 mice achieved PD with fast tumor growth (response rate 33.3%). Treatment with chidamide-HCl salt plus celecoxib-Na salt was more potent to inhibit tumor growth as compared with chidamide-K30 plus celecoxib-capsule. The treatment with chidamide-HCl salt plus celecoxib-Na salt showed that 6 mice achieved CR, 1 mouse achieved PR and no mice with PD (response rate 70%). However the treatment with chidamide-K30 plus celecoxib-capsule showed that 2 mice achieved CR, 4 mice achieved PR and 3 mice achieved PD with fast tumor growth (response rate 54.5%). When chidamide-HCl salt plus celecoxib-Na salt combined with anti-PD-1 Ab, the result demonstrated that 6 mice achieved CR (response rate 66.6%) and 1 mouse achieved PD with slow tumor growth. However the treatment with chidamide-K30 plus celecoxib-capsule combined with anti-PD-1 Ab showed that 4 mice achieved CR, 1 mouse achieved PR (response rate 62.5%) and 1 mouse achieved PD with fast tumor growth. The data suggested that chidamide-HCl salt plus celecoxib-Na salt regimen was more potent to control the tumor microenvironment and increase the anti-PD-1 Ab sensitivity in anti-PD-L1-resistance mice in comparison with chidamide-K30 plus celecoxib-capsule regimen.

In FIGS. 13F to 13O, the data showed that anti-CTLA-4 Ab second line treatment markedly inhibited tumor growth, and 2 mice achieved CR, 3 mice achieved PR and 3 mice achieved PD with fast tumor growth (response rate 55.5%). However, in the group treated with chidamide-HCl salt plus celecoxib-Na salt combined with anti-CTLA-4 Ab, the result demonstrated that 4 mice achieved CR, 3 mice achieved PR and no mice with PD (response rate 77.7%). And in chidamide-K30 plus celecoxib-capsule combined with anti-CTLA-4 Ab group, the result demonstrated that 2 mice achieved CR, 3 mice achieved PR and 1 mouse achieved PD mice with fast tumor growth (response rate 55.5%). Finally, in the group treated with the entinostat plus celecoxib-capsule combined with anti-PD-1 Ab as positive control, the result showed that 2 mice achieved CR, 1 mouse achieved PR and 3 mice achieved PD with fast tumor growth (response rate 50%). Taken together, chidamide-HCl salt plus celecoxib-Na salt regimen was potent to boost the response rate in PD-L1-resistance mice. Furthermore, chidamide-HCl salt plus celecoxib-Na salt combined with immune checkpoint inhibitor was more potent to boost response rate than chidamide-K30 plus celecoxib-capsule combined with immune checkpoint inhibitor in PD-L1-resistance mice.

Figure 13A:
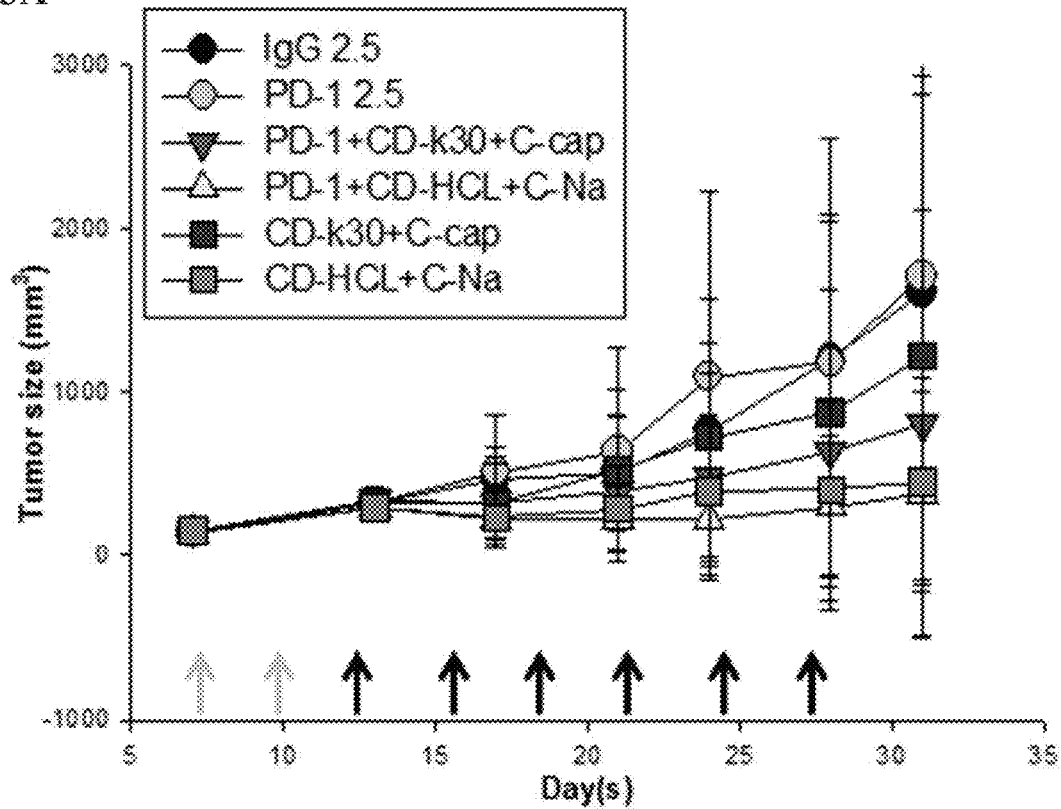
FIGS. 13A to 13R show that the resistance to PD-L1 checkpoint blockade therapy is overcome by using anti-PD-1 or anti-CTLA-4 Ab combined with chidamide-HCl salt plus celecoxib-Na salt in CT26 tumor-bearing mice. CT-26-bearing mice (the average tumor size about 160 mm³) were treated with first line of therapy of anti-PD-L1 antibody (2.5 mg/kg) administered twice (twice weekly). When tumors met the failure criteria of first line therapy, which was defined as when tumor size increased three times to average about 320 mm³ and tumor volume <600 mm³, the mice were reenrolled for the second line of therapy study. These anti-PD-L1 resistance mice were treated with seven different regimens (n=9-11 mice/group) as indicated: IgG, Anti-IgG control (vehicle, 2.5 mg/kg); PD-1, Anti-PD-1 monoclonal antibody (2.5 mg/kg); CTLA-4, anti-CTLA-4 monoclonal antibody (2.5 mg/kg); CD-HCl, chidamide-HCl salt (50 mg/kg); C—Na, amorphous celecoxib-Na salt (50 mg/kg); MS275, entinostat (20 mg/kg).
Figure 13B:
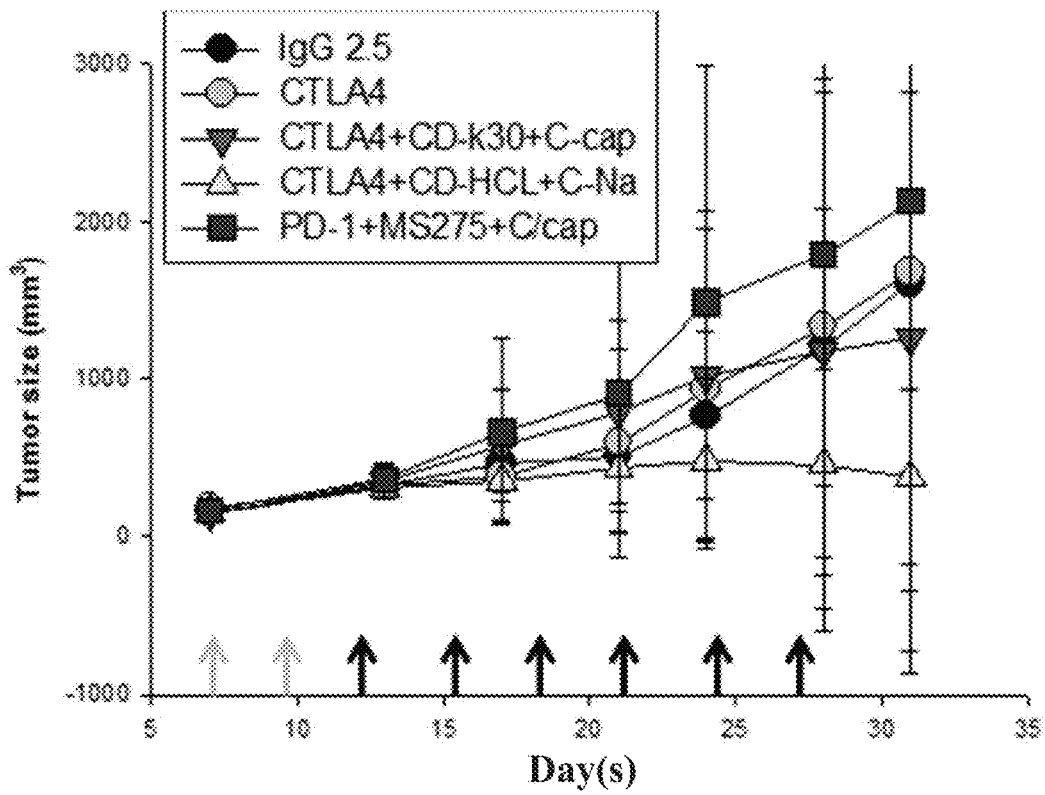
Figure 13C:
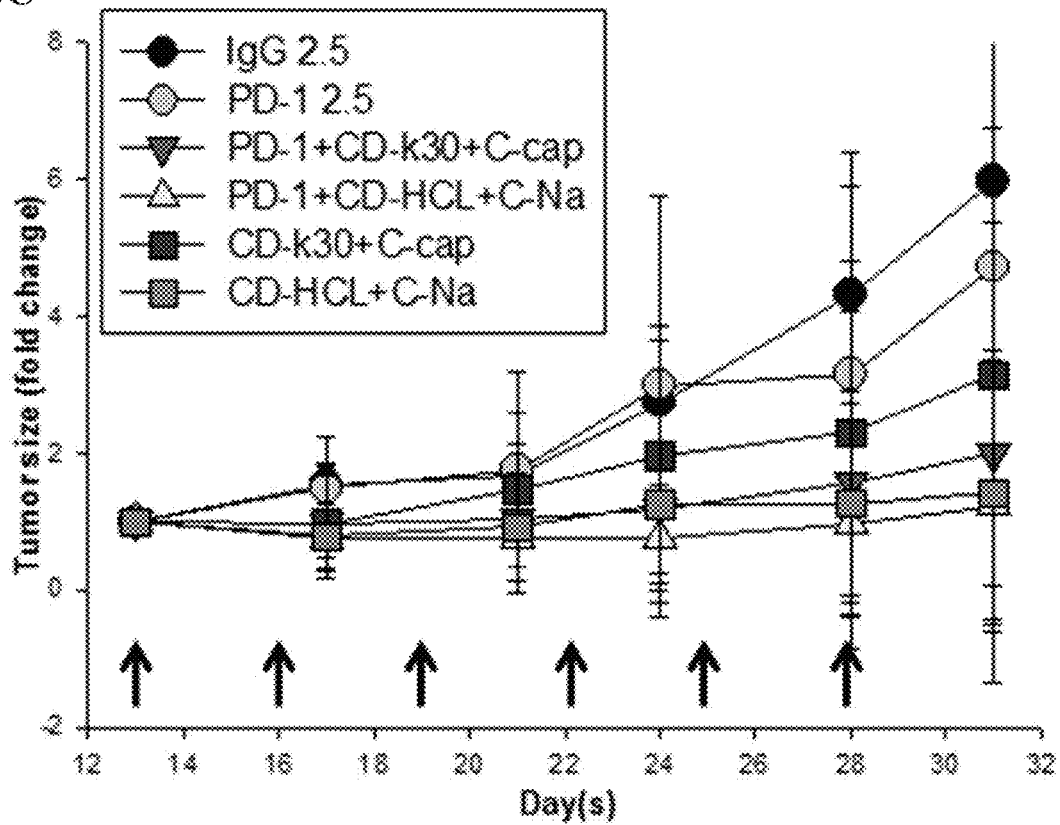
Figure 13D:
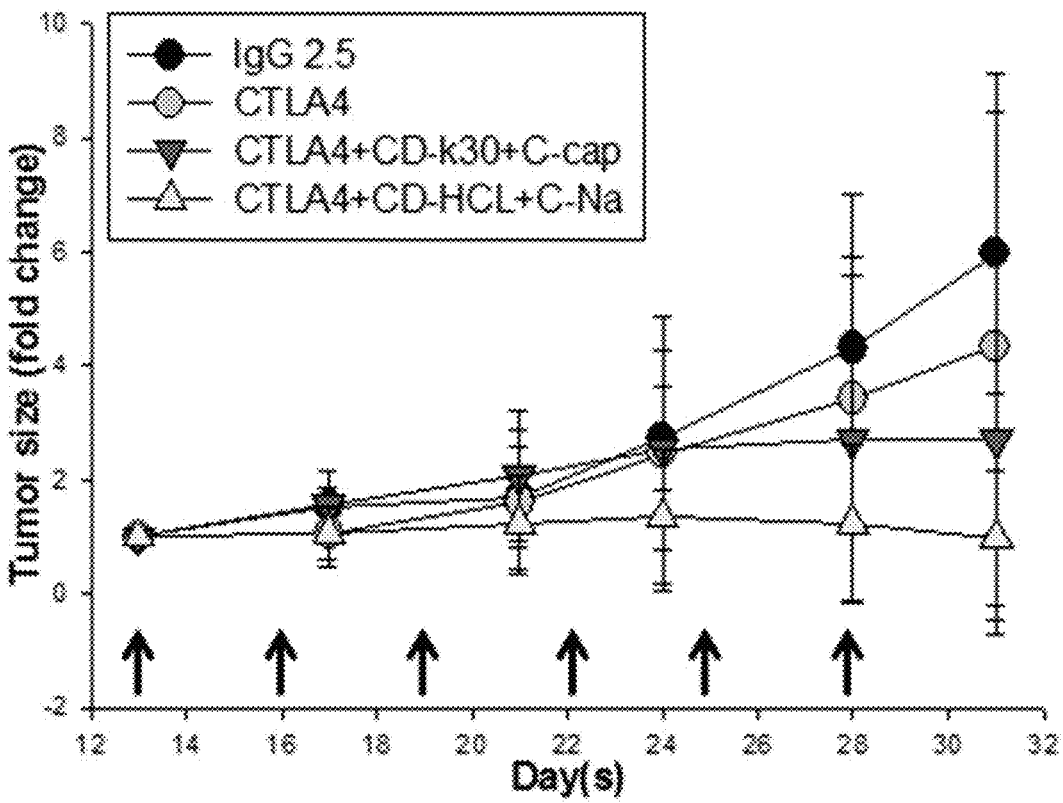
Figure 13E:
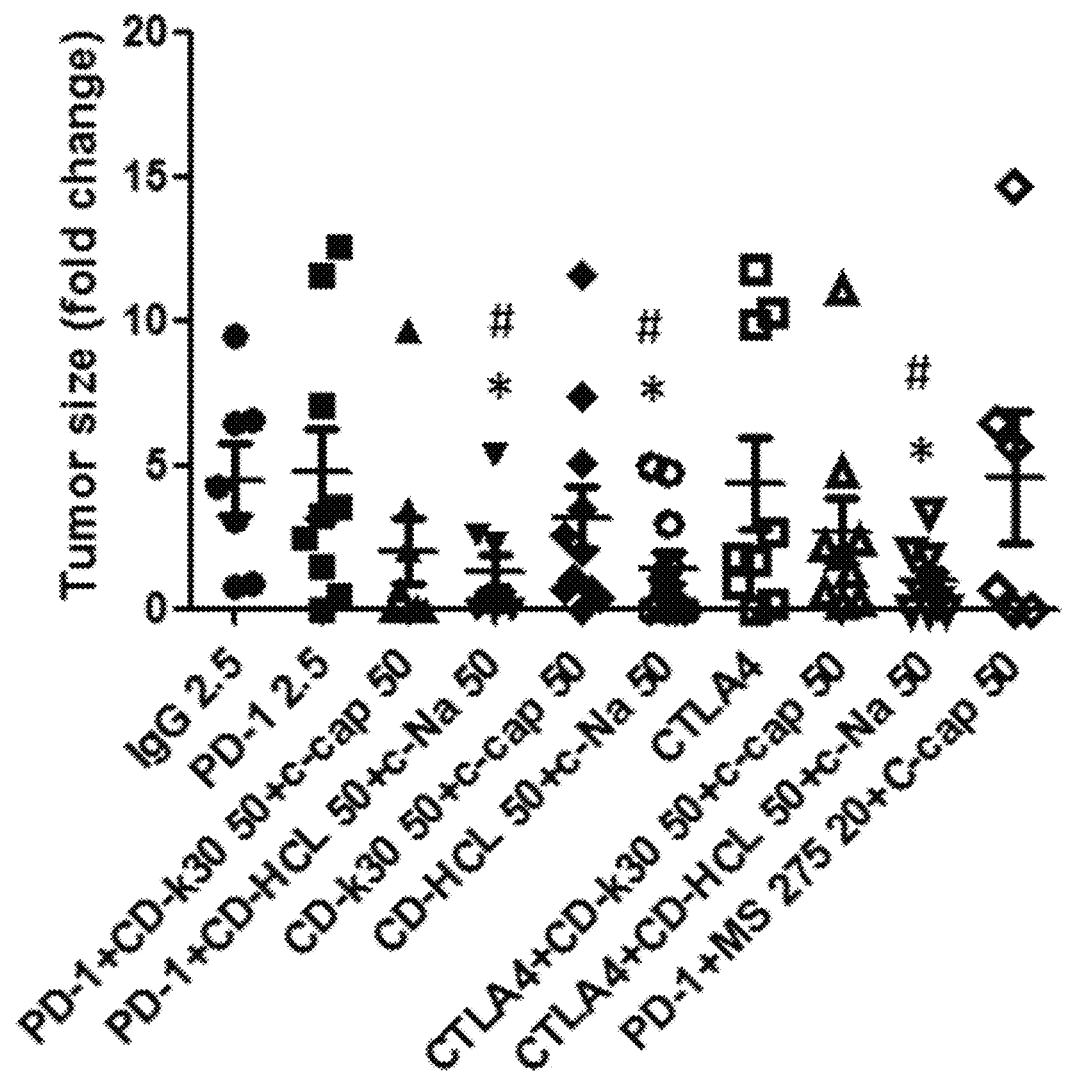
Figure 13F:
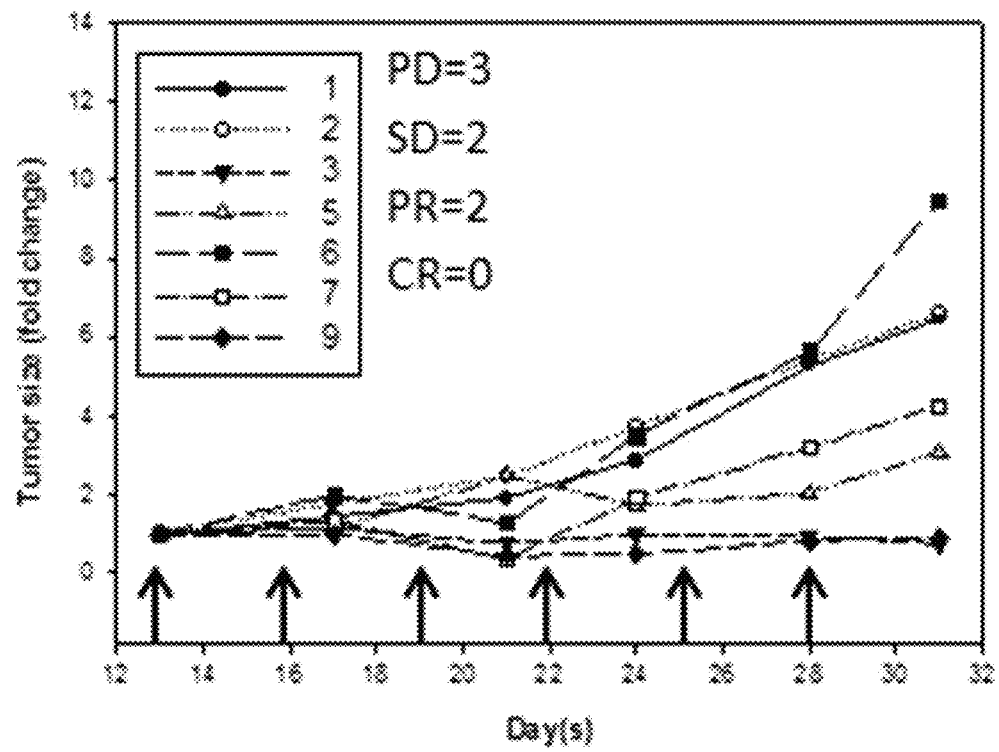
FIGS. 13F to 13O show the individual tumor volumes.
Figure 13G:
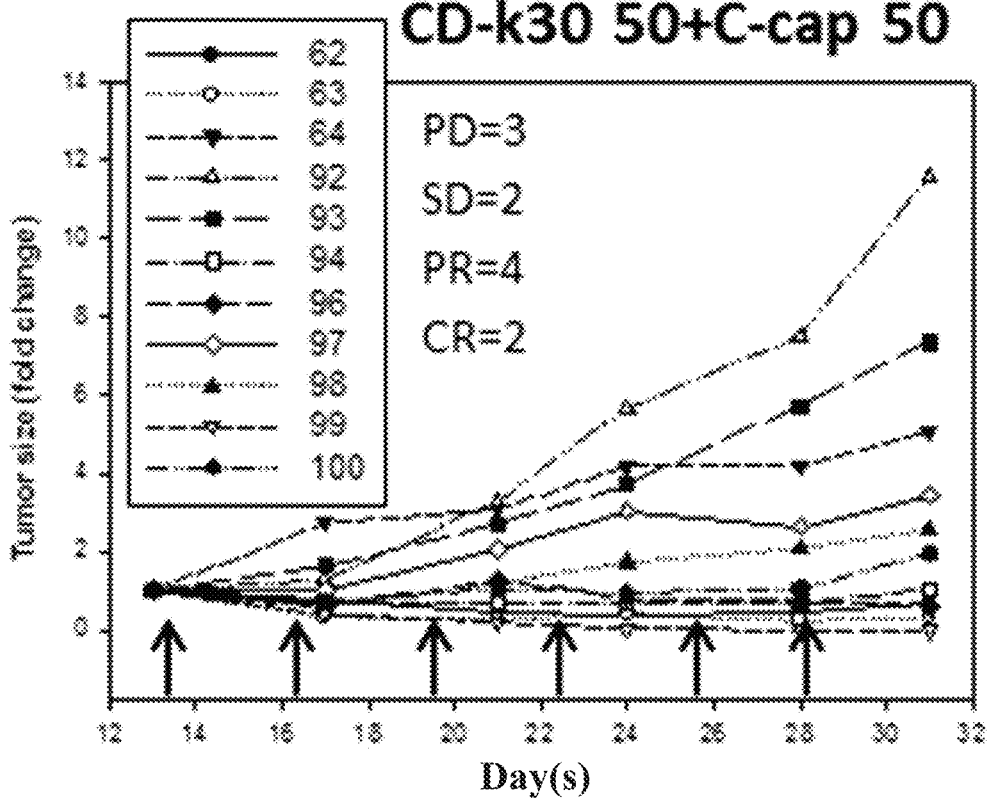
Figure 13H:
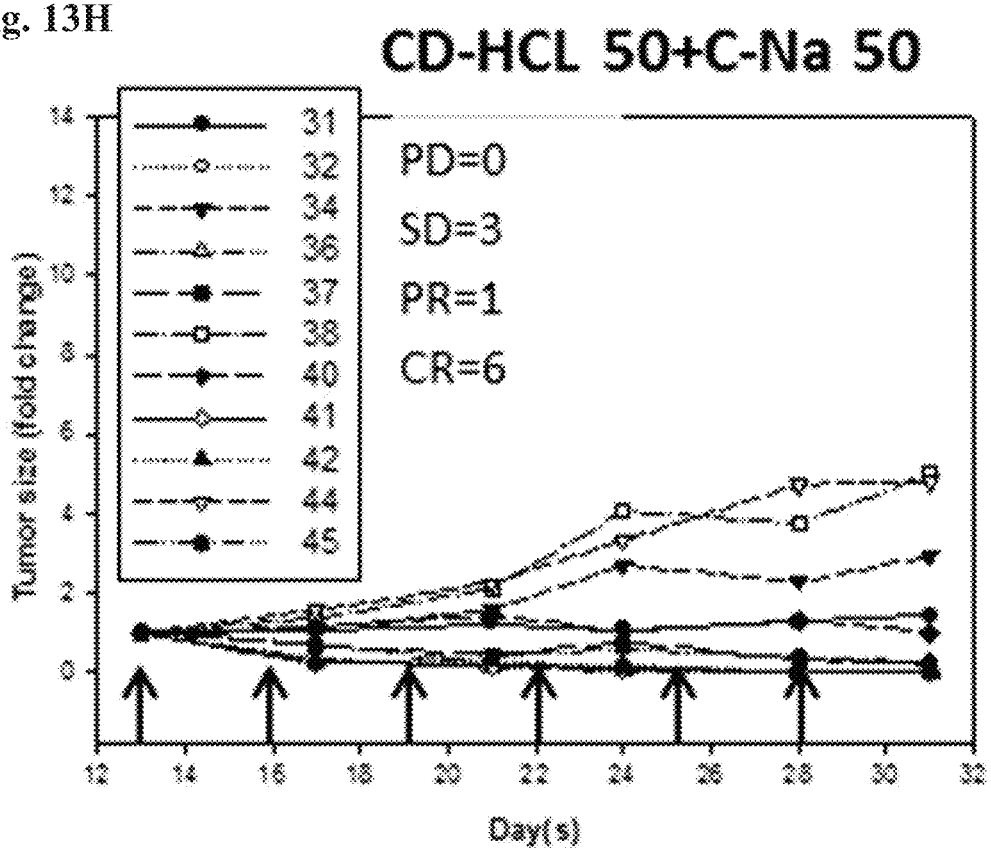
Figure 13I:
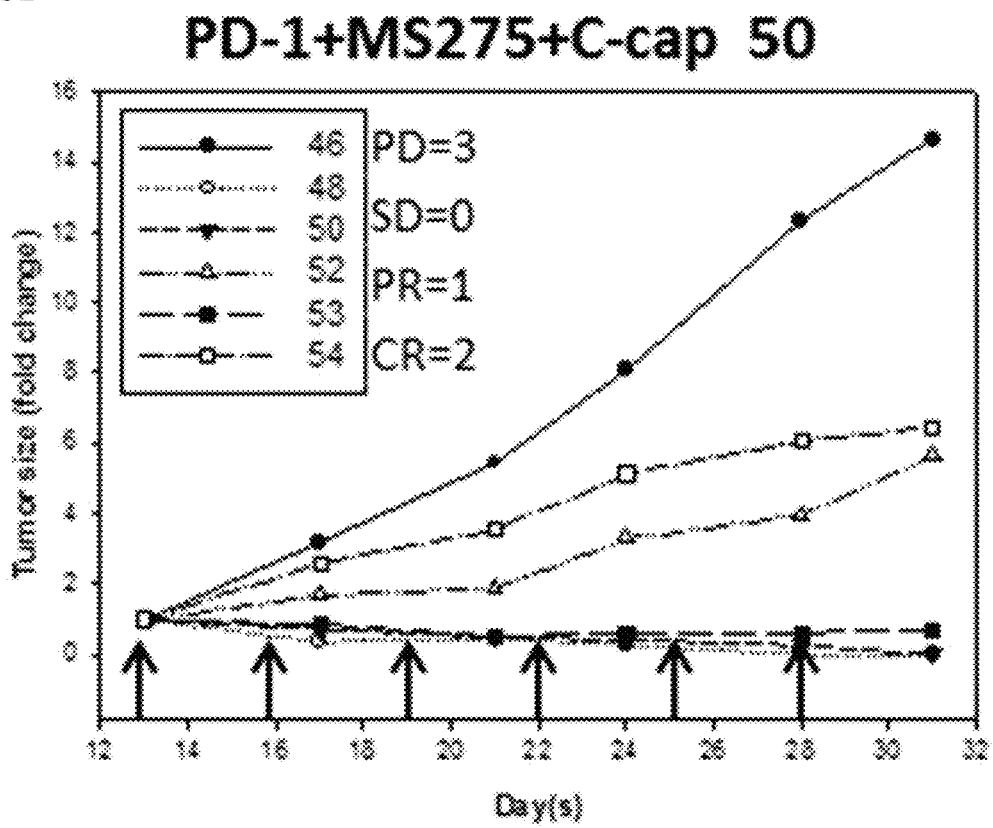
Figure 13J:
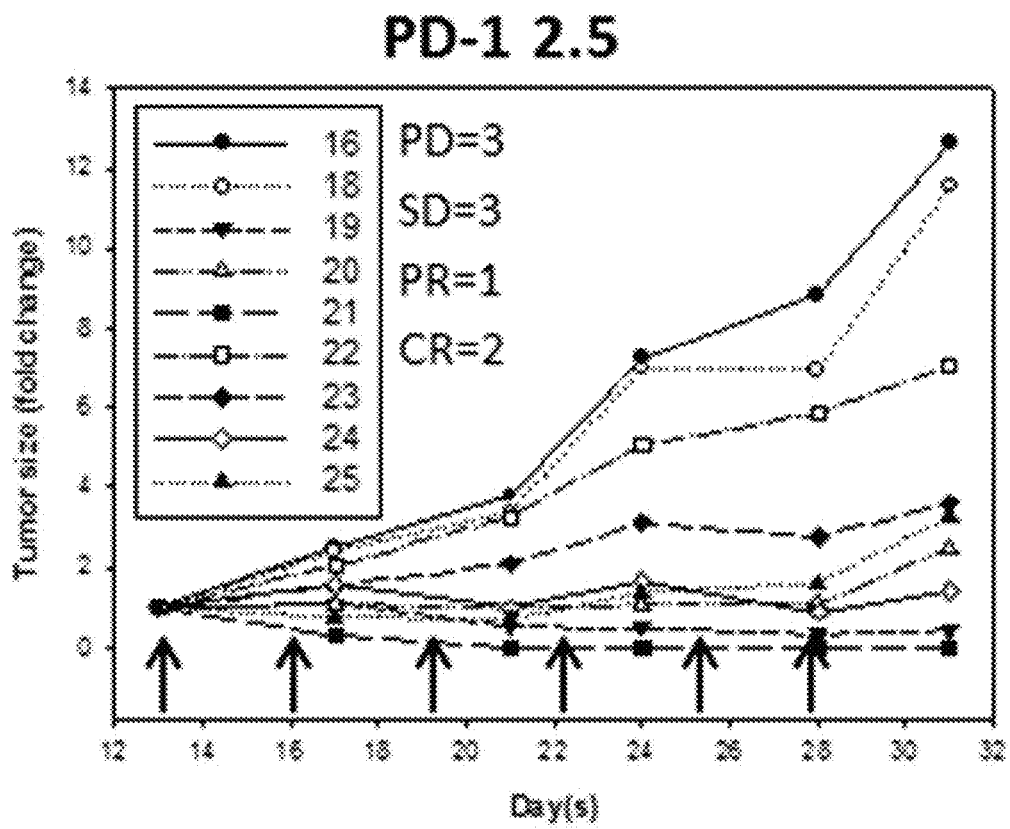
Figure 13K:
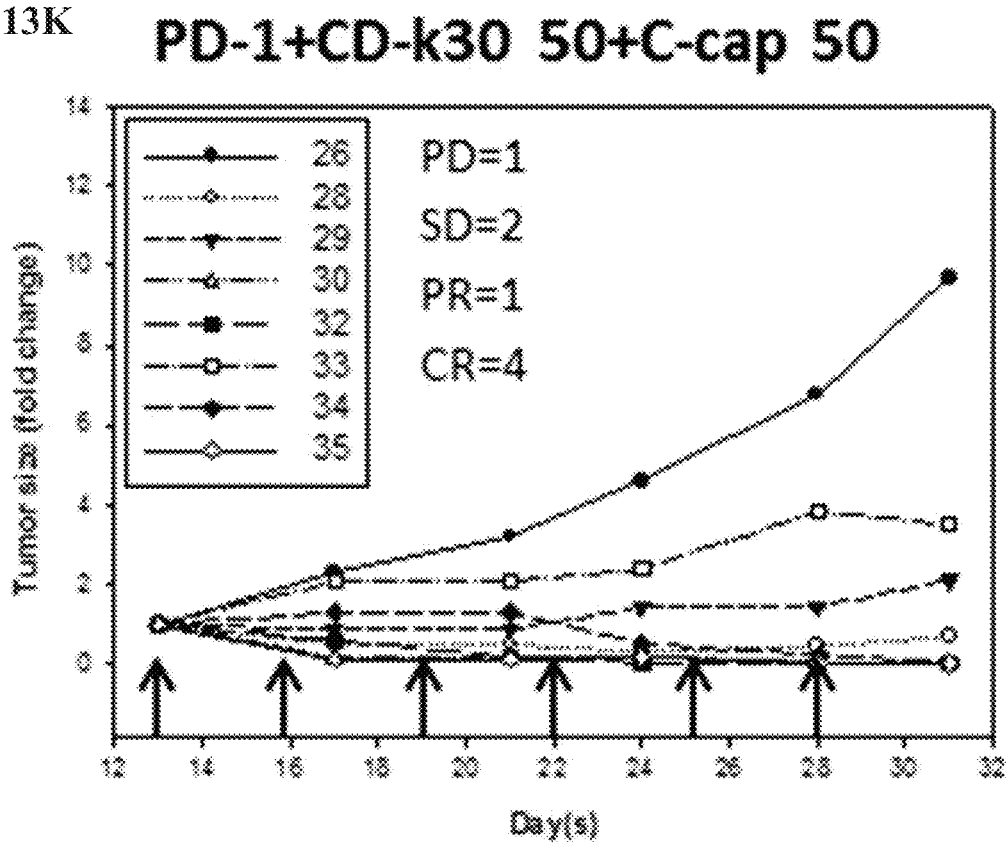
Figure 13L:
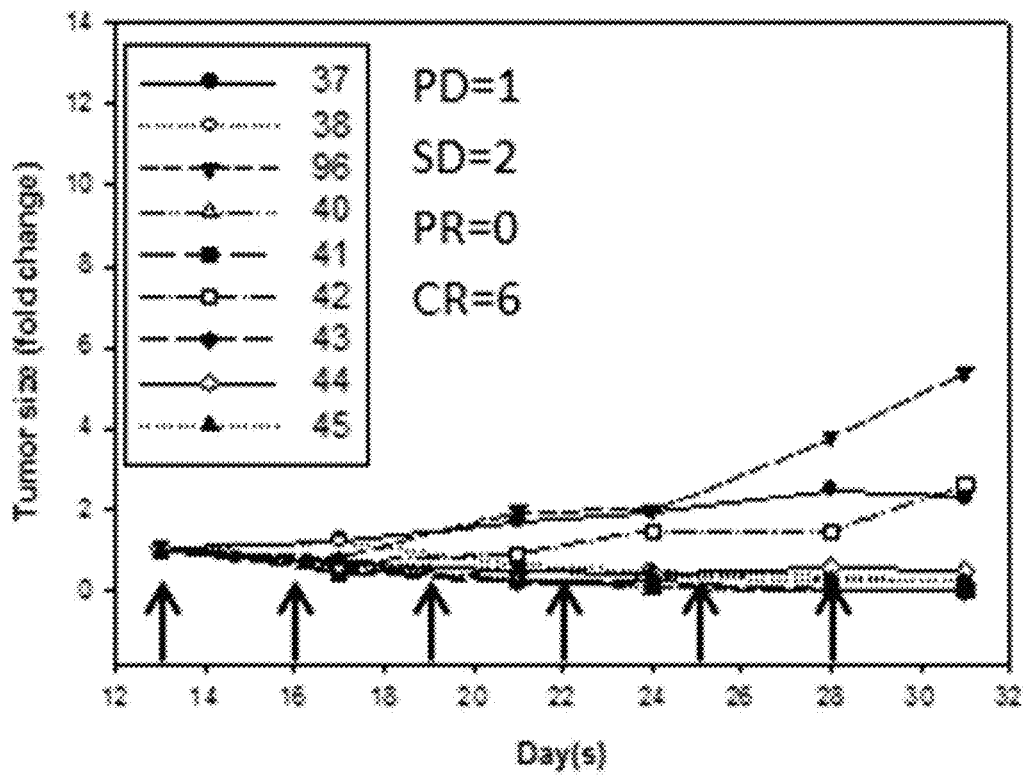
Figure 13M:
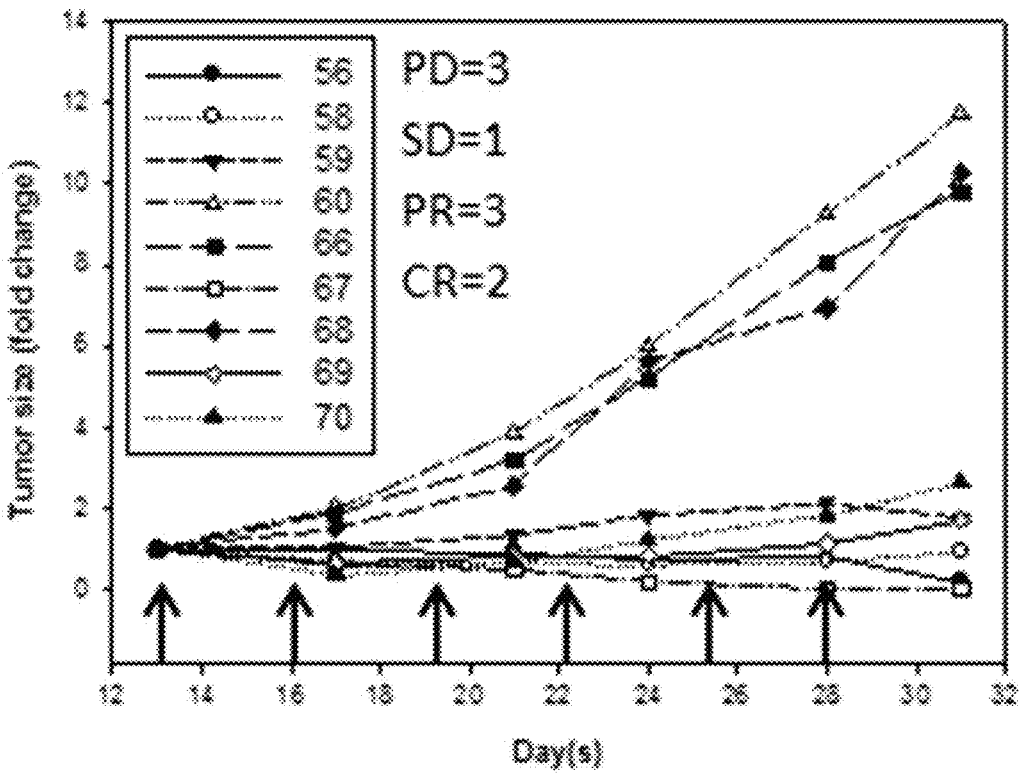
Figure 13N:
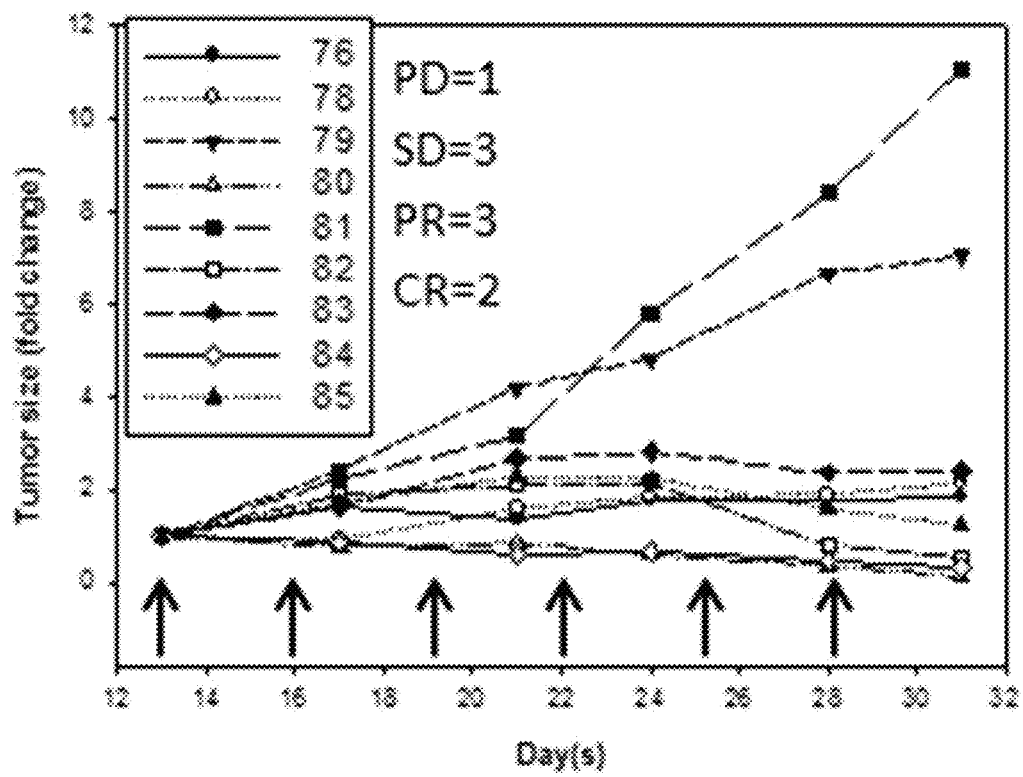
Figure 13O:
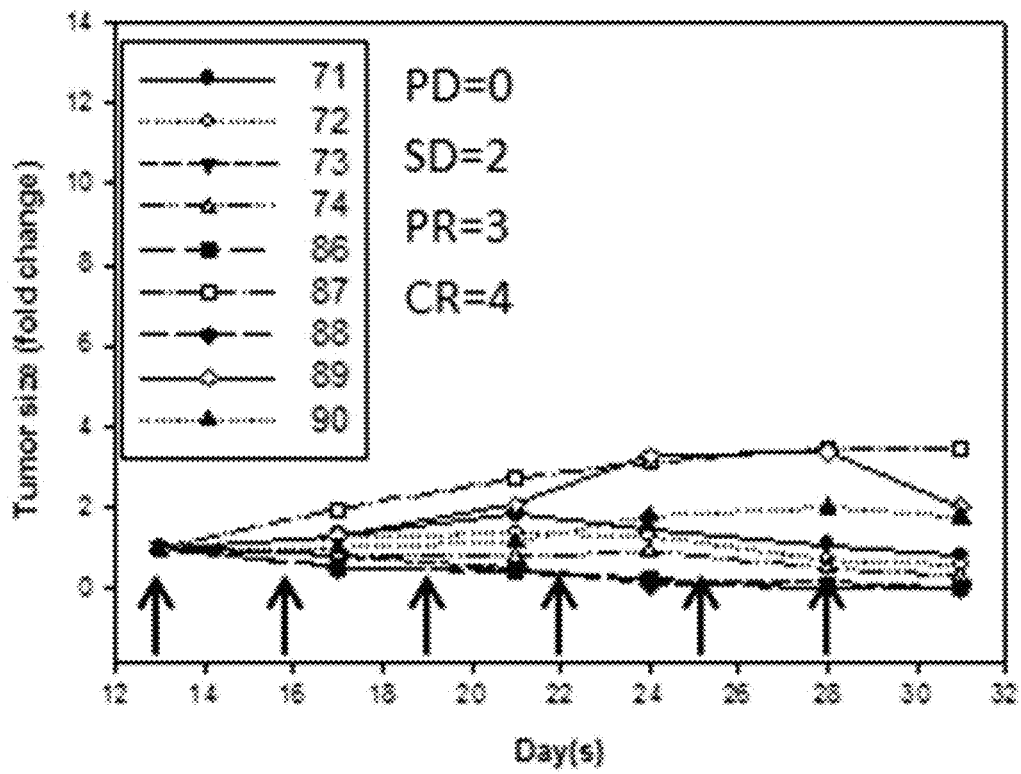
Figure 13P:
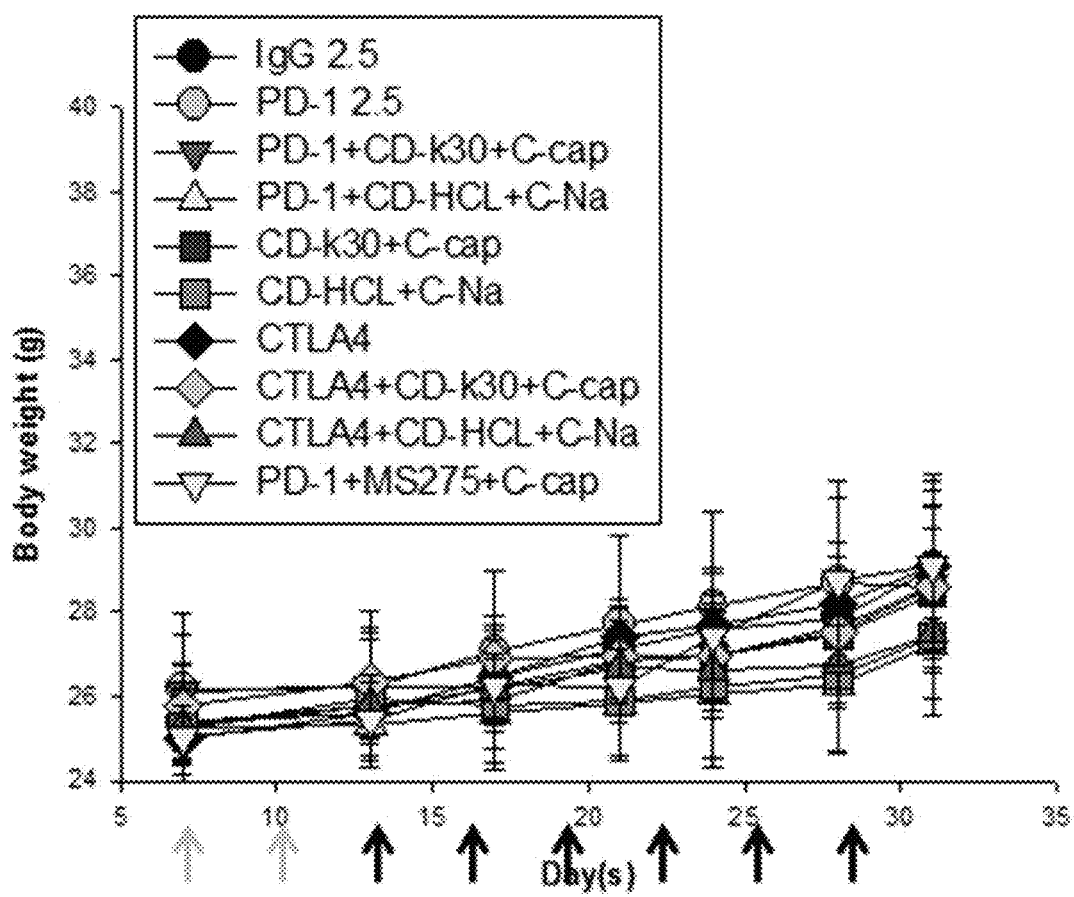
FIG. 13P shows the CT26 tumor bearing-mice body weight.
Figure 13Q:
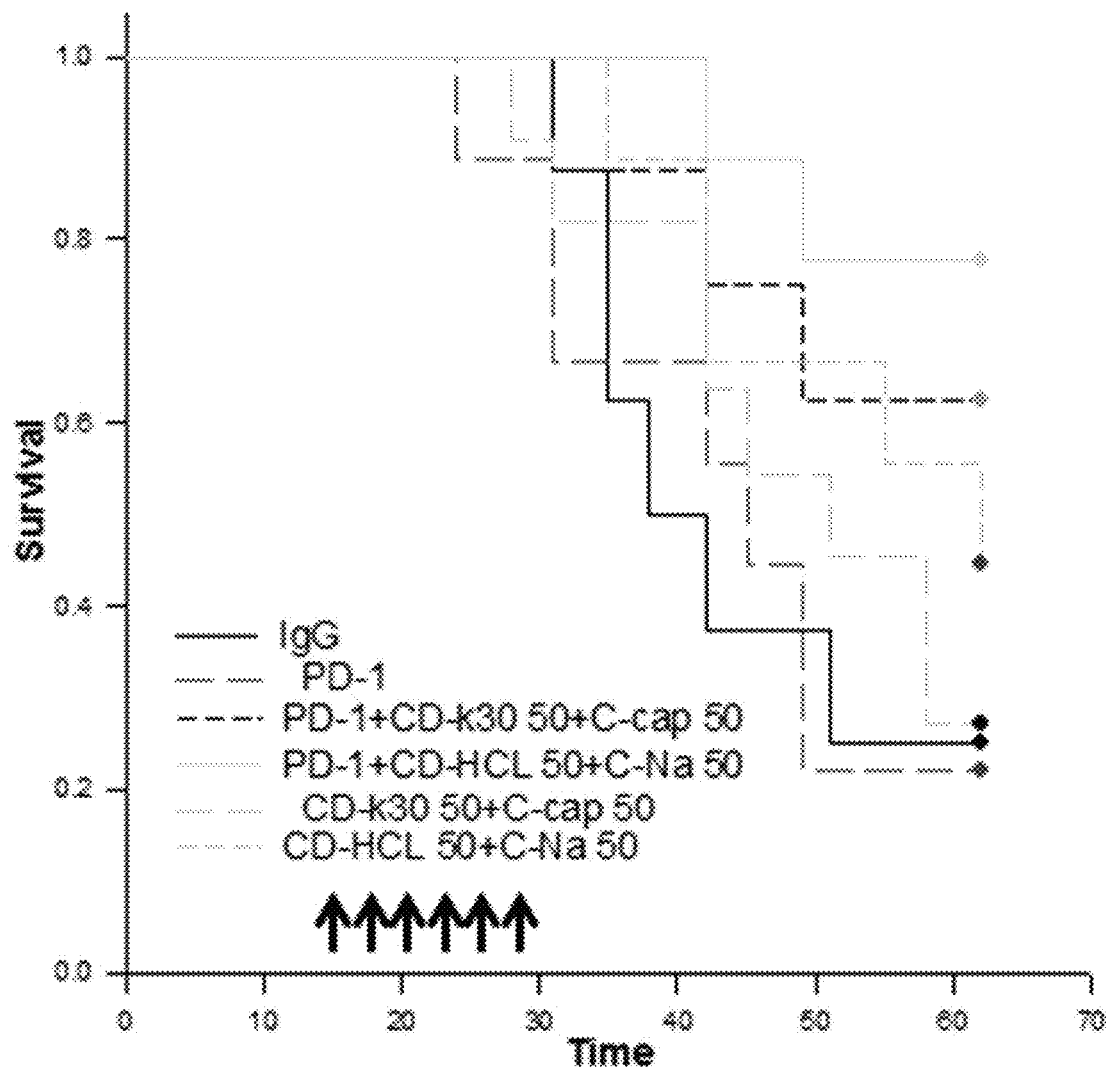
Figure 13R:
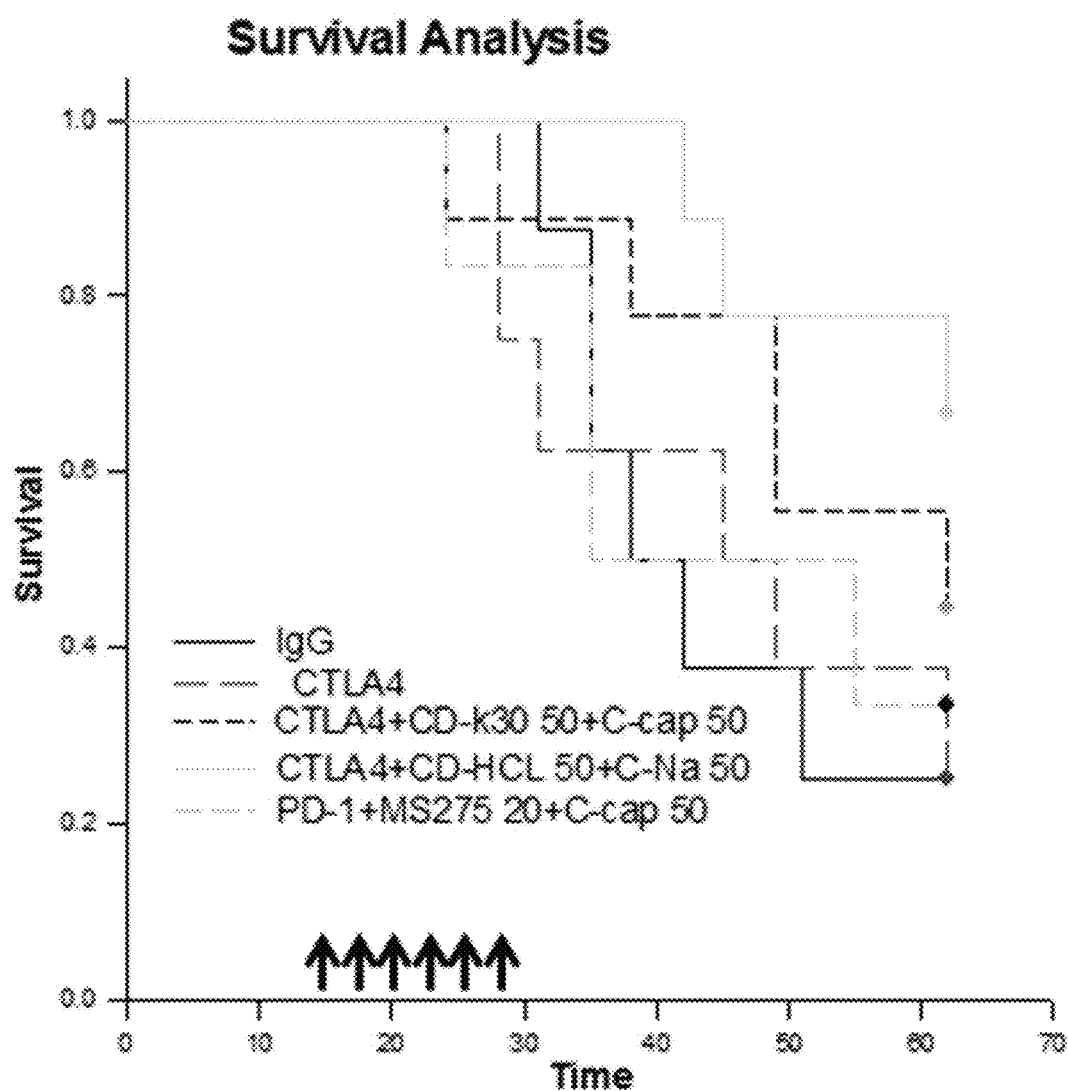

After the treatment was stopped at day 31, the tumors in the CT26 tumor-bearing mice grew faster in the anti-PD-1 and anti-CTLA-4 groups (FIGS. 13Q and 13R). The survival rate was evaluated at day 62. The treatment with chidamide-K30 plus celecoxib-capsule in combination with anti-PD-1 Ab showed better survival rate than that in the absence of anti-PD-1 Ab, achieving 62.5% and 27.2%, respectively. And the treatment with chidamide-HCl salt plus celecoxib-Na salt in combination with anti-PD-1 Ab showed better survival rate than that in the absence of anti-PD-1 Ab, achieving 77% and 44%, respectively. The result indicated that after treatment stopped chidamide-K30 plus celecoxib-capsule or chidamide-HCl salt plus celecoxib-Na salt unexpectedly showed a faster tumor growth than chidamide-K30 plus celecoxib-capsule or chidamide-HCl salt plus celecoxib-Na salt in combination with anti-PD-1 Ab. This study also proved that chidamide-HCl salt plus celecoxib-Na salt combined with anti-CTLA-4 Ab was potent to boost anti-cancer immune response. However, chidamide-HCl salt plus celecoxib-Na salt combined with anti-CTLA-4 Ab was more potent in inhibiting tumor growth than chidamide-K30 plus celecoxib-capsule combined with anti-CTLA-4 Ab, achieving survival rate 66.6%% and 44.4%, respectively (FIGS. 13Q and 13R). On the other hand, the head to head comparison between chidamide-HCl salt plus celecoxib-Na salt and MS-275 plus celecoxib-capsule when combined with anti-PD-1 Ab has demonstrated that the anti-cancer activity of combination regimen with chidamide-HCl salt plus celecoxib-Na salt is better than that of combination regimen with MS-275 plus celecoxib-capsule in anti-PD-L1 resistance condition.

Example 10

Figure 14A:
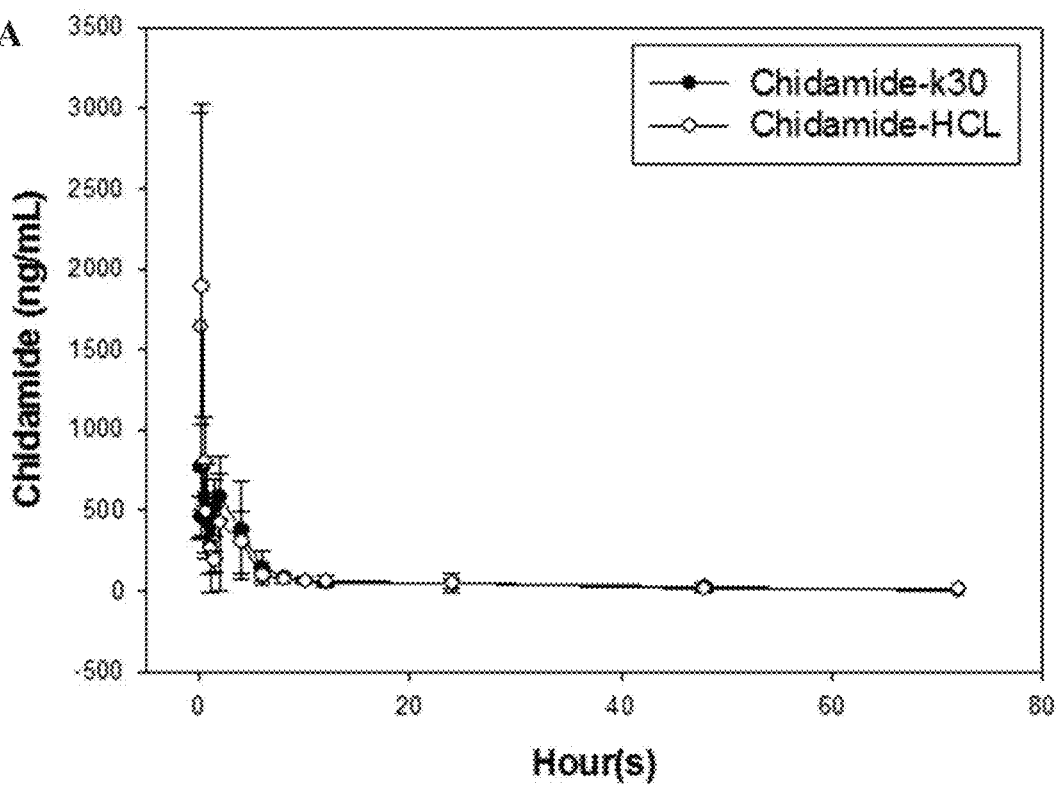
FIGS. 14A to 14I show the PK profiles of chidamide-HCl salt and celecoxib-Na salt alone or in combination in Wistar male rats. The rat was orally administered chidamide-K30, chidamide-HCl salt, celecoxib-capsule (Celebrex®, celecoxib/cap), or amorphous celecoxib-Na salt at dose of 50 mg/kg.
Figure 14B:
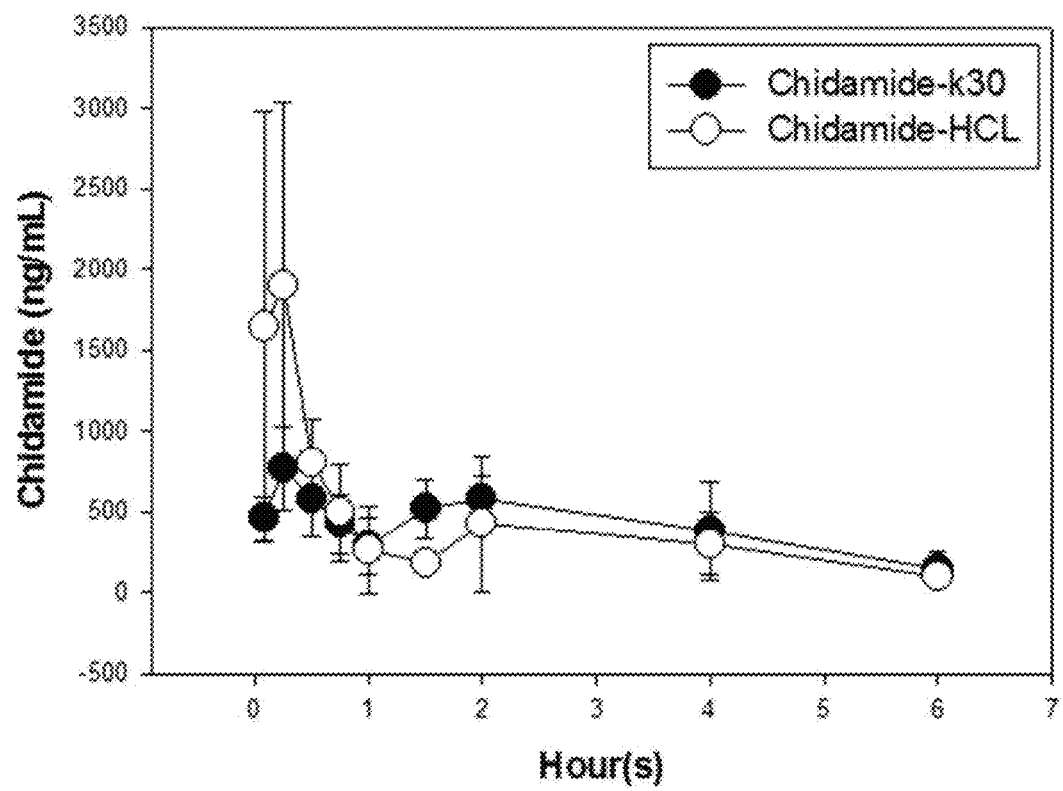
Figure 14C:
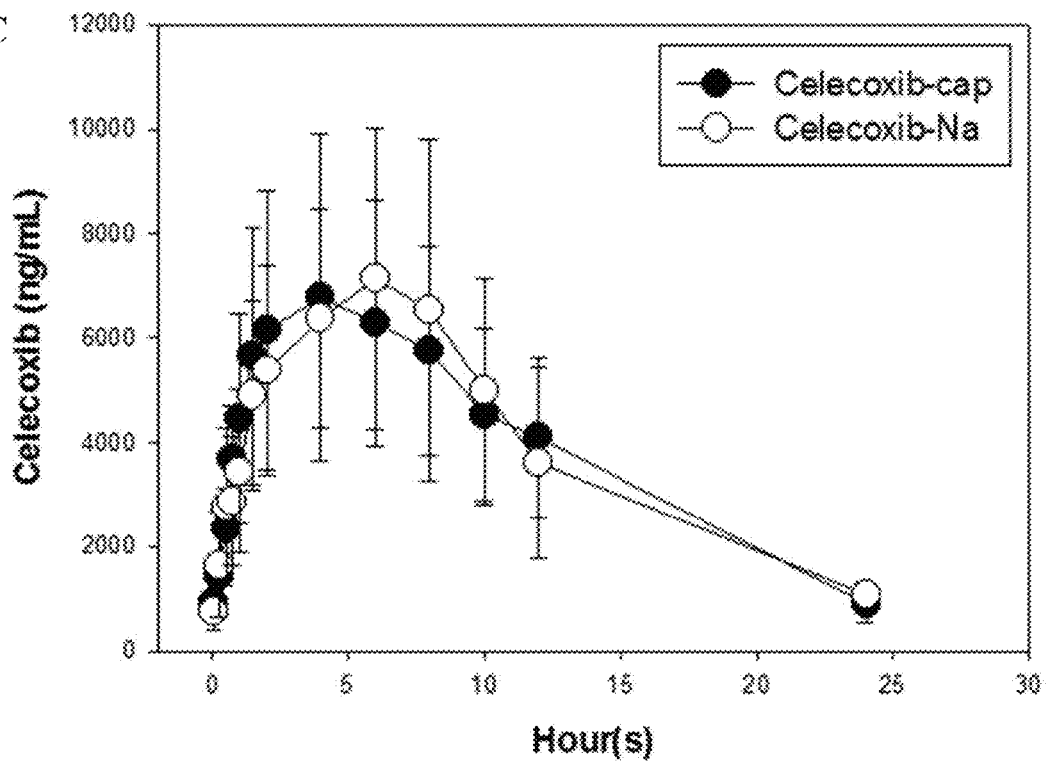

To Study the PK (pharmacokinetic) Profile of Chidamide-HCl Salt Combined with Celecoxib-Na Salt in Wistar Male Rats Chidamide-HCl salt plus amorphous form celecoxib-Na salt alone or combined with anti-PD-1 antibody possessed very potent anti-cancer immune activity. Therefore, we studied the PK profile of chidamide-HCl salt combined with celecoxib-Na salt vs. chidamide-K30 combined with celecoxib-capsule in Wistar rat. As shown in FIGS. 14A and 14B, the chidamide blood concentration-time profiles of chidamide-HCl salt (50 mg/kg) and chidamide-K30 (50 mg/kg) by oral administration in Wistar rat were analyzed. In Table 4 the result demonstrated that Cmax and Tmax of chidamide were significantly changed for salt form. In the chidamide-HCl salt group Cmax was 2065.2 (ng/mL) and Tmax was 0.14 h. However, in the chidamide-K30 group Cmax was 786.3 ng/mL and Tmax was 0.39 h. It was very markedly increased the rate of absorption of chidamide-HCl salt compared with that of chidamide-K30. However, the values of AUC, MRT, and $T_{1/2}$ were not significantly changed as shown in Table 4. These results suggested that chidamide-HCl salt possessed faster absorption properties and achieved higher Cmax, but did not increased the overall amount of the chidamide in circulation system in comparison with chidamide-K30 in Wistar rat. As shown in FIG. 14C, the celecoxib blood concentration-time profiles of 50 mg/kg of celecoxib-Na salt and 50 mg/kg of celecoxib-capsule by oral administration in Wistar rat were analyzed. This result demonstrated that the values of Tmax, Cmax, AUC, AUMC, MRT, and $T_{1/2}$ were not significantly different after oral administration between celecoxib-Na salt and celecoxib-capsule in Wistar rat as shown in Table 5.

Figure 14D:
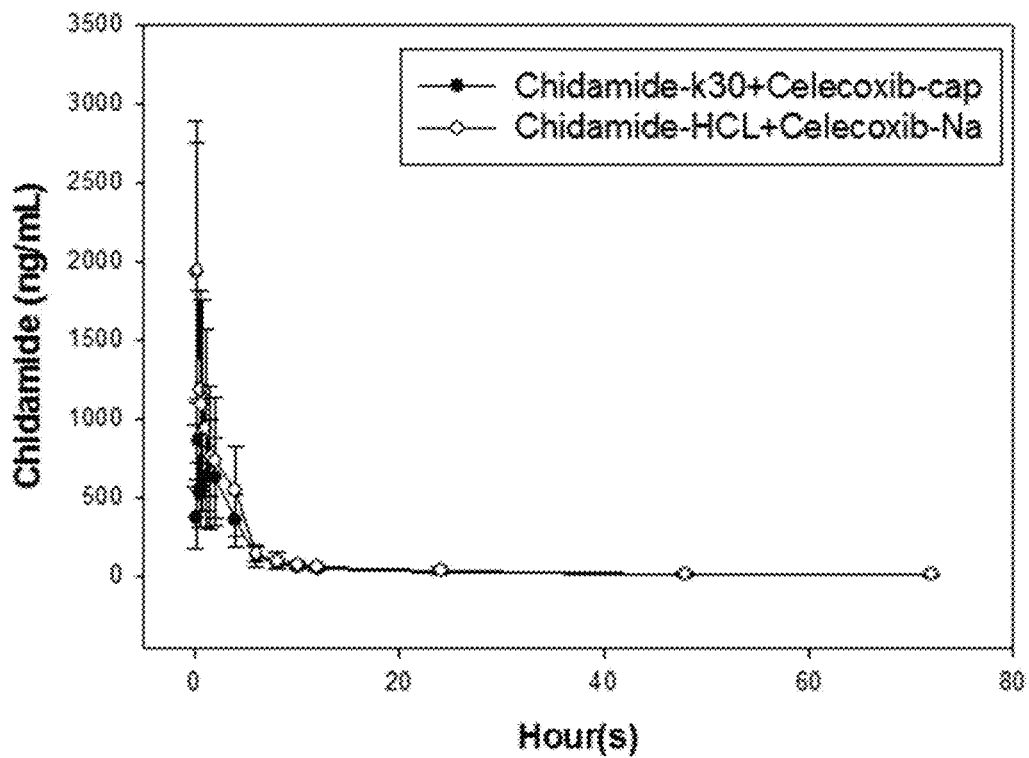
Figure 14E:
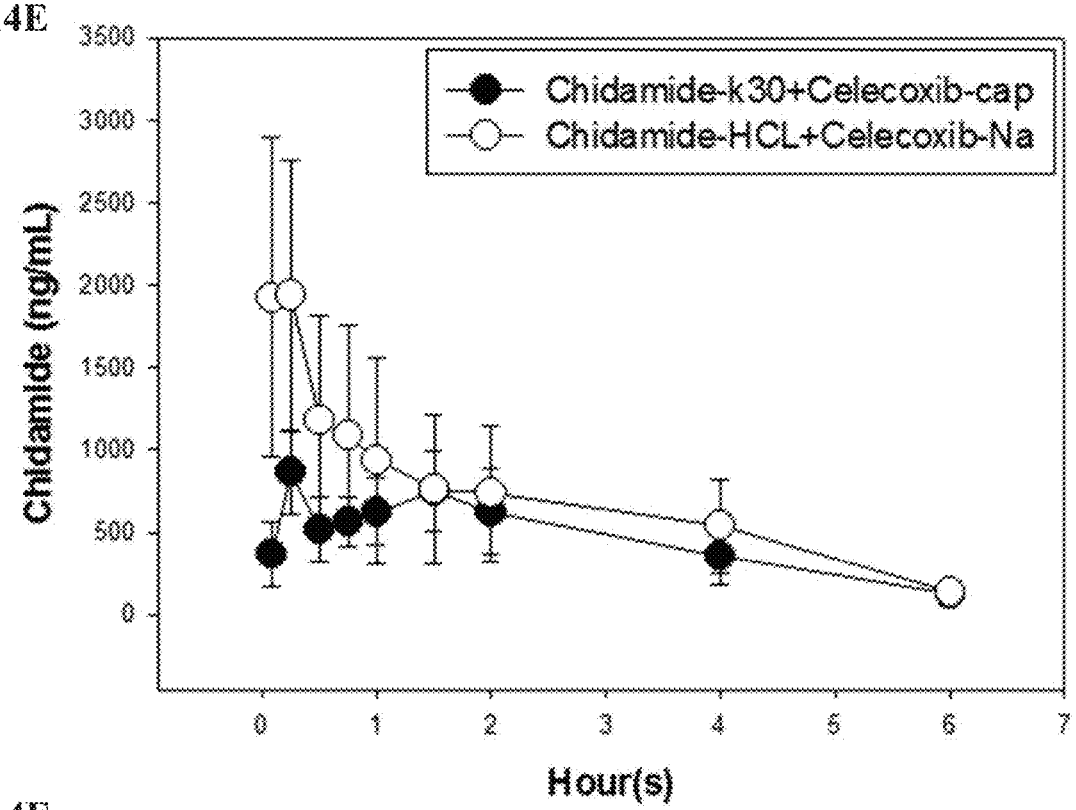

Next, the comparison of chidamide PK profiles between chidamide-HCl salt plus celecoxib-Na salt and chidamide-K30 plus celecoxib-capsule at dose of 50 mg/kg by oral administration in Wistar rat were analyzed. As shown in FIGS. 14D, 14E and Table 4, the Cmax value of chidamide was significantly increased in chidamide-HCl salt plus celecoxib-Na salt group compared with chidamide-K30 plus celecoxib-capsule group, and the values were about 2244.5 and 862.3 ng/mL, respectively. As shown in Table 4, the Tmax value of chidamide was significantly decreased in chidamide-HCl salt plus celecoxib-Na salt group compared with chidamide-K30 plus celecoxib-capsule group, and the values were about 0.14 and 0.25 h, respectively. The AUC value of chidamide was slightly increased in chidamide-HCl salt plus celecoxib-Na salt group compared with chidamide-K30 plus celecoxib-capsule group, and the values were about 5977 and 4201 ng*h/mL, respectively. The similar comparison result of AUMC value between the two combinations was shown in Table 4. The values of MRT and $T_{1/2}$ showed no difference between the two groups as shown in Table 4. The PK profile comparison between chidamide-HCl salt and chidamide-HCl salt plus celecoxib-Na salt showed slight change as shown in FIGS. 14G and 14H and Table 4. It was suggested that in the treatment with chidamide-HCl salt plus celecoxib-Na salt the chidamide PK profile was not significantly influenced by the presence of celecoxib-Na salt in term of ADME (absorption, distribution, metabolism, and excretion). But, the AUC value of chidamide was mildly influenced, and the AUC values for Chidamide-HCl and chidamide-HCl salt plus celecoxib-Na salt groups were about 4113 and 5977 ng/mL, respectively as shown in Table 4.

Figure 14F:
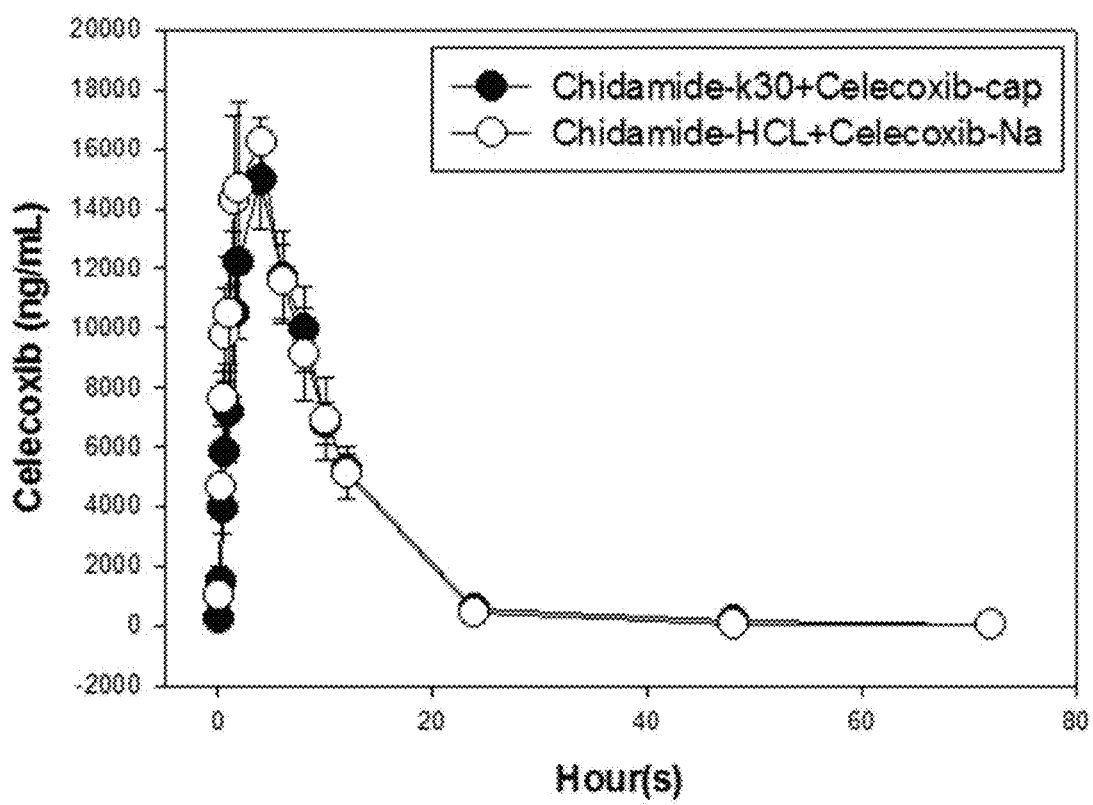
Figure 14G:
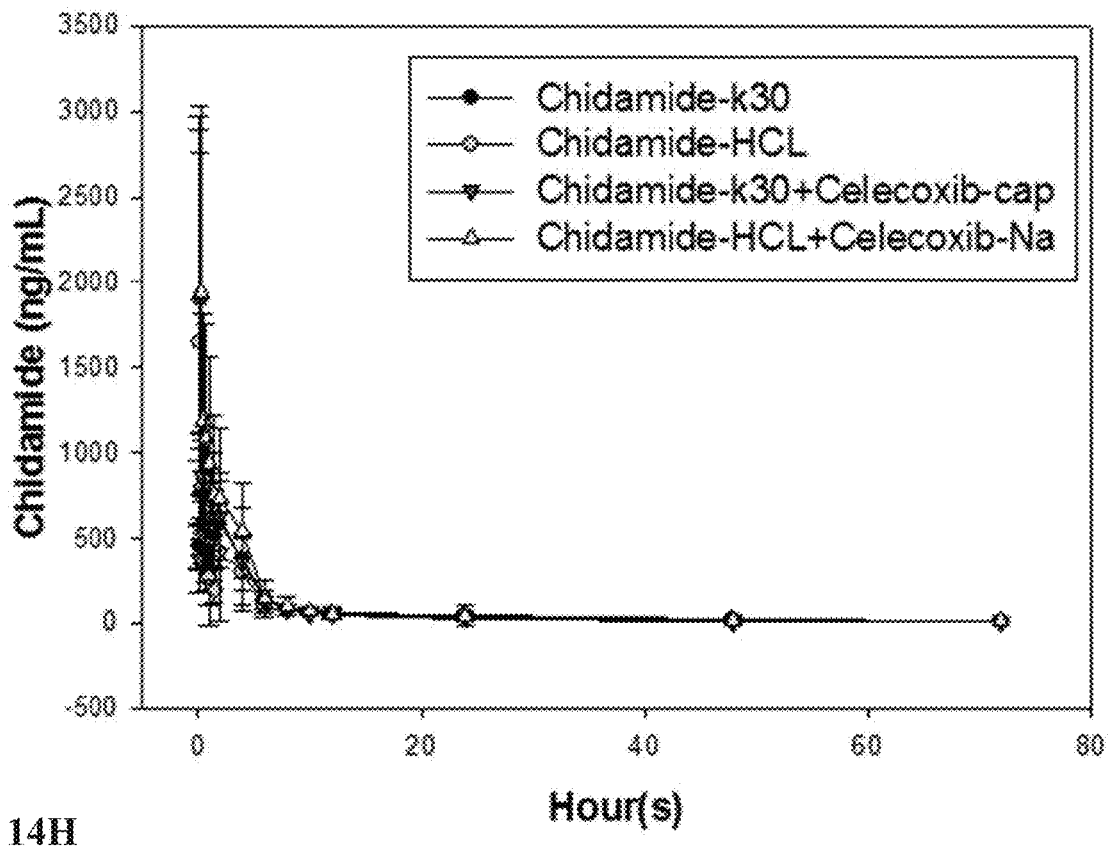
Figure 14H:
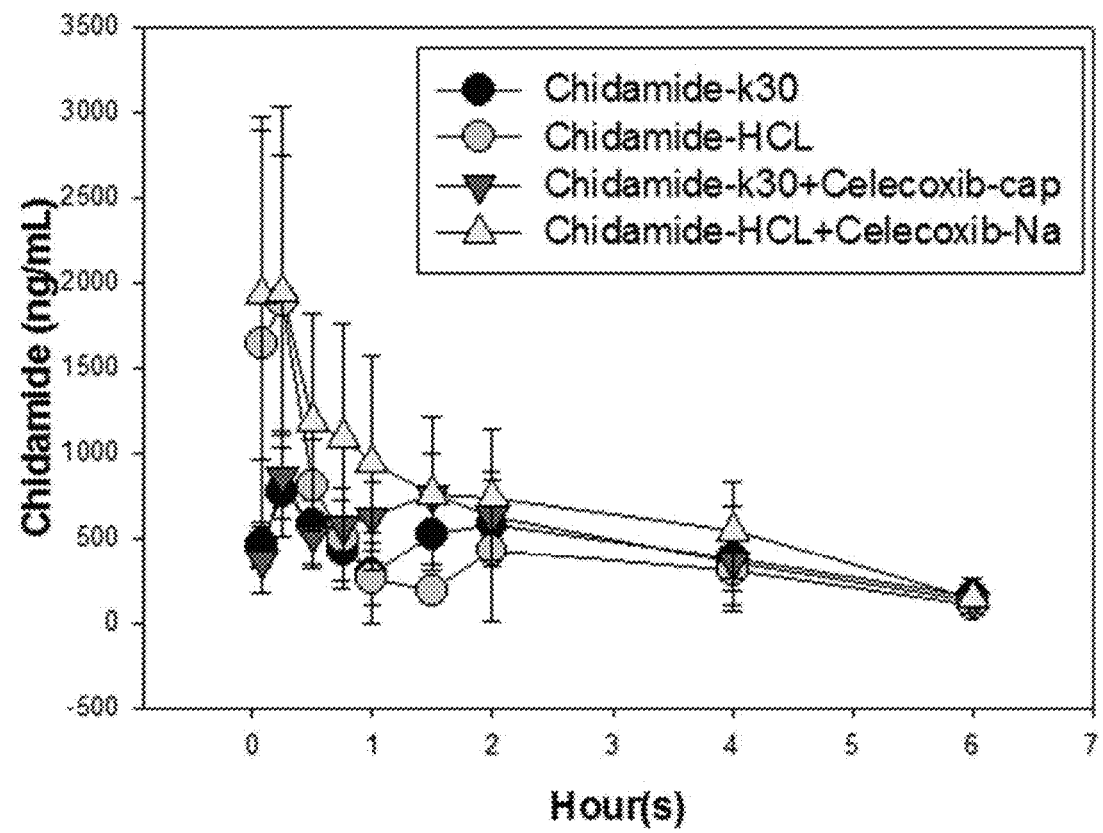
Figure 14I:
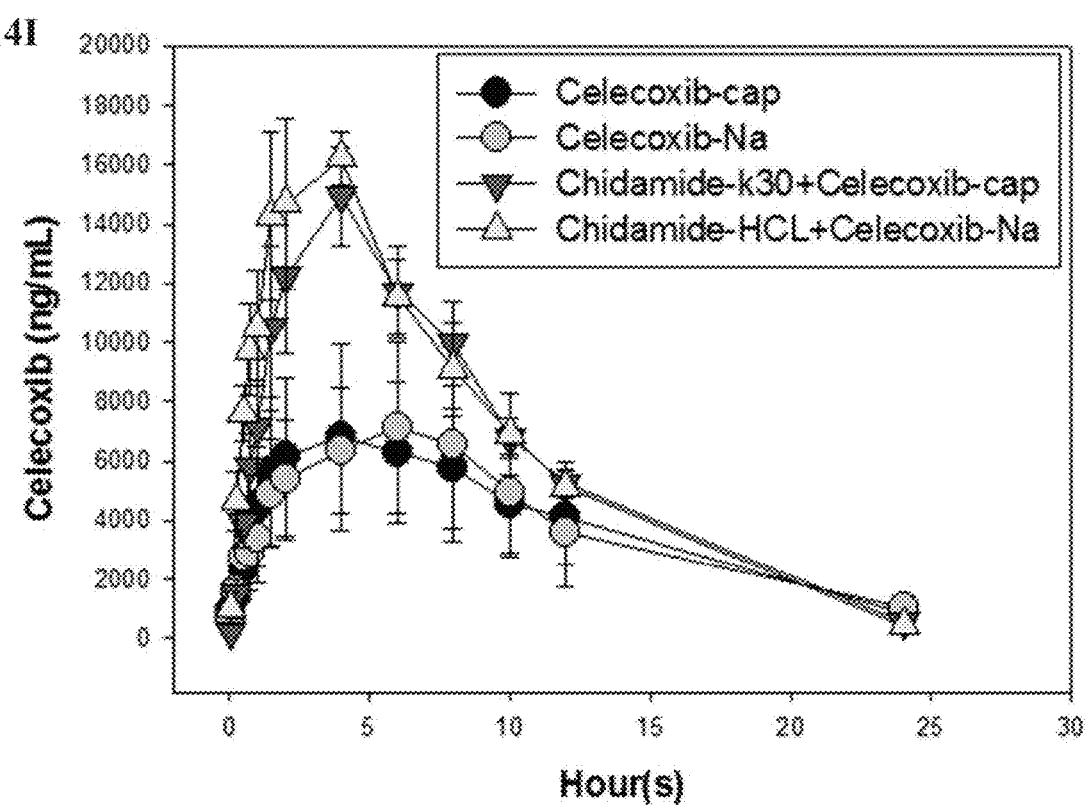

On the other hand, the celecoxib PK profile was not significantly changed when compared chidamide-K30 plus celecoxib-capsule with chidamide-HCl salt plus celecoxib-Na salt at 50 mg/kg by oral administration in Wistar rat as shown in FIG. 14F and Table 5. However, celecoxib-Na salt or celecoxib-capsule alone possessed significantly lower Cmax and AUC than chidamide-K30 plus celecoxib-capsule or chidamide-HCl salt plus celecoxib-Na salt as shown in FIG. 14I and Table 5. These results suggested that the presence of chidamide-K30 or chidamide-HCl salt significantly changed celecoxib ADME profile, and therefore markedly increased the values of Cmax and AUC of celecoxib. However, the chidamide PK profile was not significantly influenced by the presence of celecoxib-Na salt or celecoxib-capsule. In conclusion, it was demonstrated that chidamide-HCl salt plus celecoxib-Na salt possessed significantly changed ADME profile, which therefore achieved effective tumor inhibition and increased survival when in combination with immune checkpoint inhibitor, suggesting that salt forms possess better anti-cancer potency than chidamide-K30 plus celecoxib-capsule in facing challenge of second line therapy for drug resistance.

TABLE 4

Pharmacokinetics parameters of chidamide from treatment with chidamide-K30, chidamide-HCl salt, chidamide-k30 plus celecoxib-capsule, and chidamide-HCl salt plus celecoxib-Na salt in Wistar male rats.

| List | Chidamide-k30 N = 6 | Chidamide-HCl salt N = 6 | Chidamide-k30 plus Celecoxib-cap N = 6 | Chidamide-HCl salt plus celecoxib-Na salt N = 6 |
|---|---|---|---|---|
| $T_{max}$, (h) | 0.39 ± 0.2 | 0.14 ± 0.1[a] | 0.25 ± 0.01[a, b] | 0.14 ± 0.09[a, c] |
| $C_{max}$, (ng/mL) | 786 ± 243 | 2065 ± 1136[a] | 862 ± 245[a] | 2244 ± 841[b] |
| $AUC_{0 \to t}$, (ng * h/mL) | 4422 ± 1894 | 4113 ± 1773 | 4201 ± 848 | 5977 ± 2161 |
| AUMC, (ng * h²/mL) | 57808 ± 43710 | 46570 ± 25207 | 38478 ± 5671 | 53542 ± 19097 |
| MRT (h) | 12.1 ± 5.5 | 11.3 ± 2.8 | 8.9 ± 1.1 | 9.0 ± 2.9 |
| $T_{1/2}$ (h) | 16.9 ± 3.7 | 14.0 ± 4.9 | 20.7 ± 3.1 | 18.8 ± 2.2 |

Values are mean ± standard deviation (SD).
[a]$P < 0.05$, for versus chidamide-k30,
[b]$P < 0.05$, for versus chidamide-HCl salt;
[c]$P < 0.05$, for versus chidamide-k30 plus celecoxib-cap. Differences between rats treated with chidamide-k30, chidamide-HCl salt, chidamide-k30 plus celecoxib-cap, and chidamide-HCl salt plus celecoxib-Na salt were expressed as the mean ± SD and analyzed by the one-way ANOVA followed by Tukey's multiple comparisons test.
$T_{max}$: Time to reach $C_{max}$.
$C_{max}$: The peak plasma concentration of a drug after administration.
$AUC_{0 \to t}$: area under the curve.
MRT: mean residence time
$T_{1/2}$: The time required for the concentration of the drug to reach half of its original value.

TABLE 5

Pharmacokinetics parameters of celecoxib from treatment with celecoxib-capsule, celecoxib-Na salt, celecoxib-capsule plus chidamide-k30, and celecoxib-Na salt plus chidamide-HCl salt in Wistar male rats.

| List | Celecoxib-cap N = 5 | Celecoxib-Na salt N = 5 | Chidamide-k30 plus Celecoxib-cap N = 6 | chidamide-HCl salt plus celecoxib-Na salt N = 6 |
|---|---|---|---|---|
| $T_{max}$, (h) | 4.8 ± 1.0 | 5.2 ± 1 | 4.3 ± 0.8[a] | 3.3 ± 1.0[c] |
| $C_{max}$, (ng/mL) | 7104 ± 2962 | 7631 ± 2727 | 15021 ± 1563[b] | 16576 ± 1181[c] |
| $AUC_{0 \to t}$, (ng * h/mL) | 105511 ± 34816 | 106723 ± 35778 | 163453 ± 11461[b] | 168033 ± 14588[a, b] |

TABLE 5-continued

Pharmacokinetics parameters of celecoxib from treatment with celecoxib-capsule, celecoxib-Na salt, celecoxib-capsule plus chidamide-k30, and celecoxib-Na salt plus chidamide-HCl salt in Wistar male rats.

| List | Celecoxib-cap N = 5 | Celecoxib-Na salt N = 5 | Chidamide-k30 plus Celecoxib-cap N = 6 | chidamide-HCl salt plus celecoxib-Na salt N = 6 |
|---|---|---|---|---|
| AUMC, (ng * h²/mL) | 1062627 ± 301118 | 1124599 ± 333210 | 1481893 ± 243790$^a$ | 1330378+158873 |
| MRT (h) | 9.3 ± 0.4 | 9.4 ± 0.5 | 9.0 ± 1.1 | 7.9 ± 0.6$^{a, b, c}$ |
| $T_{1/2}$ (h) | 6.2 ± 2 | 7.7 ± 3.1 | 3.7 ± 0.2$^{a, b}$ | 3.4 ± 0.1$^{a, b}$ |

Values are mean ± standard deviation (SD).
$^a$P < 0.05, for versus celecoxib/cap,
$^b$P < 0.05, for versus celecoxib-Na salt;
$^c$P < 0.05, for versus chidamide-k30 plus celecoxib-cap. Differences between rats treated with chidamide-k30, chidamide-HCl salt, chidamide-k30 plus celecoxib-cap, and chidamide-HCl salt plus celecoxib-Na salt were expressed as the mean ± SD and analyzed by the one-way ANOVA followed by Tukey S multiple comparisons test.
$T_{max}$: Time to reach $C_{max}$.
$C_{max}$: The peak plasma concentration of a drug after administration.
$AUC_{0 \to t}$: area under the curve.
MRT: mean residence time
$T_{1/2}$: The time required for the concentration of the drug to reach half of its original value.

What is claimed is:

1. A combination comprising an acidic salt of chidamide and a basic salt of celecoxib; wherein the acidic salt of chidamide is a hydrochloride salt or a sulfate salt of chidamide, wherein the hydrochloride salt of chidamide is in a crystalline form (Form A) having an X-ray powder diffraction (XRPD) pattern with peaks comprising 2-theta values at about 16.12 degree, about 19.02 degree, about 21.62 degree, about 23.38 degree and about 30.16 degree, and/or wherein the sulfate salt of chidamide is in a crystalline form (Form B) having an X-ray powder diffraction (XRPD) pattern with peaks comprising 2-theta values at about 21.15 degree, about 24.65 degree, about 17.00 degree, about 18.49 degree and about 26.69 degree.

2. The combination of claim 1, wherein the amounts of the acidic salt of chidamide and the basic salt of celecoxib ranges from 5 about 5% (w/w) to about 80% (w/w) and about 95% (w/w) to about 20% (w/w), respectively.

3. The combination of claim 1, wherein the amounts of the acidic salt of chidamide and the basic salt of celecoxib are in a weight ratio of about 8:1, about 4:1, about 2:1, about 1:1, about 1:2, about 1:4 or about 1:8.

4. The combination of claim 1, wherein the acidic salt of chidamide and the basic salt of celecoxib are contained in a same dosage form or independently contained in separate dosage forms; optionally, wherein the dosage form is a tablet or capsule.

5. The combination of claim 1, wherein the hydrochloride salt of chidamide is in a crystalline form (Form A) having
a Fourier-transform infrared spectroscopy (FTIR) pattern with peaks at about 3162 cm$^{-1}$, about 3059 cm$^{-1}$, about 3036, about 2751 cm$^{-1}$, about 2588 cm$^{-1}$, about 2359 cm$^{-1}$, about 2341 cm$^{-1}$, about 1667 cm$^{-1}$, about 1658 cm$^{-1}$, about 1639 cm$^{-1}$, about 1620 cm$^{-1}$, about 1610 cm$^{-1}$, about 1562 cm$^{-1}$, about 1517 cm$^{-1}$, about 1508 cm$^{-1}$, about 1485 cm$^{-1}$, about 1468 cm$^{-1}$, about 1444 cm$^{-1}$, about 1431 cm$^{-1}$, about 1307 cm$^{-1}$, about 1282 cm$^{-1}$, about 1256 cm$^{-1}$, about 1243 cm$^{-1}$, about 1220 cm$^{-1}$, about 1182 cm$^{-1}$, about 1145 cm$^{-1}$, about 1074 cm$^{-1}$, about 1046 cm$^{-1}$.

6. The combination of claim 1, wherein the XRPD pattern of Form A further has peaks comprising 2-theta values at about 21.08 degree, about 23.76 degree, about 25.58 degree, about 27.82 degree and about 28.18 degree.

7. The combination of claim 1, wherein the sulfate salt of chidamide is in a crystalline form (Form B) having
a FTIR pattern with peaks at about 3249 cm$^{-1}$, about 3067 cm$^{-1}$, about 2578 cm$^{-1}$, about 2360 cm$^{-1}$, about 1689 cm$^{-1}$, about 1664 cm$^{-1}$, about 1647 cm$^{-1}$, about 1614 cm$^{-1}$, about 1568 cm$^{-1}$, about 1521 cm$^{-1}$, about 1510 cm$^{-1}$, about 1486 cm$^{-1}$, about 1467 cm$^{-1}$, about 1434 cm$^{-1}$, about 1412 cm$^{-1}$, about 1388 cm$^{-1}$, about 1354 cm$^{-1}$, about 1328 cm$^{-1}$, about 1283 cm$^{-1}$, about 1266 cm$^{-1}$, about 1252 cm$^{-1}$, about 1226 cm$^{-1}$, about 1184 cm$^{-1}$, about 1099 cm$^{-1}$, about 1059 cm$^{-1}$, about 1034 cm$^{-1}$ and about 1022 cm$^{-1}$.

8. The combination of claim 7, wherein the XRPD pattern of Form B further has peaks comprising 2-theta values at about 14.74 degree, about 19.45 degree, about 22.00 degree, about 23.55 degree and about 27.94 degree.

9. The combination of claim 1, wherein the basic salt of celecoxib is a sodium salt of celecoxib.

10. The combination of claim 9, wherein the sodium salt of celecoxib is in an amorphous form or a crystalline form.

11. The combination of claim 9, wherein the crystalline form (Form I) has an X-ray powder diffraction (XRPD) pattern with peaks comprising 2-theta values at about 19.85 degree, about 20.51 degree, about 21.51 degree, about 22.55 degree and about 18.25 degree.

12. The combination of claim 11, wherein the XRPD pattern of Form I further has peaks comprising 2-theta values at about 10.95 degree, about 14.05 degree, about 14.601 degree, about 17.2 degree, about 25.80 degree and about 27.30 degree.

13. The combination of claim 1, wherein the combination further comprises an immune checkpoint inhibitor and/or a chemotherapeutic agent; optionally, the immune checkpoint inhibitor is an anti-CTLA-4 antibody, anti-PD-1 antibody or an anti-PD-L1 antibody; optionally, wherein the immune checkpoint inhibitor is pembrolizumab, pidilizumab, nivolumab, durvalumab, avelumab, atezolizumab, toripalimab, sintilimab, camrelizumab, or MIHI.

14. A method of regulating tumor microenvironment in a cancer immunotherapy or treating a cancer, comprising administering an effective amount of the combination of claim 1; optionally, the method further comprises administering an immune checkpoint inhibitor, and/or administration of the acidic salt of chidamide and the basic salt of celecoxib improves the pharmacokinetics profile compared with that of chidamide free base and celecoxib free base.

15. The method of claim 14, wherein the acidic salt of chidamide and the basic salt of celecoxib are administered concurrently, separately or sequentially; optionally, the combination and the immune checkpoint inhibitor are administered concurrently, separately or sequentially.

16. The method of claim 14, wherein the cancer is glioblastoma, liver cancer, colorectal carcinoma, glioblastoma, gastric cancer, colorectal cancer, esophageal cancer, lung cancer, pancreatic cancer, renal cell carcinoma, benign prostate hyperplasia, prostate cancer, ovarian cancer, melanoma, breast cancer, chronic lymphocytic leukemia (CLL), Merkel cell carcinoma, Non-Hodgkin lymphoma, acute myeloid leukemia (AML), gallbladder cancer, cholangiocarcinoma, urinary bladder cancer, or uterine cancer.

17. The combination of claim 1, wherein the basic salt of celecoxib is anhydrous.

\* \* \* \* \*